US012186383B2

(12) United States Patent
Lai et al.

(10) Patent No.: US 12,186,383 B2
(45) Date of Patent: Jan. 7, 2025

(54) ANTIBODIES OR ANTIBODY-FRAGMENTS THEREOF TARGETING ALPHAVIRUSES, AND COMPOSITIONS AND METHODS COMPRISING SAME

(71) Applicant: Albert Einstein College of Medicine, Bronx, NY (US)

(72) Inventors: Jonathan R. Lai, Dobbs Ferry, NY (US); Jose Quiroz, Bronx, NY (US); Ryan Malonis, Bronx, NY (US); Margaret Kielian, Dobbs Ferry, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 646 days.

(21) Appl. No.: 16/972,077

(22) PCT Filed: Jun. 6, 2019

(86) PCT No.: PCT/US2019/035828
§ 371 (c)(1),
(2) Date: Dec. 4, 2020

(87) PCT Pub. No.: WO2019/236875
PCT Pub. Date: Dec. 12, 2019

(65) Prior Publication Data

US 2022/0265806 A1 Aug. 25, 2022

Related U.S. Application Data

(60) Provisional application No. 62/681,247, filed on Jun. 6, 2018.

(51) Int. Cl.
| | |
|---|---|
| *A61K 39/12* | (2006.01) |
| *A61K 33/242* | (2019.01) |
| *A61K 39/42* | (2006.01) |
| *A61P 31/14* | (2006.01) |
| *C07K 16/10* | (2006.01) |
| *C12N 7/00* | (2006.01) |
| *A61K 39/00* | (2006.01) |

(52) U.S. Cl.
CPC ............ *A61K 39/12* (2013.01); *A61K 33/242* (2019.01); *A61K 39/42* (2013.01); *A61P 31/14* (2018.01); *C07K 16/1081* (2013.01); *C12N 7/00* (2013.01); *A61K 2039/505* (2013.01); *A61K 2039/525* (2013.01)

(58) Field of Classification Search
None
See application file for complete search history.

(56) References Cited

U.S. PATENT DOCUMENTS

| | | | |
|---|---|---|---|
| 9,944,989 | B2 | 4/2018 | Xu |
| 2009/0070897 | A1 | 3/2009 | Goldman et al. |
| 2011/0286916 | A1 | 11/2011 | Aste-Amezaga et al. |
| 2016/0145323 | A1 | 5/2016 | Doranz et al. |
| 2019/0352713 | A1 | 11/2019 | Yang |
| 2022/0265806 | A1 | 8/2022 | Lai et al. |

FOREIGN PATENT DOCUMENTS

| | | | |
|---|---|---|---|
| WO | WO-2011/109440 | A1 | 9/2011 |
| WO | WO-2016/168417 | A2 | 10/2016 |
| WO | WO-2019/236875 | A1 | 12/2019 |
| WO | WO-2021/214778 | A1 | 10/2021 |

OTHER PUBLICATIONS

Schmidt and Schnierle, Drug Design, Development and Therapy, 2022, 16:3663-3673. (Year: 2022).*
Malonis et al., PNAS 2021, 118(37):e2100104118, 11 pages (Year: 2021).*
Fox et al., "Broadly neutralizing alphavirus antibodies bind an epitope on E2 and inhibit entry and egress," Cell 163(5):1095-1107 (2015).

International Search Report and Written Opinion for International Application No. PCT/US19/35828 dated Nov. 13, 2019.

UniProtKB_A0A2A2UX21, Bifunctional tetrahydrofolate synthase/dihydrofolate synthase, Accession No. AOA2A2UX21, Last Sequence Uptake: Dec. 20, 2017, Retrieved on Aug. 22, 2019, URL: <http://www.uniprot.org/uniprot/A0A2A2UX21>.

Garg et al., "Circulating cardiovascular microRNAs in critically ill COVID-19 patients", *European journal of heart failure* 23(3): 468-475 (2021).

International Search Report and Written Opinion for International Application No. PCT/US2023/019592 dated Jul. 20, 2023.

* cited by examiner

*Primary Examiner* — Stacy B Chen

(74) *Attorney, Agent, or Firm* — Foley Hoag LLP; Erik A. Huestis; Thi K. Dio

(57) ABSTRACT

Provided are high affinity anti-alphavirus antibodies or alphavirus-binding fragments thereof, as well as methods of use and devices employing such antibodies and/or fragments. Further provided are complementarity determining region (CDR) sequences of variable domain light chain (VL) and variable domain heavy chain (VH) sequences, and the methods of using the high affinity anti-alphavirus antibodies for treating different types of alphavirus infections.

26 Claims, 37 Drawing Sheets

Specification includes a Sequence Listing.

— DC1.56 to chCHK-166<sup>pMAZ</sup>
— DC2.82 to chCHK-166<sup>pMAZ</sup>
— DC2.85 to chCHK-166<sup>pMAZ</sup>
— SUDV-F4 to chCHK-166<sup>pMAZ</sup>

FIG. 7A

- p62-E1 specific
- E1 specific
- undefined epitope
- chCHK-152
- SUDV-F4

FIG. 7B

- p62-E1 specific
- E1 specific
- undefined epitope

IC$_{50}$ vs. CHIKV 181/25 (nM)

0.03, 0.07, 2.3, 4.7 mAb: DC2.429, DC2.271B, DC1.364, DC1.7, DC1.415, DC2.118, DC2.284, DC2.131, DC2.148, DC2.315, DC1.371, DC1.355, DC1.55, DC2.555, DC2.536, DC1.56, DC1.380, DC2.112, DC1.9

FIG. 7D

MAYV

| | IC$_{50}$ (nM) (95% C.I.) |
|---|---|
| DC1.55 | 63 (42-170) |
| DC2.536 | ~560 |
| DC2.555 | ~80 |
| SUDV-F4 | > |
| chCHK-265$^{MAZ}$ | <0.001 |

CHIKV 181/25

| | IC$_{50}$ (nM) (95% C.I.) |
|---|---|
| C9pMAZ | 0.04 (0.02-0.05) |
| 4N12pMAZ | 0.02 (0.01-0.03) |
| IM-CVK063pMAZ | ~14 |
| DC2.271B | 0.05 (0.03-0.08) |
| DC2.429 | 0.02 (0.02-0.03) |

FIG. 8E rVSV-CHIKV$^{E2-K230T}$

| | IC$_{50}$ (nM) (95% C.I.) |
|---|---|
| C9pMAZ | 0.1 (0.08-0.2) |
| IM-CVK063pMAZ | 24 (14-40) |
| 4N12pMAZ | 0.5 (0.3-0.8) |
| DC2.271B | > |

FIG. 8F

■ chCHK-152pMAZ
◆ SUDV-F4

ANTIBODIES OR ANTIBODY-FRAGMENTS THEREOF TARGETING ALPHAVIRUSES, AND COMPOSITIONS AND METHODS COMPRISING SAME

STATEMENT OF GOVERNMENT SUPPORT

This invention was made with government support under grant numbers AI125462 and AI075647 awarded by the National Institutes of Health. The government has certain rights in the invention.

RELATED APPLICATIONS

This application is a § 371 national stage application based on International Application No. PCT/US19/35828, filed Jun. 6, 2019, which claims the benefit of U.S. Provisional Application No. 62/681,247, filed Jun. 6, 2018, the contents of each of which are hereby incorporated by reference.

SEQUENCE LISTING

The application contains a Sequence Listing that has been filed electronically in the form of a text file, created Jul. 23, 2021, and named "AET-00301_ST25.txt" (196,006 bytes), the contents of which are incorporated herein by reference in their entirety.

BACKGROUND OF THE INVENTION

The disclosures of all publications, patents, patent application publications and books referred to herein, are hereby incorporated by reference in their entirety into the subject application to more fully describe the art to which the subject invention pertains.

Chikungunya (CHIKV) is a member of the alphavirus genus. These positive-strand RNA viruses are generally disseminated by mosquito vectors and cause severe human and animal illness (1). Human CHIKV infection causes a painful polyarthritis that can persist for years after infection and is associated with a mortality rate of ~0.1% (2,3). Other alphaviruses such as Venezuelan, eastern, and western encephalitis viruses (VEEV, EEV, and WEEV) cause severe encephalitis with human case fatality rates of up to 30%. VEEV, EEV, WEEV, and CHIKV are prioritized as NIAID categories B or C emerging pathogens.

CHIKV was discovered in Africa where it is endemic and caused large but sporadic outbreaks. Beginning in 2004, CHIKV emerged to cause a multi-year pandemic in countries around the Indian Ocean, with millions of reported cases and a number of deaths (3). CHIKV was first reported in the Americas in 2013, and rapidly spread to over 43 countries, causing more than a million cases (4). Given the spread of mosquito vectors into new regions and the adaptation of CHIKV to new vectors, continued spread of CHIKV is likely.

There are three genotypes of CHIKV (Asian, East/Central/South African (ECSA), and West African) that are ~92.5-98% identical at the amino acid level; recent epidemics have been caused by CHIKV strains of the ECSA genotype. Global spread of CHIKV was precipitated by adaptation of the envelope glycoprotein to allow human infection from both *Aedes aegypti* (Yellow Fever mosquito) and *Aedes albopictus* (Asian Tiger mosquito) (5). These two mosquitos also harbor globally significant flaviviruses such as Dengue virus (serotypes 1-4, DENV-1 to -4), Yellow Fever virus (YFV), and Zika virus (ZIKV) with the latter two being most efficiently transmitted by *A. aegypti* (6). Both mosquitos are found in the continental US, with *A. albopictus* reaching as far north as New York. A complication that has impeded ZIKV response to the epidemic in Brazil and other regions is a lack of diagnostics that can distinguish among these pathogens.

SUMMARY OF THE INVENTION

An anti-alphavirus antibody or alphavirus-binding fragment thereof, wherein said antibody or fragment thereof comprises:
(1) a heavy chain comprising (i) the CDRS set forth in GFGVNNNY (SEQ ID NO:166), IYAGGNT (SEQ ID NO:167), AREVVPTAMGGFDL (SEQ ID NO:168), or (ii) GGSISNYY (SEQ ID NO:169), MYYSGST (SEQ ID NO:170), ARSYCDIANCYTFDL (SEQ ID NO:171);
and a light chain comprising the CDRS set forth in QVTSGY (SEQ ID NO:172), AAS (SEQ ID NO:173), and QQLNSNPLVYT (SEQ ID NO:174);
(2) a heavy chain comprising the CDRS set forth in GFSFDDYV (SEQ ID NO:199), ISWDGDST (SEQ ID NO:200), ARSLADYLNYYHYTMDV (SEQ ID NO:201);
and a light chain comprising the CDRS set forth in QSVLYSSSNKSY (SEQ ID NO:202), WAS (SEQ ID NO:203), and QQYYSTPYT (SEQ ID NO:204);
(3) a heavy chain comprising the CDRs set forth in GVSFGSYS (SEQ ID NO:46), ISSSSSRI (SEQ ID NO:47), ARLDDFWSGYIVD (SEQ ID NO:48); and a light chain comprising the CDRs set forth in QSVDSN (SEQ ID NO:49); RAS (SEQ ID NO:50), QEYNTWPPYT (SEQ ID NO:51);
(4) a heavy chain comprising the CDRs set forth in GYTFHRYG (SEQ ID NO:1), ISVYTGNT (SEQ ID NO:2), ATEPNIILSYFHH (SEQ ID NO:3); and a light chain comprising the CDRs set forth in QEISAN (SEQ ID NO:4), AAS (SEQ ID NO:5), QQSYNTPRT (SEQ ID NO:6);
(5) a heavy chain comprising the CDRs set forth in GFTFSSYW (SEQ ID NO:175), INSDGSSI (SEQ ID NO:176), LTTSRFGAFDM (SEQ ID NO:177); and a light chain comprising the CDRs set forth in QSLLHSNGYNY (SEQ ID NO:178), LGS (SEQ ID NO:179), MQALQTPYT (SEQ ID NO:180);
(6) a heavy chain comprising the CDRs set forth in GFSLNTSGVT (SEQ ID NO:130), IYWDGDK (SEQ ID NO:131), SYTSYKYFDVDV (SEQ ID NO:132); and a light chain comprising the CDRs set forth in QSGNNY (SEQ ID NO:133), DTS (SEQ ID NO:134), QQRSNWPRT (SEQ ID NO:135);
(7) a heavy chain comprising the CDRs set forth in GFSLTTPGVG (SEQ ID NO:538), IFWNDEK (SEQ ID NO:539), AHSRLDLWNGYK (SEQ ID NO:540); and a light chain comprising the CDRs set forth in QSLLHINGYTY (SEQ ID NO:541), LGS (SEQ ID NO:542), MQALQTPRT (SEQ ID NO:543); or
(8) a heavy chain comprising the CDRs set forth in GFTFSDYY (SEQ ID NO:725), ISTSGSTM (SEQ ID NO:726), ARGIYYQSDAFDI (SEQ ID NO:727); and a light chain comprising the CDRs set forth in QGISNS (SEQ ID NO:728), AAS (SEQ ID NO:729), QQYYSTPPMT (SEQ ID NO:730)

An anti-alphavirus antibody or alphavirus-binding fragment thereof, wherein said antibody or fragment thereof comprises:
(1) a heavy chain comprising (i) a CDR1, CDR2, and CDR3 as set forth in any one heavy chain row of Table 1;
(2) and a light chain comprising (i) a CDR1, CDR2, and CDR3 as set forth in any one light chain row of Table 1, which light chain row belongs to the same laboratory designated antibody as the heavy chain row in (1).

A method for treating an alphavirus infection in a subject, wherein the alphavirus is a Chikungunya virus, Mayaro virus or O'nyong'nyong virus, comprising administering an antibody or antigen-binding fragment thereof as described herein in an amount effective to treat a Chikungunya virus, Mayaro virus or O'nyong'nyong virus infection in a subject.

A method for inhibiting an alphavirus infection in a subject, wherein the alphavirus is a Chikungunya virus, Mayaro virus or O'nyong'nyong virus, comprising administering an antibody or antigen-binding fragment thereof as described herein in an amount effective to inhibit a Chikungunya virus, Mayaro virus or O'nyong'nyong virus infection in a subject.

An isolated nucleic acid molecule encoding the antibody, or binding fragment thereof, as described herein.

A vector comprising the nucleic acid molecule as described herein.

A host cell comprising the nucleic acid molecule as described herein, or the vector as described herein.

A method of producing an anti-alphavirus antibody comprising culturing the host cell of as described herein, under conditions wherein the anti-alphavirus antibody is produced by the host cell.

A pharmaceutical composition comprising an anti-alphavirus antibody, or alphavirus-binding fragment thereof, as described herein, and a pharmaceutically acceptable excipient.

A method of reducing an activity of alphavirus in a subject in need thereof, comprising administering to said subject a therapeutically effective amount of the anti-alphavirus antibody, or alphavirus-binding fragment thereof, as described herein, or the pharmaceutical composition as described herein.

A method of treating a disease, disorder, or condition mediated by, or related to increased activity of an alphavirus in a subject a therapeutically effective amount of the anti-alphavirus antibody, or alphavirus-binding fragment thereof, as described herein, or the pharmaceutical composition as described herein.

An assay device is provided for selectively detecting an alphavirus in a biological sample comprising:
a first portion comprising a first plurality of anti-alphavirus antibodies as described herein, wherein the antibodies are each attached to their own reporting entity;
a second portion comprising a second plurality of anti-alphavirus antibodies.

BRIEF DESCRIPTION OF THE DRAWINGS

Figures 1A, 1B:
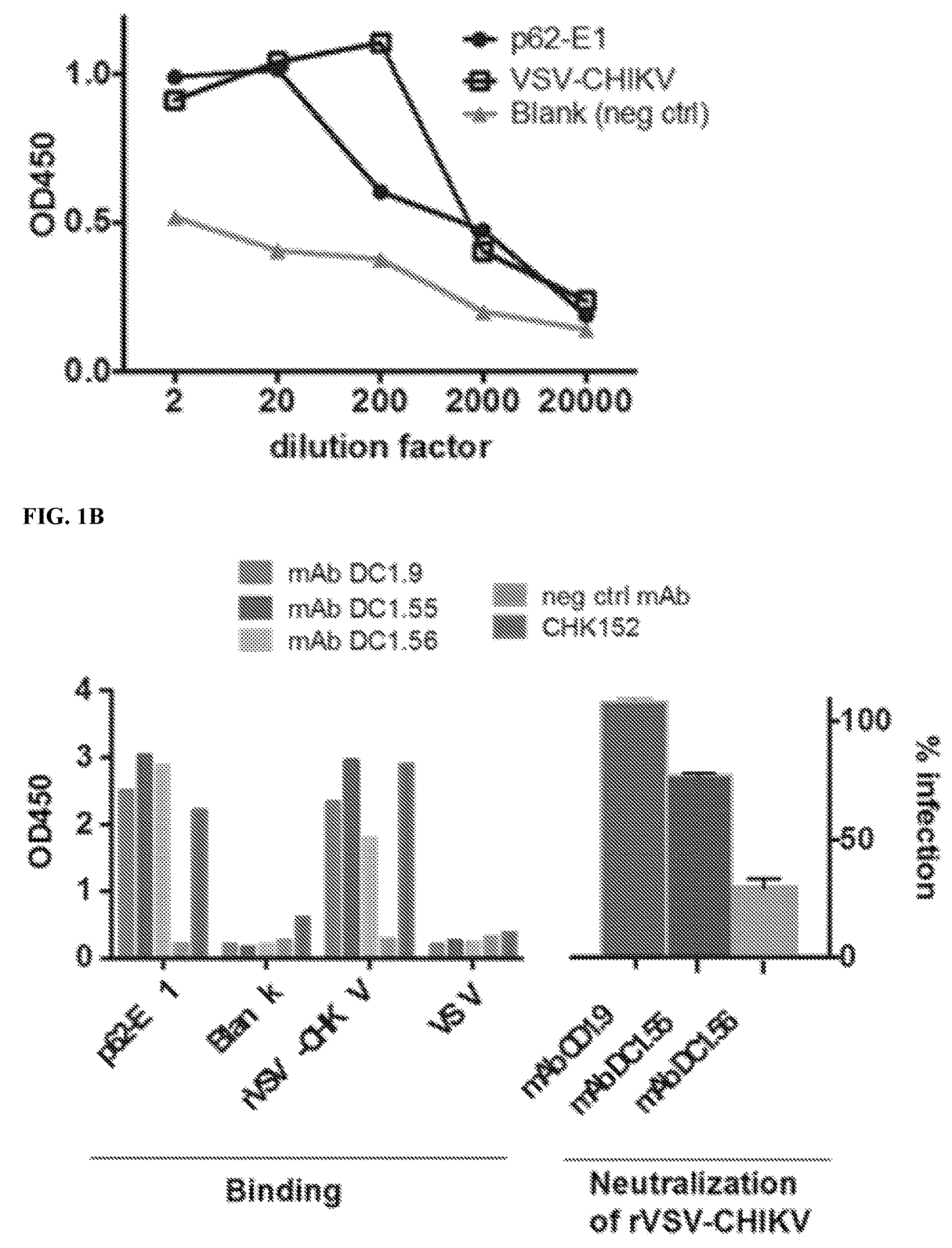

FIG. 1 contains two panels, FIGS. 1A-1B, showing sample human mAb isolation from donor DC1. FIG. 1A depicts serum ELISA showing reactivity for both p62-E1 glycoprotein and VSV-CHIKV but not blank wells. FIG. 1B shows that, for B-cell sorting, the following markers were used CD20 (Pacific Blue channel); CD27 (APC); p62-E1 (RFP); IgG (FITC). This figure shows ELISA of three human mAbs, as well as negative and positive (CHK-152) controls for binding to both p62-E1 and rVSV-CHIKV. Single-point rVSV-CHIKV neutralization assay with human mAbs.

FIG. 6 contains eight panels, FIGS. 6A-6H, showing MAb Binding Profiles and Epitope Binning.

FIG. 6F shows BLI analysis of interactions between E1-specific mAbs and p62-E1. A representative dataset from two independent experiments is shown. FIG. 6G shows ELISA analysis of binding of E1-specific mAbs to E1', p62-E1, or BSA. For p62-E1 ELISA, only DC1.7, DC2.284, DC2.315, and DC2.415 were analyzed. A representative dataset from two independent experiments performed in triplicate is shown. Each point represents mean±SD. FIG. 6H shows competition studies for E1-Specific mAbs. The ability of chCHK-166pMAZ to engage p62-E1/human mAb complexes was tested in two-phase BLI experiments. SUDV-F4 was included as a negative control.

FIG. 7 contains five panels, FIGS. 7A-7E, showing neutralization of CHIKV by Human mAbs. FIG. 7A shows Volcano plot of 46 human mAbs for their ability to inhibit infection of CHIKV 181/25 at 30 and 300 nM. FIG. 7B shows IC$_{50}$ values for 19 of the mAbs against CHIKV 181/25. The error bars represent 95% confidence interval from data fitting, all IC$_{50}$ values were measured twice independently with similar results. FIG. 7D shows cross-neutralization of MAYV by human CHIKV mAbs. A representative dataset from two experiments is shown; points represent mean±SD.

FIG. 8 contains six panels, FIG. 8A-8F, showing viral escape studies for DC2.271B and DC2.429 using rVSV-CHIKV. FIG. 8A shows schematic for the rVSV-CHIKV genome. Infection of Vero cells by rVSV-CHIKV, infection could be tracked by eGFP expression. chCHK-152$^{pMAZ}$ inhibits this infection but SUDV-F4 does not. FIG. 8D shows comparison of neutralizing potency for DC2.271B, DC2.429, C9$^{pMAZ}$, IM-CKV063$^{pMAZ}$, and 4N12$^{pMAZ}$. FIG. 8E shows neutralization of DC2.271B viral escape mutant rVSV-CHIKV$^{E2-K233T}$ by C9$^{pMAZ}$, IM-CKV063$^{pMAZ}$, and 4N12$^{pMAZ}$. For panels FIG. 8B and FIG. 8C, data are pooled from two experiments, each performed in duplicate (points represent mean±SD). For FIG. 8D, two independent experiments were performed in triplicate with similar results; a representative dataset is shown. FIG. 8F shows Characterization of rVSV-CHIKV. Neutralization of rVSV-CHIKV by chCHK-152pMAZ. A representative dataset from two independent experiments each performed in triplicate is shown. Points represent mean±SD.

FIG. 10 contains three panels, FIG. 10A-10C, showing in vivo properties of human mAbs in mice. FIG. 10A shows protective efficacy against CHIKV LR2006_OPY1 in 3-week old mice rendered immunodeficient with anti-Ifnar1 mAb. Survival curves were compared using the log-rank test with a Bonferroni correction. Results were combined from two independent experiments of five mice per treatment group (n=10). FIG. 10B shows serum mAb levels 48 hours after mAb administration in infected mice from (A) ("I", closed symbols) 60 hours after mAb administration in uninfected mice ("U", open symbols). There were three mice per group points represent mean±SD). Serum mAb levels were compared by unpaired t-test. FIG. 10C shows SEC-HPLC analysis of mAbs. Antibodies were characterized by SEC-HPLC using a ProSEC 300S 300×7.5 mm column (Agilent Technologies) on a LC 1260Infinity Series HPLC (Agilent Technologies). Column was equilibrated with 50 mM phosphatebuffer, 150 mM NaCl, Ph 7.0 at 1.00 mL/min. Chromatographs and peak area percent are reported using Agilent Openlabs software.

DETAILED DESCRIPTION OF THE INVENTION

Figure 2:
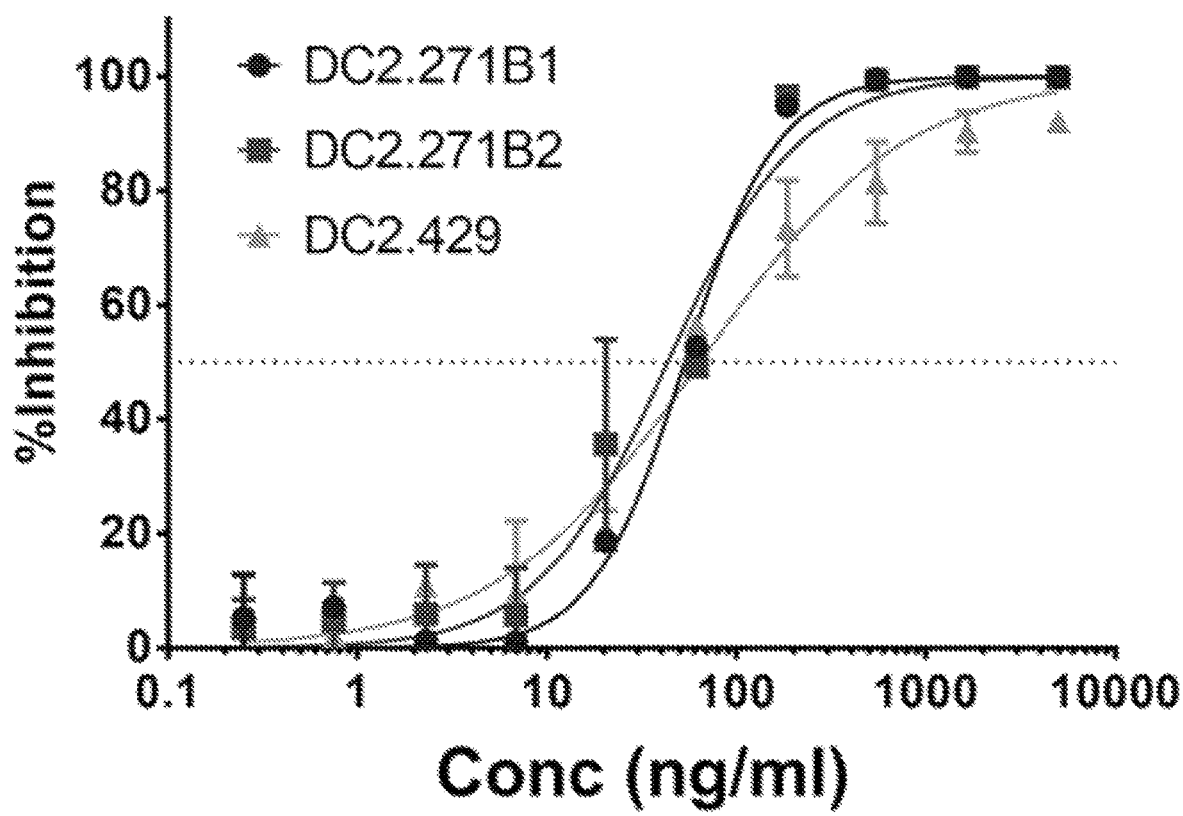
FIG. 2 shows neutralization of authentic CHIKV by DC2.271B (two different independent batches, 1 and 2) and DC2.429. These results were obtained by Dr. Courtney Cohen in Dr. John Dye's lab at USAMRIID

An anti-alphavirus antibody or alphavirus-binding fragment thereof, wherein said antibody or fragment thereof comprises:
(1) a heavy chain comprising (i) the CDRS set forth in GFGVNNNY (SEQ ID NO:166), IYAGGNT (SEQ ID NO:167), AREVVPTAMGGFDL (SEQ ID NO:168), or (ii) GGSISNYY (SEQ ID NO:169), MYYSGST (SEQ ID NO:170), ARSYCDIANCYTFDL (SEQ ID NO:171);
and a light chain comprising the CDRS set forth in QVTSGY (SEQ ID NO:172), AAS (SEQ ID NO:173), and QQLNSNPLVYT (SEQ ID NO:174);
or
(2) a heavy chain comprising the CDRS set forth in GFSFDDYV (SEQ ID NO:199), ISWDGDST (SEQ ID NO:200), ARSLADYLNYYHYTMDV (SEQ ID NO:201);
and a light chain comprising the CDRS set forth in QSVLYSSSNKSY (SEQ ID NO:202), WAS (SEQ ID NO:203), and QQYYSTPYT (SEQ ID NO:204).

An anti-alphavirus antibody or alphavirus-binding fragment thereof, wherein said antibody or fragment thereof comprises:
(1) a heavy chain comprising (i) a CDR1, CDR2, and CDR3 as set forth in any one heavy chain row of Table 1;
(2) and a light chain comprising (i) a CDR1, CDR2, and CDR3 as set forth in any one light chain row of Table 1, which light chain row belongs to the same laboratory designated antibody as the heavy chain row in (1). For example, an anti-alphavirus antibody is provided which has the laboratory designation DC1-59, with the heavy chain (HC) CDR1, 2 and 3 of SEQ ID NOS: 28, 29 and 30, respectively, and light chain (LC) CDR1, 2 and 3 of SEQ ID NOS: 31, 32 and 33, respectively, as set forth in Table 1. All antibodies, and alphavirus-binding fragments thereof, of Table 1 are individually provided.

In embodiments, the antibody comprises a non-naturally occurring Fc region. In embodiments, the antibody comprises a mutated human Fc region. In embodiments, the antibody is an Immunoglobulin G type antibody.

In embodiments, the antibody comprises antibody, or alphavirus-binding fragment thereof, binds an alphavirus with a binding affinity (KD) of from about 0.005 nM to 100 nM.

In embodiments, the antibody comprises antibody, or alphavirus-binding fragment thereof, is a monoclonal antibody.

In embodiments, the antibody comprises antibody, or alphavirus-binding fragment thereof, is a recombinant antibody.

In embodiments, the alphavirus-binding fragment comprises an Fab, F(ab)2 or scFv.

A method for treating an alphavirus infection in a subject, wherein the alphavirus is a Chikungunya virus, Mayaro virus or O'nyong'nyong virus, comprising administering an antibody or antigen-binding fragment thereof as described herein in an amount effective to treat a Chikungunya virus, Mayaro virus or O'nyong'nyong virus infection in a subject.

A method for inhibiting an alphavirus infection in a subject, wherein the alphavirus is a Chikungunya virus, Mayaro virus or O'nyong'nyong virus, comprising administering an antibody or antigen-binding fragment thereof as described herein in an amount effective to inhibit a Chikungunya virus, Mayaro virus or O'nyong'nyong virus infection in a subject.

In embodiments, the antibody binds a Chikungunya virus E2, p62, E1, p62-E1 hybrid protein, or E1-E2 glycoprotein.

In embodiments, the method is for treating or inhibiting Chikungunya virus infection.

In embodiments, the method is for treating or inhibiting Mayaro virus infection.

In embodiments, the method is for treating or inhibiting O'nyong'nyong virus infection.

An isolated nucleic acid molecule encoding the antibody, or binding fragment thereof, as described herein. In embodiments, the isolated nucleic acid molecule is DNA. n embodiments, the isolated nucleic acid molecule is cDNA.

A vector comprising the nucleic acid molecule as described herein.

A host cell comprising the nucleic acid molecule as described herein, or the vector as described herein.

A method of producing an anti-alphavirus antibody comprising culturing the host cell of as described herein, under conditions wherein the anti-alphavirus antibody is produced by the host cell.

A pharmaceutical composition comprising an anti-alphavirus antibody, or alphavirus-binding fragment thereof, as described herein, and a pharmaceutically acceptable excipient.

A method of reducing an activity of alphavirus in a subject in need thereof, comprising administering to said subject a therapeutically effective amount of the anti-alphavirus antibody, or alphavirus-binding fragment thereof, as described herein, or the pharmaceutical composition as described herein.

A method of treating a disease, disorder, or condition mediated by, or related to increased activity of an alphavirus in a subject a therapeutically effective amount of the anti-alphavirus antibody, or alphavirus-binding fragment thereof, as described herein, or the pharmaceutical composition as described herein.

An assay device is provided for selectively detecting an alphavirus in a biological sample comprising:
- a first portion comprising a first plurality of anti-alphavirus antibodies as described herein, wherein the antibodies are each attached to their own reporting entity;
- a second portion comprising a second plurality of anti-alphavirus antibodies. In embodiments, the antibody is a monoclonal antibody, or the fragment thereof is a fragment of a monoclonal antibody.

In embodiments, the reporting entity comprises a gold nanoparticle. In embodiments, the reporting entity comprises an enzyme. In embodiments, the second plurality of anti-alphavirus antibodies is affixed to a solid support of the device. In embodiments, the first plurality of anti-alphavirus antibodies is not affixed to a solid support of the device. In embodiments, the solid support comprises nitrocellulose. In embodiments, the assay device further comprises a fluid sample pad prior in sequential order to the first and second portions. In embodiments, the assay device further comprises a control portion subsequent in sequential order to the first and second portions. In embodiments, the control portion comprises a third plurality of antibodies, immobilized on a solid support of the device, and which third plurality of antibodies are capable of binding the first plurality of anti-alphavirus antibodies each attached to their own reporting molecule. In embodiments, the assay device further comprises a fluid-absorbent wicking pad subsequent in sequential order to the first and second portions, and third portion if present.

A pharmaceutical composition is provided comprising an anti-alphavirus antibody, or alphavirus-binding fragment thereof, as described herein and a pharmaceutically acceptable excipient.

A vaccine composition is provided comprising an anti-alphavirus antibody, or alphavirus-binding fragment thereof, and a carrier. In embodiments, the vaccine further comprises an immunological adjuvant.

A method is provided of detecting an alphavirus in a biological sample comprising contacting the device described herein with the sample and observing if alphavirus-bound antibodies bind to the second plurality of alphavirus-binding antibodies, wherein if such antibodies bind then alphavirus has been detected in the biological sample and wherein if no alphavirus-bound antibodies bind to the second plurality of alphavirus-binding antibodies then alphavirus has not been detected in the biological sample.

In embodiments, the method further comprises obtaining the sample from a subject.

In embodiments, the sample is urine or blood. In embodiments, the subject is human.

As used herein, the term "antibody" refers to an intact antibody, i.e. with complete Fc and Fv regions. "Fragment" refers to any portion of an antibody, or portions of an antibody linked together, such as, in non-limiting examples, a Fab, F(ab)2, a single-chain Fv (scFv), which is less than the whole antibody but which is an antigen-binding portion and which competes with the intact antibody of which it is a fragment for specific binding. In this case, the antigen is locate on the alphavirus.

As such a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

In an embodiment the linker of the scFv is 10-25 amino acids in length. In an embodiment the peptide linker comprises glycine, serine and/or threonine residues. For example, see Bird et al., *Science*, 242: 423-426 (1988) and Huston et al., *Proc. Natl. Acad. Sci. USA*, 85:5879-5883 (1988) each of which are hereby incorporated by reference in their entirety), or a polypeptide that contains at least a portion of an antibody that is sufficient to confer Mtb capsular AM-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, *J. Mol. Biol.* 196:901-917 (1987), or Chothia et al., *Nature* 342:878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an Fd fragment means an antibody fragment that consists of the VH and CH1 domains; an Fv fragment consists of the Vl and VH domains of a single arm of an antibody; and a dAb fragment (Ward et al., *Nature* 341:544-546 (1989) hereby incorporated by reference in its entirety) consists of a VH domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target on an alphavirus, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature.

As used herein, a "human antibody" unless otherwise indicated is one whose sequences correspond to (i.e. are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (e.g. Hoogenboom and Winter, *J. Mol. Biol.*, 227:381 (1991); Marks et al., *J. Mol. Biol.*, 222:581 (1991), hereby incorporated by reference in its entirety), by methods described in Cole et al., *Monoclonal Antibodies and Cancer Therapy*, Alan R. Liss, p. 77 (1985) (hereby incorporated by reference in its entirety); Boerner et al., *J. Immunol.*, 147(1):86-95 (1991) (hereby incorporated by reference in its entirety), van Dijk and van de Winkel, *Curr. Opin. Pharmacol.*, 5: 368-74 (2001) (hereby incorporated by reference in its entirety), and by administering the antigen (e.g. an alphavirus protein or glycoprotein or an entity comprising such) to a transgenic animal that has been modified to produce such antibodies in response to antigenic challenge, but whose endogenous loci have been disabled, e.g., immunized xenomice (see, e.g., U.S. Pat. Nos. 5,939, 598; 6,075,181; 6,114,598; 6,150,584 and 6,162,963 to Kucherlapati et al. regarding XENOMOUSE™ technology, each of which patents are hereby incorporated by reference in their entirety), e.g. VelocImmune® (Regeneron, Tarrytown, NY), e.g. UltiMab® platform (Medarex, now Bristol Myers Squibb, Princeton, NJ). See also, for example, Li et al., *Proc. Natl. Acad. Sci. USA*, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) *Proc. Natl. Acad. Sci. USA* 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

In an embodiment, the antibody described herein is a recombinant human antibody. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In an embodiment, the anti-alphavirus antibody described herein is capable of specifically binding or specifically binds an alphavirus. In an embodiment, the anti-alphavirus antibody described herein is capable of specifically binding alphavirus E1. In an embodiment, the anti-alphavirus antibody described herein is capable of specifically binding Chikungunya virus E1. As used herein, the terms "is capable of specifically binding" or "specifically binds" refers to the property of an antibody or fragment of binding to the (specified) antigen with a dissociation constant that is <1 µM, preferably <1 nM and most preferably <10 pM. In an embodiment, the Kd of the antibody (or fragment) for the antigen is better than 1.0 nM. In an embodiment, the Kd of the antibody (or fragment) for the antigen is better than 1.5 nM. An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy) oxolan-2-yl]-2-(2-hydroxyethoxy)ethoxy]ethyl(E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "Kd", as used herein, is intended to refer to the dissociation constant of an antibody-antigen interaction. One way of determining the Kd or binding affinity of antibodies to alphavirus by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of a fragment of an anti-alphavirus antibody can be determined by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiinide hydrochloride (EDC) and N-hydroxysuccinimide (NHS) according to the supplier's instructions. Alphavirus antigens can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated Kd) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates (kon) and dissociation rates (koff) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant (Kd) values are calculated as koff/kon. This protocol is suitable for use in determining binding affinity of an antibody or fragment to any alphavirus antigen. Other protocols known in the art may also be used. For example, ELISA of alphavirus antigen with mAb can be used to determine the kD values. The Kd values reported herein used this ELISA-based protocol.

The term Fc domain or region herein is used to define a C-terminal region of an immunoglobulin heavy chain, including native sequence Fc regions and variant Fc regions. Although the boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. The C-terminal lysine of the Fc domain may be removed, for example, by recombinantly engineering the nucleic acid encoding it.

In embodiments, the antibody comprises an Fc domain. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009). In an embodiment, the Fc domain has the same sequence as a human IgG1 Fc domain.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

| Amino Acid Substitutions | | |
|---|---|---|
| Original Residue | Conservative Substitutions | Exemplary Substitutions |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |

Amino Acid Substitutions

| Original Residue | Conservative Substitutions | Exemplary Substitutions |
|---|---|---|
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

A modification or mutation may also be made in a framework region or constant region to increase the half-life of an anti-alphavirus antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In an embodiment, an antibody described herein is recombinantly produced. In an embodiment, the antibody is produced in a eukaryotic expression system. In an embodiment, the antibody produced in the eukaryotic expression system comprises glycosylation at a residue on the Fc portion corresponding to Asn297.

This invention also provides a composition comprising an antibody, or antigen-binding fragment thereof, as described herein. In an embodiment, the composition is a pharmaceutical composition. In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

In a preferred embodiment, the antibody is an IgG1 antibody. In an embodiment, the antibody is an IgG2 antibody. In an embodiment, the antibody is an IgG3 antibody. In an embodiment, the antibody is an IgG4 antibody.

In an embodiment, the antibody comprises the following Fc region sequence:

(SEQ ID NO: 610)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGRPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLT

VDKSRWQQGNVFSCSVMHEALHNHYTQKSLSLSPGK

In embodiments, the Fc region of the antibody comprises one or more Xtend mutations, for example: M428LN434S.

In embodiments, the Fc region of the antibody comprises one or more YTE mutations, for example: M252Y/S254T/T256E.

TABLE 1

Exemplary CDRs of the antibodies are set forth in the following table:

| Laboratory Designation | CDR1 | CDR2 | CDR3 |
|---|---|---|---|
| DC1-7-HC | GYTFHRYG (SEQ ID NO: 1) | ISVYTGNT (SEQ ID NO: 2) | ATEPNIILSYFHH (SEQ ID NO: 3) |
| DC1-7-LC | QEISAN (SEQ ID NO: 4) | AAS (SEQ ID NO: 5) | QQSYNTPRT (SEQ ID NO: 6) |

TABLE 1-continued

Exemplary CDRs of the antibodies are set forth in the following table:

| Laboratory Designation | CDR1 | CDR2 | CDR3 |
|---|---|---|---|
| DC1_33-HC1 | GFTFSSYW (SEQ ID NO: 7) | INSDGSSI (SEQ ID NO: 8) | LTTSRFGAFDM (SEQ ID NO: 9) |
| DC1_33-HC2 | GFTFSDYY (SEQ ID NO: 10) | IRDKGNSYIT (SEQ ID NO: 11) | VRSYNPGRGGNSDYMDF (SEQ ID NO: 12) |
| DC1_33-LC | QSISNW (SEQ ID NO: 13) | KAS (SEQ ID NO: 14) | QQYKSYPWT (SEQ ID NO: 15) |
| DC1-43-HC | TGSISSSSYY (SEQ ID NO: 16) | MYNSGRP (SEQ ID NO: 17) | ARGRVYCDGDCHDDAFDI (SEQ ID NO: 18) |
| DC1-43-LC | QNVLYSSNNKNY (SEQ ID NO: 19) | WAS (SEQ ID NO: 20) | QQYYSTPYT (SEQ ID NO: 21) |
| DC1-56-HC | EYIFNRYG (SEQ ID NO: 22) | ITVSGTTI (SEQ ID NO: 23) | VKGPFSNKNFDI (SEQ ID NO: 24) |
| DC1-56-LC | QDISIY (SEQ ID NO: 25) | DAS (SEQ ID NO: 26) | QQHNSRPYS (SEQ ID NO: 27) |
| DC1-59-HC | GFIFDDYA (SEQ ID NO: 28) | ISWNSGNT (SEQ ID NO: 29) | AKDTNAVVIATSSHAFDI (SEQ ID NO: 30) |
| DC1-59-LC | QNINNY (SEQ ID NO: 31) | AAS (SEQ ID NO: 32) | QQSYGSPYT (SEQ ID NO: 33) |
| DC1-353-HC | GFTFDDYA (SEQ ID NO: 34) | ISWNSGDI (SEQ ID NO: 35) | AKDIDPLVSGATRFDF (SEQ ID NO: 36) |
| DC1-353-LC | QSISNW (SEQ ID NO: 37) | KAS (SEQ ID NO: 38) | QQYKSYPWT (SEQ ID NO: 39) |
| DC1-355-HC | GYRFISYW (SEQ ID NO: 40) | IYPGDSET (SEQ ID NO: 41) | ARHSWGMDV (SEQ ID NO: 42) |
| DC1-355-LC | QGISSSF (SEQ ID NO: 43) | GAS (SEQ ID NO: 44) | FIHYGDSIRP (SEQ ID NO: 45) |
| DC1-364-HC | GVSFGSYS (SEQ ID NO: 46) | ISSSSSRI (SEQ ID NO: 47) | ARLDDFWSGYIVD (SEQ ID NO: 48) |
| DC1-364-LC | QSVDSN (SEQ ID NO: 49) | RAS (SEQ ID NO: 50) | QEYNTWPPYT (SEQ ID NO: 51) |
| DC1-363-HC | GYTFTSYD (SEQ ID NO: 52) | MNANNGNT (SEQ ID NO: 53) | ARELHNSSSGYNWFDP (SEQ ID NO: 54) |
| DC1-363-LC | QTVLSSSDNKNY (SEQ ID NO: 55) | WAS (SEQ ID NO: 56) | QQYFNTQT (SEQ ID NO: 57) |
| DC2-9-HC | GFSFSDYY (SEQ ID NO: 58) | ISSSGRTI (SEQ ID NO: 59) | ARTRPTIAVAGSPLNEDY (SEQ ID NO: 60) |
| DC2-9-LC | QTVSGY (SEQ ID NO: 61) | DAS (SEQ ID NO: 62) | QQRSNWPPGIT (SEQ ID NO: 63) |
| DC2-12-HC | GGSIKRSNYY (SEQ ID NO: 64) | LFYSGST (SEQ ID NO: 65) | SRHFVGFAEAPPDGMDV (SEQ ID NO: 66) |
| DC2-12-LC | QDISNH (SEQ ID NO: 67) | DAS (SEQ ID NO: 68) | QQYDTLPLRFT (SEQ ID NO: 69) |
| DC2-64-HC | GYTFTRYA (SEQ ID NO: 70) | INTNTGEP (SEQ ID NO: 71) | AQQVIAFDV (SEQ ID NO: 72) |
| DC2-64-LC | QSLLSSSNNKNF (SEQ ID NO: 73) | WAS (SEQ ID NO: 74) | QQYYSTPPYS (SEQ ID NO: 75) |
| DC2-65-HC | GFTFNVYS (SEQ ID NO: 76) | IWYDGVDK (SEQ ID NO: 77) | ARGPGWSGYLDS (SEQ ID NO: 78) |
| DC2-65-LC | QSLVYSDGGTY (SEQ ID NO: 79) | KVS (SEQ ID NO: 80) | MQATHWPHT (SEQ ID NO: 81) |

TABLE 1-continued

Exemplary CDRs of the antibodies are set forth in the following table:

| Laboratory Designation | CDR1 | CDR2 | CDR3 |
|---|---|---|---|
| DC2-69-HC | GGSMSSGDYY (SEQ ID NO: 82) | ISYSGSA (SEQ ID NO: 83) | ARVFSGYYYSDY (SEQ ID NO: 84) |
| DC2-69-LC | QSISSW (SEQ ID NO: 85) | KAS (SEQ ID NO: 86) | QQYNTYPWT (SEQ ID NO: 87) |
| DC2-74-HC | GFTLSNYG (SEQ ID NO: 88) | ILYDGGNR (SEQ ID NO: 89) | AKDDSVFETDRTGTLNY (SEQ ID NO: 90) |
| DC2-74-LC | QSIGIY (SEQ ID NO: 91) | ASS (SEQ ID NO: 92) | QQSYSSPPA (SEQ ID NO: 93) |
| DC2-77-HC | GFAVNYYA (SEQ ID NO: 94) | IVGYGATT (SEQ ID NO: 95) | AKLTHPHDGSSFET (SEQ ID NO: 96) |
| DC2-77-LC | QDVTTA (SEQ ID NO: 97) | WAS (SEQ ID NO: 98) | QQHYSTPLT (SEQ ID NO: 99) |
| DC2-80-HC | GFSLSTSEVG (SEQ ID NO: 100) | IYWDDDK (SEQ ID NO: 101) | AHIKSYCSTITCYPTTFDY (SEQ ID NO: 102) |
| DC2-80-LC | QSVLDSSNNNYY (SEQ ID NO: 103) | WAS (SEQ ID NO: 104) | QQYYSTPWT (SEQ ID NO: 105) |
| DC2-82-HC | GYSFSSYS (SEQ ID NO: 106) | IYPGDSYT (SEQ ID NO: 107) | VRGMATNN (SEQ ID NO: 108) |
| DC2-82-LC | QTLVHSDGNTY (SEQ ID NO: 109) | KIS (SEQ ID NO: 110) | MQATHFPWT (SEQ ID NO: 111) |
| DC2-85-HC | GFTFRNYV (SEQ ID NO: 112) | ISYDGNNK (SEQ ID NO: 113) | ARDTQTQNSDWYLFGA (SEQ ID NO: 114) |
| DC2-85-LC | QSVFIN (SEQ ID NO: 115) | GAS (SEQ ID NO: 116) | QQYNDWPPIT (SEQ ID NO: 117) |
| DC2-112HC | GYTFNNHY (SEQ ID NO: 118) | IAPSGDNT (SEQ ID NO: 119) | ARDQLNRHSTNRGFFDL (SEQ ID NO: 120) |
| DC2-112LC | QSVGSY (SEQ ID NO: 121) | DAS (SEQ ID NO: 122) | HQRGNWPPS (SEQ ID NO: 123) |
| DC2-114HC | GFNFDDYG (SEQ ID NO: 124) | ITWNSGLI (SEQ ID NO: 125) | AKDMGRLYTVGWYNFHF (SEQ ID NO: 126) |
| DC2-114LC | LNIGTF (SEQ ID NO: 127) | AVS (SEQ ID NO: 128) | QESYNTPEDLT (SEQ ID NO: 129) |
| DC2-131-HC | GFSLNTSGVT (SEQ ID NO: 130) | IYWDGDK (SEQ ID NO: 131) | SYTSYKYFDVDV (SEQ ID NO: 132) |
| DC2-131-LC | QSGNNY (SEQ ID NO: 133) | DTS (SEQ ID NO: 134) | QQRSNWPRT (SEQ ID NO: 135) |
| DC2-134-HC | GYTLTTYP (SEQ ID NO: 136) | INTHTGNP (SEQ ID NO: 137) | ARDLAVAEYHGY (SEQ ID NO: 138) |
| DC2-134-LC | QDVTTA (SEQ ID NO: 139) | WAS (SEQ ID NO: 140) | QQHYSTPLT (SEQ ID NO: 141) |
| DC2-148-HC | GFIFDDHA (SEQ ID NO: 142) | ISWNSGDI (SEQ ID NO: 143) | VKDTPYCGGGGCLNWFDS (SEQ ID NO: 144) |
| DC2-148-LC | QSLLHSNGYNY (SEQ ID NO: 145) | LGS (SEQ ID NO: 146) | MQTLQTPRT (SEQ ID NO: 147) |
| DC2-159-HC | GFTFDDYA (SEQ ID NO: 148) | IKSETYGGTT (SEQ ID NO: 149) | SIVVAQVVRGIPLPNVFDI (SEQ ID NO: 150) |
| DC2-159-LC | QGIGNY (SEQ ID NO: 151) | SAS (SEQ ID NO: 152) | LKYHGAPYT (SEQ ID NO: 153) |
| DC2-160-HC | GFTFSNYV (SEQ ID NO: 154) | ISYDGSNK (SEQ ID NO: 155) | ARDTQTQSSDYYLFGA (SEQ ID NO: 156) |

TABLE 1-continued

Exemplary CDRs of the antibodies are set forth in the following table:

| Laboratory Designation | CDR1 | CDR2 | CDR3 |
|---|---|---|---|
| DC2-160-LC | QSVINN (SEQ ID NO: 157) | GAS (SEQ ID NO: 158) | QQYNDWPPIT (SEQ ID NO: 159) |
| DC2-164-HC | GESFSGYY (SEQ ID NO: 160) | INHSGST (SEQ ID NO: 161) | ARGYADTPVFRRAAAAGMDV (SEQ ID NO: 162) |
| DC2-164-LC | QYIGTF (SEQ ID NO: 163) | DAS (SEQ ID NO: 164) | QQGYSPLYS (SEQ ID NO: 165) |
| DC2-271B_HC | GFGVNNNY (SEQ ID NO: 166) | IYAGGNT (SEQ ID NO: 167) | AREVVPTAMGGFDL (SEQ ID NO: 168) |
| DC2-271A_HC | GGSISNYY (SEQ ID NO: 169) | MYYSGST (SEQ ID NO: 170) | ARSYCDIANCYTFDL (SEQ ID NO: 171) |
| DC2-271_LC | QVTSGY (SEQ ID NO: 172) | AAS (SEQ ID NO: 173) | QQLNSNPLVYT (SEQ ID NO: 174) |
| DC2-283-HC | GFTFSSYW (SEQ ID NO: 175) | INSDGSSI (SEQ ID NO: 176) | LTTSRFGAFDM (SEQ ID NO: 177) |
| DC2-283-LC | QSLLHSNGYNY (SEQ ID NO: 178) | LGS (SEQ ID NO: 179) | MQALQTPYT (SEQ ID NO: 180) |
| DC2-284-HC | GYTLTRFA (SEQ ID NO: 181) | INTNTGNP (SEQ ID NO: 182) | ARDGYNHGYNDL (SEQ ID NO: 183) |
| DC2-284-LC | QSVSSE (SEQ ID NO: 184) | DAS (SEQ ID NO: 185) | QQRSSWPLFT (SEQ ID NO: 186) |
| DC2-416-HC | GFSLSTNGVG (SEQ ID NO: 187) | IYWDDDE (SEQ ID NO: 188) | AHKGYYCSSSSCYAGGKAFNI (SEQ ID NO: 189) |
| DC2-416-LC | QGINSY (SEQ ID NO: 190) | AAS (SEQ ID NO: 191) | QQPSSHPLT (SEQ ID NO: 192) |
| DC2-422-HC | GYTFTDYT (SEQ ID NO: 193) | INTKTGNP (SEQ ID NO: 194) | ARIRLVHYYGSGNYFKSFQSFGMGB (SEQ ID NO: 195) |
| DC2-422-LC | QTLLHSNGYNY (SEQ ID NO: 196) | MGS (SEQ ID NO: 197) | MQGLQTPHT (SEQ ID NO: 198) |
| DC2-429-HC | GFSFDDYV (SEQ ID NO: 199) | ISWDGDST (SEQ ID NO: 200) | ARSLADYLNYYHYTMDV (SEQ ID NO: 201) |
| DC2-429-LC | QSVLYSSSNKSY (SEQ ID NO: 202) | WAS (SEQ ID NO: 203) | QQYYSTPYT (SEQ ID NO: 204) |
| DC2-432-HC | GFTFSAHY (SEQ ID NO: 205) | ISSRGSTI (SEQ ID NO: 206) | AGAITWNDVFFWY (SEQ ID NO: 207) |
| DC2-432-LC | QSLVHSDGNTY (SEQ ID NO: 208) | KVS (SEQ ID NO: 209) | MQATQFLWT (SEQ ID NO: 210) |
| DC2-463-HC | GFSLTTSGMC (SEQ ID NO: 211) | IDWDDDK (SEQ ID NO: 212) | ARSPPGASVAILPTTKYYFDS (SEQ ID NO: 213) |
| DC2-463-LC | HSVTSSY (SEQ ID NO: 214) | GAS (SEQ ID NO: 215) | QQYGSSAMYT (SEQ ID NO: 216) |
| SC-91-LC | QDVTTA (SEQ ID NO: 217) | WAS (SEQ ID NO: 218) | QQHYSTPLT (SEQ ID NO: 219) |
| SC-95-HC | GFTFGNYG (SEQ ID NO: 220) | IWFDGSNK (SEQ ID NO: 221) | ARADGYCSDDACYDWFDP (SEQ ID NO: 222) |
| DC2-502-HC | GFTFSSYV (SEQ ID NO: 223) | ISYDGSNK (SEQ ID NO: 224) | ARDTQTQSSDYYLFGA (SEQ ID NO: 225) |
| DC2-502-LC | QSIINN (SEQ ID NO: 226) | GAS (SEQ ID NO: 227) | QQYNDWPPIT (SEQ ID NO: 228) |
| DC2-507-HC | SGDSMSYY (SEQ ID NO: 229) | IFISGNT (SEQ ID NO: 230) | AKGSRSFIA (SEQ ID NO: 231) |

TABLE 1-continued

Exemplary CDRs of the antibodies are set forth in the following table:

| Laboratory Designation | CDR1 | CDR2 | CDR3 |
|---|---|---|---|
| DC2-507-LC | QDVSIY (SEQ ID NO: 232) | DAS (SEQ ID NO: 233) | QQHDNLPPT (SEQ ID NO: 234) |
| DC2-541-HC | GFTFSSYE (SEQ ID NO: 235) | ISGGGDTI (SEQ ID NO: 236) | AKFWNDYYNDFEY (SEQ ID NO: 237) |
| DC2-541-LC | QSVSSY (SEQ ID NO: 238) | DAS (SEQ ID NO: 239) | QQRTNWPPWT (SEQ ID NO: 240) |
| DC2-547-HC | GYSFTSFD (SEQ ID NO: 241) | MNPNSGSS (SEQ ID NO: 242) | ATITVTGTLGF (SEQ ID NO: 243) |
| DC2-547-LC | QGIRHY (SEQ ID NO: 244) | AAS (SEQ ID NO: 245) | QQLNSYPPVT (SEQ ID NO: 246) |
| DC2-572-HC | GDTFSSYG (SEQ ID NO: 247) | IIPIVDIT (SEQ ID NO: 248) | ARISAYYYDGSGSNPGITDYGMDV (SEQ ID NO: 249) |
| DC2-572-LC | QSLLHSNGYNY (SEQ ID NO: 250) | LGS (SEQ ID NO: 251) | MQGLQTPHT (SEQ ID NO: 252) |
| DC2-580-HC | GFSFSDYY (SEQ ID NO: 253) | IYSGGST (SEQ ID NO: 254) | ARAPSWGLRVGPFDF (SEQ ID NO: 255) |
| DC2-580-LC | RSINSY (SEQ ID NO: 256) | AAS (SEQ ID NO: 257) | HQTYTTPPGT (SEQ ID NO: 258) |
| DC1-426-HC | GYTFSDYD (SEQ ID NO: 259) | ISTYSGDA (SEQ ID NO: 260) | ARAAHLSYDFWNGPKGWYHFMDV (SEQ ID NO: 261) |
| DC1-426-LC | QSITTW (SEQ ID NO: 262) | KTS (SEQ ID NO: 263) | QQCDSNLWS (SEQ ID NO: 264) |
| DC1-435-HC | GYTFIDYY (SEQ ID NO: 265) | INPNSGDT (SEQ ID NO: 266) | ARDPLPETMDIDY (SEQ ID NO: 267) |
| DC1-435-LC | QSVSSNY (SEQ ID NO: 268) | TAS (SEQ ID NO: 269) | QQYGSAPRT (SEQ ID NO: 270) |
| DC1-450-HC 1 | GDSISTETYY (SEQ ID NO: 271) | IYASGST (SEQ ID NO: 272) | AREWYYYNSSGFYLEAFDI (SEQ ID NO: 273) |
| DC1-450-HC 2 | GGSFGGYY (SEQ ID NO: 274) | INHSGST (SEQ ID NO: 275) | ARGPYFDY (SEQ ID NO: 276) |
| DC1-450-LC | QSVSSD (SEQ ID NO: 277) | GAS (SEQ ID NO: 278) | QQYKSWPYT (SEQ ID NO: 279) |
| DC2-149-HC | GFSLSTSGVG (SEQ ID NO: 280) | IYWDDDK (SEQ ID NO: 281) | AHLTSYPINAFDI (SEQ ID NO: 282) |
| DC2-149-LC | HTISTN (SEQ ID NO: 283) | RAS (SEQ ID NO: 284) | QQYNNWPT (SEQ ID NO: 285) |
| DC2-154-HC | GESFSGYY (SEQ ID NO: 286) | INHSGST (SEQ ID NO: 287) | ARGYADTPVFRRYYYYGMDV (SEQ ID NO: 288) |
| DC2-154-LC | QTVSSK (SEQ ID NO: 289) | GAS (SEQ ID NO: 290) | QQYDNWPPYT (SEQ ID NO: 291) |
| DC2-158-HC | GFTFSNYG (SEQ ID NO: 292) | ISGGGAST (SEQ ID NO: 293) | AKGGRWDGSIAEFDY (SEQ ID NO: 294) |
| DC2-158-LC | QSVRGN (SEQ ID NO: 295) | GAS (SEQ ID NO: 296) | QQYNNWPLYT (SEQ ID NO: 297) |
| DC2-121-HC | GASISSGDYY (SEQ ID NO: 298) | IYYTGRT (SEQ ID NO: 299) | ARDRGVRGGYGIDY (SEQ ID NO: 300) |
| DC2-121-LC | QSVGSSY (SEQ ID NO: 301) | GSS (SEQ ID NO: 302) | LQYAGTPRT (SEQ ID NO: 303) |
| DC2-129-HC | GYWFTSYW (SEQ ID NO: 304) | IYPGDSDA (SEQ ID NO: 305) | ARHSVGEAPRQLEF (SEQ ID NO: 306) |

TABLE 1-continued

Exemplary CDRs of the antibodies are set forth in the following table:

| Laboratory Designation | CDR1 | CDR2 | CDR3 |
|---|---|---|---|
| DC2-129-LC | ASQSVSR DAS (SEQ ID NO: 307) | QQYGSTPYT (SEQ ID NO: 308) | (SEQ ID NO: 309) |
| DC2-618-HC | GFTFSSYS (SEQ ID NO: 310) | ISTTSSYI (SEQ ID NO: 311) | ARDGVSGAHDI (SEQ ID NO: 312) |
| DC2-618-LC | QSISSY (SEQ ID NO: 313) | AAS (SEQ ID NO: 314) | QQTYSTLWT (SEQ ID NO: 315) |
| DC2-643-HC | GFTFGTYA (SEQ ID NO: 316) | ISGSGAGT (SEQ ID NO: 317) | AKDNSASVWDLAY (SEQ ID NO: 318) |
| DC2-643-LC | HSLLHTNGYNY (SEQ ID NO: 319) | LGS (SEQ ID NO: 32) | MQALQTLYT (SEQ ID NO: 321) |
| DC2-645-HC | GFTFSNYA (SEQ ID NO: 322) | MSYDGINT (SEQ ID NO: 323) | ARDLQYRGWGSGLDS (SEQ ID NO: 324) |
| DC2-645-LC | QTINTY (SEQ ID NO: 325) | AAS (SEQ ID NO: 326) | QQTYSTPFT (SEQ ID NO: 327) |
| DC2-647-HC | GYTFTRYA (SEQ ID NO: 328) | INTNTGNP (SEQ ID NO: 329) | AHIPGIAAGEMFP (SEQ ID NO: 330) |
| DC2-647-LC | QSVGSY (SEQ ID NO: 331) | DVS (SEQ ID NO: 332) | QHGSNWRVA (SEQ ID NO: 333) |
| DC2-682-HC | GFTFDDYA (SEQ ID NO: 334) | ISWNGDTV (SEQ ID NO: 335) | AKDMAAGEGDYYNHYFDP (SEQ ID NO: 336) |
| DC2-682-LC | QSISSS (SEQ ID NO: 337) | DAV (SEQ ID NO: 338) | QQRRSWLFT (SEQ ID NO: 339) |
| DC2-684-HC | GFTFDDSA (SEQ ID NO: 340) | ISWNSDTI (SEQ ID NO: 341) | AKDHSPYYYGYRGNNWFDS (SEQ ID NO: 342) |
| DC2-684-LC | QGIHNY (SEQ ID NO: 343) | AAS (SEQ ID NO: 344) | QQSYSTPRT (SEQ ID NO: 345) |
| DC4-7-HC | GLTLSGYW (SEQ ID NO: 346) | INSDGSST (SEQ ID NO: 347) | TIQKVGEI (SEQ ID NO: 348) |
| DC4-7-LC | QSVSFY (SEQ ID NO: 349) | DAS (SEQ ID NO: 350) | QQRSNWAWT (SEQ ID NO: 351) |
| DC4-8-HC | GFTFSSYA (SEQ ID NO: 352) | ISGSGGST (SEQ ID NO: 353) | AFGGRSIPWVLSVADTTALDY (SEQ ID NO: 354) |
| DC4-8-LC | QSVSSSY (SEQ ID NO: 355) | GAS (SEQ ID NO: 356) | QQYGSSRGT (SEQ ID NO: 357) |
| DC4-10-HC | SNVFTSSGVG (SEQ ID NO: 358) | IYGDDDK (SEQ ID NO: 359) | AHSNYDFWGGFYIKSYIDY (SEQ ID NO: 360) |
| DC4-10-LC | QSVSSN (SEQ ID NO: 361) | GAS (SEQ ID NO: 362) | QQYDNWPYT (SEQ ID NO: 363) |
| DC1-366-HC | GGSFGGYY (SEQ ID NO: 364) | INHSGST (SEQ ID NO: 365) | ARGPYFDY (SEQ ID NO: 366) |
| DC1-366-LC | QSVSSRY (SEQ ID NO: 367) | GAS (SEQ ID NO: 368) | QQYSSSYT (SEQ ID NO: 369) |
| DC1-371-HC | GHAFASYY (SEQ ID NO: 370) | INPSGGST (SEQ ID NO: 371) | ARGLYSNSWSTRGVFDI (SEQ ID NO: 372) |
| DC1-371_LC | QSVSTY (SEQ ID NO: 373) | GAS (SEQ ID NO: 374) | QQYGGSPFT (SEQ ID NO: 375) |
| DC1-374-HC | GFTFSNYA (SEQ ID NO: 376) | ISGSDSST (SEQ ID NO: 377) | ATGGYSDY (SEQ ID NO: 378) |
| DC1-374-LC | QGISSW (SEQ ID NO: 379) | AAS (SEQ ID NO: 380) | QQAYRFPYT (SEQ ID NO: 381) |

TABLE 1-continued

Exemplary CDRs of the antibodies are set forth in the following table:

| Laboratory Designation | CDR1 | CDR2 | CDR3 |
|---|---|---|---|
| DC1-349-HC | GDSFTNYW (SEQ ID NO: 382) | IYPDDSDI (SEQ ID NO: 383) | ARHRRTAYQIGDGLDI (SEQ ID NO: 384) |
| DC1-349-LC | TSNYLAW (SEQ ID NO: 385) | DAS (SEQ ID NO: 386) | QQYRSSPYT (SEQ ID NO: 387) |
| DC1-370-HC | GFLFGSYW (SEQ ID NO: 388) | IKQDGSEK (SEQ ID NO: 389) | ARDWPLDPLDY (SEQ ID NO: 390) |
| DC1-370-LC | QSISSF (SEQ ID NO: 391) | TAS (SEQ ID NO: 392) | QQSYTSPRT (SEQ ID NO: 393) |
| DC1-371-HC | GHAFASYY (SEQ ID NO: 394) | INPSGGST (SEQ ID NO: 395) | ARGLYSNSWSTRGVFDI (SEQ ID NO: 396) |
| DC1-371-LC | QSVSTY (SEQ ID NO: 397) | GAS (SEQ ID NO: 398) | QQYGGSPFT (SEQ ID NO: 399) |
| DC2-410-HC | GFNFGSYA (SEQ ID NO: 400) | ISYLGDNE (SEQ ID NO: 401) | ARSLDDYYDTLGYGRGAFDL (SEQ ID NO: 402) |
| DC2-410-LC | QSVLDNSNNKNY (SEQ ID NO: 403) | WAS (SEQ ID NO: 404) | QQYYSTPDT (SEQ ID NO: 405) |
| DC2-416-HC | GFSLSTNGVG (SEQ ID NO: 406) | IYWDDDE (SEQ ID NO: 407) | AHKGYYCSSSSCYAGGKAFNI (SEQ ID NO: 408) |
| DC2-416-LC | QGINSY (SEQ ID NO: 409) | AAS (SEQ ID NO: 410) | QQPSSHPLT (SEQ ID NO: 411) |
| DC2-446-HC | GLTLKNYA (SEQ ID NO: 412) | ISFDGTYK (SEQ ID NO: 413) | ARGPQLYSHQPAKFGDLLFGAFDI (SEQ ID NO: 414) |
| DC2-446-LC | QDVSHY (SEQ ID NO: 415) | DTS (SEQ ID NO: 416) | QQYDTLPLT (SEQ ID NO: 417) |
| DC2-435-HC | GFTFSAHY (SEQ ID NO: 418) | ISSRGSTI (SEQ ID NO: 419) | AGAITWNDVFFWY (SEQ ID NO: 420) |
| DC2-435-LC | QSVRSY (SEQ ID NO: 421) | DAT (SEQ ID NO: 422) | QLRSTLGVT (SEQ ID NO: 423) |
| DC2-448-HC | GFTFRNYW (SEQ ID NO: 424) | INRNGNEK (SEQ ID NO: 425) | VRDSSPSFGPGNYYDAFDI (SEQ ID NO: 426) |
| DC2-448-LC | QDIRNE (SEQ ID NO: 427) | AAS (SEQ ID NO: 428) | LQDFNYPRT (SEQ ID NO: 429) |
| DC2-456-HC | GFSLTTYSMG (SEQ ID NO: 430) | IYGDGVK (SEQ ID NO: 431) | AHSSTVDWDVD (SEQ ID NO: 432) |
| DC2-456-LC | QSVSSF (SEQ ID NO: 433) | DAS (SEQ ID NO: 434) | HQRSNWPRT (SEQ ID NO: 435) |
| DC2-458-HC | GESFSGYY (SEQ ID NO: 436) | INHSGST (SEQ ID NO: 437) | ARGYADTPVFRRAAAAGMDV (SEQ ID NO: 438) |
| DC2-458-LC | QRIDSW (SEQ ID NO: 439) | QAS (SEQ ID NO: 440) | QQYKSFSYT (SEQ ID NO: 441) |
| DC2-463-HC | GFSLTTSGMC (SEQ ID NO: 442) | IDWDDDK (SEQ ID NO: 443) | ARSPPGASVAILPTTKYYFDS (SEQ ID NO: 444) |
| DC2-463-LC | HSVTSSY (SEQ ID NO: 445) | GAS (SEQ ID NO: 446) | QQYGSSAMYT (SEQ ID NO: 447) |
| DC2-504-HC | GYIFNRYA (SEQ ID NO: 448) | INTNSGDA (SEQ ID NO: 449) | ARDRWSSGYQYYGLDA (SEQ ID NO: 450) |
| DC2-504-LC | QGVRNDY (SEQ ID NO: 451) | GAS (SEQ ID NO: 452) | QQYGRSPMT (SEQ ID NO: 453) |
| DC2-513-HC | GFTFKDYA (SEQ ID NO: 454) | VSVDGSLQ (SEQ ID NO: 455) | AREFSGTNVRCFDL (SEQ ID NO: 456) |

TABLE 1-continued

Exemplary CDRs of the antibodies are set forth in the following table:

| Laboratory Designation | CDR1 | CDR2 | CDR3 |
|---|---|---|---|
| DC2-513-LC | QGIHRW (SEQ ID NO: 457) | AAS (SEQ ID NO: 458) | QQGNSFPLT (SEQ ID NO: 459) |
| DC2-514-HC | GGSIRSHY (SEQ ID NO: 460) | IYTSGTT (SEQ ID NO: 461) | ARGSSEVTI (SEQ ID NO: 462) |
| DC2-514-LC | QDISNY (SEQ ID NO: 463) | AAS (SEQ ID NO: 464) | QQYDNLPLT (SEQ ID NO: 465) |
| DC2-524-HC | GFTFSSYE (SEQ ID NO: 466) | TNHSGSTI (SEQ ID NO: 467) | AREHYDILTGFGGYLDY (SEQ ID NO: 468) |
| DC2-524-LC | QSVSNN (SEQ ID NO: 469) | GAS (SEQ ID NO: 470) | QQYNDWPRWT (SEQ ID NO: 471) |
| DC2-536-HC | GESFSGYY (SEQ ID NO: 472) | INHSGST (SEQ ID NO: 473) | ARGYADTPVFRRAAAAG MDV(SEQ ID NO: 474) |
| DC2-536-LC | QSISSY (SEQ ID NO: 475) | GAS (SEQ ID NO: 476) | LQSYSSWT (SEQ ID NO: 477) |
| DC2-541-HC | GFTFSSYE (SEQ ID NO: 478) | ISGGGDTI (SEQ ID NO: 479) | AKFWNDYYNDFEY (SEQ ID NO: 480) |
| DC2-541-LC - | QSVSSY (SEQ ID NO: 481) | DAS (SEQ ID NO: 482) | QQRTNWPPWT (SEQ ID NO: 483) |
| DC2-549-HC | GFTFGTYA (SEQ ID NO: 484) | ISGSGAGT (SEQ ID NO: 485) | AKDNSASVWDLAY (SEQ ID NO: 486) |
| DC2-549-LC | RSINSY (SEQ ID NO: 487) | AAS (SEQ ID NO: 488) | HQTYTTPPGT (SEQ ID NO: 489) |
| DC2-555-HC - | GFAFSDYA (SEQ ID NO: 490) | ISYAGNNK (SEQ ID NO: 491) | ARPFSRGWFEGCDS (SEQ ID NO: 492) |
| DC2-555-LC | QTINDF (SEQ ID NO: 493) | SAS (SEQ ID NO: 494) | QQSYIAPLT (SEQ ID NO: 495) |
| DC2-550-HC | GFTFRSYA (SEQ ID NO: 496) | ISLDGSHK (SEQ ID NO: 497) | VRGGWHEVGSFDY (SEQ ID NO: 498) |
| DC2-550-LC | QSINSNY (SEQ ID NO: 499) | AAS (SEQ ID NO: 500) | QXYGNTPFT (SEQ ID NO: 501) |
| DC2-572-HC | GDTFSSYG (SEQ ID NO: 502) | IIPIVDIT (SEQ ID NO: 503) | ARISAYYYDGSGSNPGITDYGMDV (SEQ ID NO: 504) |
| DC2-572-LC | QSLLHSNGYNY (SEQ ID NO: 505) | LGS (SEQ ID NO: 506) | MQGLQTPHT (SEQ ID NO: 507) |
| DC2-307-HC | GFTFSSYD (SEQ ID NO: 508) | AWYDGSNK (SEQ ID NO: 509) | ARGTHTYTYGYRTDYCMGVWGTHTYTY GYRTDYCMGV (SEQ ID NO: 510) |
| DC2-307-LC | QGIGNY (SEQ ID NO: 511) | SAS (SEQ ID NO: 512) | LKYHGAPYI (SEQ ID NO: 513) |
| DC2-324-HC | GYIFTTYT (SEQ ID NO: 514) | INAGNGVT (SEQ ID NO: 515) | ARAWKYSSTWFYYDY (SEQ ID NO: 516) |
| DC2-324-LC | QTINNY (SEQ ID NO: 517) | AAS (SEQ ID NO: 518) | QQSYSAPFT (SEQ ID NO: 519) |
| DC2-326-HC | GLTLSTNA (SEQ ID NO: 520) | IRGSGEST (SEQ ID NO: 521) | AKSGMGELVRCWFDA (SEQ ID NO: 522) |
| DC2-326-LC | QSVLYSSNNKNY (SEQ ID NO: 523) | WAS (SEQ ID NO: 524) | QQYYSNPPPGT (SEQ ID NO: 525) |
| DC2-345-HC | GFSLTTPGVG (SEQ ID NO: 526) | IFWNDEK (SEQ ID NO: 527) | AHSRLDLWNGYK (SEQ ID NO: 528) |

TABLE 1-continued

Exemplary CDRs of the antibodies are set forth in the following table:

| Laboratory Designation | CDR1 | CDR2 | CDR3 |
|---|---|---|---|
| DC2-345-LC | QSLLHINGYTY (SEQ ID NO: 529) | LGS (SEQ ID NO: 530) | MQALQTPRT (SEQ ID NO: 531) |
| DC2-657-HC | QSLVHRDGNTY (SEQ ID NO: 532) | GVS (SEQ ID NO: 533) | MQATHWGYT (SEQ ID NO: 534) |
| DC2-657-LC | RFIFSNYG (SEQ ID NO: 535) | IRSDGSNT (SEQ ID NO: 536) | AKGCCGGVPDFGLDV (SEQ ID NO: 537) |
| DC2-315-HC | GFSLTTPGVG (SEQ ID NO: 538) | IFWNDEK (SEQ ID NO: 539) | AHSRLDLWNGYK (SEQ ID NO: 540) |
| DC2-315-LC | QSLLHINGYTY (SEQ ID NO: 541) | LGS (SEQ ID NO: 542) | MQALQTPRT (SEQ ID NO: 543) |
| DC2-316-HC | GYTFTSYD (SEQ ID NO: 544) | MSPHTGNT (SEQ ID NO: 545) | GRLVGAPLYNYYGFDV (SEQ ID NO: 546) |
| DC2-316-LC | QDISDW (SEQ ID NO: 547) | AAS (SEQ ID NO: 548) | QQSSSFPLT (SEQ ID NO: 549) |
| DC2-317-HC | GFSFDDYG (SEQ ID NO: 550) | ISWNSGTI (SEQ ID NO: 551) | AKDFYAGFGGNTAFDI (SEQ ID NO: 552) |
| DC2-317-LC | QGIHNY (SEQ ID NO: 553) | AAS (SEQ ID NO: 554) | QQSYSVPRNT (SEQ ID NO: 555) |
| DC2-321-HC | GFTFKSYG (SEQ ID NO: 556) | ISNHGHNK (SEQ ID NO: 557) | AKGLNSDYDNEPFGD (SEQ ID NO: 558) |
| DC2-321-LC | QSFDSSY (SEQ ID NO: 559) | GAS (SEQ ID NO: 560) | QQYASTPFT (SEQ ID NO: 561) |
| DC2-68-HC | GGSMSSGDYY (SEQ ID NO: 562) | ISYSGSA (SEQ ID NO: 563) | ARVFSGYYYFDY (SEQ ID NO: 564) |
| DC2-68-LC 1 | QSISSW (SEQ ID NO: 565) | KAS (SEQ ID NO: 566) | QQYNTYPWT (SEQ ID NO: 567) |
| DC2-64-HC | GYTFTRYA (SEQ ID NO: 568) | INPGIGNT (SEQ ID NO: 569) | ARDLDLGIPTLGY (SEQ ID NO: 570) |
| DC2-64-LC | QSLLSSSNNKNF (SEQ ID NO: 571) | WAS (SEQ ID NO: 572) | QQYYSTPPYS (SEQ ID NO: 573) |
| DC2-70-HC | GYTFTRYA (SEQ ID NO: 574) | INTNTGEP (SEQ ID NO: 575) | AQQVIAFDV (SEQ ID NO: 576) |
| DC2-70-LC | QSLLSSSNNKNF (SEQ ID NO: 577) | WAS (SEQ ID NO: 578) | QQYYSTPPYS (SEQ ID NO: 579) |
| DC2-76-HC | GFTFNDYA (SEQ ID NO: 580) | ITWNGGPL (SEQ ID NO: 581) | AKVYCSSSTCSNALDV (SEQ ID NO: 582) |
| DC2-76-LC | QDISIY (SEQ ID NO: 583) | DAS (SEQ ID NO: 584) | QQHNSRPYS (SEQ ID NO: 585) |
| DC2-78-HC | GVSINNYDYY (SEQ ID NO: 586) | IIYSGST (SEQ ID NO: 587) | VRANLCNVASCYYYFDF (SEQ ID NO: 588) |
| DC2-78-LC | QDVTTA (SEQ ID NO: 589) | WAS (SEQ ID NO: 590) | QQHYSTPLT (SEQ ID NO: 591) |
| DC2-93-HC | GFTLSRYD (SEQ ID NO: 592) | IGTATTG (SEQ ID NO: 593) | YC IRAMVRGLDIFDY (SEQ ID NO: 594) |
| DC2-93-LC | QSVSSK (SEQ ID NO: 595) | GAS (SEQ ID NO: 596) | QQYNSWPMCT (SEQ ID NO: 597) |
| DC2-95-HC | GFTFSHYW (SEQ ID NO: 598) | IRPDGTTT (SEQ ID NO: 599) | ARDLTPGDDSAWYDFFDY (SEQ ID NO: 600) |
| DC2-95-LC | QPIRNE (SEQ ID NO: 601) | AAS (SEQ ID NO: 602) | LQDYRYPRT (SEQ ID NO: 603) |

TABLE 1-continued

Exemplary CDRs of the antibodies are set forth in the following table:

| Laboratory Designation | CDR1 | CDR2 | CDR3 |
| --- | --- | --- | --- |
| DC-415-HC | GFDLSDYY (SEQ ID NO: 604) | TARTGSTE (SEQ ID NO: 605) | ARDLVSHDVFDI (SEQ ID NO: 606) |
| DC1-415-LC | QRISTN (SEQ ID NO: 607) | DAS (SEQ ID NO: 608) | QQYINWPRT (SEQ ID NO: 609) |
| DC2_M1_HC | GFTFSSFA (SEQ ID NO: 611) | ISYEGKNK (SEQ ID NO: 612) | ARPFSMSWFEGFEF (SEQ ID NO: 613) |
| DC2_M1_LC | QNINSF (SEQ ID NO: 614) | EAS (SEQ ID NO: 615) | QQSYTAPLT (SEQ ID NO: 616) |
| DC2_M10_HC | GYTFTNYY (SEQ ID NO: 617) | IYPSGGDT (SEQ ID NO: 618) | ARDHLNRDSSSRGFMDY (SEQ ID NO: 619) |
| DC2_M10_LC | QSISHY (SEQ ID NO: 620) | DAS (SEQ ID NO: 621) | QQRGTWPPS (SEQ ID NO: 622) |
| DC2_M101_HC | GYTFTNYP (SEQ ID NO: 623) | INTNTGKP (SEQ ID NO: 624) | ARGRGATTVTTYYFDY (SEQ ID NO: 625) |
| DC2_M101_LC | QSVSSN (SEQ ID NO: 626) | GAS (SEQ ID NO: 627) | QHYINRPGRT (SEQ ID NO: 628) |
| DC2_M105_HC | GYTFIAFY (SEQ ID NO: 629) | INPYSGDT (SEQ ID NO: 630) | ARTVYVDKGMVMVRRLYQYFGMDV (SEQ ID NO: 631) |
| DC2_M105_LC | QTVSSSY (SEQ ID NO: 632) | GAS (SEQ ID NO: 633) | QQYGISPEFT (SEQ ID NO: 634) |
| DC2_M106_HC | GFTFSDYY (SEQ ID NO: 635) | ISSSGSTL (SEQ ID NO: 636) | ARAERIVGSVQTPFI (SEQ ID NO: 637) |
| DC2_M106_LC | QSLVYRDGNTY (SEQ ID NO: 638) | KVS (SEQ ID NO: 639) | MQGTDSFT (SEQ ID NO: 640) |
| DC2_M108_HC | GFTFSDYF (SEQ ID NO: 641) | ISDNGNTI (SEQ ID NO: 642) | ARGLYIQSDAFDL (SEQ ID NO: 643) |
| DC2_M108_LC | QGLSNS (SEQ ID NO: 644) | AAS (SEQ ID NO: 645) | QQYYNTPPIT (SEQ ID NO: 646) |
| DC2_M109_HC | GYNFTNYW (SEQ ID NO: 647) | IYPGDSDS (SEQ ID NO: 648) | ARRPREQLGRLLLGDVVPHGRNDAFDI (SEQ ID NO: 649) |
| DC2_M109_LC | QSISTY (SEQ ID NO: 650) | SAS (SEQ ID NO: 651) | QQSYGTLWT (SEQ ID NO: 652) |
| DC2_M11_HC | GFNFNIFP (SEQ ID NO: 653) | ISDDVTKK (SEQ ID NO: 654) | ARASGWQRTGTKYYYYGMDV (SEQ ID NO: 655) |
| DC2_M11_LC | QDISNN (SEQ ID NO: 656) | DAS (SEQ ID NO: 657) | LQYDNLPYS (SEQ ID NO: 658) |
| DC2_M112_HC | GFIFKTYG (SEQ ID NO: 659) | IWYDGSNE (SEQ ID NO: 660) | ARDEAVGPYQYAAEYFHH (SEQ ID NO: 661) |
| DC2_M112_LC | KSVTSN (SEQ ID NO: 662) | GAS (SEQ ID NO: 663) | QQYNNWLT (SEQ ID NO: 664) |
| DC2_M123_HC | GFTFSSSA (SEQ ID NO: 665) | ISSDGTYK (SEQ ID NO: 666) | AKSGWELHPFGV (SEQ ID NO: 667) |
| DC2_M123_LC | QSVSSN (SEQ ID NO: 668) | GAS (SEQ ID NO: 669) | QHYINRPGRT (SEQ ID NO: 670) |
| DC2_M124_HC | GGSISGYF (SEQ ID NO: 671) | VHYSGST (SEQ ID NO: 672) | ARASTGGFDP (SEQ ID NO: 673) |
| DC2_M124_LC | QSVSSN (SEQ ID NO: 674) | GAS (SEQ ID NO: 675) | QHYINRPGRT (SEQ ID NO: 676) |
| DC2_M125_HC | GFTFSSYA (SEQ ID NO: 677) | ISPSGSTI (SEQ ID NO: 678) | VRGVYVQSDAFDI (SEQ ID NO: 679) |

TABLE 1-continued

Exemplary CDRs of the antibodies are set forth in the following table:

| Laboratory Designation | CDR1 | CDR2 | CDR3 |
| --- | --- | --- | --- |
| DC2_M125_LC | QGISYS (SEQ ID NO: 680) | AAS (SEQ ID NO: 681) | QQYYSTPPIT (SEQ ID NO: 682) |
| DC2_M129_HC | GVTFSDYD (SEQ ID NO: 683) | IRSSGGTT (SEQ ID NO: 684) | VRDKDGVFDY (SEQ ID NO: 685) |
| DC2_M129_LC | QDISSW (SEQ ID NO: 686) | KAS (SEQ ID NO: 687) | QQYNTYPHST (SEQ ID NO: 688) |
| DC2_M131_HC | GFTFSDYY (SEQ ID NO: 689) | ISISGSTI (SEQ ID NO: 690) | ARGIYHQSDAFDI (SEQ ID NO: 691) |
| DC2_M131_LC | QGISNS (SEQ ID NO: 692) | AAS (SEQ ID NO: 693) | QQYYSTPPIT (SEQ ID NO: 694) |
| DC2_M132_HC | GYTLSTYP (SEQ ID NO: 695) | INTYTGDP (SEQ ID NO: 696) | VRQKDPFDY (SEQ ID NO: 697) |
| DC2_M132_LC | HTVSSVY (SEQ ID NO: 698) | GAS (SEQ ID NO: 699) | QQYAISPPPMYT (SEQ ID NO: 700) |
| DC2_M133_HC | GFTFRDYW (SEQ ID NO: 701) | INRNGNEK (SEQ ID NO: 702) | VRDNSPSFGPGNYYDAFDI (SEQ ID NO: 703) |
| DC2_M133_LC | QDIRNE (SEQ ID NO: 704) | AAS (SEQ ID NO: 705) | LQDYNYPRT (SEQ ID NO: 706) |
| DC2_M135_HC | GYTFTSYA (SEQ ID NO: 707) | INTNTGNP (SEQ ID NO: 708) | AREHLVALEYYYYGVDV (SEQ ID NO: 709) |
| DC2_M135_LC | QRISNY (SEQ ID NO: 710) | AAS (SEQ ID NO: 711) | QQSYSVPLT (SEQ ID NO: 712) |
| DC2_M14_HC | RFIFSNFG (SEQ ID NO: 713) | IRSDGSNE (SEQ ID NO: 714) | AKGCCGGVPDFGLDV (SEQ ID NO: 715) |
| DC2_M14_LC | QSLVHRDGSTY (SEQ ID NO: 716) | QVS (SEQ ID NO: 717) | MQATHWGYT (SEQ ID NO: 718) |
| DC2_M15_HC | GYTLSTYP (SEQ ID NO: 719) | INTYTGDP (SEQ ID NO: 720) | VRQKDPFDY (SEQ ID NO: 721) |
| DC2_M15_LC | QDVTTA (SEQ ID NO: 722) | WAS (SEQ ID NO: 723) | QQHYSTPLT (SEQ ID NO: 724) |
| DC2_M16_HC | GFTFSDYY (SEQ ID NO: 725) | ISTSGSTM (SEQ ID NO: 726) | ARGIYYQSDAFDI (SEQ ID NO: 727) |
| DC2_M16_LC | QGISNS (SEQ ID NO: 728) | AAS (SEQ ID NO: 729) | QQYYSTPPMT (SEQ ID NO: 730) |
| DC2_M2_HC | GFTFSSSA (SEQ ID NO: 731) | ISSDGTYK (SEQ ID NO: 732) | AKSGWELHPFGV (SEQ ID NO: 733) |
| DC2_M2_LC | QDVTTA (SEQ ID NO: 734) | WAS (SEQ ID NO: 735) | QQHYSTPLT (SEQ ID NO: 736) |
| DC2_M21_HC | GYTFTSSY (SEQ ID NO: 737) | IYPSGGNT (SEQ ID NO: 738) | ARDHLNRDSTSRGFIDS (SEQ ID NO: 739) |
| DC2_M21_LC | QSVGNY (SEQ ID NO: 740) | DAS (SEQ ID NO: 741) | EQRGDWPLT (SEQ ID NO: 742) |
| DC2_M22_HC | GGSISSDIYY (SEQ ID NO: 743) | IYYSGST (SEQ ID NO: 744) | ARRGEWLRLGYFDY (SEQ ID NO: 745) |
| DC2_M22_LC | QSVSSSY (SEQ ID NO: 746) | GAS (SEQ ID NO: 747) | QQYGSSPWT (SEQ ID NO: 748) |
| DC2_M24_HC | GGSISGYF (SEQ ID NO: 749) | VHYSGST (SEQ ID NO: 750) | ARASTSGGFDP (SEQ ID NO: 751) |
| DC2_M24_LC | QGIRND (SEQ ID NO: 752) | AAS (SEQ ID NO: 753) | LQHNSYPYT (SEQ ID NO: 754) |

TABLE 1-continued

Exemplary CDRs of the antibodies are set forth in the following table:

| Laboratory Designation | CDR1 | CDR2 | CDR3 |
|---|---|---|---|
| DC2_M137_HC | GFSFSNYE (SEQ ID NO: 755) | ISSGSSYR (SEQ ID NO: 756) | VRDEDYRNGSRHYDGLHV (SEQ ID NO: 757) |
| DC2_M137_LC | QGIRND (SEQ ID NO: 758) | AAS (SEQ ID NO: 759) | LQDYNYPRT (SEQ ID NO: 760) |
| DC2_M141_HC | GFTFSSSA (SEQ ID NO: 761) | ISSDGTYK (SEQ ID NO: 762) | AKSGWELHPFGV (SEQ ID NO: 763) |
| DC2_M141_LC | QSVLYSSNNKNY (SEQ ID NO: 764) | WAS (SEQ ID NO: 765) | QQYYSTLPLT (SEQ ID NO: 766) |
| DC2_M150_HC | GFTFRDYW (SEQ ID NO: 767) | INRNGNEK (SEQ ID NO: 768) | VRDNSPPFGPGNYYDALDI (SEQ ID NO: 769) |
| DC2_M150_LC | QDIRNE (SEQ ID NO: 770) | AAS (SEQ ID NO: 771) | LQDYNYPRT (SEQ ID NO: 772) |
| DC2_M151_HC | GFTFKDYW (SEQ ID NO: 773) | INRNGNEK (SEQ ID NO: 774) | VRDSSPSFGPGNYYDAFDI (SEQ ID NO: 775) |
| DC2_M151_LC | QDIRNE (SEQ ID NO: 776) | AAS (SEQ ID NO: 777) | LQDYNYPRT (SEQ ID NO: 778) |
| DC2_M152_HC | GYTFTDYY (SEQ ID NO: 779) | ISPKSGGT (SEQ ID NO: 780) | TRDNYNSWRGPDFYTGVDV (SEQ ID NO: 781) |
| DC2_M152_LC | QSVSSY (SEQ ID NO: 782) | NAS (SEQ ID NO: 783) | QQRSSLGLS (SEQ ID NO: 784) |
| DC2_M167_HC | GYTFTGYY (SEQ ID NO: 785) | IDPNGGDT (SEQ ID NO: 786) | ARDRAGSVWFRGVYFFDA (SEQ ID NO: 787) |
| DC2_M167_LC | QDVHYY (SEQ ID NO: 788) | GVS (SEQ ID NO: 789) | QQYSNWPPGA (SEQ ID NO: 790) |
| DC2_M171_HC | GFSFSNYG (SEQ ID NO: 791) | ISYDGNNI (SEQ ID NO: 792) | VKAGGFS (SEQ ID NO: 793) |
| DC2_M171_LC | QGIRSA (SEQ ID NO: 794) | DAS (SEQ ID NO: 795) | QHFSTYPYT (SEQ ID NO: 796) |
| DC2_M173_HC | GYSLTRYY (SEQ ID NO: 797) | ISPSGGGT (SEQ ID NO: 798) | ARDACSGGSCYTPFDY (SEQ ID NO: 799) |
| DC2_M173_LC | QSVSSN (SEQ ID NO: 800) | GAS (SEQ ID NO: 801) | QQYNNWPRT (SEQ ID NO: 802) |
| DC2_M182_HC | GFSFSDHY (SEQ ID NO: 803) | IRNKAKDYST (SEQ ID NO: 804) | TRVNYYDRSGWSLDAFDI (SEQ ID NO: 805) |
| DC2_M182_LC | QGISNS (SEQ ID NO: 806) | AAS (SEQ ID NO: 807) | QQYYSTPPIT (SEQ ID NO: 808) |
| DC2_M186_HC | GFSFSNYE (SEQ ID NO: 809) | ISSGSSYR (SEQ ID NO: 810) | ARRWHGIDI (SEQ ID NO: 811) |
| DC2_M186_LC | QDIRSD (SEQ ID NO: 812) | AAS (SEQ ID NO: 813) | LQDFNYPRI (SEQ ID NO: 814) |
| DC2_M190_HC | GYTFSRYA (SEQ ID NO: 815) | INTNTGEP (SEQ ID NO: 816) | ARDGTLRSADGETSAFDI (SEQ ID NO: 817) |
| DC2_M190_LC | QGISNS (SEQ ID NO: 818) | AAS (SEQ ID NO: 819) | QQYYSTPPIT (SEQ ID NO: 820) |
| DC2_M192_HC | GFTFSSYG (SEQ ID NO: 821) | IWLDGTNK (SEQ ID NO: 822) | ARRGFHYDSSGYYYYGMDV (SEQ ID NO: 823) |
| DC2_M192_LC | QSLLHSNGYNY (SEQ ID NO: 824) | LGS (SEQ ID NO: 825) | MQALQTPPFT (SEQ ID NO: 826) |
| DC2_M193_HC | GVTFSDYD (SEQ ID NO: 827) | IRSSGGTT (SEQ ID NO: 828) | VRDKDGVFDY (SEQ ID NO: 829) |

TABLE 1-continued

Exemplary CDRs of the antibodies are set forth in the following table:

| Laboratory Designation | CDR1 | CDR2 | CDR3 |
|---|---|---|---|
| DC2_M193_LC | QSVLYSSNNKNY (SEQ ID NO: 830) | WAS (SEQ ID NO: 831) | QQYYRTPL (SEQ ID NO: 832) |
| DC2_M198_HC | GFTFSSYA (SEQ ID NO: 833) | ISPSGSTI (SEQ ID NO: 834) | VRGVYVQSDAFDI (SEQ ID NO: 835) |
| DC2_M198_LC | QGISNS (SEQ ID NO: 836) | AAS (SEQ ID NO: 837) | QQYYSTPPIT (SEQ ID NO: 838) |
| DC2_M199_HC | GYTFTTYA (SEQ ID NO: 839) | INTNTGNP (SEQ ID NO: 840) | ARDRYSSSWYQFDP (SEQ ID NO: 841) |
| DC2_M199_LC | QGISNS (SEQ ID NO: 842) | AAS (SEQ ID NO: 843) | QQYNTYPHST (SEQ ID NO: 844) |
| DC2_M203_HC | GFTFSNYD (SEQ ID NO: 845) | IDTSGNT (SEQ ID NO: 846) | VRLGGYIGNDRDAFDI (SEQ ID NO: 847) |
| DC2_M203_LC | QDISSW (SEQ ID NO: 848) | KAS (SEQ ID NO: 849) | QQYNTYPHST (SEQ ID NO: 850) |
| DC2_M204_HC | GYTFISYG (SEQ ID NO: 851) | ISAKNGNT (SEQ ID NO: 852) | ARDRTGTLDS (SEQ ID NO: 853) |
| DC2_M204_LC | QDIKKFLNWYQQ (SEQ ID NO: 854) | DAF (SEQ ID NO: 855) | QQYDILPYT (SEQ ID NO: 856) |
| DC2_M208_HC | GYTFISYG (SEQ ID NO: 857) | ISAKSGNT (SEQ ID NO: 858) | ARDRTGTLDS (SEQ ID NO: 859) |
| DC2_M208_LC | QSIDDY (SEQ ID NO: 860) | AAS (SEQ ID NO: 861) | QQTYGTSIT (SEQ ID NO: 862) |
| DC2_M209_HC | GFIFGDFA (SEQ ID NO: 863) | IRSQAHGGTT (SEQ ID NO: 864) | TREGVVVAARYYYYIMDV (SEQ ID NO: 865) |
| DC2_M209_LC | HNISRY (SEQ ID NO: 866) | AAS (SEQ ID NO: 867) | QQNYRTPRT (SEQ ID NO: 868) |
| DC2_M212_HC | GFAFNYYD (SEQ ID NO: 869) | IKPGGGNT (SEQ ID NO: 870) | ARQLYGNSFFDY (SEQ ID NO: 871) |
| DC2_M212_LC | QGISNS (SEQ ID NO: 872) | AAS (SEQ ID NO: 873) | QQYYSTPPIT (SEQ ID NO: 874) |
| DC2_M213_HC | GFTFRDYW (SEQ ID NO: 875) | INRNGNEK (SEQ ID NO: 876) | VRDSSPSFGPGNYYDAFDI (SEQ ID NO: 877) |
| DC2_M213_LC | QDIRNE (SEQ ID NO: 878) | AAS (SEQ ID NO: 879) | LQDYNYPRT (SEQ ID NO: 880) |
| DC2_M215_HC | GYTFIDYY (SEQ ID NO: 881) | INPKSGAT (SEQ ID NO: 882) | STFWDGVDAFDV (SEQ ID NO: 883) |
| DC2_M215_LC | QSVSSY (SEQ ID NO: 884) | DTS (SEQ ID NO: 885) | LQRRNWPPFT (SEQ ID NO: 886) |
| DC2_M218_HC | GFSFSNYE (SEQ ID NO: 887) | ISSGSSYR (SEQ ID NO: 888) | ARRWHGLDI (SEQ ID NO: 889) |
| DC2_M218_LC | QSLLHINGYNY (SEQ ID NO: 890) | LGS (SEQ ID NO: 891) | MQALQTPWT (SEQ ID NO: 892) |
| DC2_M220_HC | GFIFSSTG (SEQ ID NO: 893) | IGRDGNYK (SEQ ID NO: 894) | ILSSALVPGATFDK (SEQ ID NO: 895) |
| DC2_M220_LC | QSISTS (SEQ ID NO: 896) | TAS (SEQ ID NO: 897) | CQQSYSVPYT (SEQ ID NO: 898) |
| DC2_M221_HC | GFTFRSFE (SEQ ID NO: 899) | ISVGANP (SEQ ID NO: 900) | VRKIPGTSHFDY (SEQ ID NO: 901) |
| DC2_M221_LC | QSVSSY (SEQ ID NO: 902) | DAS (SEQ ID NO: 903) | QHFSTYPYT (SEQ ID NO: 904) |

TABLE 1-continued

Exemplary CDRs of the antibodies are set forth in the following table:

| Laboratory Designation | CDR1 | CDR2 | CDR3 |
|---|---|---|---|
| DC2_M222_HC | GGIFSNYA (SEQ ID NO: 905) | FIPIVNIG (SEQ ID NO: 906) | ARDLEAANSVILPRLFY (SEQ ID NO: 907) |
| DC2_M222_LC | QGISNS (SEQ ID NO: 908) | AAS (SEQ ID NO: 909) | QQYYSTPPIT (SEQ ID NO: 910) |
| DC2_M223_HC | GFTLSDHY (SEQ ID NO: 911) | SRNKAKTYTT (SEQ ID NO: 912) | TRPGYFDRSGDSFDALDI (SEQ ID NO: 913) |
| DC2_M223_LC | QGIRSA (SEQ ID NO: 914) | DAS (SEQ ID NO: 915) | QHFSTYPYT (SEQ ID NO: 916) |
| DC2_M229_HC | GFSFSNYE (SEQ ID NO: 917) | ISTIRPYI (SEQ ID NO: 918) | ARDAFTSTSYDGFSGNFDY (SEQ ID NO: 919) |
| DC2_M229_LC | QGIRSA (SEQ ID NO: 920) | DAS (SEQ ID NO: 921) | QHFSTYPYT (SEQ ID NO: 922) |
| DC2_M230_HC | GFTFTDYY (SEQ ID NO: 923) | ISPSGSTI (SEQ ID NO: 924) | ARGIYYQSDAFDT (SEQ ID NO: 925) |
| DC2_M230_LC | QVIRNS (SEQ ID NO: 926) | AAS (SEQ ID NO: 927) | QQYYSTPPIT (SEQ ID NO: 928) |
| DC2_M233_HC | GFTFTSYA (SEQ ID NO: 929) | ISYNGRNK (SEQ ID NO: 930) | VRSMGDFDWLLTDY (SEQ ID NO: 931) |
| DC2_M233_LC | QSVSTH (SEQ ID NO: 932) | DAS (SEQ ID NO: 933) | QQYNTWPR (SEQ ID NO: 934) |
| DC2_M240_HC | GVTFSDYD (SEQ ID NO: 935) | IRSSGGTT (SEQ ID NO: 936) | VRDKDGVFDY (SEQ ID NO: 937) |
| DC2_M240_LC | QSVTRTF (SEQ ID NO: 938) | DAS (SEQ ID NO: 939) | QQYGTSPLT (SEQ ID NO: 940) |
| DC2_M241_HC | GFTFSHYW (SEQ ID NO: 941) | INGNGGAT (SEQ ID NO: 942) | VGGSNDWVGIDY (SEQ ID NO: 943) |
| DC2_M241_LC | QSIRTF (SEQ ID NO: 944) | DAS (SEQ ID NO: 945) | QQSYSSPLT (SEQ ID NO: 946) |
| DC2_M242_HC | GYTFIDYF (SEQ ID NO: 947) | IYPKSGET (SEQ ID NO: 948) | ARDIAPTGAWWFDS (SEQ ID NO: 949) |
| DC2_M242_LC | QMLSSSR (SEQ ID NO: 950) | GAS (SEQ ID NO: 951) | QQYGSPRT (SEQ ID NO: 952) |
| DC2_M243_HC | GYTFISYG (SEQ ID NO: 953) | ISAKNGNT (SEQ ID NO: 954) | ARDRTGTLDS (SEQ ID NO: 955) |
| DC2_M243_LC | QSISDF (SEQ ID NO: 956) | TAS (SEQ ID NO: 957) | QQSYSAPLT (SEQ ID NO: 958) |
| DC2_M244_HC | GYTFIAFY (SEQ ID NO: 959) | INPYSGDT (SEQ ID NO: 960) | ARTVYVDKGMVMVRRLYQYFGMDV (SEQ ID NO: 961) |
| DC2_M244_LC | QSISNNF (SEQ ID NO: 962) | ASS (SEQ ID NO: 963) | QQYGTSPAT (SEQ ID NO: 964) |
| DC2_M245_HC | GFIFKTYG (SEQ ID NO: 965) | IWYDGSNE (SEQ ID NO: 966) | ARDEAVGPYQYAAEYFHH (SEQ ID NO: 967) |
| DC2_M245_LC | QSLLHGNGYNF (SEQ ID NO: 968) | LGS (SEQ ID NO: 969) | MQALQTPWT (SEQ ID NO: 970) |
| DC2_M249_HC | GFTFSGHY (SEQ ID NO: 971) | IRDQPHKYST (SEQ ID NO: 972) | ARAPFYDTTGYSLDALDI (SEQ ID NO: 973) |
| DC2_M249_LC | QSVSSN (SEQ ID NO: 974) | GAS (SEQ ID NO: 975) | QHYINRPGRT (SEQ ID NO: 976) |
| DC2_M251_HC | GFSFSNYE (SEQ ID NO: 977) | ISSGSSYR (SEQ ID NO: 978) | ARQDNSGRPFSH (SEQ ID NO: 979) |

TABLE 1-continued

Exemplary CDRs of the antibodies are set forth in the following table:

| Laboratory Designation | CDR1 | CDR2 | CDR3 |
|---|---|---|---|
| DC2_M251_LC | QGISNS (SEQ ID NO: 980) | AAS (SEQ ID NO: 981) | QQYYSTPPIT (SEQ ID NO: 982) |
| DC2_M261_HC | GFTFSSHA (SEQ ID NO: 983) | ISYDGSNK (SEQ ID NO: 984) | VRWVAYYFDN (SEQ ID NO: 985) |
| DC2_M261_LC | QSVSSSS (SEQ ID NO: 986) | GTS (SEQ ID NO: 987) | QYYGSLPPIT (SEQ ID NO: 988) |
| DC2_M262_HC | GDSISSYY (SEQ ID NO: 989) | ISYTGST (SEQ ID NO: 990) | ARLGYSHPYWYFDL (SEQ ID NO: 991) |
| DC2_M262_LC | QSISNF (SEQ ID NO: 992) | AAS (SEQ ID NO: 993) | QQSYSPPLIT (SEQ ID NO: 994) |
| DC2_M263_HC | GFTFSRYW (SEQ ID NO: 995) | IEADGSVK (SEQ ID NO: 996) | ARDANYHDGSAYYDAFDV (SEQ ID NO: 997) |
| DC2_M263_LC | QAIRND GAS (SEQ ID NO: 998) | LQDYNYPRT (SEQ ID NO: 999) | (SEQ ID NO: 1000) |
| DC2_M264_HC | GYSFSAHA (SEQ ID NO: 1001) | INGGNGNT (SEQ ID NO: 1002) | ARHLPEPWNYYDSSGYFGFDY (SEQ ID NO: 1001) |
| DC2_M264_LC | QSVSNY (SEQ ID NO: 1004) | YTS (SEQ ID NO: 1005) | QQRYNWPLT (SEQ ID NO: 1006) |
| DC2_M266_HC | GFTFSDYY (SEQ ID NO: 1007) | ISGSGKIT (SEQ ID NO: 1008) | ARVQGEQWRGLHFDS (SEQ ID NO: 1009) |
| DC2_M266_LC | QDISNY (SEQ ID NO: 1010) | DAS (SEQ ID NO: 1011) | QHRSNWPA (SEQ ID NO: 1012) |
| DC2_M280_HC | GFRFGDYA (SEQ ID NO: 1013) | INWDSGDI (SEQ ID NO: 1014) | AKDSGWLRRGDYDTSGFYGPIDY (SEQ ID NO: 1015) |
| DC2_M280_LC | QYISTY (SEQ ID NO: 1016) | SAS (SEQ ID NO: 1017) | QQSYGTLLT (SEQ ID NO: 1018) |

HC = Heavy chain; LC = Light chain

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention may be better understood from the Experimental Details, which follow.

EXEMPLIFICATIONS

Example 1

Experimental Details

The alphavirus envelope glycoproteins E1 and E2 are responsible for mediating viral attachment (E2) and membrane fusion (E1) (FIG. 1) (1, 7, 8). The prefusion E1/E2 heterodimer is arranged into trimers with an icosahedral organization on the CHIKV particle (9,10). Mature E1/E2 is generated by furin cleavage of a penultimate precursor that consists of a non-covalent heterodimer of E1 and p62. The p62 polypeptide contains E2 and E3, which is a small domain that accompanies the glycoprotein throughout the viral assembly and prevents premature conformational changes (11). Furin cleavage in the region between E2 and E3 releases E3 and primes the glycoprotein for membrane fusion (1, 7, 8). A hybrid p62-E1 protein is used as "bait" for mAb discovery, in which the ectodomains of p62 and E1 are joined by a polypeptide linker. Rey and coworkers used this construct for X-ray studies of the CHIKV prefusion assembly and provided the DNA used for p62-E1 expression at Einstein (8).

In recent years, advances in human monoclonal antibody (mAb) isolation methods have greatly accelerated the pace and extent of characterization of human responses to viral pathogens. In particular, B-cell sorting and single cell cloning methods have led to the isolation and development of HIV-1 mAbs VRC01 and 3BNC117 that have exceptional breadth and potency and are undergoing clinical trials as immunotherapies (12-14). In flaviviruses, similar approaches led to the identification of novel human mAbs that target epitopes that span the E glycoprotein prefusion dimer ("envelope dimer epitope", EDE mAbs) (15, 16). More recently, rapid and high-throughput B-cell sorting was used to profile the antibody response of a human Ebola virus survivor (elaborated below) (17). A common aspect to the work-flow in the above cases is the use of FACS and single-cell sorting to identify antigen-specific B-cells (generally memory B-cells) from seropositive donors. The power of this approach lies in the ability to rapidly isolate and screen hundreds of mAbs from any one patient sample, allowing for a comprehensive set of human mAbs. Thus, rare human mAbs with enhanced properties such as cross-neutralization or that target unique/unusual epitopes can be identified readily.

The characterization of human mAbs from convalescent patients is advantageous for two reasons. While isolation of murine mAbs from inoculations or immunizations can be very insightful for understanding sites of vulnerability on viral glycoproteins, it has been shown in many pathogens that the immunodominant neutralization sites in mice and humans do not correlate. It is only through the isolation and characterization of human mAbs that one can characterize which epitopes are most likely to elicit desirable neutralizing or protective responses for a human vaccine. Second, human mAbs are less likely to elicit anti-idiotypic and rare anaphylactic responses when used therapeutically than murine/human chimeric mAbs. Human mAbs are potentially more clinical useful as immunotherapies than mAbs from other species.

There are no effective therapeutic drugs or licensed vaccines for human alphavirus infections and new antiviral strategies are urgently needed. For CHIKV, two vaccines have entered into Phase II clinical studies (18, 19). In addition, several groups have demonstrated that neutralizing mAbs administered as monotherapies or as a cocktail can provide protection in a lethal mouse model (20-25). Similarly, immunotherapeutic mAbs against other alphaviruses (e.g., VEEV) are under development (26, 27). In a recent study, a cross-protective alphavirus murine mAb (CHK-265) was shown to be effective in murine models of CHIKV, Mayaro virus (MAYV), and O'nyong'nyong virus (ONNV) (28). However, no such cross-protective human mAb has yet been described.

Previous human CHIKV mAb isolation methods provide an incomplete profile of the human response. Both phage display and hybridoma approaches have been previously used to isolate human CHIKV mAbs (23-25, 29). Despite these advances, the most potent and broadly protective CHIKV mAbs are of murine origin (28). While it is possible that species difference or inoculation methods (e.g., natural infection vs. vaccination) belie these discrepancies, a more likely explanation is that the ~40 human CHIKV mAbs that have been isolated thus far do not provide a comprehensive profile of the human antibody response. Furthermore, these two human mAb methods both suffer from intrinsic biases. Phage display recovery of human V regions from B-cells does not allow for proper heavy and light chain pairing, and is subject to expression biases in non-native bacterial systems. Human hybridoma fusions are low-throughput and are preferential toward B-cell clones with high intrinsic ability to be immortalized with Epstein Barr Virus or to fuse with myeloma partners. Here, we propose to rapidly and comprehensively profile the human antibody response to CHIKV infection using two complementary and nascent strategies: B-cell sorting and de novo antibody sequencing by mass spectrometry.

Figure 3:
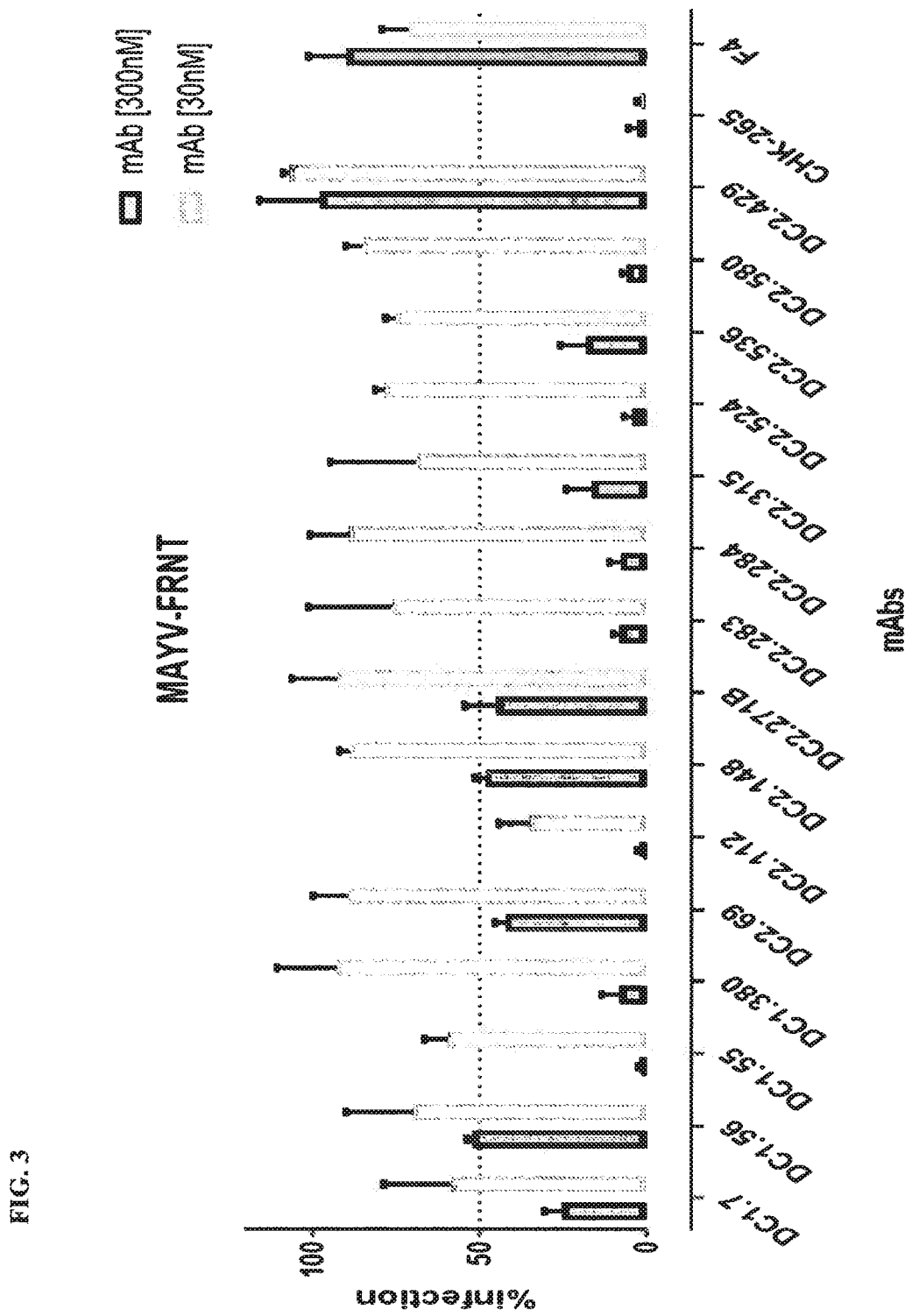
FIG. 3 shows neutralization of MAYV by human CHIKV mAbs. CHK-265 is a positive control murine mAb with reported cross neutralizing activity toward MAYV, and F4 is a negative control.

The human antibody response to CHIKV was examined herein. PBMC samples were obtained from a convalescent patient who was diagnosed with CHIKV 18 months ago in the Dominican Republic (donor Dominican Republic CHIKV 1 or "DC1"). Serum ELISA indicated a strong reactivity toward CHIKV p62-E1 hybrid protein, which represents the immature form of the prefusion E1-E2 glycoprotein assembly (FIG. 3A). From these samples, B-cell sorting experiments were performed pilot. FIG. 3B shows representative data from sorting of the CD20+ CD27+ IgG+ p62-E1(CHIKV)+ population (antigen-specific memory B-cells). From these studies, it was found that ~0.1% of B-cells are CHIKV-specific. A number of mAbs were cloned from single sequenced B-cells. FIG. 3C shows sample ELISA binding and neutralization data from three cloned mAbs DC1.9, DC1.55, and DC1.56; all three mAbs exhibited specific binding to p62-E1 as well as a recombinant vesicular stomatitis virus particle that bears the CHIKV E1/E2 glycoproteins in place of the native glycoprotein G (rVSV-CHIKV). Furthermore, mAb DC1.56 was found to neutralize rVSV-CHIKV in a single high-point test, DC1.55 was less effective and DC1.9 had no neutralizing activity.

Isolation of a Panel of Human CHIKV mAbs

Human single B-cell sorting was utilized to isolate a total of 108 mAbs from two convalescent donors (DC1 and DC2) who were exposed to CHIKV infection in the Dominican Republic. In general, the sorting procedure involved positive gating of CD19 or CD20+, IgG+ and p62-E1+ B-cells, followed by single cell cloning of variable domains. Recombinant mAbs from this procedure were produced as human IgG1 from HEK293 cells, and purified by protein A chromatography. A focus was placed on mAb containing κ light chains because of their generally favorable stability properties, abundance in human blood, and for technical simplicity during the variable domain PCR recovery. Of the isolated mAbs, 40 have been demonstrated to have functional activity, either binding or neutralization, and an additional 40 mAbs are currently being characterized. Sequences of the 40 functional mAbs showed they were from diverse IGHV and IGKV lineages and contained a wide range of CDR-H3 lengths. Dr. Daniel Hoffman assisted with these experiments. Of the 40 mAbs, two pairs were contained identical light chains paired with unique heavy chains. ELISA at two different antibody concentrations (300 and 30 nM) demonstrated that 28 of the mAbs exhibited strong reactivity toward p62-E1 (OD450>2 at 30 nM) and 8 mAbs had more moderate reactivity. A few of the mAbs did not show any significant binding activity toward p62-E1 in this format, including mAb DC2.429, one of the more potent neutralizing mAbs (see below).

Neutralizing Activity Against the CHIKV Vaccine Strain 181/25 and Authentic CHIKV mAbs were screened for neutralization of the CHIKV 181/25 vaccine strain at 300 nM and 30 nM by focus reduction neutralization test. A majority of the mAbs exhibited greater than 50% neutralization at 300 nM, but only a handful (5) were active at 30 nM. Based on these results, 8 mAbs were selected for IC50 determination with the CHIKV 181/25 vaccine strain (Table 1).

TABLE 1

IC$_{50}$ values for human CHIKV mAbs against CHIKV 181/25 vaccine strain by FRNT

| mAb | IC$_{50}$ (nM) |
| --- | --- |
| DC1.7 | 11 |
| DC1.33 | <0.01 |
| DC1.56 | 72 |
| DC2.1 | 0.08 |
| DC2.112 | 78 |
| DC2.118 | 5.1 |
| DC2.148 | 11 |
| DC2.271B | <0.01 |
| DC2.315 | 44 |
| DC2.429 | <0.01 |

As shown, potencies against CHIKV 181/25 ranged from <0.01 to 78 nM. The two most potent mAbs were DC2.429 and DC2.271B. Interestingly, DC2.429 had no observable binding to p62-E1, despite potent neutralizing activity against authentic CHIKV as well as the vaccine strain and ability to bind the E1-E2 glycoprotein presented on vesicular stomatitis virus particles (data not shown), suggesting that binding of this mAb may be dependent on quarternary structures. mAbs DC2.429 and DC2.271B were carried forward for neutralization studies with authentic CHIKV (Asian lineage) under BSL3 conditions in collaboration with the USAMRIID. Both mAbs were found to neutralize authentic virus with high potency (IC50~40 ng/mL or 0.27 nM).

Cross-Neutralizing Activity against Mayaro Virus (MAYV).

The potential cross-neutralizing capacity of human CHIKV mAbs was explored against MAYV. MAYV is a member of the alphavirus family. At present, there are several mAbs that have been reported to harbor cross-neutralizing activity between CHIKV and MAYV, but all of these mAbs are of murine origin (28). Neutralizing activity of 18 CHIKV mAbs was determined against MAYV. DC2.429 was also included in the analysis, since it has the unusual property of neutralizing CHIKV but not binding p62-E1 and has very potent activity. However, DC2.429 did not neutralize MAYV.

Epitope Binning

Figure 4:
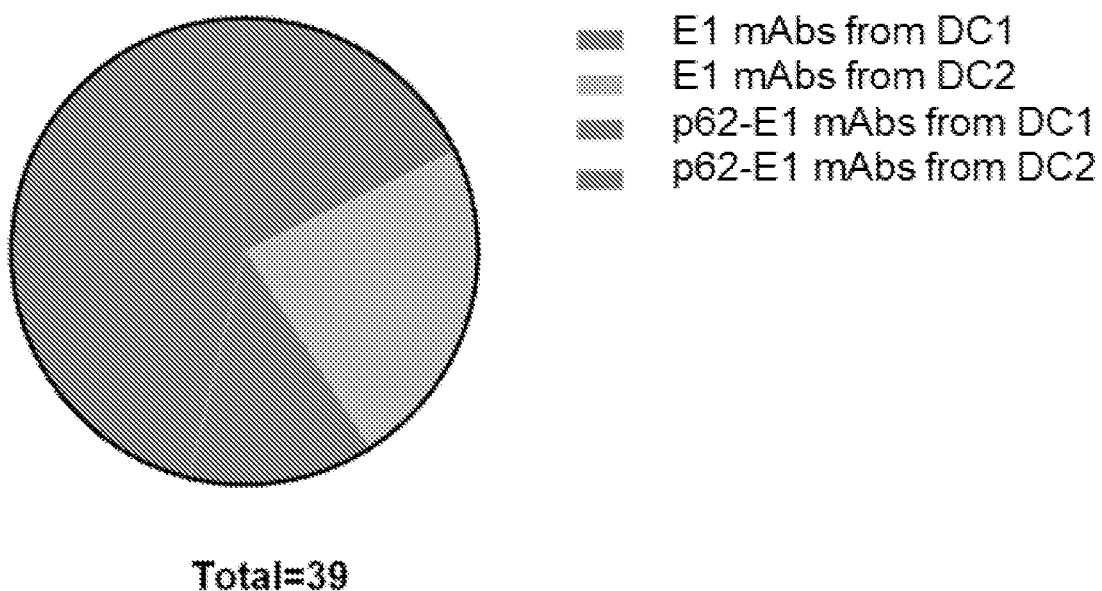
FIG. 4 shows breakdown of binding for 39 of the human CHIKV mAbs (DC2.429 did not bind to either protein).

A previous study described the identification of human CHIKV mAbs by a different mAb isolation method (human hybridoma technology). All of these previously reported mAbs were found by mutational studies to bind the E2 subunit. To determine the location of epitopes for our novel human CHIKV mAbs, immunoprecipitation studies were performed (Table 2).

previously been shown to afford protective efficacy in a mouse model. Epitope binning experiments indicate that the human E1-specific mAbs that were isolated do not compete with CHK-166 suggesting an entirely novel epitope (not shown). A summary of the breakdown for binding to p62-E1 or E1 by mAbs obtained from patients DC1 and DC2 is shown in FIG. 4.

Example 2

Materials and Methods (for Example 3)

CHIKV p62-E1 and E1' production. The CHIKV-115 p62-E1 construct was a gift from Dr. Felix Rey (Institut Pasteur), and the recombinant protein was purified from S2 cells as previously described (Voss J E, et al. *Nature*. 2010; 468(7324):709-12). The construct contained the p62 and E1 ectodomains joined by a glycine-serine linker with a double strep-tag at the C-terminus (IBA Lifesciences). The p62 furin cleavage site (between E2 and E3) was mutated to prevent furin cleavage (Voss J E, et al. *Nature*. 2010; 468(7324):709-12). E1' was expressed in S2 cells and purified as above and as previously described (Sanchez-San Martin C, et al. *Journal of virology*. 2013; 87(13):7680-7).

Viruses. The Chikungunya 181/25 virus was obtained from Dr. Robert B. Tesh (University of Texas Medical Branch, Galveston, TX). The Mayaro Guyane virus (NR-49911) was obtained through BEI Resources, NIAID, NIH,

TABLE 2

Summary of immunoprecipitation (IP) and E1 or p62-E1 ELISA results.

| E1-specific | | | | p62-E1 specific (likely E2) | | |
|---|---|---|---|---|---|---|
| mAb | IP | E1 ELISA | p62-E1 ELISA | mAb | IP | p62-E1 ELISA |
| DC1.7 | E1 | ++ | + | DC1.33 | No IP | ++ |
| DC1.9 | E1 | ND | ++ | DC1.43 | E2 + p62 | ++ |
| DC1.55 | No IP | ++ | ++ | DC1.55 | E2 + p62 | ++ |
| DC1.56 | E1 | ++ | ++ | DC1.159 | E1, E2, p62 | ND |
| DC1.353 | E1 | ND | ND | DC1.364 | E1, E2, p62 | ND |
| DC1.355 | E1 | ND | ND | DC2.1 | E2 + p62 | ++ |
| DC1.380 | E1 | ND | ND | DC2.3 | E1, E2, p62 | ++ |
| DC2.23 | No IP | ND | + | DC2.12 | E2 + p62 | ++ |
| DC2.74 | E1 | ++ | ++ | DC2.80 | ND | ++ |
| DC2.82 | E1 | ++ | ++ | DC2.95 | ND | + |
| DC2.112 | E1 | ++ | ++ | DC2.118 | ND | + |
| DC2.131 | E1 | ND | ++ | DC2.148 | No IP | ++ |
| DC2.134 | E1 | ND | + | DC2.159 | E1, E2, p62 | ++ |
| DC2.284 | E1 | ++ | ++ | DC2.271B | E1, E2 | ++ |
| DC2.315 | E1 | ND | ++ | DC2.422 | ND | + |
| | | | | DC2.432 | E2 + p62 | ++ |
| | | | | DC2.446 | E2 + p62 | ND |
| | | | | DC2.502 | No IP | ++ |
| | | | | DC2.507 | No IP | ++ |
| | | | | DC2.541 | No IP | ++ |
| | | | | DC2.547 | E1, E2, p62 | ++ |
| | | | | DC2.572 | No IP | ++ |
| | | | | DC2.580 | No IP | ++ |

++ Strong binding
+ Moderate binding
ND not determined
Immunoprecipitation data obtained by Dr. Rebecca Brown.

While many of the mAbs immunoprecipitated E2 as well as p62, a number of mAbs appeared specific to E1, a previously undescribed target for the human antibody response. Binding to E1 was confirmed in these cases by ELISA and BLI studies with recombinantly expressed E1 subunit (lacking E2) (Table 2). While human mAbs against E1 have not previously been described, mouse mAbs against E1 have been described, including CHK-166 which has as part of the WRCEVA program. The Chikugunya 181/25 and Mayaro Guyane viruses were propagated and titered on BHK-21 cells.

Study subjects and sample collection. To study naturally acquired antibodies to CHIKV, healthy adult patients were recruited who had a history of symptomatic CHIKV infection. Patients were identified either through the Montefiore Medical Center Microbiology laboratory with a positive CHIKV serology or from the community with a self-reported diagnosis of CHIKV. After informed consent, details of their CHIKV illness was recorded and blood samples were collected. The study protocol was approved by the Institutional Review Board of the Albert Einstein College of Medicine (protocol IRB #2016-6137). CHIKV immune status was confirmed by serum ELISA.

Forty mL of whole blood was collected from patients using K2EDTA blood collection tubes (BD Vacutainer, Franklin Lakes, New Jersey). ~15 mls of plasma was separated, aliquoted and frozen. To isolate PBMCs using a density gradient separation, blood was mixed with 1:1 ratio of Hanks Balanced Salt Solution (HBSS) and layered over equal volume of Ficoll-Paque™ (GE: 17-5442-02) and centrifuged per the manufacturer's protocol. The PBMC layer was collected, washed with HBSS, centrifuged at 400 g, and frozen at $4 \times 10^6$ cells/m 467 L in heat inactivated FBS (Gibco) and 5% DMSO and then stored in liquid nitrogen.

Isolation of CHIKV mAbs by single B cell sorting. Approximately $8 \times 10^6$ cells/mL were stained using anti-human CD8(PE-Cy7), CD3(PE-Cy7), CD14(PE-Cy7), CD20 (PB), CD27 (APC), IgG (FITC), and biotinylated p62-E1 hybrid protein. p62-E1 was biotinylated using EZ-Link™ Sulfo-NHS-LC-Biotin (Life Technologies) followed by buffer exchange using Amicon® 30,000 MW cut-off spin columns (Millipore) into PBS pH 7.4. Biotinylated p62-E1 was used at a concentration of 100 nM and detected using streptavidin-PE (Invitrogen) at 1:500 dilution. Single B cells were sorted into 8-strip PCR tubes (USA scientific) containing 4 μl/well of lysis buffer [RNasin® Ribonuclease Inhibitors (Promega) 2 U/well, 0.005 M DTT (Invitrogen), PBS, nuclease free $H_2O$] using FACS Aria high-speed cell sorter flow cytometer (Becton Dickinson). Tubes were frozen on dry ice and stored at stored at $-80°$ C.

IgH and IgK variable gene transcripts were amplified using an RT-PCR and two-step nested PCR strategy. A primer set specific to IgG leader sequences, constant regions and V-region heavy/light chain families was used for antibody variable region recovery (Tiller T, et al. *J Immunol Methods*. 2008; 329(1-2):112-24). The second round PCR primer set had 35 base pairs of 5' and 3' homology to the heavy and light chain expression vectors pMAZ-IgH and pMAZ-IgL (Mazor Y, et al. *J Immunol Methods*. 2007; 321(1-2):41-59). Gibson cloning reactions were performed using 100 ng of purified PCR and 50 ng of cut heavy and light chain plasmids containing IgG1 constant-region framework. Chemical transformations were done using 10 μl DH5-α (New England BioLabs) and 1 μl of Gibson reaction mix. Individual colonies were picked and sequenced for downstream analysis and characterization.

Expression and purification of mAbs and Fab fragments. Antibodies used for binding and neutralization screens were expressed in FreeStyle™ 293-F cells by transient co-transfection of 1:1 ratio of heavy and light chain plasmids (ThermoFisher). HEK293 cells were passaged to $5.0 \times 10^5$ cells per ml. A transfection mixture of DNA diluted in PBS (0.67 μg total plasmid DNA per ml of culture) was prepared on day of transfection. Addition of transfection agent Polyethylieneimine "MAX" (PEI) (Polysciences Inc) at a DNA-to-PEI ratio of 1:3 to diluted DNA and incubated at room temperature for 15 min. The transfection mixture was then added to culture via drop-wise addition. At six days post-transfection, cultures were harvested by centrifugation at 4,000 g× for 15 min, and incubated with Protein A agarose (Thermo Scientific) at $4°$ C. for 90 min. Protein A resin containing bound mAbs was then passed through a protein purification column (BioRad) and washed twice with Pierce™ Gentle Ag/Ab Binding Buffer, pH 8.0 (Thermo Scientific). Antibodies were eluted Pierce™ Gentle Ag/Ab Elution Buffer, pH 6.6 (Thermo Scientific) and desalted into 150 mM Hepes, 200 mM NaCl, pH 7.4 using PD-10 Desalting Columns (GE Healthcare). Fab fragments were generating by digestion of IgG1 using Pierce™ Fab preparation kit (Thermo Scientific) as per manufacturers protocol. Briefly IgG was incubated with papain for 4 h at $37°$ C. and the Fab and the Fc mixtures were passed over Protein A agarose to remove Fc fragments and undigested Fc. Fab fraction was then buffer exchanged into 150 mM Hepes, 200 mM NaCl, pH 7.4.

Immunoprecipitation of viral proteins from infected cells. BHK-21 cells were cultured at $37°$ C. in complete media (Dulbecco's modified Eagle's medium (DMEM) with 5% fetal bovine serum, 10% tryptose phosphate broth, 100 U penicillin/mL, and 100 μg streptomycin/ml) and seeded 24 h prior to infection. Cells were infected with CHIKV 181/25 at 10 PFU/cell for 4 h, washed three times, and placed back into complete media. At 8 h post-infection, cells were washed once with minimal essential media (MEM) lacking cysteine and methionine and then labeled with 50 μCi/mL of [35S]methionine/cysteine for 2 h. The cells were washed three times with ice-cold PBS before solubilizing on ice with lysis buffer (50 mM Tris-Cl pH 7.4, 100 mM NaCl, 1% Triton-x-100, 1 mM EDTA, and one complete protease inhibitor tablet/10 ml (Roche)). Cell debris was removed by centrifugation at 20,000 g $4°$ C. 10 min. The soluble lysate was aliquoted and frozen at $-80°$ C. Approximately 1 μg of each candidate antibody was incubated with an individual lysate aliquot for 1 h in the presence of 0.1% SDS and the immunoprecipitate was retrieved with Protein A agarose (Pierce) for 3 h at $4°$ C. The beads were washed four times with RIPA buffer and once with PBS. The samples were then boiled in SDS sample buffer supplemented with dithiothreitol, alkylated with iodoacetaminde at $37°$ C., and analyzed by SDS-PAGE and fluorography.

Biolayer interferometry (BLI). IgG binding to p62-E1 and E1' was determined by BLI measurements using OctetRed™ system (ForteBio, Pall LLC). For single-phase binding experiments, global data fitting to a 1:1 binding model was used to estimate values for the $k_{on}$ (association rate constant), $k_{off}$ (dissociation rate constant), and $K_D$ (equilibrium dissociation constant). IgGs were immobilized on anti-human Fc capture sensors (Pall Life sciences). Data were analyzed using ForteBio Data Analysis Software 9. For double phase binning experiments, biotinylated p62-E1 was first bound to streptavidin-coated sensor, and then the first mAb bound to saturation. The sensor was then transferred to a second well containing equimolar amounts of the first and competing mAbs.

p62-E1 ELISA. Initial antibody binding screening against p62-E1 was performed by coating 250 ng/well diluted in PBS in half-area 96-well high binding plates (Costar). Wells were blocked with 3% BSA at $37°$ C. for 2 h. Antibody dilutions at 300 nM and 30 nM were performed in PB-T (PBS pH 7.4, 0.5% BSA, 0.05% Tween) and incubated 1 h at $37°$ C. After antibody binding plates were washed with PBS-T (PBS pH 7.4, 0.005% Tween-20) five times. Horseradish peroxidase conjugated-(HRP)-Protein A (life technologies) diluted at 1:2000 in PB-T was added in for 1 h at $37°$ C. Plates were washed five times with PBS-T and developed using TMB (Thermo Fischer). Optical density at 450 nm was read on Synergy H4 Hybrid reader (BioTek). Procedures were similar for full (8-point) ELISA curves and serum ELISA, except that initial stock of mAb or serum were serially diluted.

Focus reduction neutralization test with CHIKV 181/25. Serial dilution of mAbs were incubated with 100-150 FFU of CHIKV 181-25 vaccine strain for 1 h at 37° C. Antibody-virus complexes were then added to Vero cell monolayers in 96-well plates. Infection proceeded for 90 min at 37° C. and cells were then overlaid with 0.5% carboxylmethylcellulose in Modified Eagle Media (MEM), supplemented with heat inactivated 2% FBS and 10 mM Hepes pH 7.4. Plates were fixed 16 h post-infection with 1% PFA diluted in PBS. After fixation, plates were incubated with 250 ng/mL of 5G11 (USAMRIID) and horseradish peroxidase (HRP)-conjugated goat anti-mouse IgG in PBS supplemented with 0.1% Saponin and 0.1% BSA. Foci were then visualized using TrueBlue Peroxidase substrate (KPL). Developed foci where quantified on ImmunoSpot® S6 macroanalyzer (Cellular Technologies Ltd.). Infection in wells containing mAb was calculated relative to wells containing CHIKV 181/25 alone. Non-linear regression analysis was performed using Prism 7 software (GraphPad Software, La Jolla CA).

CHIKV-AF15561 Microneutralization Assay. Serial dilutions of mAbs were prepared in infection media (2% FBS MEM) and incubated with CHIKV-AF15561 virus for 1 hr at 37° C. Vero E6 cells were then exposed to antibody/virus inoculum at an MOI of 1.5 plaque-forming units (PFUs)/cell for 1 h at 37° C. before it was removed and replaced with fresh culture media (5% FBS MEM). At 24 h post-infection, cells were fixed in 10% formalin for 24 h prior to removal from containment. Cells were permeabilized with 0.2% Triton™ X-100 (Sigma-Aldrich) for 10 min, blocked and incubated with 2 μg/ml CHIKV-specific 5G11 (USAMRIID) for 1 h at RT. Cells were washed with PBS, incubated with anti-mouse IgG 559 conjugated to Alexa488 (Sigma-Aldrich), washed again and counterstained with Hoechst stain (Invitrogen). Infection was quantitated by automated fluorescence microscopy, as described (46).

Focus Reduction Neutralization Test with CHIKV LR2006 OPY1. Focus reduction neutralization tests (FRNT) were performed as previously described (26). Briefly, serial dilutions of mAb were incubated with 100 FFU of CHIKV LR2006_OPY1 for 1 h at 37° C. MAb-virus complexes were added to Vero cells in 96-well plates. After 1 h, cells were overlaid with 1% (w/v) methylcellulose in Modified Eagle Media (MEM) supplemented with 4% FBS. Plates were fixed with 1% PFA in PBS 18 h later. Plates were incubated sequentially with 500 ng/ml of mouse anti-CHK-11 (26) and horseradish peroxidase (HRP)-conjugated goat anti-mouse IgG in PBS supplemented with 0.1% saponin and 0.1% BSA. CHIKV LR2006_OPY1 foci were visualized using TrueBlue peroxidase substrate (KPL) and quantitated on an ImmunoSpot macroanalyzer (Cellular Technologies Ltd). The IC50 was calculated using non-linear regression analysis constraining the bottom to 0 and top to 100 after comparison to wells infected with CHIKV-LR in the absence of antibody.

Generation of recombinant vesicular stomatitis virus (rVSVs) bearing CHIKV glycoproteins (rVSV-CHIKV). Human codon optimized sequence of the CHIKV E3-E2-6K-E1 protein from the African prototype S27 strain (UniProt Accession no. Q8JUX5) was synthesized (Epoch Biosciences) and cloned in the VSV antigenome plasmid to replace its native glycoprotein G as previously reported (Chattopadhyay A, et al. *Journal of virology*. 2013; 87(1): 395-402). The VSV genome also carries an enhanced green fluorescent proteion (eGFP) marker to score infected cells. A plasmid-based rescue system was used to generate rVSV-CHIKV (Whelan S P, et al. *Proceedings of the National Academy of Sciences of the United States of America*. 1995; 92(18):8388-92.). Rescued virus was grown on Vero cells and Sanger sequencing was used to confirm the glycoprotein gene sequence.

rVSV-CHIKV neutralization assay and escape mutant generation. For antibody neutralization experiments, pre-titrated amounts of rVSV-CHIKV particles were incubated with increasing concentrations of test antibody at 37° C. for 1 h prior to addition to cell monolayers in 96-well plates. After 1 h of infection, 20 mM of NH4Cl was added to halt subsequent rounds of infection. The infection rate of rVSV-CHIKV was measured by automated enumeration of eGFP+ cells (infectious units) using a Cell Insight CX5 imager (Thermo Fisher) at 16 h post-infection.

Escape mutant selections were performed by serial passage of rVSV-CHIKV particles in the presence of test mAb. Serial 10-fold dilutions of virus were preincubated with a concentration of mAb corresponding to the IC90 value derived from neutralization assays, and then added to 70% confluent monolayers of Vero cells in 12-well plates, in duplicate. Infection was allowed to proceed to completion (>90% cell death by eye), and supernatants were harvested from the infected wells that received the highest dilution (i.e., the least amount) of viral inoculum.

Following three to four subsequent passages under mAb selection with virus-containing supernatants as above, supernatants were tested for viral neutralization escape. If viral populations demonstrated resistance to test antibody, individual viral clones were plaque-purified on Vero cells, and amplified for sequencing. Viral RNA isolation was performed on each viral clone using Viral RNA Kit™ (Zymo research) and cDNA synthesis was performed. Glycoprotein gene was amplified by using primers flanking the upstream and downstream of CHIKV glycoprotein and subsequently sequenced.

In vivo challenge with CHIKV LR2006_OPY1. This study was carried out in accordance with the recommendations in the Guide for the Care and Use of Laboratory Animals of the National Institutes of Health. The protocols were approved by the Institutional Animal Care and Use Committee at the Washington University School of Medicine. Footpad injections were performed under anesthesia that was induced and maintained with ketamine hydrochloride and xylazine, and all efforts were made to minimize suffering. MAbs (100 μg in PBS, 6 mg/kg) were administered to 3-week-old male C57BL/6 mice treated with 0.25 mg of an anti-Ifnar1 blocking mouse Mab (MAR1-5A3) (40) via intraperiontal injection 1 day prior to CHIKV-LR inoculation. Mice were inoculated subcutaneously in the footpad with $10^3$ FFU of CHIKV-LR diluted in PBS and survival followed for 21 days.

Pharmacokinetic studies in uninfected mice. Eight to ten week-old ICR mice (n=3) received 100 μg/mouse of antibody intravenously on Day 0. Blood draws were obtained on Day 3 and then Day 6. Serum collected was then evaluated by ELISA to detect human IgG. Mouse serum samples were tested using a commercial ELISA (Abcam cat No. ab100547) for quantifying human IgG. Data was analyzed and graphed using GraphPad Prism v6.0.

Negative stain electron microscopy (nsEM). 800 pmol of purified DC2.271B Fab was mixed with 100 pmol purified p62/E1 and incubated overnight at 4° C. The resulting complex was recovered by size-exclusion chromatography using an S200i column (GE Healthcare, IL) mounted on a fast protein liquid phase system (Äkta pure; GE Healthcare, IL). Pure antigen alone or purified Fab-antigen complex were deposited on plasma-cleaned (Gatan Solarus 950 Plasma system, CA) carbon-coated 400 mesh copper EM grids (Protochips Inc, NC) and embedded in 2% w/V uranyl formate. The resulting p62/E1 nsEM specimen was introduced into an FEI Tecnai G2 F20 electron microscope mounted with a Tietz TemCamCF416 CMOS camera. Data was collected under low-dose conditions at 200 kV, 60,000× nominal magnification and 1 um nominal underfocus. The resulting data pixel size was 1.79 Å. Similarly, the p62-E1/DC2.271B Fab nsEM specimen was introduced into an FEI Tecnai T12 electron microscope mounted with a Tietz TemCamCF-CMOS camera. Data were collected under low-627 dose conditions at 120 kV, 60,000× nominal magnification and 1 um nominal underfocus. The resulting data pixel size was 2.54 Å.

Contrast transfer functions for each micrograph were modeled using GCTF (Zhang K. *Journal of structural biology.* 2016; 193(1):1-12). Both data sets were Fourier cropped by a factor of 2. Identification of particles in the micrographs was performed with a difference-of-Gaussian approach (Voss N R, et al. *Journal of structural biology.* 2009; 166(2):205-13). Particle images were extracted and reference-free 2D class averaging was performed correcting the data for microscope contrast transfer functions by phase flipping (Relion 3.0) (Scheres S H. *Journal of structural biology.* 2012; 180(3):519-30). Particles contributing to meaningful class averages were selected for further processing. A simulated density map (PDB ID 3N40) (Voss J E, et al. *Nature.* 2010; 468(7324):709-12) was low-pass filtered to 40 Å and used as reference for iterative Euler angle recovery and 3D object reconstruction of the data (Relion 3.0). Nominal FSC 0.5 resolutions of the resulting density maps were 16 Å (p62/E1) and 16 Å (p62-E1/DC2.271B Fab).

Example 3

Figure 5A:
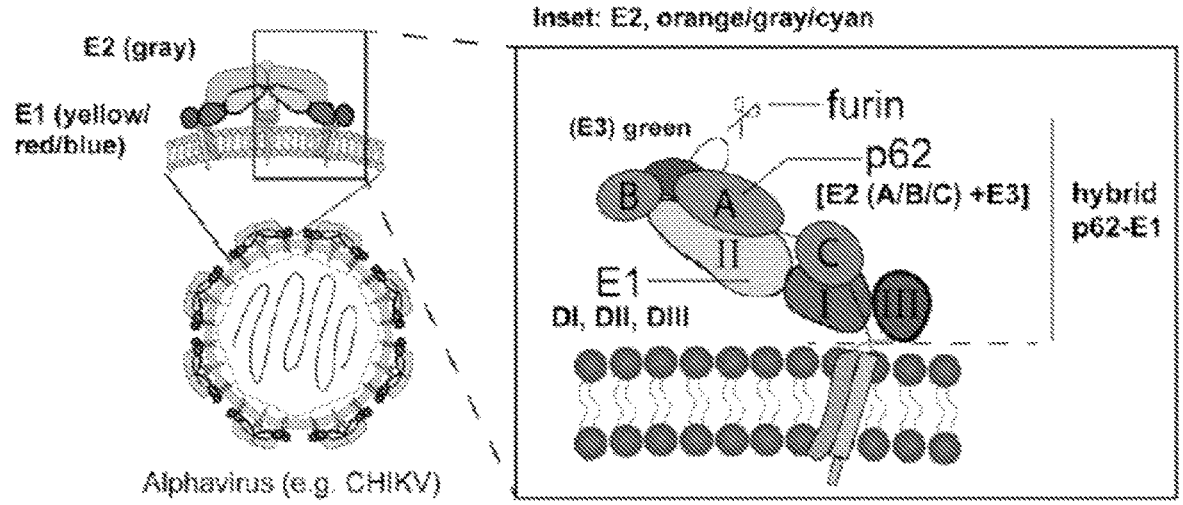
FIG. 5A shows the CHIKV glycoprotein spike consists of three copies each of E1 and E2 each in the prefusion form (modified from (Sanchez-San Martin C, et al. *Trends Microbiol.* 2009; 17(11):514-21)). The inset shows the arrangement of E1 (comprised of DI, DII, and DIII) and E2 (comprised of domains A, B, and C). The location of E3 and the furin cleavage site are also shown. The hybrid protein "p62-E1", consisting of p62 ectodomain linked to the E1 ectodomain by a polypeptide linker, was used for binding and sorting experiments.
Figure 5B:
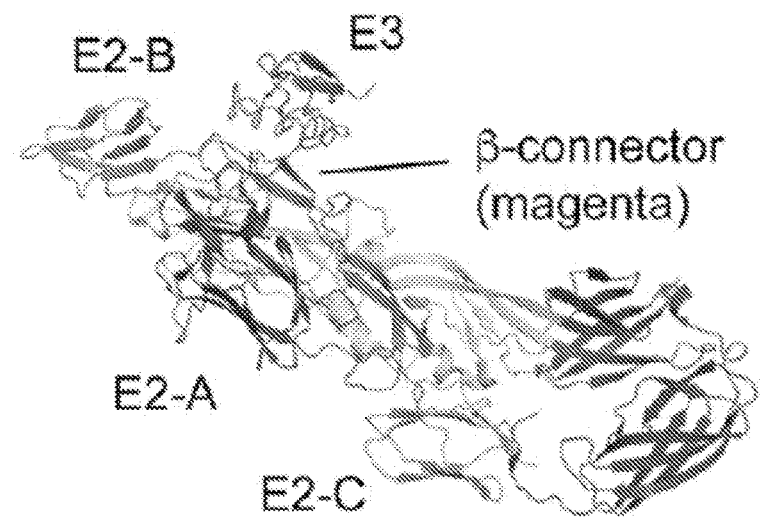
FIG. 5B show X-ray crystallographic structure of CHIKV p62-E1 (PDB ID: 3N40) (Sanchez-San Martin C, et al. *Trends Microbiol.* 2009; 17(11):514-21) with domains colored and labeled according to panel FIG. 5A, and with the (β-connector colored magenta (identified at end of black line).
Figure 5C:
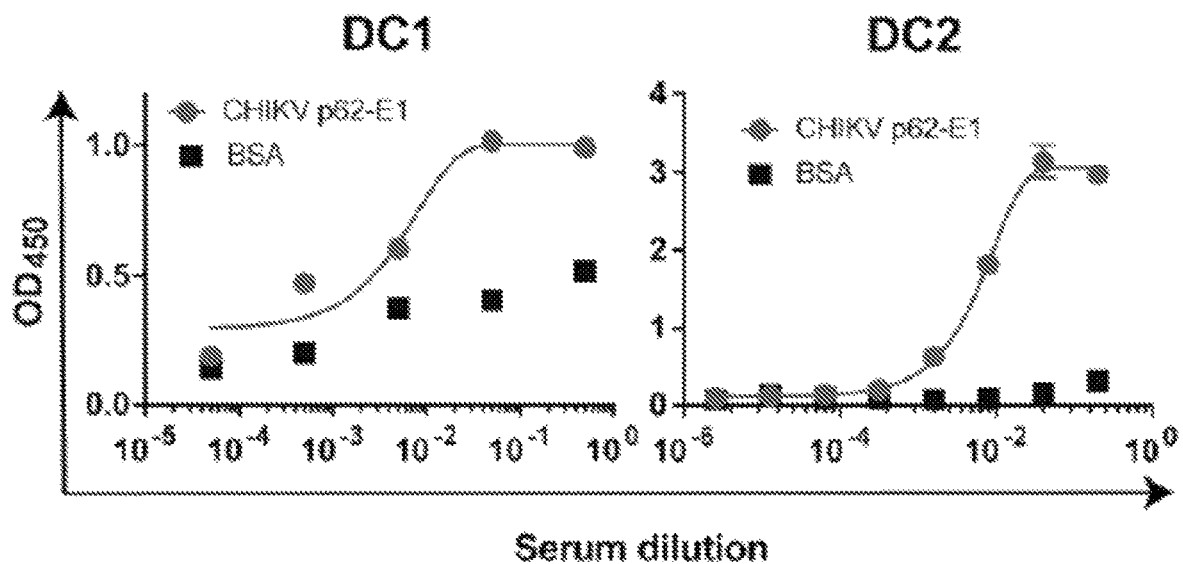
FIG. 5C depicts reactivity of plasma from convalescent patients DC1 and DC2 toward CHIKV p62-E1 in comparison to negative control wells (3% BSA). A representative dataset is shown for the DC2 ELISA from two experiments, each performed in triplicate (points represent mean±SD). Sera for DC1 were limited and thus data presented here are from a single experiment with no replicates.

Single B-cell cloning and screening of CHIKV human mAbs. As in Example 1, plasma from two convalescent donors (DC1 and DC2) was tested for their capacity to bind recombinant CHIKV p62-E1 protein (FIGS. 5A and 5B). Both donors were exposed to CHIKV in the Dominican Republic (Dominican Republic, Chikungunya) within two years of sample collection and experienced fever, joint pain, and in the case of DC2, persistent arthritis. In both cases, serum reactivity against p62-E1 was observed relative to wells coated with BSA, indicating the presence of circulating CHIKV130 specific antibodies (FIG. 5C).

Peripheral blood mononuclear cells (PBMCs) from both patients were isolated and sorted for individual p62-E1-reactive B cells by fluorescence activated cell sorting (FACS). P62-E1 was chosen as the sorting antigen because it can be efficiently expressed in and purified from *Drosophila* S2 cells. Furthermore, previous isolation of human CHIKV antibodies via hybridoma methods resulted in the isolation of numerous mAbs that bind in the β-connector region of E2 (Smith S A, et al. *Cell host & microbe.* 2015; 18(1):86-95), part of which lies underneath E3 in p62-E1. Thus, it was reasoned that use of p62-E1 as a sorting antigen, in which parts of the β-connector were occluded by E3, might favor isolation of antibodies that target previously unrecognized epitopes of the glycoprotein. PBMCs were sorted for viability and size/granularity consistent with single lymphocytes. These populations were then negatively gated for T cells, macrophages, and other lymphocytes (CD3$^+$/CD8$^+$/CD14$^+$); followed by positive gating for CD20$^{hi/lo}$ CD27$^+$ IgG$^+$ p62-E1$^+$ B cells (FIGS. 5H-5K).

B cells that met these criteria were sorted into individual wells (generally less than 0.1% of PBMCs per sorting sample), lysed, and cDNA was generated and used for nested PCR with human-specific degenerate primers to recover variable domains of immunoglobulin heavy and light chains (Tiller T, et al. *J Immunol Methods.* 2008; 329(1-2):112-24). The κ light chains were focused on due to their high abundance in natural human antibody repertoires and generally favorable biochemical properties. The recovered variable domains were cloned and expressed as recombinant human IgG1 antibodies.

Figure 5D:
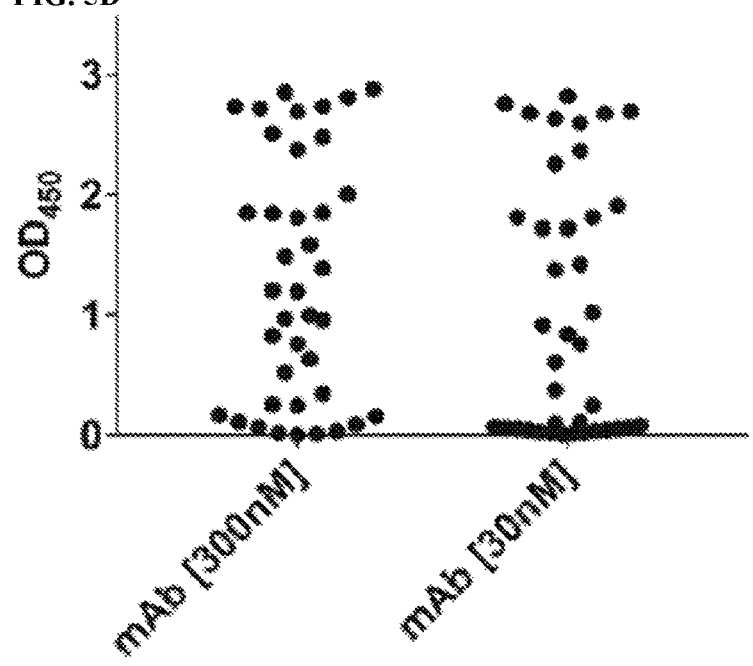
FIG. 5D shows Volcano plot of ELISA (OD450) for 46 of the isolated mAbs at 30 nM and 300 nM. Each data point represents the mean from 2 or more replicates. Distribution of IGHV families (FIG. 5E), CDR-H3 lengths (FIG. 5F), and IGKV families (FIG. 5G) for the mAbs.
Figure 5E:
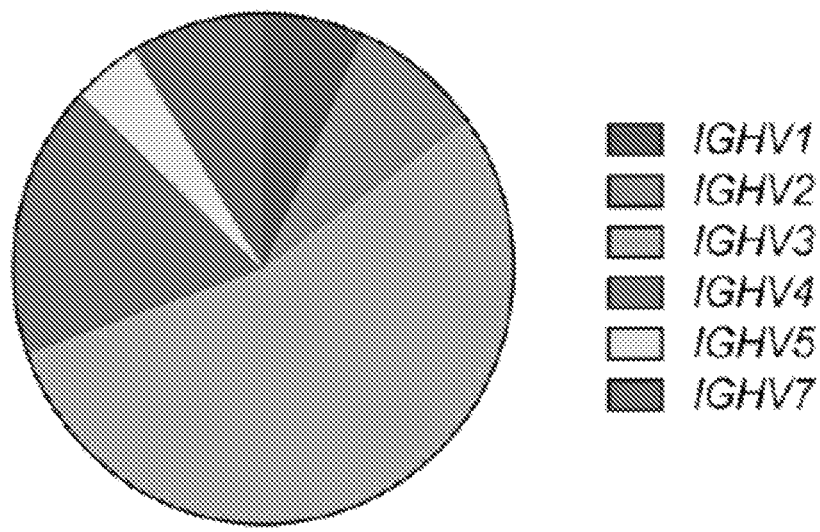
FIG. 5 contains eleven panels, FIGS. 5A-5K, showing Chikungunya virus Glycoprotein Architecture and Overview of Human Monoclonal Antibodies.
FIG. 5H-5K shows representative FACS sort of patient-derived PBMCs. Cells were filtered for size and granularity (FIG. 5H), then (in this case) CD3+/CD8+/CD14+ cells eliminated (FIG. 5I). The CD27+/CD20hi/IgG+/p62-E1+B cells (FIGS. 5J and 5K) were collected in individual wells. In some samples, both CD20hi/lo populations were carried forward.
Figure 5F:
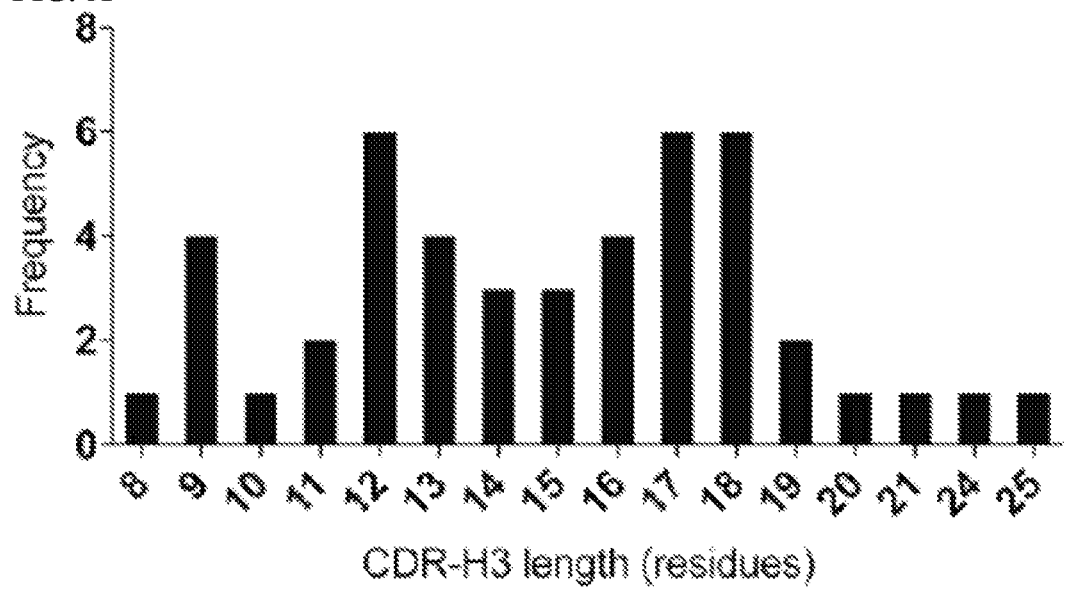
Figure 5G:
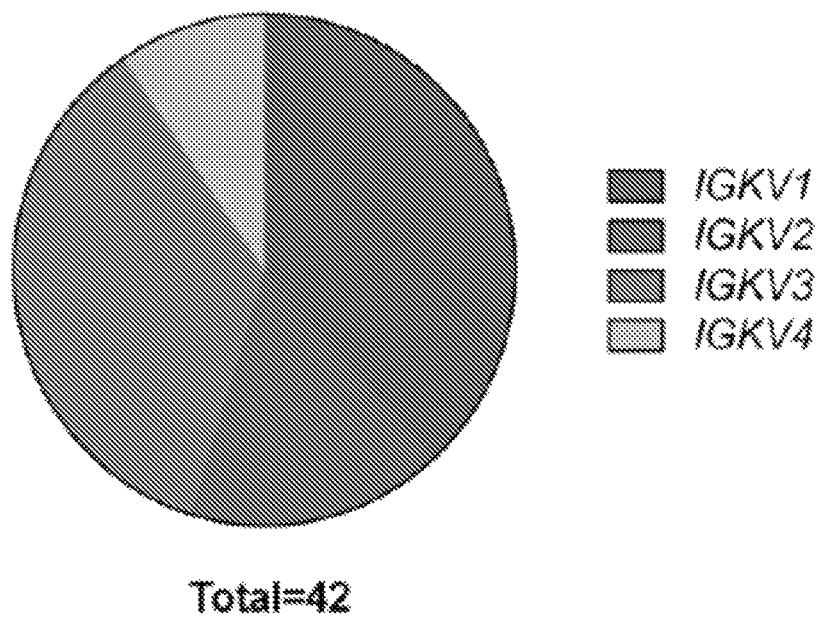
Figure 5H:
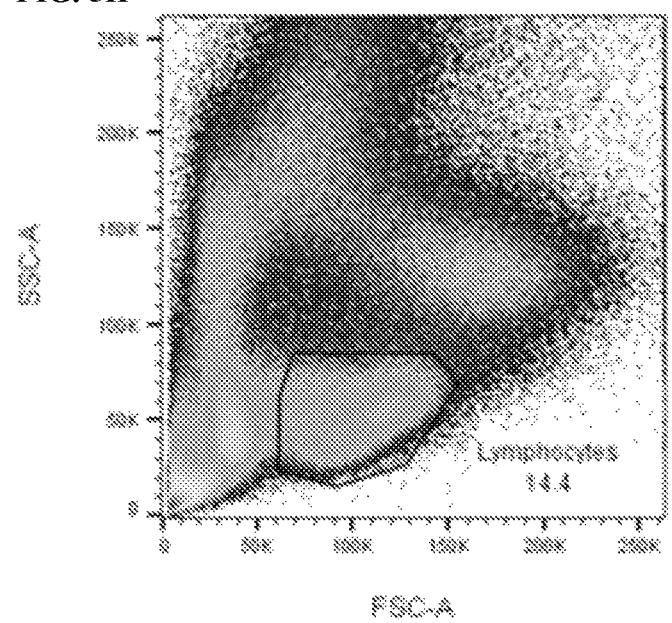
Figure 5I:
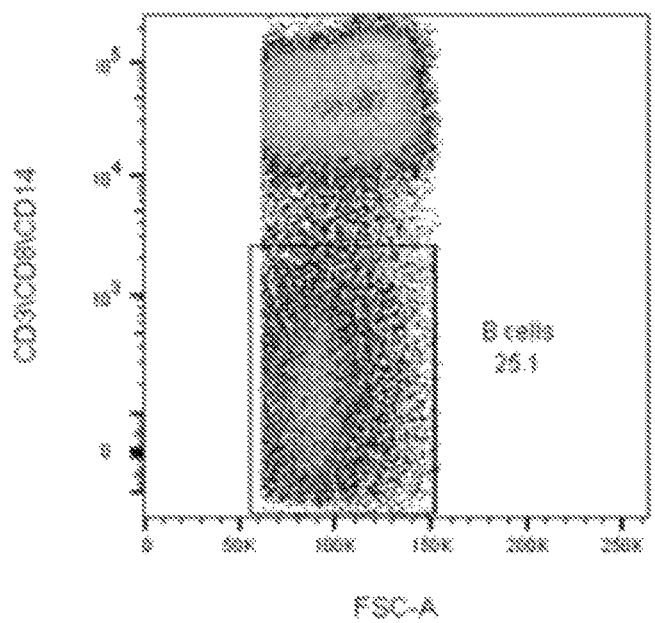
Figure 5J:
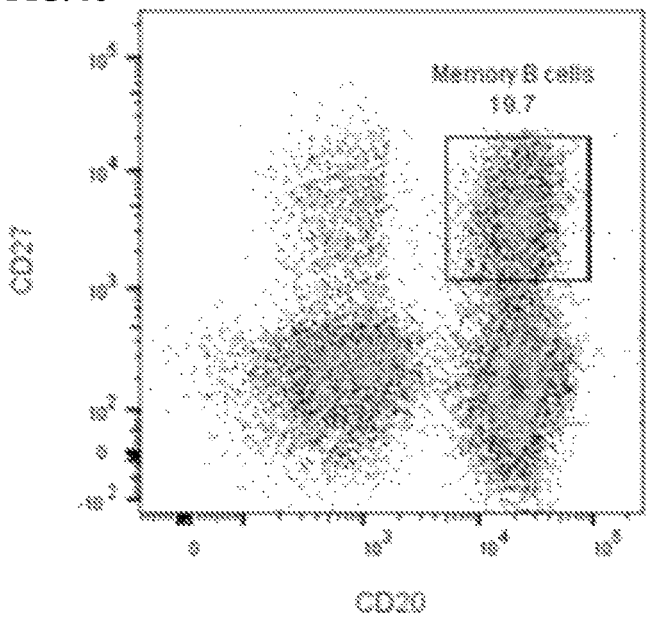
Figure 5K:
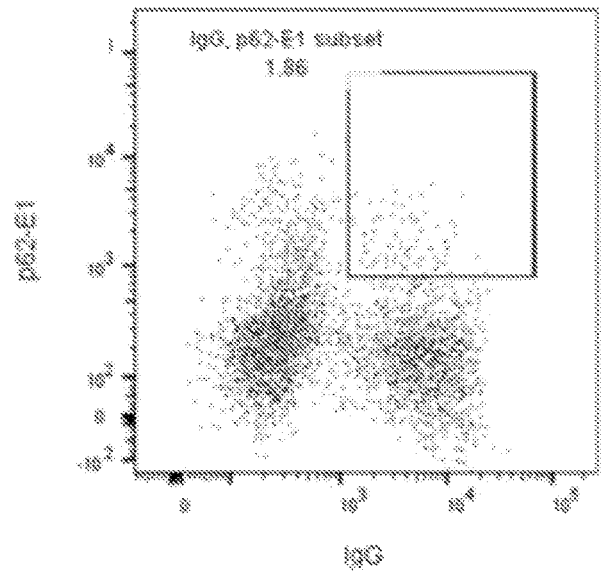

From 108 cloned human mAbs, the analysis was focused on 46 mAbs due to favorable functional and/or expression properties. All 46 of these mAbs were subjected to an ELISA against p62-E1 using 30 and 300 nM concentrations of mAb (FIG. 5D). The mAbs bound p62-E1 with a range of OD$_{450}$ values from 0 (non-binding) to 3 (high binding), but a number of mAbs exhibited strong reactivity (OD$_{450}$>1.5) even at the lower concentration (30 nM). The binding was specific as none of the mAbs showed any significant binding toward control wells coated with 3% BSA at 300 nM mAb concentration (data not shown). Sequence analysis revealed that the majority of the mAbs belonged to the IGHV3 family, consistent with the prevalence of this family in human repertoires; other IGHV families (Jose J, et al. *Future Microbiol.* 2009; 4(7):837-56, Sourisseau M, et al. *PLoS Pathog.* 2007; 3(6):e89, Morrison T E. *Journal of virology.* 2014; 88(20): 11644-7, Halstead S B. *Emerging infectious diseases.* 2015; 21(4):557-61, Tsetsarkin K A, et al. *PLoS Pathog.* 2007; 3(12):e201, Kraemer M U, et al. *Elife.* 2015; 4:e08347) comprised the remainder of the mAb population (FIG. 5E). The CDR-H3 lengths ranged from 8-25, with a bimodal distribution at 12 and 17-18 residues (FIG. 5F). The light chains were distributed among IGKV1-4 families, with the IGKV1 family representing almost half (16/42, four light chain sequences were shared by pairs of heavy chains, thus bringing the total to 42 distinct VK sequences) (FIG. 5G). The diversity of IGHV and IGKV families, as well as CDR-H3 lengths suggests a range of potential modes of interaction between mAbs and the CHIKV glycoprotein.

Figure 6A:
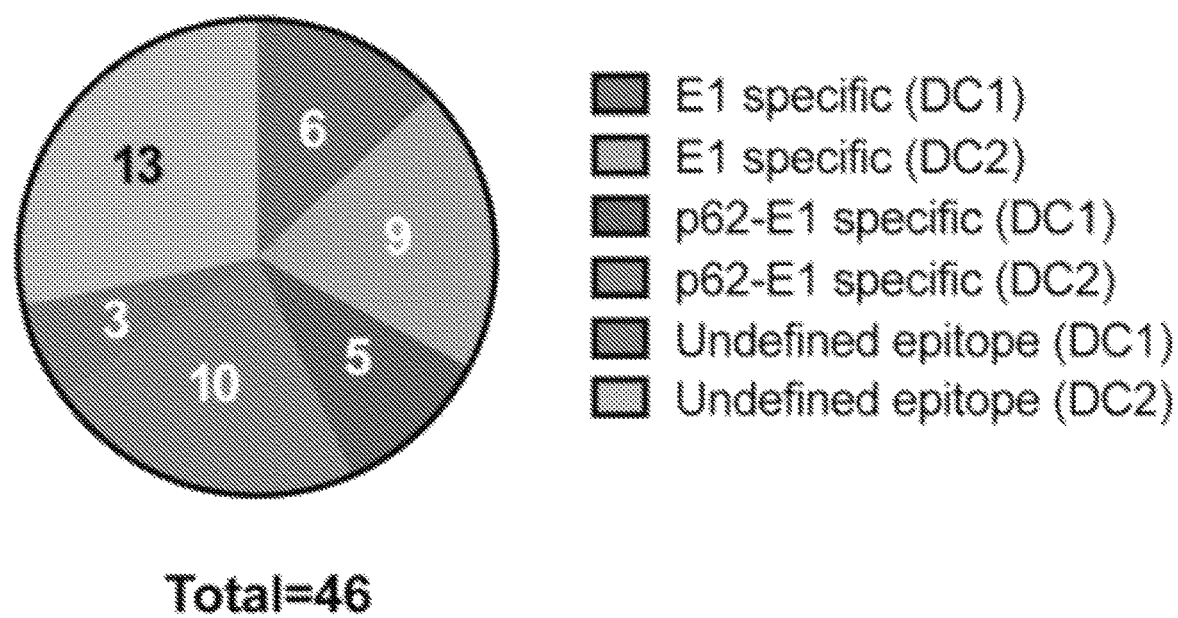
FIG. 6A shows distribution of specificities for mAbs isolated from DC1 and DC2, based on IP, ELISA and/or BLI studies. "p62-E1" specificity refers to mAbs that were confirmed to bind p62-E1 by ELISA and/or BLI, or that immunoprecipitated p62-E1 or E2. These mAbs likely have epitopes contained in E2 or shared epitopes across E1 and E2. "E1" specificity refers to mAbs that were confirmed to bind bacterially expressed E1' by ELISA and/or BLI.
Figure 6B:
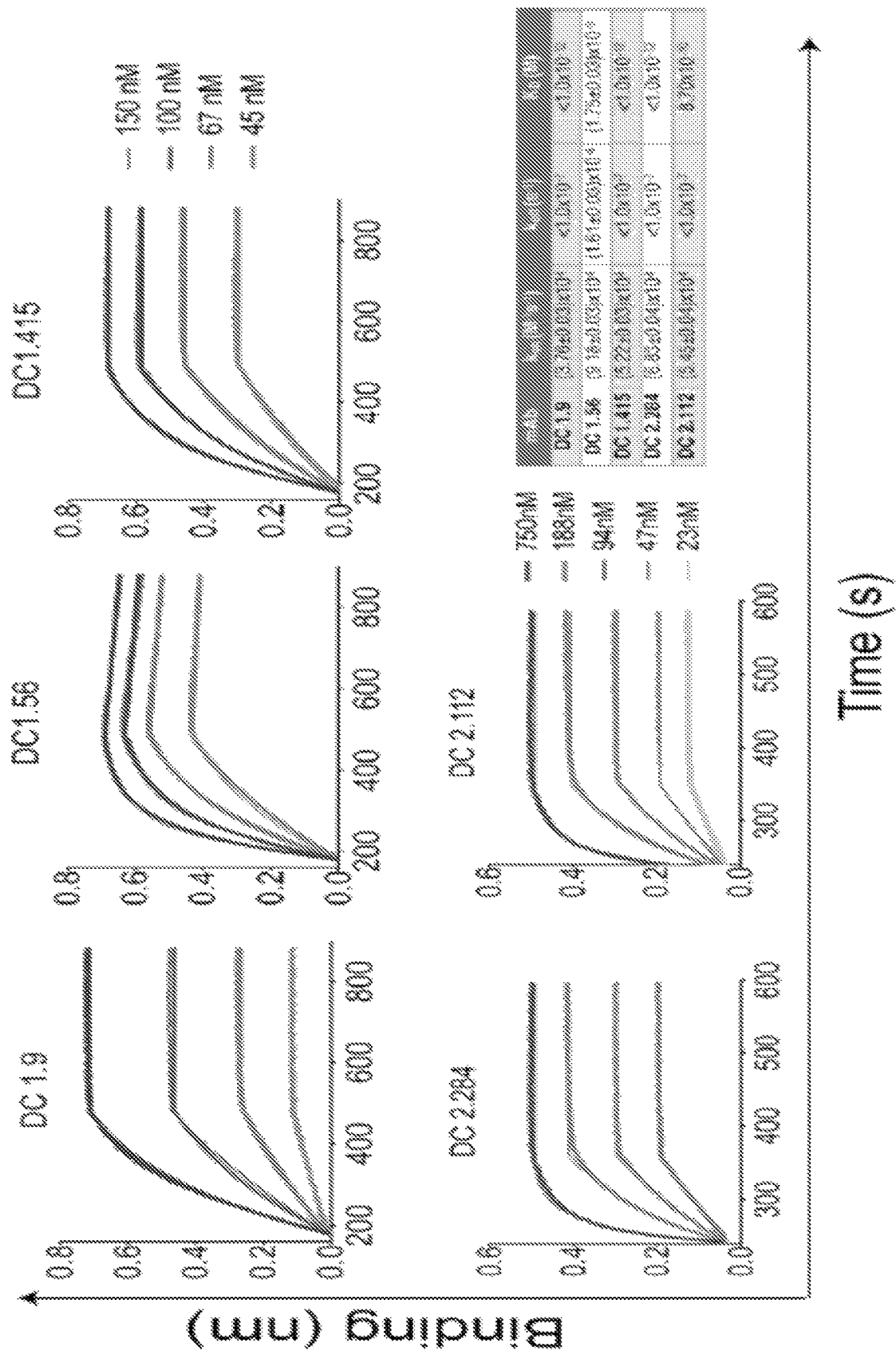
FIG. 6B shows binding of E1 mAbs to E1' by BLI. A representative dataset from two experiments is shown.
Figure 6C:
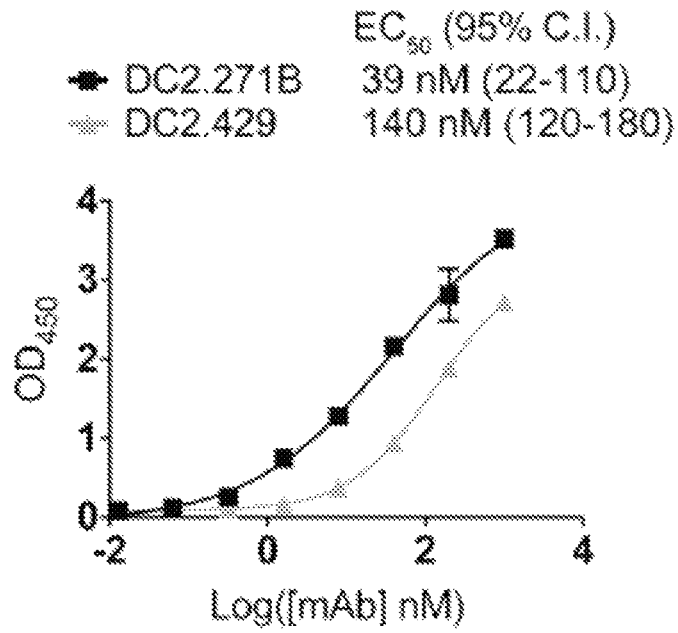
FIG. 6C shows full ELISA binding curves for DC2.271B and DC2.429 against p62-E1; a representative dataset 829 from two experiments each performed in triplicate is shown (points represent mean±SD).
Figure 6D:
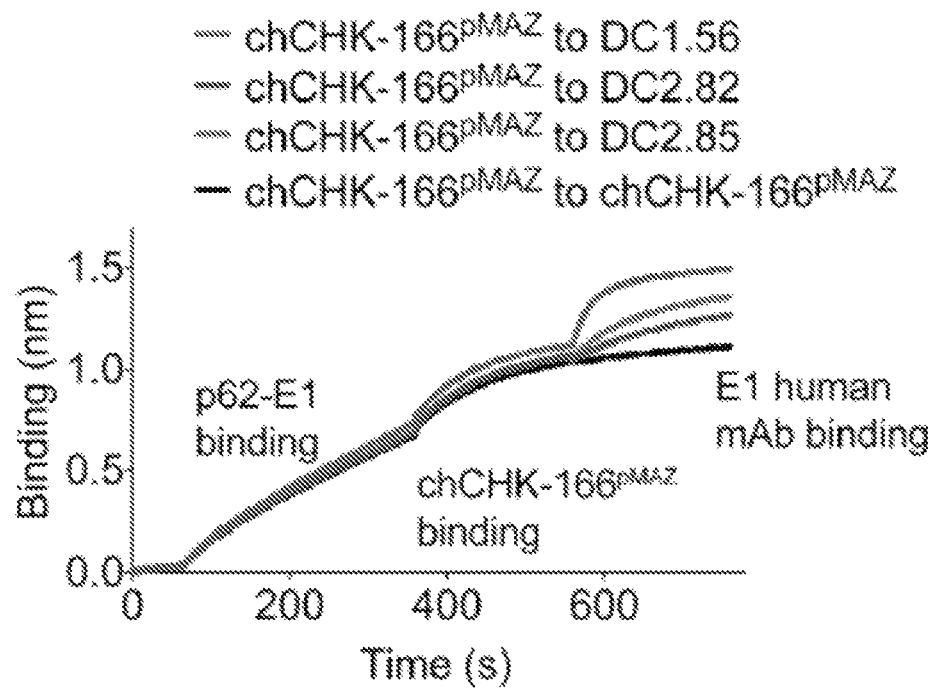
FIG. 6D shows two-phase binding by BLI of E1 mAbs DC1.56, DC2.82, and DC2.85 against E1 mAb chCHK-166pMAZ. In all cases, the human mAbs were able to engage p62-E1 simultaneously as CHK-166, regardless of order of addition, thus indicating that they do not share epitopes with CHK-166. A representative dataset from two experiments is shown.
Figure 6E:
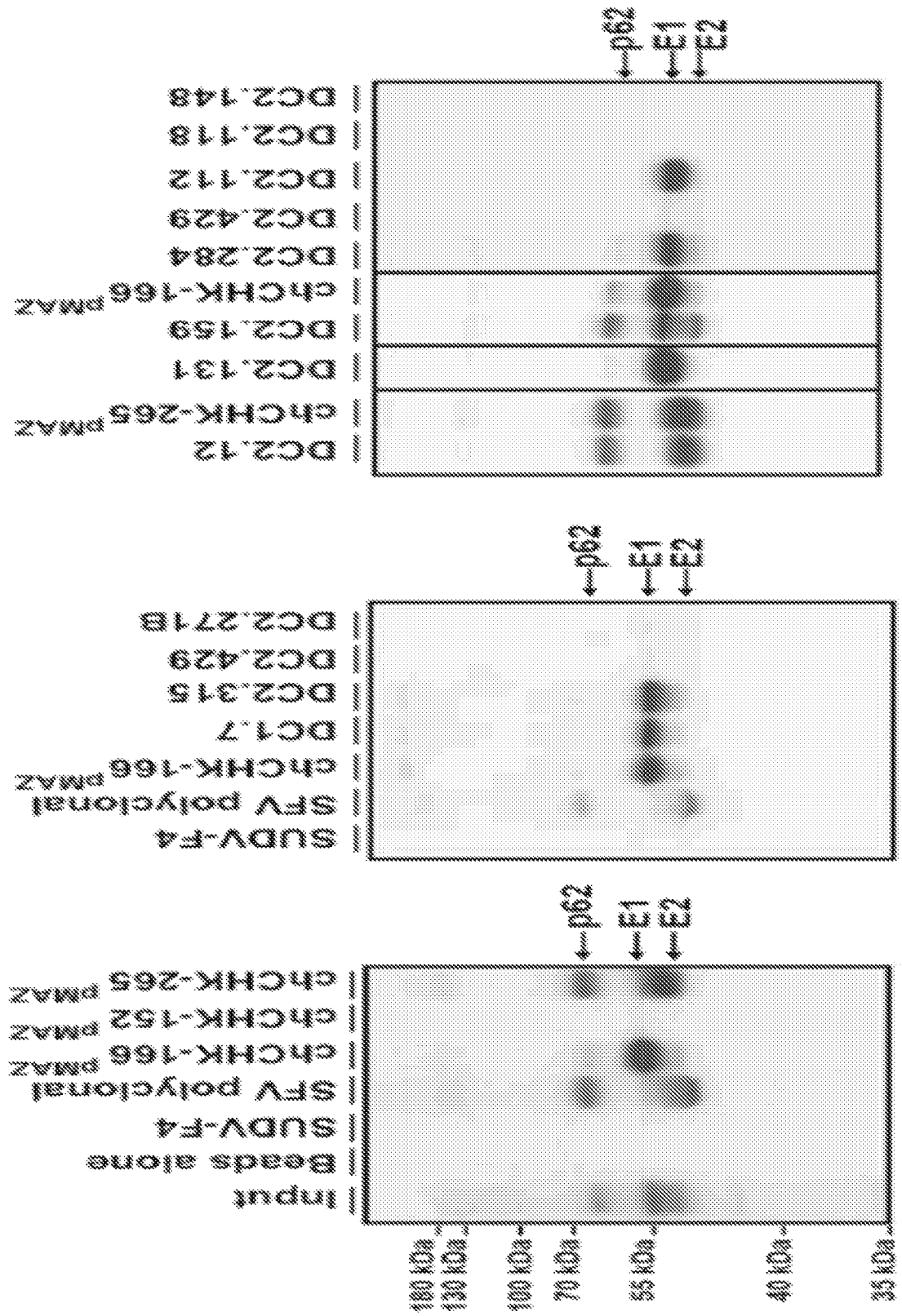
FIG. 6E shows immunoprecipitation of viral proteins from infected cells. BHKs were infected with CHIK 181/25 for 8 h, labeled with [$^{35}$S]methionine/cysteine for 2 h, and lysed on ice. Approximately 1 μg of the indicated mAbs or 2 μL of a control SFV polyclonal antibody (Sanchez-San Martin et al., 2013 *Journal of virology* 87, 7680-7687) was incubated with lysate for 1 h in the presence of 0.1% SDS. The immunoprecipitate was retrieved with Protein A agarose and the samples were reduced and alkylated and analyzed by SDS-PAGE and fluorography. The lower migrating immunoprecipitated protein is E2, the middle is E1, and the upper is p62 (arrows) as demonstrated by control antibodies (chCHK-166$^{pMAZ}$:E1, chCHK-265$^{pMAZ}$:E2/p62, and SFV polyclonal antibody:E2/p62).

Binding profiles and epitope binning. As in Example 1, a combination of methods was used to bin the epitopes of the 46 mAbs (FIG. 6A, FIG. 6E, and Table 2). Immunoprecipitation (IP) experiments with lysates of radiolabeled virus-infected cells revealed a number of reactivity profiles, with some mAbs targeting E1 alone (11 mAbs) and others targeting a combination of p62 (containing both E2 and E3) and E2, with or without E1 (9 mAbs). For unknown reasons, a number of mAbs did not result in an IP signal. For many of the E1-specific mAbs, binding to the E1 subunit was confirmed by ELISA against an S2-expressed E1 ectodomain construct (E1'). Similarly, the majority of p62-E1-specific mAbs exhibited strong reactivity toward p62-E1 by ELISA, including several mAbs (e.g., DC1.43, DC1.55, DC2.12, DC2.432. and DC2.446) that lacked E1 reactivity and therefore likely engage epitopes completely contained on E2. Although murine mAbs targeting CHIKV E1 have previously been described (Pal P, et al. *PLoS Pathog.* 2013; 9(4):e1003312), no human E1-specific CHIKV antibodies have been reported. E2 is thought to be the predominant antigenic target of antibodies that arise in response to infection. Cryo-electron microscopy (cryoEM) studies of CHIKV virus-like particles (VLPs) suggest that E1 is not abundantly exposed in the prefusion form (Long F, et al. *Proceedings of the National Academy of Sciences of the United States of America.* 2015; 112(45):13898-903., Sun S, et al. *Elife.* 2013; 2:e00435). Nonetheless, it was demonstrated here that E1 antibodies are elicited in response to natural human infection.

Figure 6F:
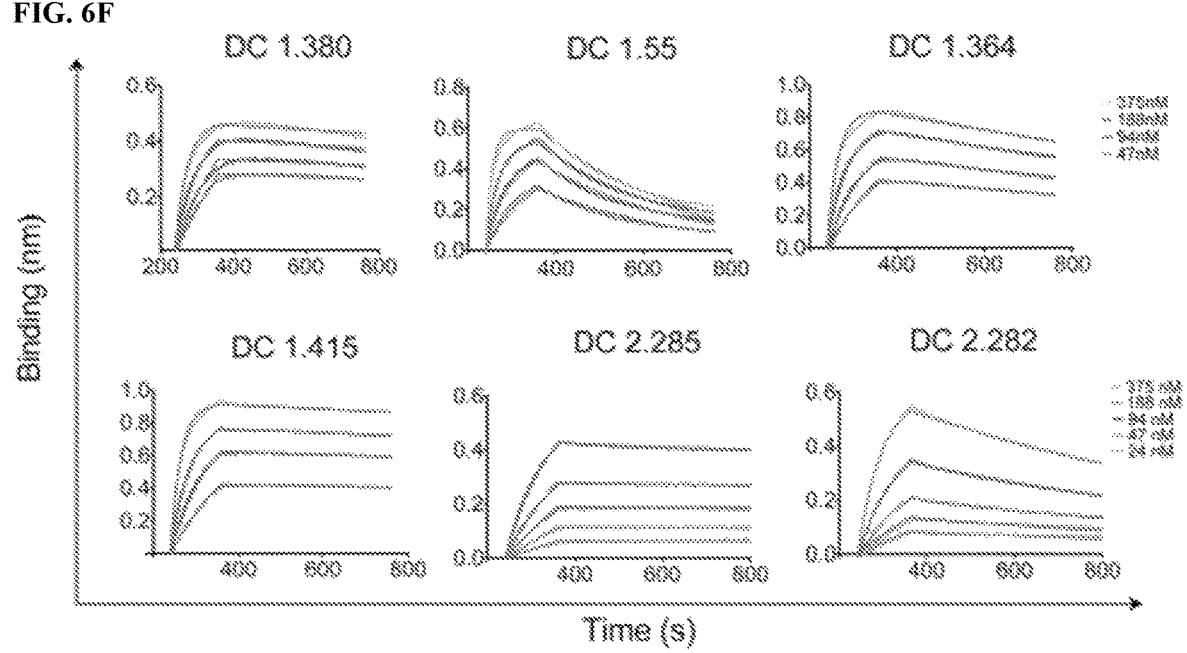
FIGS. 6F-6G shows binding of E1-Specific mAbs.
Figure 6G:
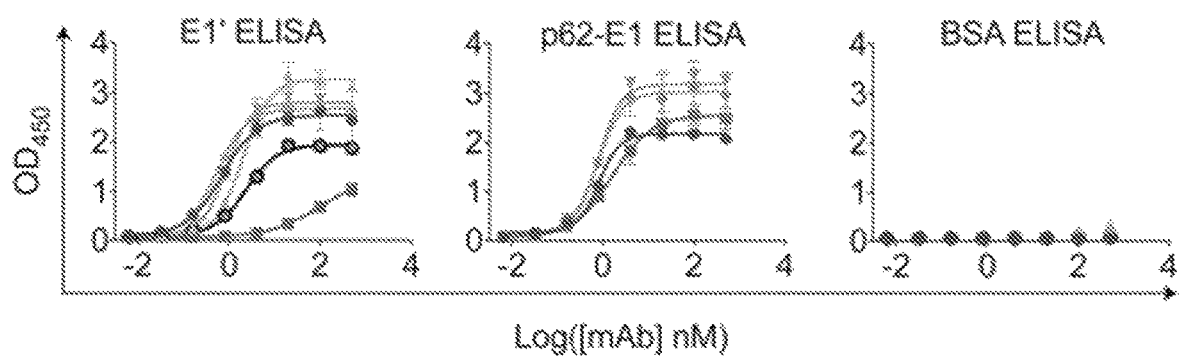

The binding affinity of a subset of mAbs was examined by Biolayer Interferometry (BLI) or full 8-point ELISA curves. The E1 mAbs DC1.9, DC1.56, DC1.415, DC2.284, and DC2.112 bound E1' with subnanomolar affinity, due to slow off-rates ($k_{off} \sim 10^{-7}$-$10^{-4}$ s$^{-}$) (FIG. 6B and FIGS. 6F-6G). In comparison, binding of DC2.315 to E1 as well as binding of DC2.271B and DC2.429 to p62-E1 was less avid, and binding sensorgrams had poor signal-to-noise ratios (not shown). An ELISA of p62-E1-specific mAbs DC2.271B and DC2.429 confirm that reactivity to p62-E1 is moderate, since the binding curves for DC2.271B and DC2.429 were relatively non-cooperative and had EC50 values in mid-nanomolar range (39 and 140 nM, respectively, FIG. 6C), in comparison to E1-specific mAbs whose EC50 values were in single-digit nanomolar range or below (FIGS. 6F-6G). As DC2.271B and DC2.429 were among the most potent neutralizing mAbs (see below); their binding to the soluble p62-E1 does not directly correlate with neutralizing potency and more likely, these mAbs bind efficiently to infectious virions.

Given that no prior human mAbs against E1 have been reported, it was determined whether E1-specific mAbs had overlapping epitopes with the murine mAb CHK-166, which targets the E1 DII fusion loop. The published variable domain sequences CHK-166 (Pal P, et al. *PLoS Pathog.* 2013; 9(4):e1003312) were cloned into the pMAZ-IgH (heavy chain) and pMAZ-IgL (light chain) plasmids that were used for expression of all DC1 and DC2-derived mAbs to generate a chimerized isotype-matched variant of CHK-166 (chCHK-166$^{pMAZ}$) (Mazor Y, et al. *J Immunol Methods.* 2007; 321(1-2):41-59). Two-phase BLI experiments in which biotinylated p62-E1 was captured on a streptavidin-coated sensor, followed by binding to chCHK-166$^{pMAZ}$ and then binding of a human mAb while in the presence of chCHK-166pMAZ, were used to determine if E1 mAbs compete for binding (FIG. 6D). DC1.56, DC2.82, and 199 DC2.85 yielded a binding signal to the p62-E1/chCHK-166$^{pMAZ}$ complex whereas incubation of the p62-E1/chCHK-166$^{pMAZ}$ complex-loaded sensors in a solution containing equimolar amounts of chCHK-166$^{pMAZ}$ resulted in no additional binding signal. When the order of binding was reversed (human mAb first, then p62-E1, then chCHK-166$^{pMAZ}$) a similar trend was observed, with chCHK-166$^{pMAZ}$ able to engage all human mAb/p62-E1 complexes (FIG. 6H). Thus, our human E1 mAbs bind to epitopes that differ spatially from CHK-166.

Neutralizing activity. To evaluate capacity of the mAbs to inhibit viral infection, a focus reduction neutralization test (FRNT) using the CHIKV 181/25 vaccine strain was performed at mAb concentrations of 300 nM and 30 nM for all 46 mAbs (FIG. 7A). At 300 nM, the majority of the mAbs could inhibit infection by >50%. These neutralizing mAbs included those binding E1 or p62-E1, and others for which the precise epitope was not identified. However, at 30 nM, only 12 mAbs showed >50% inhibition, including some with E1, p62-E1, or undefined specificities. As a comparative control, the variable domains of murine mAb CHK-152 were expressed onto identical human constant domain background, as described above. The resulting mAb, chCHK-152$^{pMAZ}$ strongly neutralized CHIKV infection at both 30 and 300 nM whereas the negative control mAb SUDV-F4, a Sudan virus-specific mAb with identical constant regions (Chen G, et al. *ACS Chemical Biology.* 2014; 9(10):2263-73), did not.

Figure 7C:
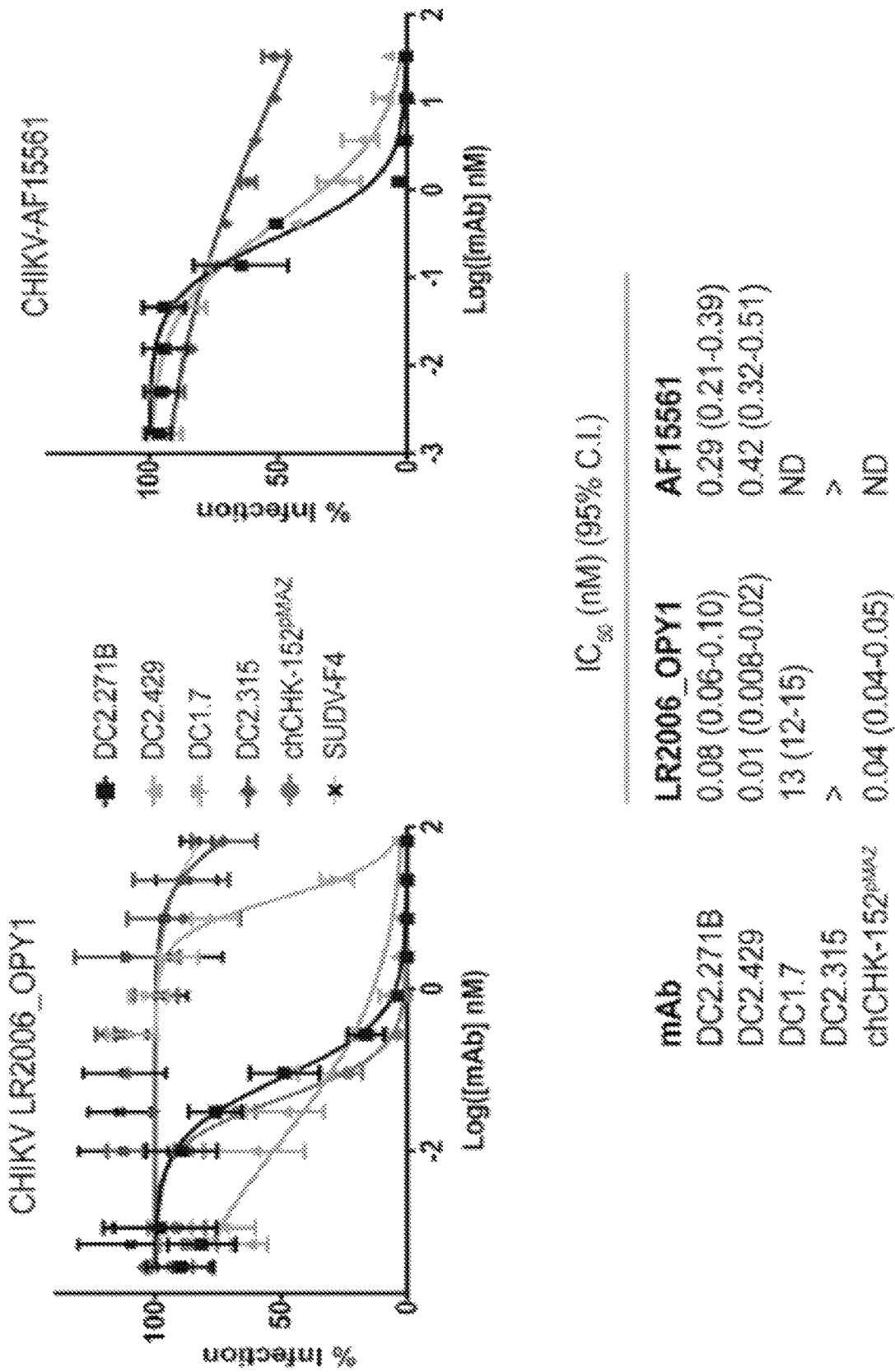
FIG. 7C shows neutralization of ESCA African genotype LR2006_OPY1 and Asian genotype AF15561 by human mAbs.
Figure 7E:
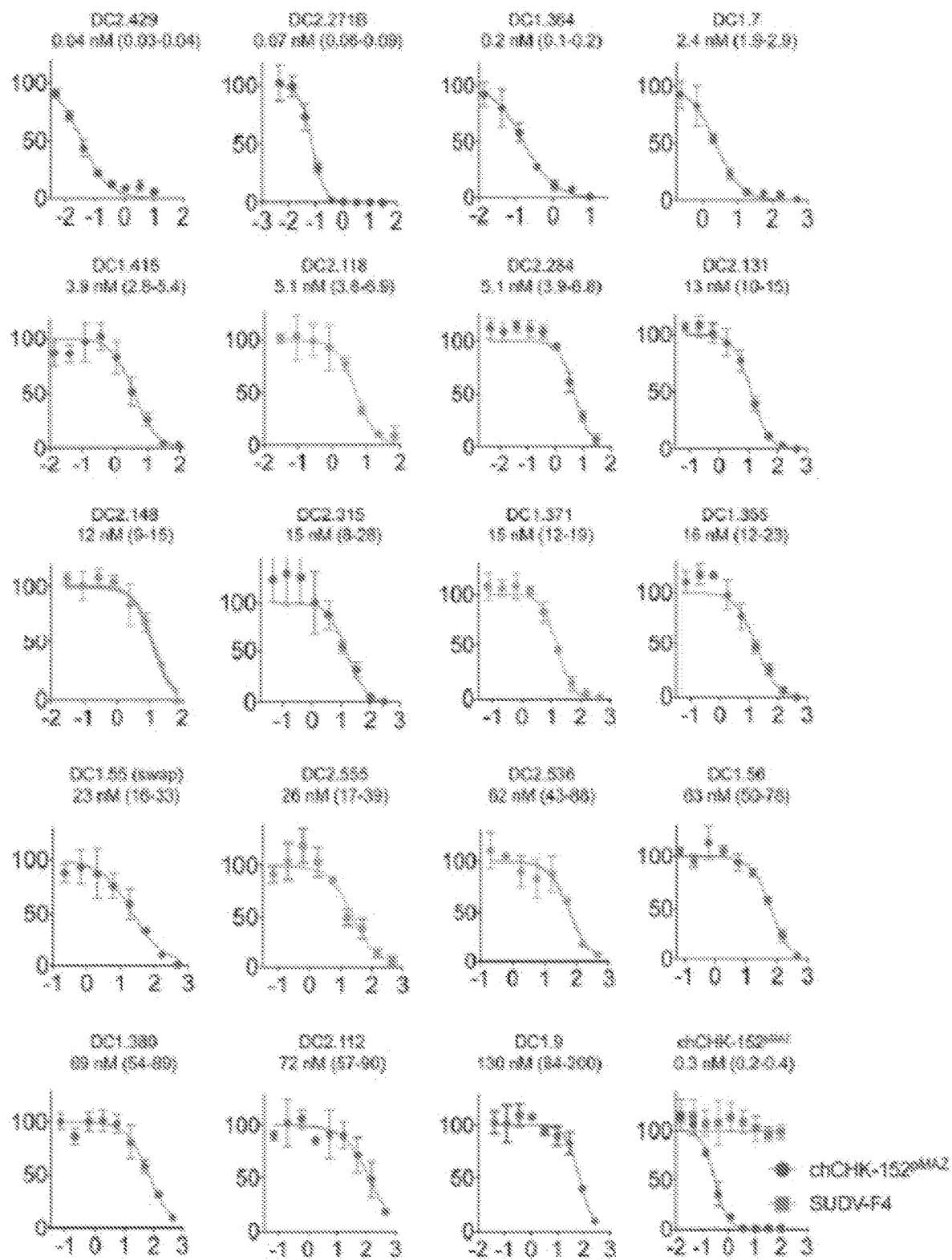
FIG. 7E shows full neutralization curves of human mAbs against CHIKV 181/25. For each mAb, a representative dataset performed in triplicate from two or more independent experiments is shown (IC$_{50}$ values were consistent among experiments). Points represent the mean±SD. Curves are color-coded according to epitope designation (blue (bar columns 1-3), p62-E1 specific; red (bar columns 4-5, 7-8, 10, 12-13, 16-19), E1-specific; gray (bar columns 6, 9, 11, 14-15), undefined). The IC$_{50}$ value is provided, along with 95% confidence interval from curve fitting (these values are also shown graphically in FIG. 6).

Full dose response neutralization curves against CHIKV 181/25 were performed for 19 of the mAbs (FIG. 7B and FIG. 7E). Overall the IC$_{50}$ values ranged from 0.03 nM to 130 nM, with those mAbs binding p62-E1 (DC2.271B, DC2.429, and DC1.364) among the most potent. A number of E1-specific mAbs (e.g., DC1.7, DC2.283, DC2.131, and DC2.315) also neutralized CHIKV 181/25 with IC$_{50}$ values in the low/midnanomolar range (2.3-23 nM), indicating that some of the neutralization epitopes identified by our mAbs lie within the E1 subunit. The two most potent p62-E1-specific mAbs (DC2.271B and DC2.429) were tested against pathogenic CHIKV strains AF15561 (Asian genotype) and LR2006_OPY1 (East/Central/South African genotype); they potently neutralized infection of these strains with subnanomolar IC$_{50}$ values (FIG. 7C), which agreed with results obtained using the CHIKV 181/25 vaccine strain. chCHK-152$^{pMAZ}$ potently neutralized CHIKV LR2006_OPY1, consistent with previous reports on fully murine, chimeric murine/human, or fully humanized CHK-152 variants (Pal P, et al. *PLoS Pathog.* 2013; 9(4):e1003312 (FIG. 7C). Additionally, two of the E1-specific mAbs (DC1.7 and DC2.315) were tested against CHIKV LR2006 OPY1. DC1.7 neutralized infection with an IC$_{50}$ of 13 nM, again consistent with results using the CHIKV 181/25 vaccine strain, albeit with a higher value. In contrast, DC2.315 did not neutralize LR2006_OPY1; this mAb was additionally tested against AF15561 and exhibited modest and incomplete neutralization. The basis for the difference in neutralization properties for DC2.315 against CHIKV 181/25 vs. LR2006_OPY1 is unknown.

To explore the potential for cross-neutralization with other alphaviruses, mAbs were screened for their ability to neutralize Mayaro virus (MAYV) at 300 nM and 30 nM in an FRNT. The MAYV p62 and E1 glycoproteins are 58% and 62% identical to CHIKV p62 and E1, respectively, and previous reports have indicated that broadly neutralizing epitopes exist within domain B of E2, as typified by murine mAb CHK-265 (Fox J M, et al. *Cell.* 2015; 163(5):1095-107). Of the human mAbs, only three neutralized MAYV infection (DC1.55, DC2.536, DC2.555; FIG. 7D), albeit with lower potency relative to a chimerized human constant domain-matched variant of CHK-265 (chCHK-265$^{pMAZ}$). Negative control mAb SUDV-F4 had no activity against MAYV.

Figure 8A:
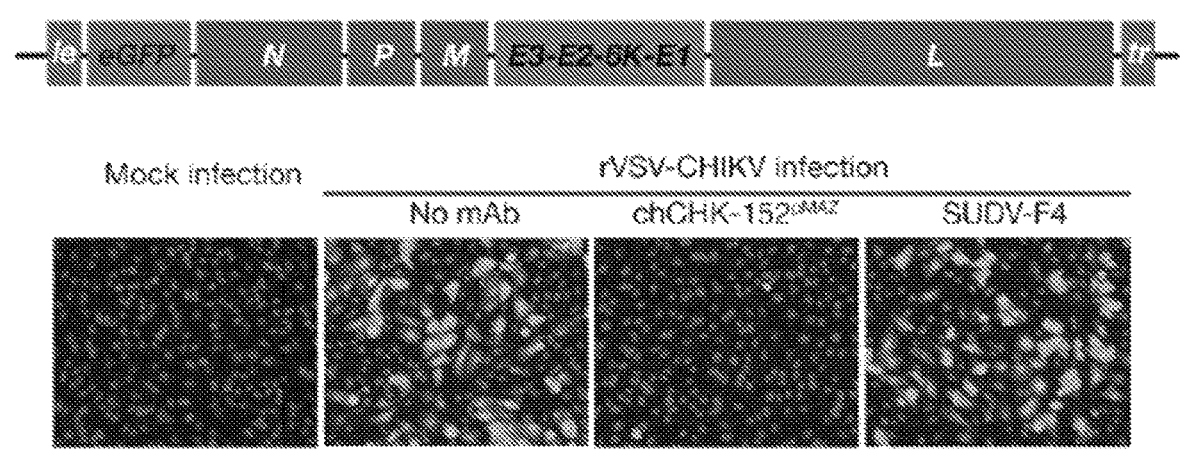
Figure 8B:
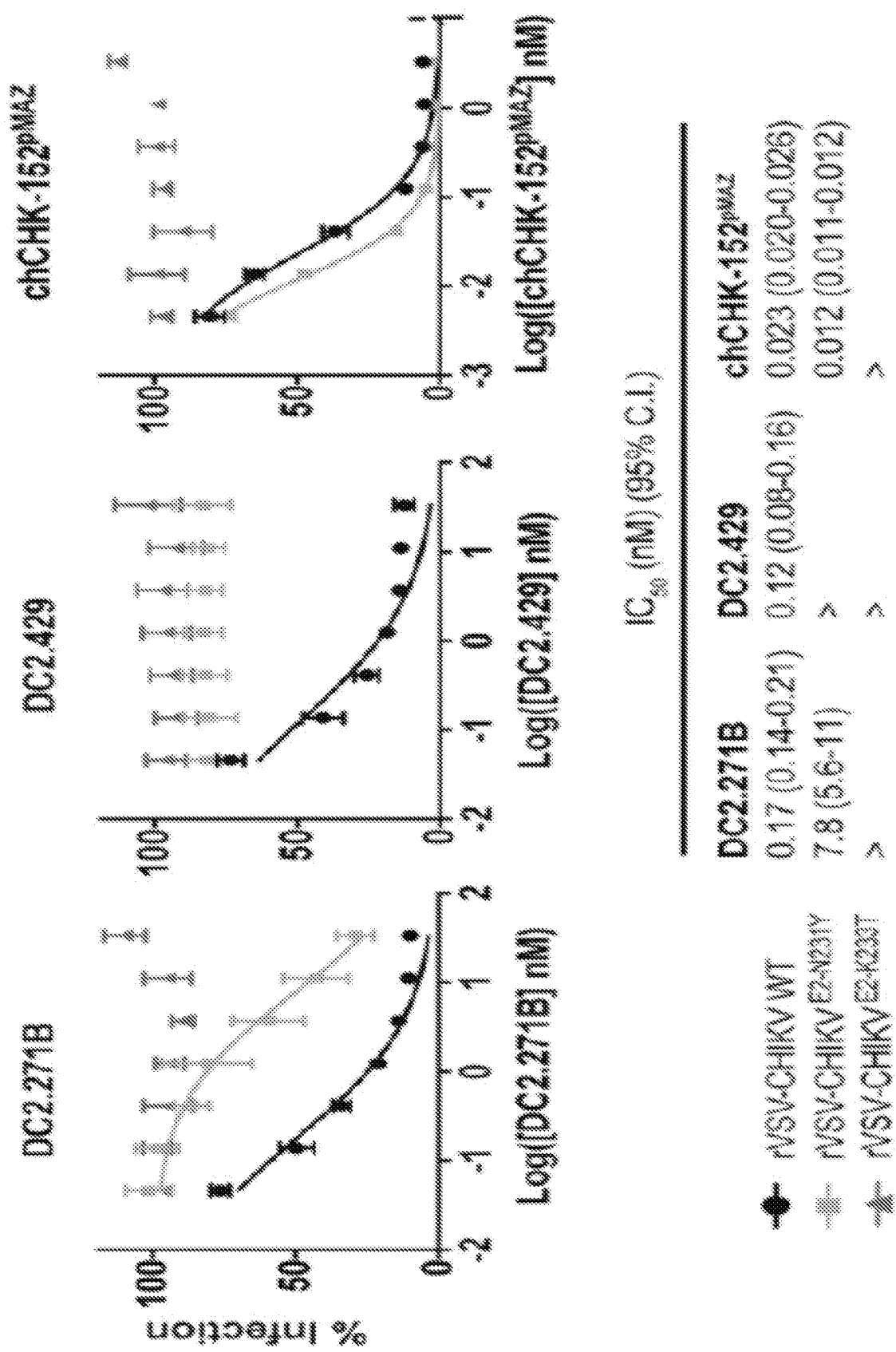
FIG. 8B shows neutralization assay for rVSV-CHIKV WT and E2 viral escape mutations by DC2.271B, DC2.429, and chCHK-152$^{pMAZ}$. Data are pooled from two experiments, each performed in duplicate, were (points represent mean±SD).

Isolation of neutralization escape viruses. To map the potential epitopes of the two most potent p62-E1-specific mAbs (DC2.271B and DC2.429) as well as two of the E1-specific mAbs (DC1.7 and DC2.315), a replication-competent vesicular stomatitis virus clone was generated bearing CHIKV E3-E2-6K-E1 genes in place of the native glycoprotein G (rVSV-CHIKV) (FIG. 8A). Similar viruses have been generated and evaluated as potential vaccine candidates for CHIKV, ebolaviruses, and arenaviruses (Chattopadhyay A, et al. *Journal of virology.* 2013; 87(1): 395-402; Agnandji S T, et al. *N Engl J Med.* 2015; Whitt M A, et al. *Methods in molecular biology* (Clifton, NJ). 2016; 1403:295-311). The rVSV-CHIKV particle encodes an enhanced green fluorescent protein (eGFP) as an additional transcription unit that allows quantification of infection of Vero cells by automated fluorescence microscopy (FIG. 8A). rVSV-CHIKV was efficiently neutralized by chCHK-152$^{pMAZ}$ but not by SUDV-F4 (FIGS. 8A, 8B, and FIG. 8F). Despite the different morphologies of VSV and CHIKV particles (bullet-shaped and spheroid, respectively) (Sun S, et al *Elife.* 2013; 2:e00435; Ge P, et al. *Science* (New York, NY). 2010; 327(5966):689-93), the entry properties of rVSV-CHIKV and the fact that it is efficiently neutralized by chCHK-152$^{pMAZ}$ suggest that it recapitulates the critical features of CHIKV entry.

Figure 8C:
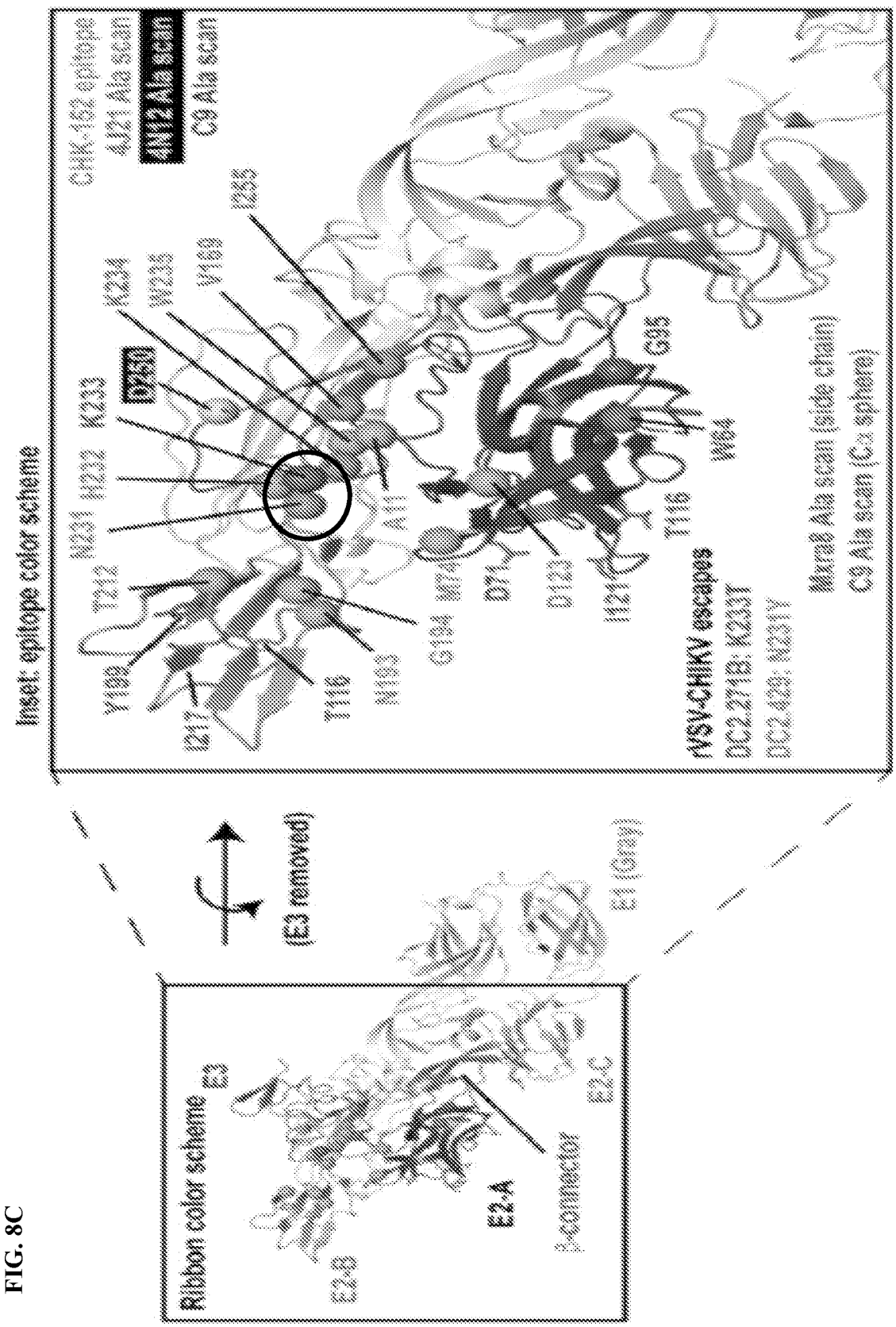
FIG. 8C shows location of rVSV-CHIKV escape mutations for DC2.429 and DC2.271B (orange and red Cα spheres, respectively (circled in figure)) mapped onto the p62-E1 X-ray structure. E2 domains as well as E3 are colored and labeled as in FIG. 5A; E1 is labeled and colored gray. Also 850 shown are previously reported alanine scanning mutations that ablate binding for 4N12 (parent of SVIR001, yellow Cα sphere), 4J21 (green Cα spheres), C9 (magenta Cα sphere), and IMCV-063 (blue Cα sphere). The structural epitope for murine 852 mAb CHK-152, as mapped by cryo-EM is shown as cyan Cα spheres. The alanine scanning mutations that reduced Mxra8 binding are shown as magenta side chains.

It was found that DC2.271B and DC2.429 efficiently neutralized rVSV-CHIKV (FIG. 8B). rVSV-CHIKV was serially passaged against each mAb, and individual plaques from the resulting escape populations were isolated, sequenced, and characterized. For DC2.271B and DC2.429, single escape mutations of E2 K233T or E2 N231Y were isolated, respectively (FIGS. 8B and 8C). Both of these residues are located at the junction between the β-connector and B domains of E2 and just outside the region that is occluded by E3 on the p62-E1 hybrid protein. The epitopes for previously reported human neutralizing mAbs against CHIKV E2 1H12, 814, 4J21, and 3N23 include an adjacent residue, K234, as mapped by an alanine scanning library of cell-surface expressed E1/E2 (the 3N23 epitope also includes K233) (FIG. 8C) (Long F, et al. *Proceedings of the National Academy of Sciences of the United States of America*. 2015; 112(45): 13898-903; Smith S A, et al. *Cell host & microbe*. 2015; 18(1):86-95). Furthermore, the cryo-electron microscopy-mapped structural epitope of CHK-152 includes residues in this region (H232 and W235) as well as residues on the B domain (Sun S, et al. *Elife*. 2013; 2:e00435). The epitope of the non-neutralizing human mAb 1M9 includes N231, although DC2.429 is potently neutralizing while likely engaging a similar epitope as 1M9. The viral escape mutations for other human neutralizing mAbs 4N12 (parent of SVIR001), C9, and IM-CKV063 were located on distal regions of the E2 subunit (Jin J, et al. *Cell host & microbe*. 2018; 24(3):417-28.e5, Jin J, et al. *Cell Rep*. 2015; 13(11):2553-64). Together, these results indicate that the β-connector and B domain regions constitute epitopes recognized by a number of anti-CHIKV neutralizing antibodies. This region is distal to the putative Mxra8 receptor binding region, as inferred by escape mutations (FIG. 8C).

The viral escape mutations for DC2.271B and DC2.429 on rVSV-CHIKV are proximal to one another and lie in the middle of the cluster of residues identified as the structural epitope of CHK-152 by cryoEM studies (FIG. 8C), suggesting that some or all of the epitopes for these three antibodies may be shared. To further investigate this hypothesis, all three mAbs were tested against both the rVSV-CHIKV$^{E2-K233T}$ (DC2.271B viral escape) and the rVSV-CHIKVK$^{E2-N231Y}$ (DC2.429 viral escape) (FIG. 8C). chCHK-152$^{pMAZ}$ neutralized rVSV-CHIKV$^{E2-N231Y}$ with similar potency as WT rVSV-CHIKV but did not neutralize rVSV-CHIKV$^{E2-K233T}$. DC2.429 did not neutralize either viral escape mutant, and DC2.271B weakly neutralized rVSV-CHIKV$^{E2-N231Y}$. These data suggest that the DC2.271B epitope includes residues for binding both DC2.429 and CHK-152, as neither of these mAbs could neutralize the rVSV-CHIKV$^{E2-K233T}$ viral escape mutant that was selected against DC2.271B. In contrast, the epitope for DC2.429 may be only partially shared with DC2.271B and may not be shared at all with CHK-152, since the DC2.429 viral escape mutant (rVSV-CHIKV$^{E2-N231Y}$) was still neutralized by chCHK-152$^{pMAZ}$ and partially neutralized by DC2.271B. However, these studies do not rule out the possibility that the viral escape mutations described here induce conformational effects, rather than directly ablating binding interactions. Furthermore, these data do not unequivocally demonstrate competition of the three mAbs. Competition ELISA and BLI experiments with DC2.271B, DC2.429, and chCHK-152$^{pMAZ}$ did not yield interpretable results, likely due to the weak binding of the human mAbs toward the monomeric p62-E1 hybrid protein (above).

To compare neutralizing activity of DC2.271B 290 and DC2.429 with the most efficacious of the previously reported human mAbs (Selvarajah S, et al. *PLoS neglected tropical diseases*. 2013; 7(9):e2423, Smith S A, et al. *Cell host & microbe*. 2015; 18(1):86-95), versions of C9, IM-CKV063 and 4N12 (parent of SINV001) expressed from the pMAZ platform (C9$^{pMAZ}$, IM-CKV063$^{pMAZ}$, and 4N12$^{pMAZ}$) were generated and their capacity to neutralize CHIKV 181/25 infection were assessed. It was found that C9P$^{pMAZ}$ and 4N12$^{pMAZ}$ neutralized CHIKV 181/25 similarly to DC2.271B and DC2.429, whereas IM-CKV063$^{pMAZ}$ was over 200-fold less potent (FIG. 4D). To further examine the degree to which the DC2.271B epitope overlapped with these three human mAbs, they were tested for their capacity to neutralize rVSV-CHIKV$^{E2-K233T}$ (DC2.271B viral escape mutant, FIG. 8E). Both C9P$^{pMAZ}$ and 4N12$^{pMAZ}$ potently neutralized rVSV-CHIKV$^{E2-K233T}$; IM-CKV063 was less potent but could nonetheless inhibit infection. These results indicate that the DC2.271B epitope is distinct from those of previously reported human mAbs.

Figure 9A:
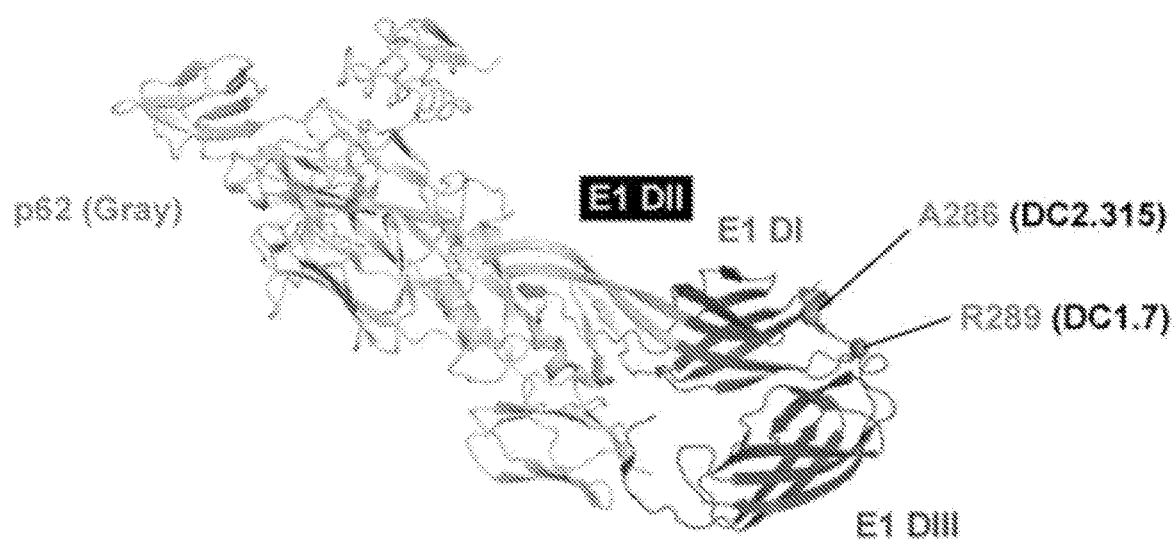
FIG. 9 contains three panels, FIGS. 9A-9C, showing viral escape studies with E1-targeting mAbs. Location of A286 and R289 on the p62-E1 X-ray structure (FIG. 9A, PDB ID: 3N40) (Voss J E, et al. *Nature*. 2010; 468(7324):709-12) or on the E1/E2 cryoEM heterohexamer (FIG. 9B, PDB ID: 3J2W) (Sun S, et al. *Elife*. 2013; 2:e00435). For clarity, p62 or E2 subunits are labeled and colored gray while E1 domains DI, DII, and DIII colored and labeled as per FIG. 5.
In FIG. 9B, a complete prefusion E1/E2 hexameric spike (outlined with dotted line) is illustrated, along with an E1/E2 heterodimer from an adjacent spike, to depict relative orientation within adjacent spikes.
FIG. 9C shows neutralization studies with WT VSV-CHIKV and viral escape mutants. Data are pooled from two experiments, each performed in duplicate or triplicate (points represent mean±SD).
Figure 9B:
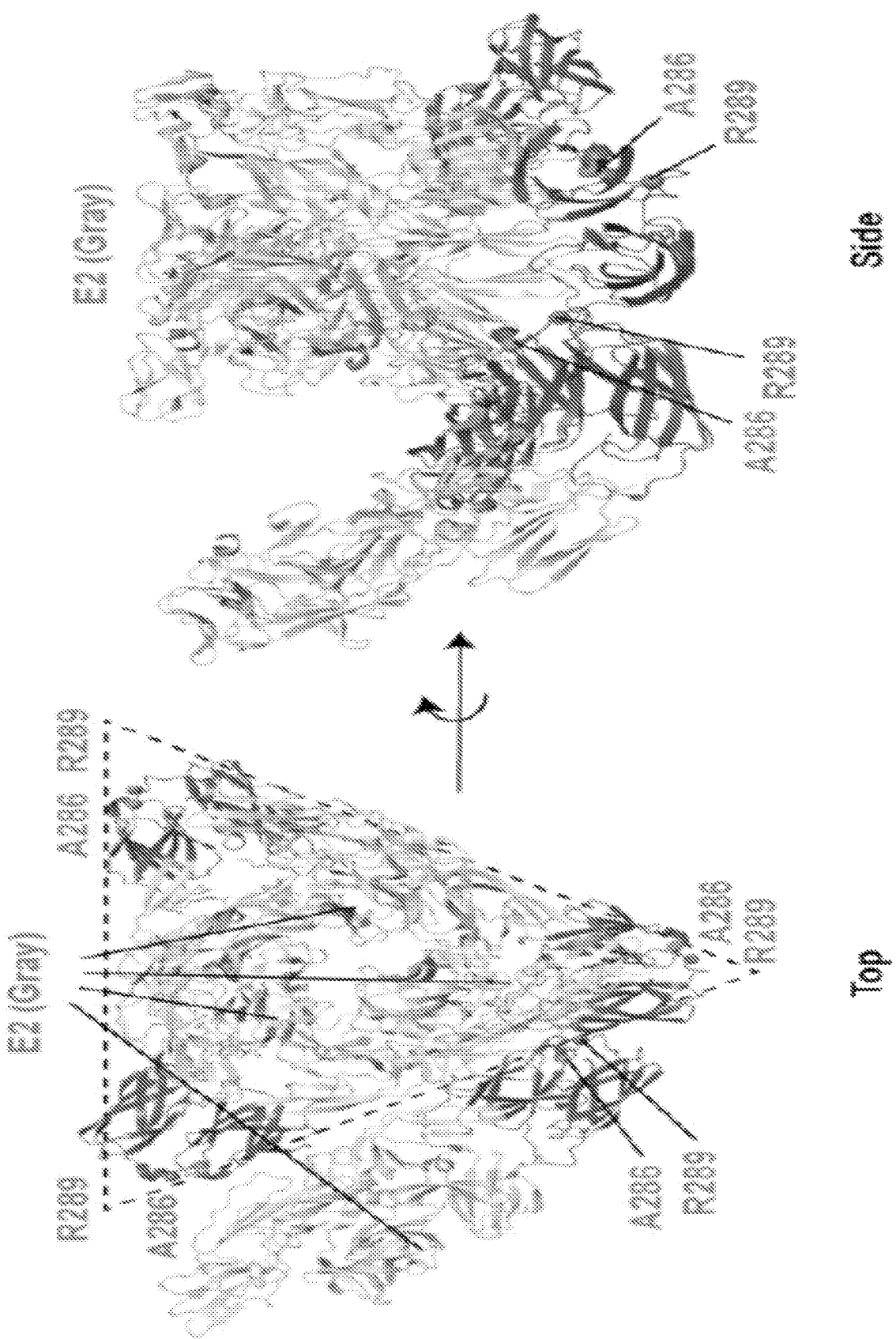
Figure 9C:
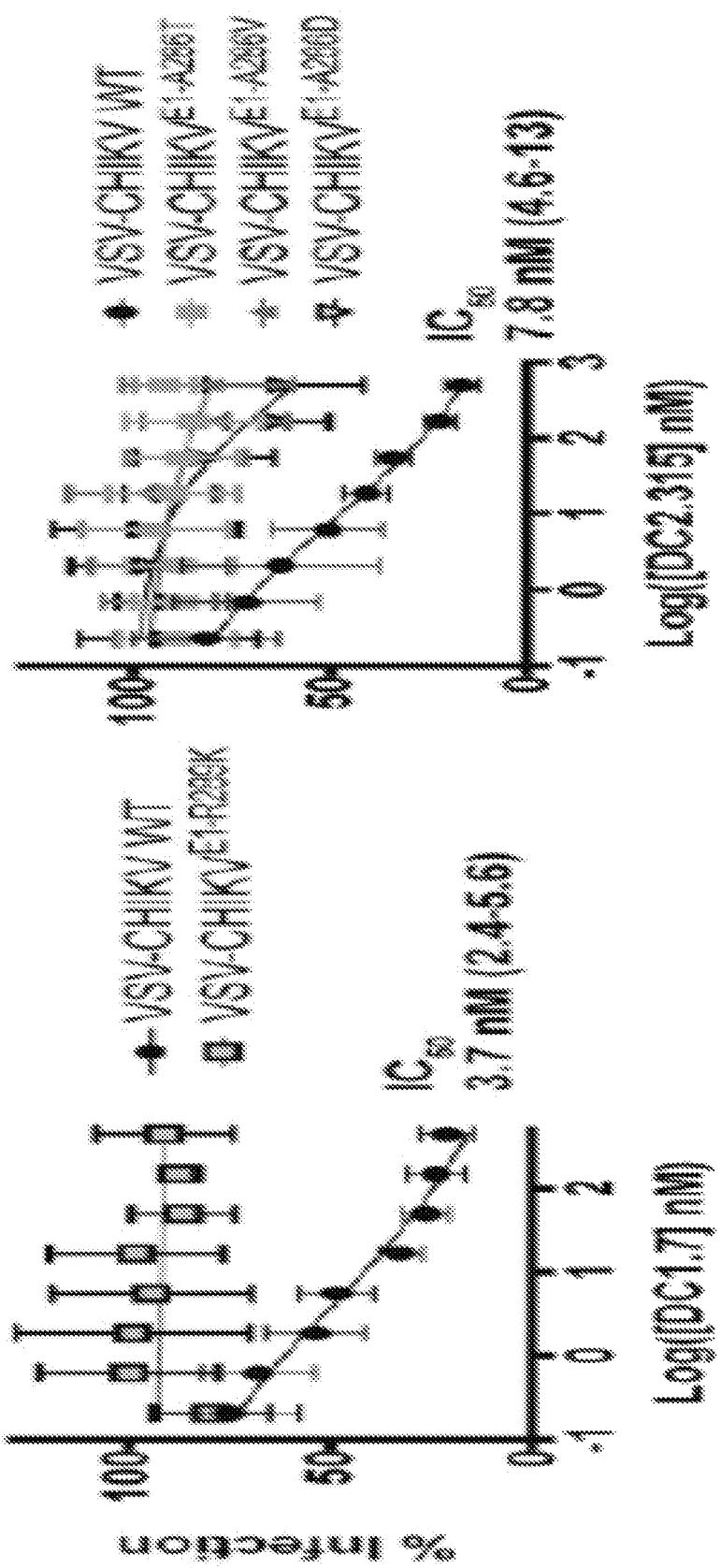

A similar viral escape study was performed with rVSV-CHIKV and E1-specific mAbs D1.7 and DC2.315 (FIG. 9). For E1-specific mAb DC1.7, a single escape mutation of E1 R289K was isolated, which lies in the linker region leading into domain III (DIII) (FIGS. 9A and 9B). For DC2.315, three independent escape mutants at position E1 A286 were identified (A286T, A286V, and A286D, FIG. 9C). This residue is located at the border of domain I (DI), immediately preceding the linker that leads into DIII (FIG. 9A). When considered within the context of the E1/E2 prefusion hexamer, the escape mutations for both DC1.7 and DC2.315 lie near the edge of the triangular spike (FIG. 9B). Topologically, one potential mechanism by which these mAbs could access this site is by engaging the underlying E1 subunit in between adjacent E2 subunits (see FIG. 9B, side view). The observation that this region is targeted by neutralizing mAbs, albeit strain-dependently and with modest potency, is notable since DIII is the most structurally mobile region of E1 during its conformational rearrangements to mediate viral membrane fusion (Sanchez-San Martin C, et al. *Journal of virology*. 2013; 87(13):7680-7; Gibbons D L, et al. *Nature*. 2004; 427(6972):320-5). MAbs that bind this region could neutralize infection by preventing the DIII movements required for viral fusion. However, the relatively modest potency as well as the fact the DC1.7 and DC2.315 neutralization varies per strain suggests that this epitope is not a site of universal susceptibility.

Protective capacity of mAbs in mice. Four mAbs (DC2.271B, DC2.429, DC1.7, and DC2.315) were tested for their ability to protect mice from lethal viral challenge with CHIKV LR2006_OPY1, using 3-week old C57BL/6 mice rendered immunodeficient by treatment with the anti-Ifnar1 mAb MAR1-5A3 (Sheehan K C, et al. *Journal of interferon & cytokine research*. 2006; 26(11):804-19). The CHIKV mAbs (100 µg, ~6 mg/kg) were administered one day prior to virus infection. DC2.271B and DC2.429 were the most potently neutralizing among the E2 mAbs. Although neutralization by DC1.7 was relatively modest, and that by DC2.315 was strain-dependent (non-neutralizing against CHIKV LR2006 OPY1), it was nonetheless determined if mAbs binding E1 in this region could afford protection. In other pathogens, such as ebolaviruses, some non-neutralizing mAbs can afford in vivo protection (Saphire E O, et al. *Cell*. 2018; 174(4):938-52.e13). Human mAbs targeting E1 DI, DIII, or the DI-DIII linker have not previously been studied for protection against CHIKV in vivo.

Figures 10A, 10B:
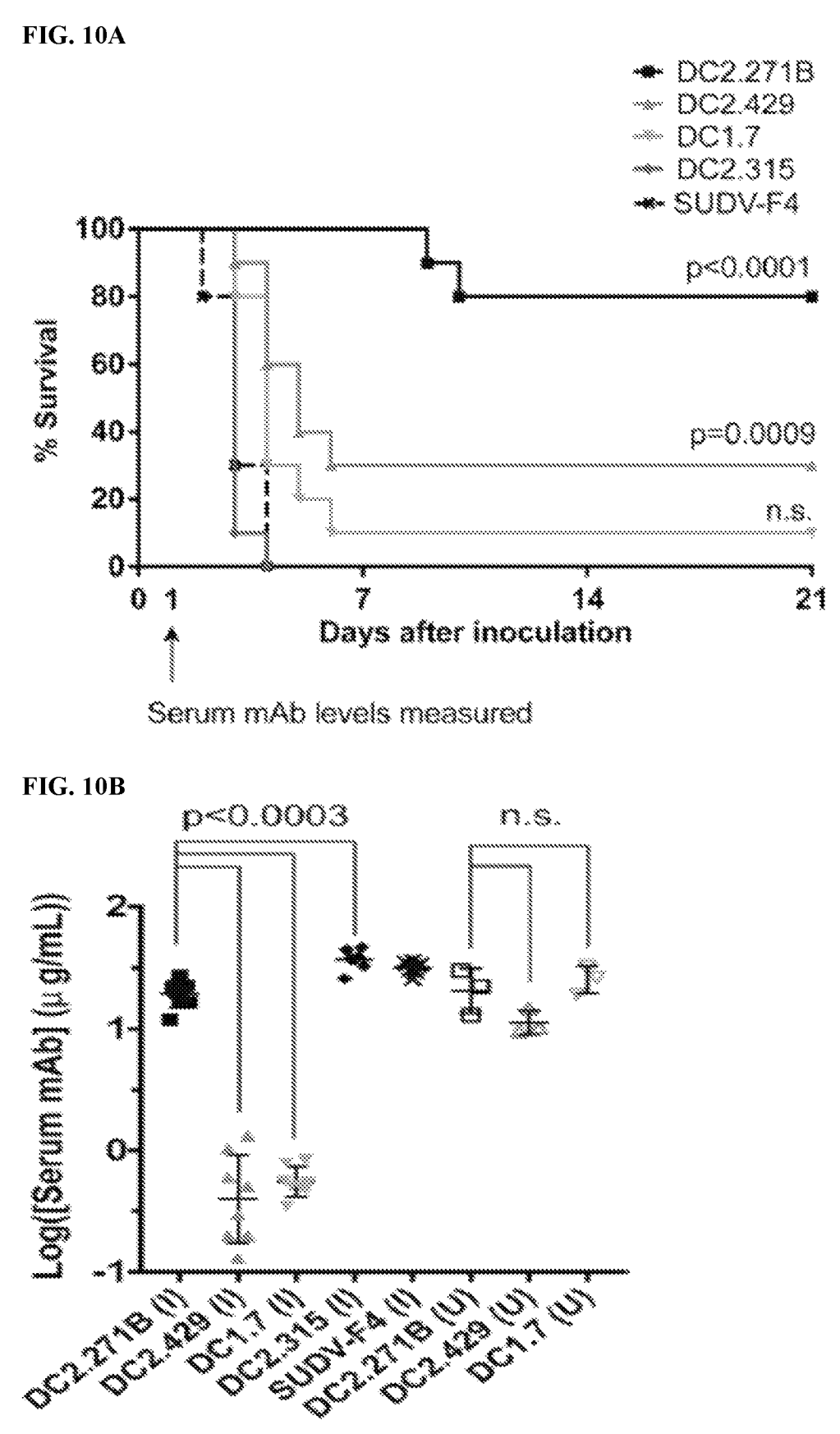
Figure 10C:
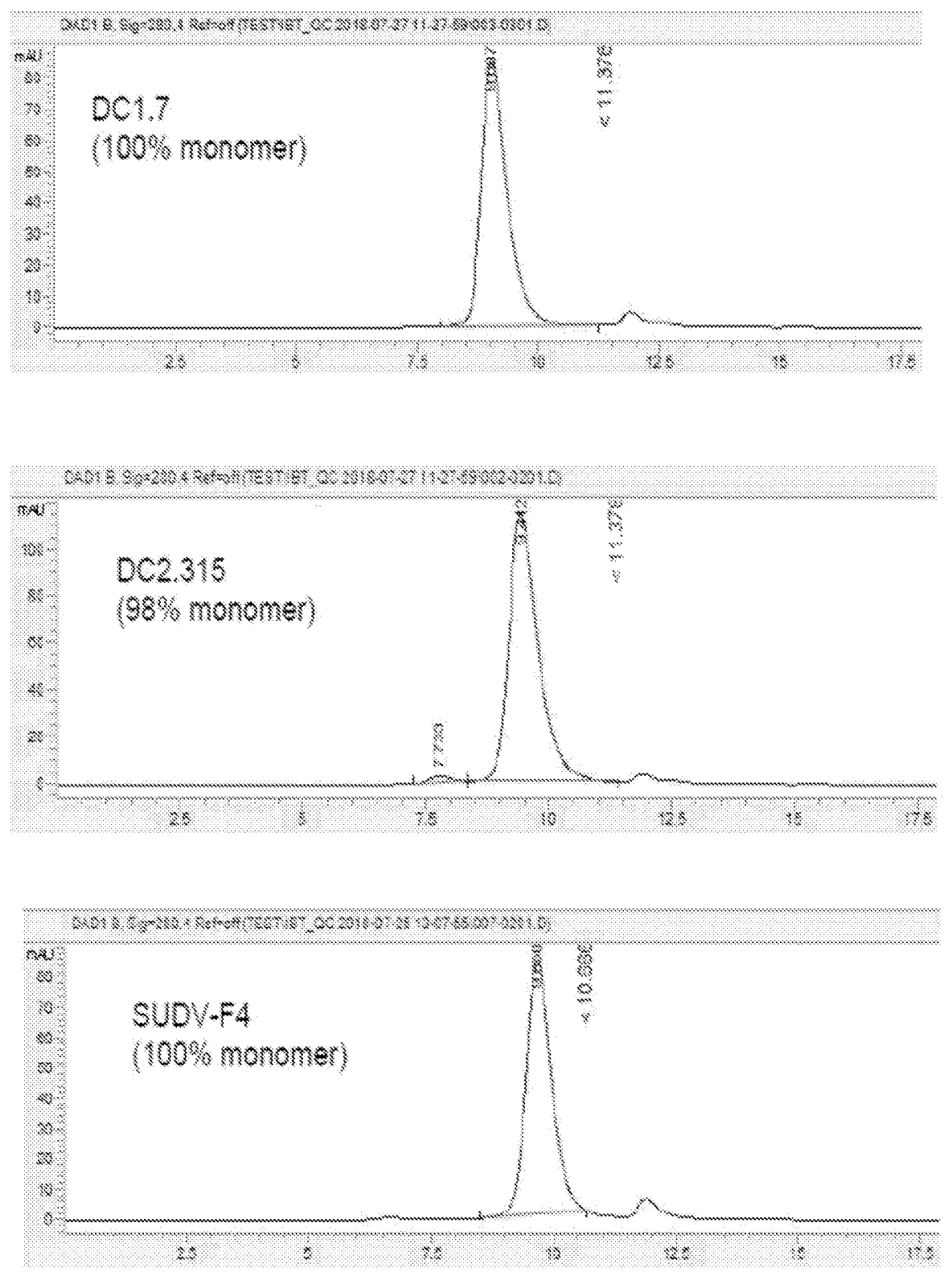

All mice receiving the SUDV-F4 negative control mAb succumbed to infection within four days. In contrast, 80% of mice receiving DC2.271B survived the challenge. mAb DC2.429 afforded a lesser but significant survival advantage (30%). Neither DC1.7 nor DC2.315 provided significant in vivo protection from CHIKV infection (FIG. 10A). To gain insight into factors contributing to in vivo efficacy, the serum mAb levels during the challenge were measured by sampling 2 days after IP administration of the mAb and 1 day after infection (FIG. 10B). DC2.271B, DC2.315, and negative control mAb SUDV-F4 were present at average (across mice) serum concentrations of 20±2 µg/mL, 38±3 µg/mL and 32±1 µg/mL, respectively, whereas DC2.429 and DC1.7 were present at >30-fold lower serum concentrations (0.5±0.1 and 0.6±0.1 µg/mL, respectively). Early clearance of mAb could be due to the presence of aggregates. To explore this possibility, mAbs were subjected to SEC-HPLC analysis and 336 a small (n=3) pharmacokinetic study in uninfected mice. All of the DC1.7, DC2.315, and SUDV-F4 were found to be >98% monomeric (FIG. 10C). The serum levels of DC2.271B, DC2.429, and DC1.7 were found to be 26±4, 22±5, and 12±2 µg/mL (average across three mice) when administered at protective doses (FIG. 10B). Together, these results indicate that DC2.429 and DC1.7 are cleared from serum more rapidly during the course of CHIKV infection and treatment than DC2.271B and DC2.315, but that this early clearance is not due to aggregates and depends on the presence of virus. Perhaps related to this effect, the half-life of HIV-1 bNAbs has been found to be reduced in human clinical trials (~3 days) when used therapeutically for patients coming off antiretroviral therapy (Caskey M, et al. *Nature.* 2015; 522(7557):487-91). A possible mechanism for this observation is that mAbs bind virus in the bloodstream, and the antibody-virus complex is cleared. However, why this affects DC2.429 and DC1.7 but not DC2.271B or DC2.315 warrants further investigation.

Figure 11A:
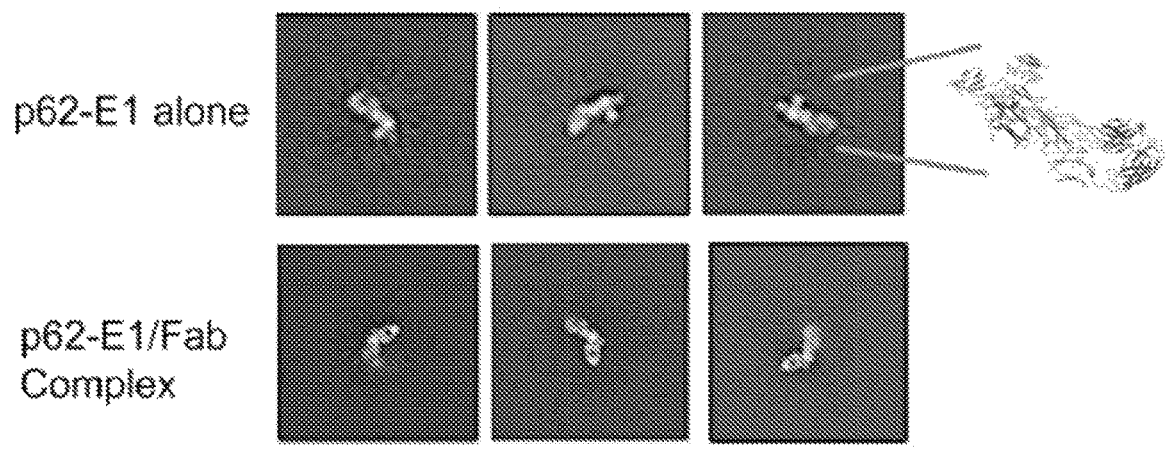
FIG. 11 contains three panels, FIGS. 11A-11C, showing recognition requirements for DC2.271B. CryoEM visualization (FIG. 11A) and single particle three-dimensional reconstruction (FIG. 11B) of p62-E1 alone and in complex with DC2.271B Fab.
FIG. 11C shows neutralization of CHIKV 181/25 by DC2.271B IgG1 and Fab. Data are pooled from two experiments each performed in triplicate (points represent mean±SD).
Figure 11B:
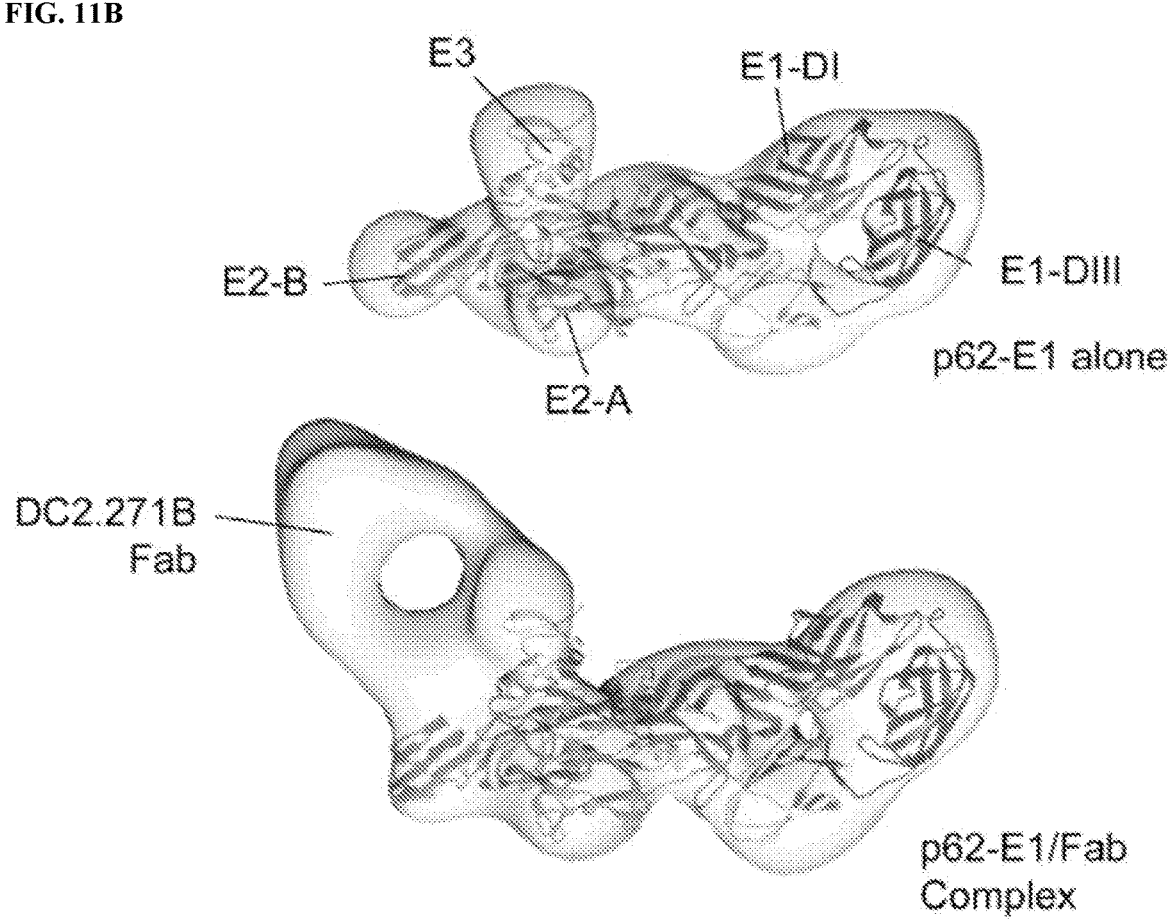
Figure 11C:
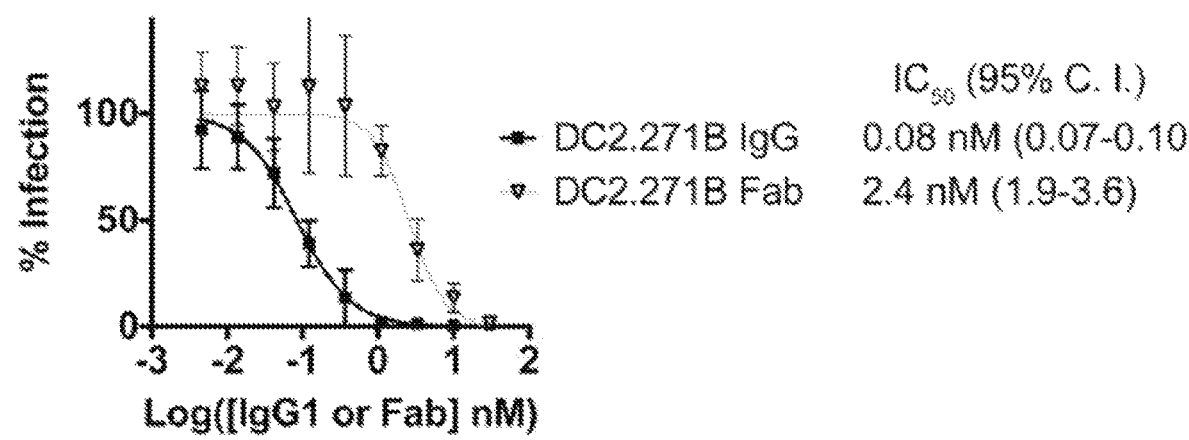
Figure 12:
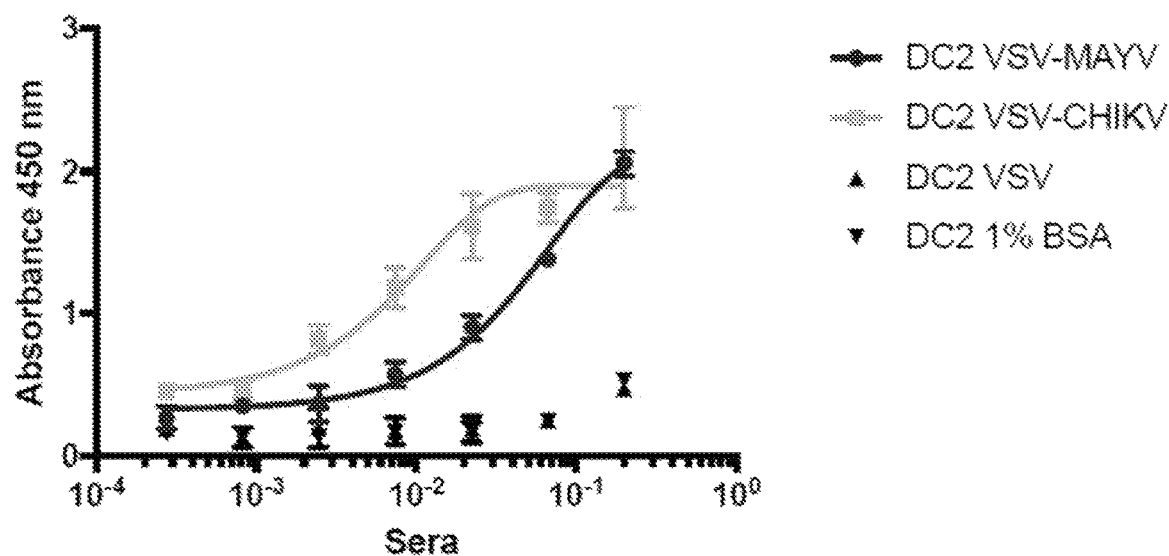
FIG. 12 shows that CHIKV patient DC2 sera reacts with VSV-MAYV. ELISA binding curve of patient sera to VSV- CHIKV and VSV-MAYV pseudotyped viruses. Negative control serum was used from uninfected patient.
Figure 13:
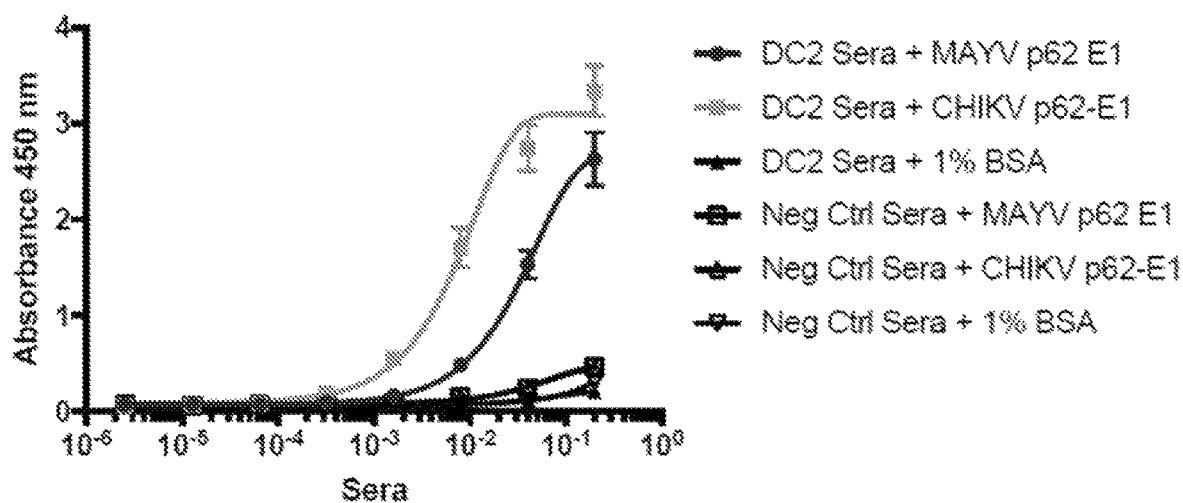
FIG. 13 shoes DC2 sera binds MAYV p62-E1. ELISA binding curve of DC2 sera to CHIKV and MAYV p62-E1 glycoprotein. Negative control serum was used from uninfected patient.
Figure 14:
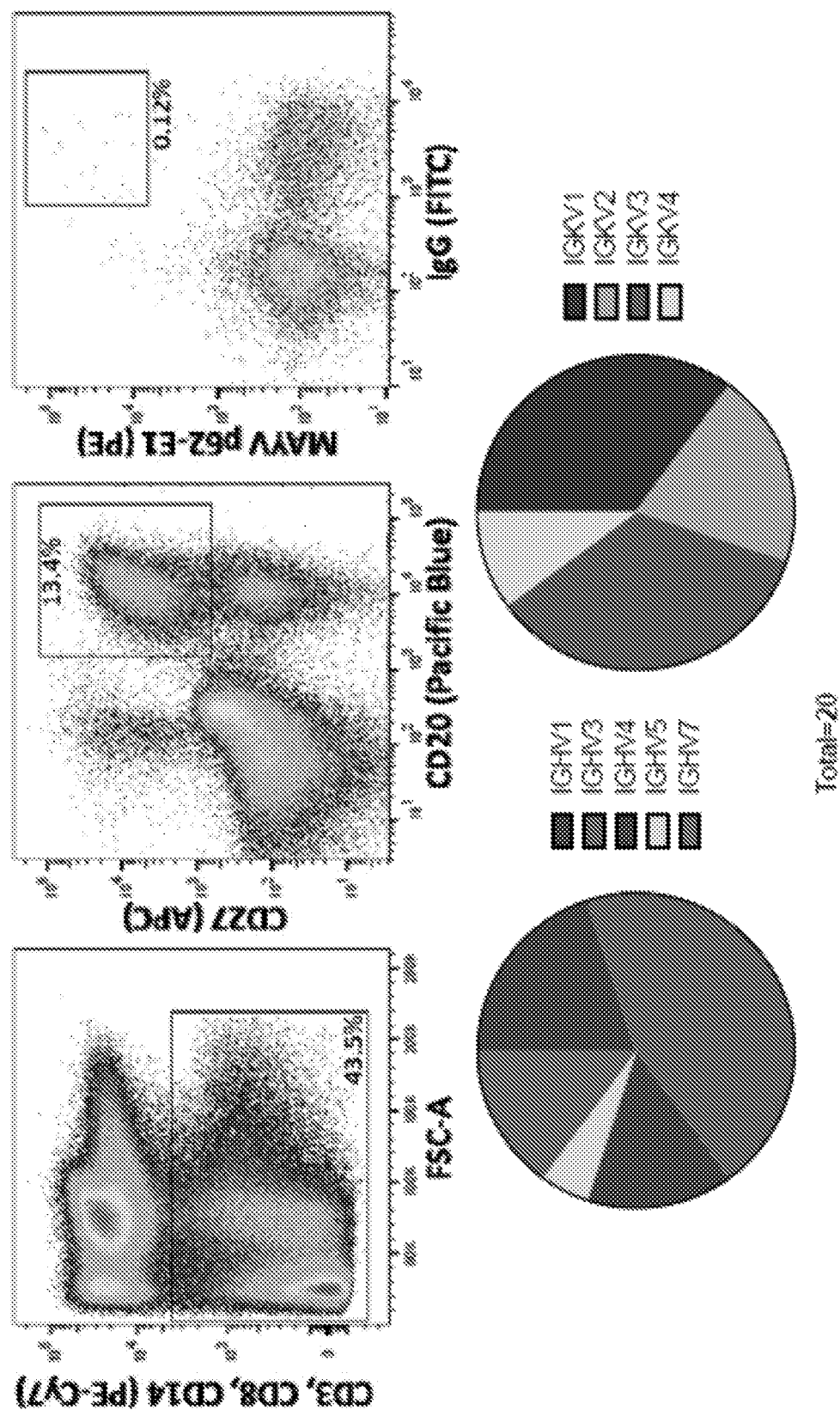
FIG. 14 shows sorting MAYV-reactive B cells from DC2. (Top) Gating strategy for isolation of antigen-reactive IgG memory B cells. (Bottom) Distribution of IGHV and IGKV families of 20 isolated mAbs.
Figure 15:
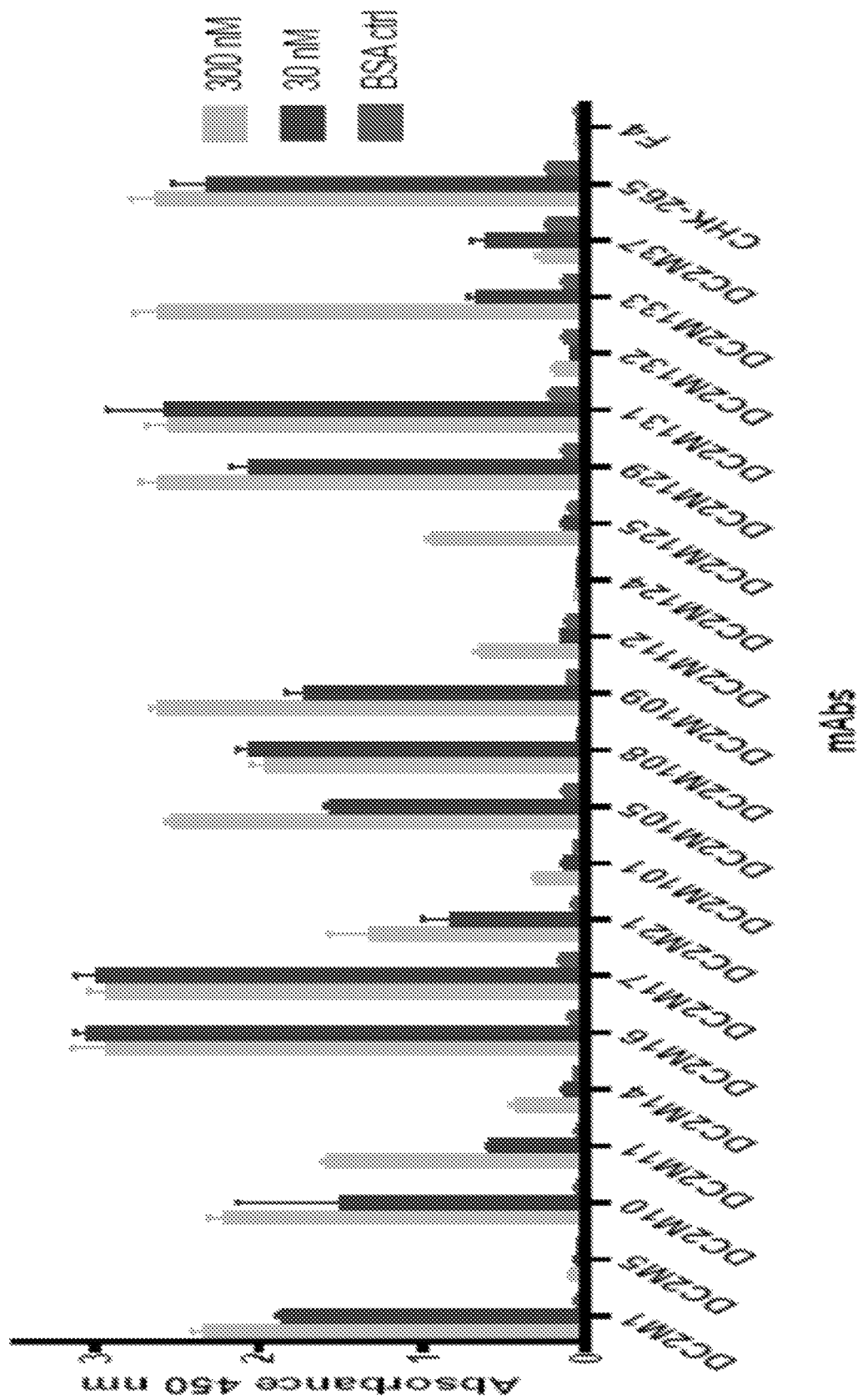
FIG. 15 shows MAYV p62-E1 ELISA of mAbs from DC2. Binding ELISA of immobilized MAYV p62-E1 to mAb panel at 300 nM and 30 nM. Reactivity of mAbs to BSA is shown as a negative control.
Figure 16:
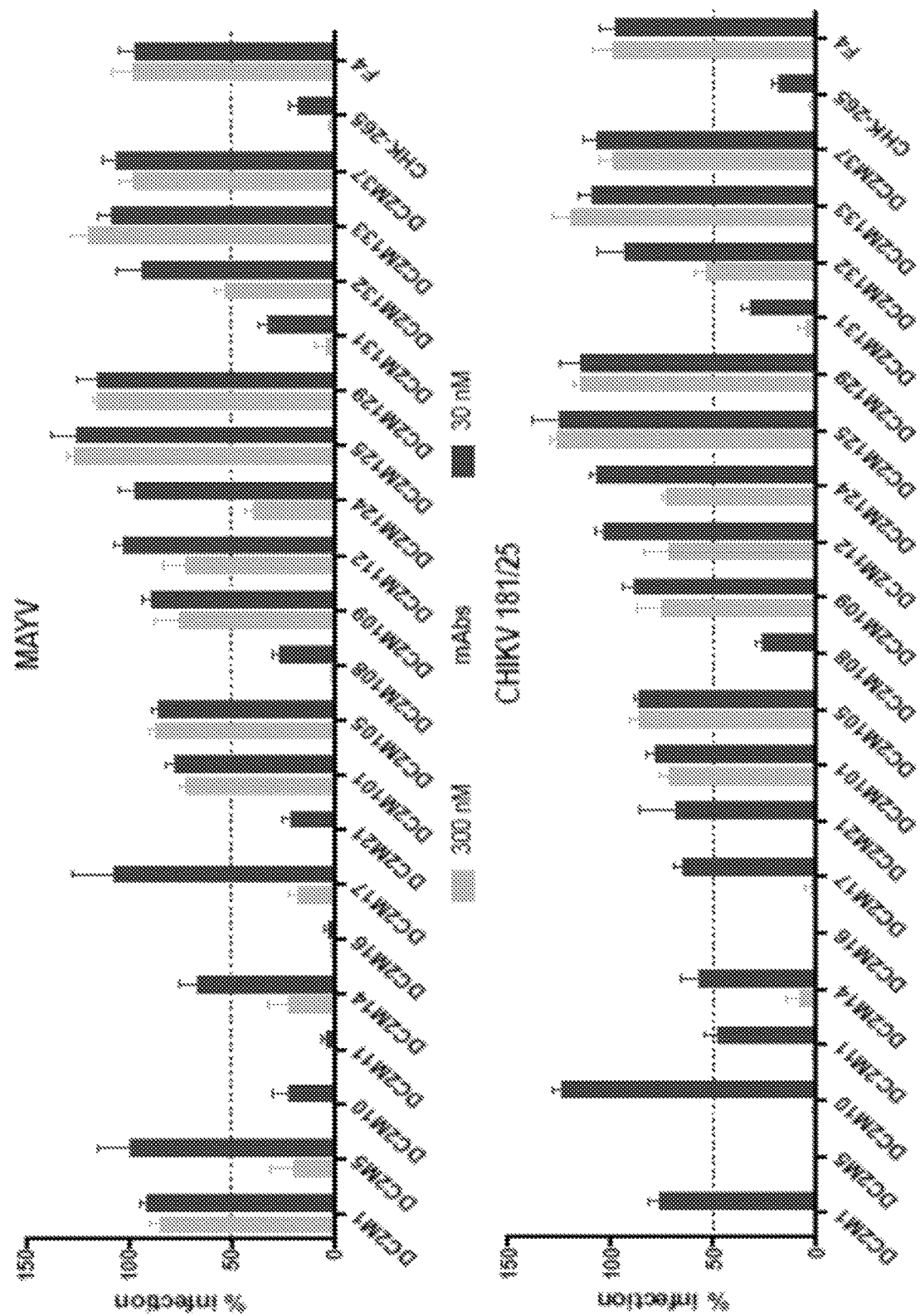
FIG. 16 shows neutralization of MAYV and CHIKV 181/25 by cross-reactive human mAbs. Focus Reduction Neutralization Test assay performed with 300 nM and 30 nM of each mAb with MAYV (top) and CHIKV 181/25 vaccine strain (bottom). CHK265 and F4 are positive and negative control mAbs, respectively.
Figure 17:
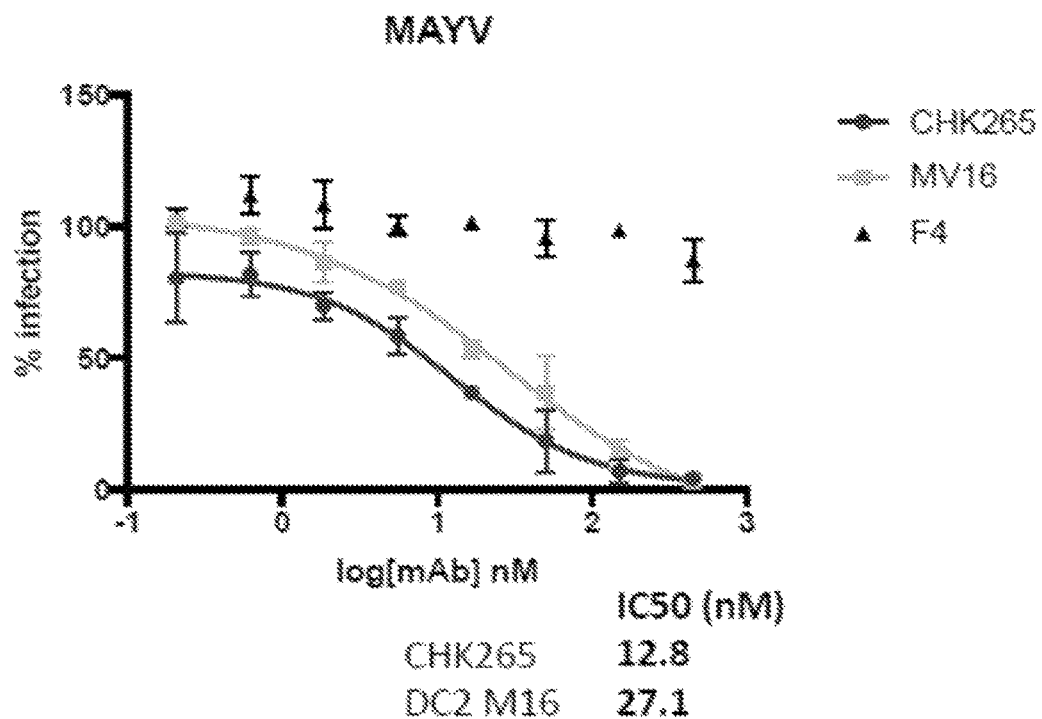
FIG. 17 shows MAYV neutralization curve by DC2 M16. Focus Reduction Neutralization Test assay was performed for DC2 M16 mAb against MAYV and the IC50 determined. CHK265 and F4 are positive and negative control mAbs, respectively.
Figure 18:
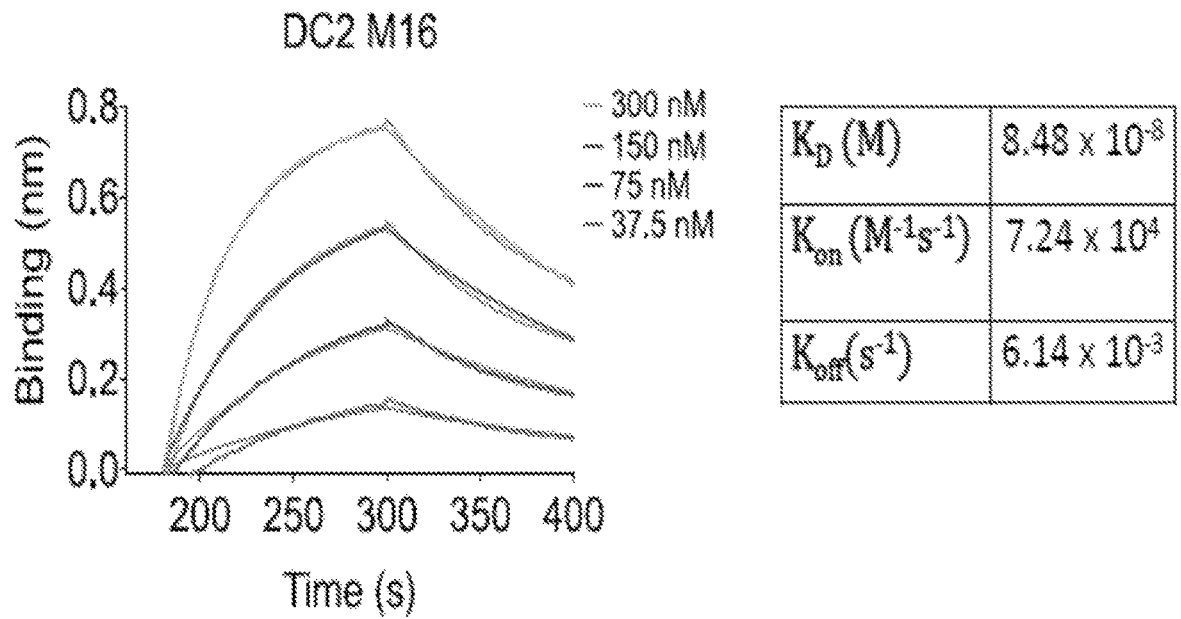
FIG. 18 shows DC2 M16 binding kinetics by BLI. Binding kinetics of mAb DC2 M16 to MAYV p62-E1 were determined by bio-layer interferometry (BLI).
Figure 19:
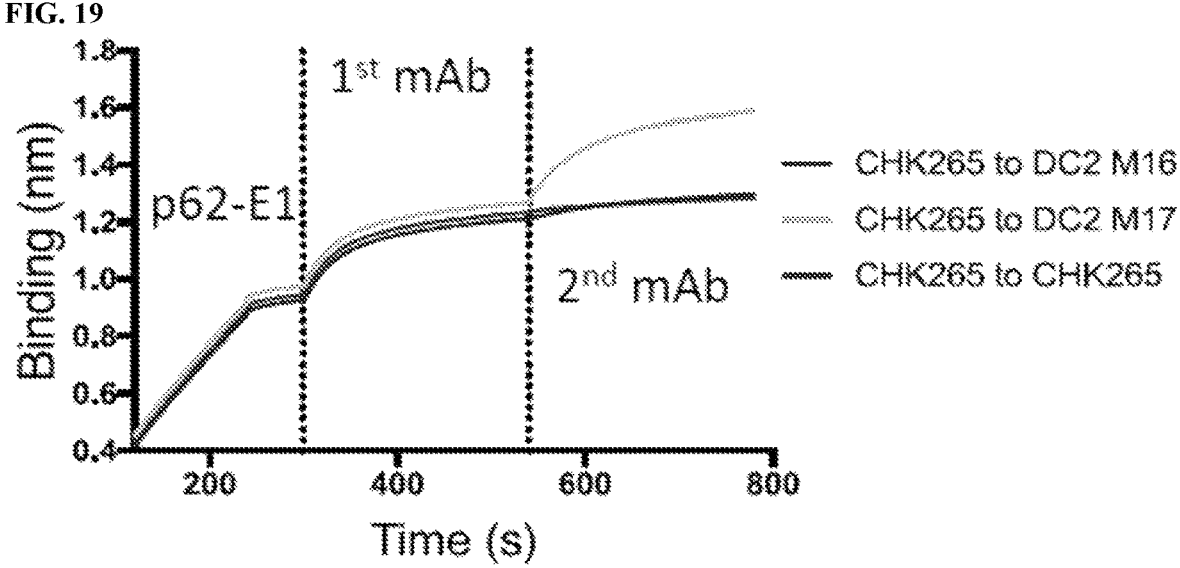
FIG. 19 shows epitope binning of cross-neutralizing mAbs. Two-phase binding by BLI of DC2 M16 and M17 against CHK265 bound to immobilized MAYV p62-E1 antigen.

Recognition requirements of DC2.271B. Given the highly protective properties of DC2.271B, we explored the recognition requirements of this mAb in the context of the isolated glycoprotein and viral particle. The antigen-binding fragment (Fab) of DC2.271B was generated by papain digestion, and then the complex of Fab with p62-E1 was purified. Both the p62-E1 hybrid protein alone as well as the p62-E1/DC2.271B complex (1:1) were visualized by negative stain electron microscopy (FIGS. 11A and 11B), with the twisted β-plate architecture of the p62-E1 evident as well as the characteristic "hole" between the heavy and light chains of the DC2.271B Fab. Three-dimensional reconstruction from the p62-E1 and p62-E1/DC2.271B revealed that the Fab density appears offset to E3, near the B domain (FIG. 11B). This structural model is consistent with the location of the viral escape mutation (VSV-CHIKV$^{E2-K233T}$). Together, these data indicate that the epitope for DC2.271B lies in the loop region between the β-connector and the B domain. This structural epitope is proximal to, but not occluded by E3, and in the reconstruction of the Fab/p62-E1 complex, density corresponding to what is presumably E3 abuts the Fab. Notably, viral escape rVSV-CHIKV$^{E2-K233T}$ 's proximal to E3 yet E3 does not sterically block binding of DC2.271B. To examine effects of bivalent binding of IgG, the DC2.271B Fab was tested for neutralization against CHIKV 181/25 and found to have neutralizing activity, but showed a 30-fold reduced potency relative to the intact IgG (FIG. 11C). Thus, bivalent crosslinking of epitopes from adjacent subunits is not a requirement for neutralization by DC2.271B.

The data in FIGS. 12-19 suggest that cross-neutralizing mAbs against distinct alphaviruses can be isolated from human patients with previous alphavirus infection. More specifically, a CHIKV-infected patient was found to have cross-reactive mAbs that could neutralize a related alphavirus, Mayaro. These mAbs come from diverse V gene families and have differential binding and neutralization capacity against CHIKV and MAYV.

REFERENCES

1 Jose, J., Snyder, J. E. & Kuhn, R. J. A structural and functional perspective of alphavirus replication and assembly. *Future microbiology* 4, 837-856, doi:10.2217/fmb.09.59 (2009).
2 Sourisseau, M. et al. Characterization of reemerging chikungunya virus. *PLoS pathogens* 3, e89, doi:10.1371/journal.ppat.0030089 (2007).
3 Schuffenecker, I. et al. Genome microevolution of chikungunya viruses causing the Indian Ocean outbreak. *PLoS medicine* 3, e263, doi:10.1371/journal.pmed.0030263 (2006).
4 Morrison, T. E. Reemergence of chikungunya virus. *Journal of virology* 88, 11644-11647, doi:10.1128/jvi.01432-14 (2014).
5 Tsetsarkin, K. A., Vanlandingham, D. L., McGee, C. E. & Higgs, S. A single mutation in chikungunya virus affects vector specificity and epidemic potential. *PLoS pathogens* 3, e201, doi:10.1371/journal.ppat.0030201 (2007).
6 Kraemer, M. U. et al. The global distribution of the arbovirus vectors *Aedes aegypti* and *Ae. albopictus. eLife* 4, e08347, doi:10.7554/eLife.08347 (2015).
7 Sanchez-San Martin, C., Liu, C. Y. & Kielian, M. Dealing with low pH: entry and exit of alphaviruses and flaviviruses. *Trends in microbiology* 17, 514-521, doi:10.1016/j.tim.2009.08.002 (2009).
8 Voss, J. E. et al. Glycoprotein organization of Chikungunya virus particles revealed by X-ray crystallography. *Nature* 468, 709-712, doi:10.1038/nature09555 (2010).
9 Long, F. et al. Cryo-EM structures elucidate neutralizing mechanisms of anti-chikungunya human monoclonal antibodies with therapeutic activity. *Proceedings of the National Academy of Sciences of the United States of America* 112, 13898-13903, doi:10.1073/pnas.1515558112 (2015).
10 Sun, S. et al. Structural analyses at pseudo atomic resolution of Chikungunya virus and antibodies show mechanisms of neutralization. *eLife* 2, e00435, doi:10.7554/eLife.00435 (2013).
11 Uchime, O., Fields, W. & Kielian, M. The role of E3 in pH protection during alphavirus assembly and exit. *Journal of virology* 87, 10255-10262, doi:10.1128/jvi.01507-13 (2013).
12 Caskey, M. et al. Viraemia suppressed in HIV-1-infected humans by broadly neutralizing antibody 3BNC117. *Nature* 522, 487-491, doi:10.1038/nature14411 (2015).
13 Tiller, T. et al. Efficient generation of monoclonal antibodies from single human B cells by single cell RT-PCR and expression vector cloning. *Journal of immunological methods* 329, 112-124, doi:10.1016/j.jim.2007.09.017 (2008).
14 Ledgerwood, J. E. et al. Safety, pharmacokinetics and neutralization of the broadly neutralizing HIV-1 human monoclonal antibody VRC01 in healthy adults. *Clinical and experimental immunology* 182, 289-301, doi:10.1111/cei.12692 (2015).
15 Dejnirattisai, W. et al. A new class of highly potent, broadly neutralizing antibodies isolated from viremic patients infected with dengue virus. *Nature immunology* 16, 170-177, doi:10.1038/ni.3058 (2015).

16 Rouvinski, A. et al. Recognition determinants of broadly neutralizing human antibodies against dengue viruses. *Nature* 520, 109-113, doi:10.1038/nature14130 (2015).
17 Bornholdt, Z. A. et al. Isolation of potent neutralizing antibodies from a survivor of the 2014 Ebola virus outbreak. *Science* (New York, N.Y.) 351, 1078-1083, doi:10.1126/science.aad5788 (2016).
18 Chang, L. J. et al. Safety and tolerability of chikungunya virus-like particle vaccine in healthy adults: a phase 1 dose-escalation trial. *Lancet* (London, England) 384, 2046-2052, doi:10.1016/s0140-6736(14)61185-5 (2014).
19 Edelman, R. et al. Phase II safety and immunogenicity study of live chikungunya virus vaccine TSI-GSD-218. *The American journal of tropical medicine and hygiene* 62, 681-685 (2000).
20 Fric, J., Bertin-Maghit, S., Wang, C. I., Nardin, A. & Warter, L. Use of human monoclonal antibodies to treat Chikungunya virus infection. *The Journal of infectious diseases* 207, 319-322, doi:10.1093/infdis/jis674 (2013).
21 Jin, J. et al. Neutralizing Monoclonal Antibodies Block Chikungunya Virus Entry and Release by Targeting an Epitope Critical to Viral Pathogenesis. *Cell reports* 13, 2553-2564, doi:10.1016/j.celrep.2015.11.043 (2015).
22 Pal, P. et al. Development of a Highly Protective Combination Monoclonal Antibody Therapy against Chikungunya Virus. *PLoS pathogens* 9, e1003312, doi:10.1371/journal.ppat.1003312 (2013).
23 Selvarajah, S. et al. A neutralizing monoclonal antibody targeting the acid-sensitive region in chikungunya virus E2 protects from disease. *PLoS neglected tropical diseases* 7, e2423, doi:10.1371/journal.pntd.0002423 (2013).
24 Smith, S. A. et al. Isolation and Characterization of Broad and Ultrapotent Human Monoclonal Antibodies with Therapeutic Activity against Chikungunya Virus. *Cell host & microbe* 18, 86-95, doi:10.1016/j.chom.2015.06.009 (2015).
25 Warter, L. et al. Chikungunya virus envelope-specific human monoclonal antibodies with broad neutralization potency. *Journal of immunology* (Baltimore, Md.: 1950) 186, 3258-3264, doi:10.4049/jimmunol.1003139 (2011).
26 Hunt, A. R. et al. Treatment of mice with human monoclonal antibody 24 h after lethal aerosol challenge with virulent Venezuelan equine encephalitis virus prevents disease but not infection. *Virology* 414, 146-152, doi:10.1016/j.virol.2011.03.016 (2011).
27 O'Brien, L. M., Goodchild, S. A., Phillpotts, R. J. & Perkins, S. D. A humanised murine monoclonal antibody protects mice from Venezuelan equine encephalitis virus, Everglades virus and Mucambo virus when administered up to 48 h after airborne challenge. *Virology* 426, 100-105, doi:10.1016/j.virol.2012.01.038 (2012).
28 Fox, J. M. et al. Broadly Neutralizing Alphavirus Antibodies Bind an Epitope on E2 and Inhibit Entry and Egress. *Cell* 163, 1095-1107, doi:10.1016/j.cell.2015.10.050 (2015).
29 Fong, R. H. et al. Exposure of epitope residues on the outer face of the chikungunya virus envelope trimer determines antibody neutralizing efficacy. *Journal of virology* 88, 14364-14379, doi:10.1128/jvi.01943-14 (2014).
30 Hunt, A. R. & Roehrig, J. T. Biochemical and biological characteristics of epitopes on the E1 glycoprotein of western equine encephalitis virus. *Virology* 142, 334-346 (1985).

---

What is claimed is:

1. An anti-Chikungunya (CHIKV) antibody or CHIKV-binding fragment thereof, wherein said antibody or fragment thereof comprises:
   (1) a heavy chain comprising (i) a CDR1, CDR2, and CDR3 as set forth in any one heavy chain row of Table 1;
   (2) and a light chain comprising (i) a CDR1, CDR2, and CDR3 as set forth in any one light chain row of Table 1, which light chain row belongs to the same laboratory designated antibody as the heavy chain row in (1).

2. The anti-CHIKV antibody of claim 1, comprising a non-naturally occurring Fc region.

3. The anti-CHIKV antibody of claim 1, comprising a mutated human Fc region.

4. The anti-CHIKV antibody of claim 1, which is an Immunoglobulin G type antibody.

5. The anti-CHIKV antibody, or CHIKV-binding fragment thereof, of claim 1, wherein the antibody, or CHIKV-binding fragment thereof, binds an CHIKV or both CHIKV/MAYV with a binding affinity (KD) of from about 0.005 nM to 100 nM.

6. The anti-CHIKV antibody, or CHIKV-binding fragment thereof, of claim 1, which is a monoclonal antibody.

7. The anti-CHIKV antibody, or CHIKV-binding fragment thereof, of claim 1, which is a recombinant antibody.

8. The CHIKV-binding fragment of claim 1, which is an Fab, F(ab)2 or scFv.

9. A method for inhibiting a CHIKV or MAYV infection in a subject, the method comprising administering an anti-CHIKV antibody or anti-CHIKV antigen-binding fragment thereof of claim 1 in an amount effective to inhibit the infection in the subject.

10. The method of claim 9, wherein the antibody binds a Chikungunya virus E2, p62, E1, p62-E1 hybrid protein, or E1-E2 glycoprotein.

11. The method of claim 9, wherein the method is for inhibiting Chikungunya virus infection.

12. The method of claim 9, wherein the method is for inhibiting Mayaro virus infection.

13. The method of claim 9, wherein the method is for inhibiting O'nyong'nyong virus infection and comprises administering the anti-CHIKV antibody or CHIKV-binding fragment of claim 2, wherein said antibody fragment thereof comprises: (i) a heavy chain comprising the CDRs set forth in GFTFSDYF (SEQ ID NO: 641), ISDNGNTI (SEQ ID NO: 642), and ARGLYIQSDAFDL (SEQ ID NO: 643); and a light chain comprising the CDRs set forth in QGLSNS (SEQ ID NO: 644), AAS (SEQ ID NO: 645), and QQYYN-TPPIT (SEQ ID NO: 646), or (ii) a heavy chain comprising the CDRs set forth in GFTFTDYY (SEQ ID NO:923), ISPSGSTI (SEQ ID NO:924), and ARGIYYQSDAFDT (SEQ ID NO: 925); and a light chain comprising the CDRs set forth in QVIRNS (SEQ ID NO:926), AAS (SEQ ID NO:927), and QQYYSTPPIT (SEQ ID NO:928).

14. An isolated nucleic acid molecule encoding the antibody, or binding fragment thereof, of claim 1.

15. A vector comprising the nucleic acid molecule of claim 14.

16. An isolated host cell comprising the vector of claim 15.

17. A method of producing an anti-CHIKV antibody comprising culturing the isolated host cell of claim 16, under conditions wherein the anti-CHIKV antibody is produced by the isolated host cell.

18. A pharmaceutical composition comprising an anti-CHIKV antibody, or CHIKV-binding fragment thereof, of claim 1, and a pharmaceutically acceptable excipient.

19. The anti-CHIKV antibody or CHIKV-binding fragment of claim 1, wherein said antibody or fragment thereof comprises:

(1) a heavy chain comprising the CDRs set forth in GFSFDDYV (SEQ ID NO:199), ISWDGDST (SEQ ID NO:200), and ARSLADYLNYYHYTMDV (SEQ ID NO:201); and a light chain comprising the CDRs set forth in QSVLYSSSNKSY (SEQ ID NO:202), WAS (SEQ ID NO:203), and QQYYSTPYT (SEQ ID NO:204);

(2) a heavy chain comprising the CDRs set forth in GVSFGSYS (SEQ ID NO:46), ISSSSSRI (SEQ ID NO:47), and ARLDDFWSGYIVD (SEQ ID NO:48); and a light chain comprising the CDRs set forth in QSVDSN (SEQ ID NO:49); RAS (SEQ ID NO:50), and QEYNTWPPYT (SEQ ID NO:51);

(3) a heavy chain comprising the CDRs set forth in GFSLNTSGVT (SEQ ID NO:130), IYWDGDK (SEQ ID NO:131), and SYTSYKYFDVDV (SEQ ID NO:132); and a light chain comprising the CDRs set forth in QSGNNY (SEQ ID NO:133), DTS (SEQ ID NO:134), and QQRSNWPRT (SEQ ID NO:135);

(4) a heavy chain comprising the CDRs set forth in GYSFSSYS (SEQ ID NO: 106), IYPGDSYT (SEQ ID NO: 107), and VRGMATNN (SEQ ID NO: 108); and a light chain comprising the CDRs set forth in QTLVHSDGNTY (SEQ ID NO: 109), KIS (SEQ ID NO: 110), and MQATHFPWT (SEQ ID NO: 111);

(5) a heavy chain comprising the CDRs set forth in TGSISSSSYY (SEQ ID NO: 16), MYNSGRP (SEQ ID NO: 17), and ARGRVYCDGDCHDDAFD (SEQ ID NO: 18); and a light chain comprising the CDRs set forth in QNVLYSSNNKNY (SEQ ID NO: 19), WAS (SEQ ID NO: 20), and QQYYSTPYT (SEQ ID NO: 21);

(6) a heavy chain comprising the CDRs set forth in EYIFNRYG (SEQ ID NO: 22), ITVSGTTI (SEQ ID NO: 23), and VKGPFSNKNFDI (SEQ ID NO: 24); and a light chain comprising the CDRs set forth in QDISIY (SEQ ID NO: 25), DAS (SEQ ID NO: 26), and QQHNSRPYS (SEQ ID NO: 27);

(7) a heavy chain comprising the CDRs set forth in GFTFSAHY (SEQ ID NO: 205), ISSRGSTI (SEQ ID NO: 206), and AGAITWNDVFFWY (SEQ ID NO: 207); and a light chain comprising the CDRs set forth in QSLVHSDGNTY (SEQ ID NO: 208), KVS (SEQ ID NO: 209), and MQATQFLWT (SEQ ID NO: 210); or (8) a heavy chain comprising the CDRs set forth in GLTLKNYA (SEQ ID NO: 412), ISFDGTYK (SEQ ID NO: 413), and ARGPQLYSHQPAKFGDLLFGAFDI (SEQ ID NO: 414); and a light chain comprising the CDRs set forth in QDVSHY (SEQ ID NO: 415), DTS (SEQ ID NO: 416), and QQYDTLPLT (SEQ ID NO: 417).

20. The anti-CHIKV antibody or CHIKV-binding fragment of claim 1, wherein said antibody or fragment thereof comprises:

(1) a heavy chain comprising (i) the CDRS set forth in GFGVNNNY (SEQ ID NO:166), IYAGGNT (SEQ ID NO:167), and AREVVPTAMGGFDL (SEQ ID NO:168), or (ii) GGSISNYY (SEQ ID NO:169), MYYSGST (SEQ ID NO:170), and ARSYCDIANCYTFDL (SEQ ID NO: 171); and a light chain comprising the CDRS set forth in QVTSGY (SEQ ID NO:172), AAS (SEQ ID NO:173), and QQLNSNPLVYT (SEQ ID NO:174);

(2) a heavy chain comprising the CDRs set forth in GYTFHRYG (SEQ ID NO:1), ISVYTGNT (SEQ ID NO:2), and ATEPNIILSYFHH (SEQ ID NO:3); and a light chain comprising the CDRs set forth in QEISAN (SEQ ID NO:4), AAS (SEQ ID NO:5), and QQSYNTPRT (SEQ ID NO: 6);

(3) a heavy chain comprising the CDRs set forth in GFTFSSYW (SEQ ID NO:175), INSDGSSI (SEQ ID NO:176), and LTTSRFGAFDM (SEQ ID NO:177); and a light chain comprising the CDRs set forth in QSLLHSNGYNY (SEQ ID NO:178), LGS (SEQ ID NO:179), and MQALQTPYT (SEQ ID NO:180);

(4) a heavy chain comprising the CDRs set forth in GFSLTTPGVG (SEQ ID NO:538), IFWNDEK (SEQ ID NO:539), and AHSRLDLWNGYK (SEQ ID NO:540); and a light chain comprising the CDRs set forth in QSLLHINGYTY (SEQ ID NO:541), LGS (SEQ ID NO:542), and MQALQTPRT (SEQ ID NO:543);

(5) a heavy chain comprising the CDRs set forth in GFTFSDYY (SEQ ID NO:725), ISTSGSTM (SEQ ID NO:726), and ARGIYYQSDAFDI (SEQ ID NO:727); and a light chain comprising the CDRs set forth in QGISNS (SEQ ID NO:728), AAS (SEQ ID NO:729), and QQYYSTPPMT (SEQ ID NO:730);

(6) a heavy chain comprising the CDRs set forth in GESFSGYY (SEQ ID NO: 472), INHSGST (SEQ ID NO: 473), and ARGYADTPVFRRAAAAGMDV (SEQ ID NO: 474); and a light chain comprising the CDRs set forth in QSISSY (SEQ ID NO: 475), GAS (SEQ ID NO: 476), and LQSYSSWT (SEQ ID NO: 477);

(7) a heavy chain comprising the CDRs set forth in GFAFSDYA (SEQ ID NO: 490), ISYAGNNK (SEQ ID NO: 491), and ARPFSRGWFEGCDS (SEQ ID NO: 492); and a light chain comprising the CDRs set forth in QTINDF (SEQ ID NO: 493), SAS (SEQ ID NO: 494), and QQSYIAPLT (SEQ ID NO: 495);

(8) a heavy chain comprising the CDRs set forth in GYTFTNYY (SEQ ID NO: 617), IYPSGGDT (SEQ ID NO: 618), and ARDHLNRDSSSRGFMDY (SEQ ID NO: 619); and a light chain comprising the CDRs set forth in QSISHY (SEQ ID NO: 620), DAS (SEQ ID NO: 621), and QQRGTWPPS (SEQ ID NO: 622);

(9) a heavy chain comprising the CDRs set forth in GFTFSDYF (SEQ ID NO: 641), ISDNGNTI (SEQ ID NO: 642), and ARGLYIQSDAFDL (SEQ ID NO: 643); and a light chain comprising the CDRs set forth in QGLSNS (SEQ ID NO: 644), AAS (SEQ ID NO: 645), and QQYYNTPPIT (SEQ ID NO: 646);

(10) a heavy chain comprising the CDRs set forth in GENFNIFP (SEQ ID NO: 653), ISDDVTKK (SEQ ID NO: 654), and ARASGWQRTGTKYYYY (SEQ ID NO: 655); and a light chain comprising the CDRs set forth in QDISNN (SEQ ID NO: 656), DAS (SEQ ID NO: 657), and LQYDNLPYS (SEQ ID NO: 658);

(11) a heavy chain comprising the CDRs set forth in GGSISGYF (SEQ ID NO: 671), VHYSGST (SEQ ID NO: 672), and ARASTSGGFDP (SEQ ID NO: 673); and a light chain comprising the CDRs set forth in QSVSSN (SEQ ID NO: 674), GAS (SEQ ID NO: 675), and QHYINRPGRT (SEQ ID NO: 676);

(12) a heavy chain comprising the CDRs set forth in GFTFSDYY (SEQ ID NO: 689), ISISGSTI (SEQ ID NO: 690), and ARGIYHQSDAFDI (SEQ ID NO: 691); and a light chain comprising the CDRs set forth in QGISNS (SEQ ID NO: 692), AAS (SEQ ID NO: 693), and QQYYSTPPIT (SEQ ID NO: 694);

(13) a heavy chain comprising the CDRs set forth in RFIFSNFG (SEQ ID NO: 713), IRSDGSNE (SEQ ID NO: 714), and AKGCCGGVPDFGLDV (SEQ ID NO: 715); and a light chain comprising the CDRs set forth in QSLVHRDGSTY (SEQ ID NO: 716), QVS (SEQ ID NO: 717), and MQATHWGYT (SEQ ID NO: 718);

(14) a heavy chain comprising the CDRs set forth in GYTFTSSY (SEQ ID NO: 737), IYPSGGNT (SEQ ID NO: 738), and ARDHLNRDSTSRGFIDS (SEQ ID NO: 739); and a light chain comprising the CDRs set forth in QSVGNY (SEQ ID NO: 740), DAS (SEQ ID NO: 741), and EQRGDWPLT (SEQ ID NO: 742);

(15) a heavy chain comprising the CDRs set forth in GGSMSSGDYY (SEQ ID NO: 82), ISYSGSA (SEQ ID NO: 83), and ARVFSGYYYSDY (SEQ ID NO: 84); and a light chain comprising the CDRs set forth in QSISSW (SEQ ID NO: 85), KAS (SEQ ID NO: 86), and QQYNTYPWT (SEQ ID NO: 87);

(16) a heavy chain comprising the CDRs set forth in GYTFNNHY (SEQ ID NO: 118), IAPSGDNT (SEQ ID NO: 119), and ARDQLNRHSTNRGFFDL (SEQ ID NO: 120); and a light chain comprising the CDRs set forth in QSVGSY (SEQ ID NO: 121), DAS (SEQ ID NO: 122), and HQRGNWPPS (SEQ ID NO: 123);

(17) a heavy chain comprising the CDRs set forth in GFIFDDHA (SEQ ID NO: 142), ISWNSGDI (SEQ ID NO: 143), and VKDTPYCGGGGCLNWFD (SEQ ID NO: 144); and a light chain comprising the CDRs set forth in QSLLHSNGYNY (SEQ ID NO: 145), LGS (SEQ ID NO: 146), and MQTLQTPRT (SEQ ID NO: 147);

(18) a heavy chain comprising the CDRs set forth in GYTLTRFA (SEQ ID NO: 181), INTNTGNP (SEQ ID NO: 182), and ARDGYNHGYNDL (SEQ ID NO: 183); and a light chain comprising the CDRs set forth in QSVSSE (SEQ ID NO: 184), DAS (SEQ ID NO: 185), and QQRSSWPLFT (SEQ ID NO: 186);

(19) a heavy chain comprising the CDRs set forth in GFTFSSYE (SEQ ID NO: 466), TNHSGSTI (SEQ ID NO: 467), and AREHYDILTGFGGYLDY (SEQ ID NO: 468); and a light chain comprising the CDRs set forth in QSVSNN (SEQ ID NO: 469), GAS (SEQ ID NO: 470), and QQYNDWPRWT (SEQ ID NO: 471); or

(20) a heavy chain comprising the CDRs set forth in GFSFSDYY (SEQ ID NO: 253), IYSGGST (SEQ ID NO: 254), and ARAPSWGLRVGPFDF (SEQ ID NO: 255); and a light chain comprising the CDRs set forth in RSINSY (SEQ ID NO: 256), AAS (SEQ ID NO: 257), and HQTYTTPPGT (SEQ ID NO: 258).

21. The anti-CHIKV antibody or CHIKV-binding fragment of claim 20, wherein said antibody or fragment thereof comprises:
a heavy chain comprising (i) the CDRS set forth in GFGVNNNY (SEQ ID NO:166), IYAGGNT (SEQ ID NO:167), and AREVVPTAMGGFDL (SEQ ID NO:168); and
a light chain comprising the CDRS set forth in QVTSGY (SEQ ID NO:172), AAS (SEQ ID NO: 173), and QQLNSNPLVYT (SEQ ID NO:174).

22. The anti-CHIKV antibody or CHIKV-binding fragment of claim 20, wherein said antibody or fragment thereof comprises:
a heavy chain comprising the CDRs set forth in GYTFNNHY (SEQ ID NO: 118), IAPSGDNT (SEQ ID NO: 119), and ARDQLNRHSTNRGFFDL (SEQ ID NO: 120); and
a light chain comprising the CDRs set forth in QSVGSY (SEQ ID NO: 121), DAS (SEQ ID NO: 122), and HQRGNWPPS (SEQ ID NO: 123).

23. The anti-CHIKV antibody or CHIKV-binding fragment of claim 20, wherein said antibody or fragment thereof comprises:
a heavy chain comprising the CDRs set forth in GFTFSDYY (SEQ ID NO:725), ISTSGSTM (SEQ ID NO:726), and ARGIYYQSDAFDI (SEQ ID NO:727); and
a light chain comprising the CDRs set forth in QGISNS (SEQ ID NO:728), AAS (SEQ ID NO: 729), and QQYYSTPPMT (SEQ ID NO:730).

24. The anti-CHIKV antibody or CHIKV-binding fragment of claim 20, wherein said antibody or fragment thereof comprises:
a heavy chain comprising the CDRs set forth in GFTFSDYF (SEQ ID NO: 641), ISDNGNTI (SEQ ID NO: 642), and ARGLYIQSDAFDL (SEQ ID NO: 643); and
a light chain comprising the CDRs set forth in QGLSNS (SEQ ID NO: 644), AAS (SEQ ID NO: 645), and QQYYNTPPIT (SEQ ID NO: 646).

25. The anti-CHIKV antibody or CHIKV-binding fragment of claim 20, wherein said antibody or fragment thereof comprises:
a heavy chain comprising the CDRs set forth in GFSLTTPGVG (SEQ ID NO:538), IFWNDEK (SEQ ID NO:539), and AHSRLDLWNGYK (SEQ ID NO:540); and
a light chain comprising the CDRs set forth in QSLLHINGYTY (SEQ ID NO:541), LGS (SEQ ID NO:542), and MQALQTPRT (SEQ ID NO:543).

26. The anti-CHIKV antibody or CHIKV-binding fragment of claim 19, wherein said antibody or fragment thereof comprises:
a heavy chain comprising the CDRs set forth in GFSLNTSGVT (SEQ ID NO:130), IYWDGDK (SEQ ID NO:131), and SYTSYKYFDVDV (SEQ ID NO:132); and
a light chain comprising the CDRs set forth in QSGNNY (SEQ ID NO:133), DTS (SEQ ID NO: 134), and QQRSNWPRT (SEQ ID NO:135).

* * * * *

SEQUENCE LISTING

<160> NUMBER OF SEQ ID NOS: 1018

<210> SEQ ID NO 1
<211> LENGTH: 8
<212> TYPE: PRT
<213> ORGANISM: Artificial Sequence
<220> FEATURE:
<223> OTHER INFORMATION: synthetic peptide

<400> SEQUENCE: 1

Gly Tyr Thr Phe His Arg Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Ile Ser Val Tyr Thr Gly Asn Thr
1               5

<210> SEQ ID NO 3
<211> LENGTH: 13
<212> TYPE: PRT
<213> ORGANISM: Artificial Sequence
<220> FEATURE:
<223> OTHER INFORMATION: synthetic peptide

```
<400> SEQUENCE: 3

Ala Thr Glu Pro Asn Ile Ile Leu Ser Tyr Phe His His
1               5                   10

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Gln Glu Ile Ser Ala Asn
1               5

<210> SEQ ID NO 5
<211> LENGTH: 3
<212> TYPE: PRT
<213> ORGANISM: Artificial Sequence
<220> FEATURE:
<223> OTHER INFORMATION: synthetic peptide

<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Gln Gln Ser Tyr Asn Thr Pro Arg Thr
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic peptide

<400> SEQUENCE: 7

Gly Phe Thr Phe Ser Ser Tyr Trp
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic peptide

<400> SEQUENCE: 8

Ile Asn Ser Asp Gly Ser Ser Ile
1               5

<210> SEQ ID NO 9
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 9

Leu Thr Thr Ser Arg Phe Gly Ala Phe Asp Met
1               5                   10

<210> SEQ ID NO 10
<211> LENGTH: 8
<212> TYPE: PRT
<213> ORGANISM: Artificial Sequence
<220> FEATURE:
<223> OTHER INFORMATION: synthetic peptide

<400> SEQUENCE: 10

Gly Phe Thr Phe Ser Asp Tyr Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: synthetic peptide

<400> SEQUENCE: 11

Ile Arg Asp Lys Gly Asn Ser Tyr Ile Thr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: synthetic peptide

<400> SEQUENCE: 12

Val Arg Ser Tyr Asn Pro Gly Arg Gly Gly Asn Ser Asp Tyr Met Asp
1               5                   10                  15

Phe

<210> SEQ ID NO 13
<211> LENGTH: 6
<212> TYPE: PRT
<213> ORGANISM: Artificial Sequence
<220> FEATURE:
<223> OTHER INFORMATION: synthetic peptide

<400> SEQUENCE: 13

Gln Ser Ile Ser Asn Trp
1               5

<210> SEQ ID NO 14
<211> LENGTH: 3
<212> TYPE: PRT
<213> ORGANISM: Artificial Sequence
<220> FEATURE:
<223> OTHER INFORMATION: synthetic peptide

<400> SEQUENCE: 14

Lys Ala Ser
1

<210> SEQ ID NO 15
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 15

Gln Gln Tyr Lys Ser Tyr Pro Trp Thr
1               5

<210> SEQ ID NO 16
<211> LENGTH: 10
<212> TYPE: PRT
<213> ORGANISM: Artificial Sequence
<220> FEATURE:
<223> OTHER INFORMATION: synthetic peptide

<400> SEQUENCE: 16

Thr Gly Ser Ile Ser Ser Ser Ser Tyr Tyr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: synthetic peptide

<400> SEQUENCE: 17

Met Tyr Asn Ser Gly Arg Pro
1               5

<210> SEQ ID NO 18
<211> LENGTH: 18
<212> TYPE: PRT
<213> ORGANISM: Artificial Sequence
<220> FEATURE:
<223> OTHER INFORMATION: synthetic peptide

<400> SEQUENCE: 18

Ala Arg Gly Arg Val Tyr Cys Asp Gly Asp Cys His Asp Asp Ala Phe
1               5                   10                  15
Asp Ile

<210> SEQ ID NO 19
<211> LENGTH: 12
<212> TYPE: PRT
<213> ORGANISM: Artificial Sequence
<220> FEATURE:
<223> OTHER INFORMATION: synthetic peptide

<400> SEQUENCE: 19

Gln Asn Val Leu Tyr Ser Ser Asn Asn Lys Asn Tyr
1               5                   10

<210> SEQ ID NO 20
<211> LENGTH: 3
<212> TYPE: PRT
<213> ORGANISM: Artificial Sequence
<220> FEATURE:
<223> OTHER INFORMATION: synthetic peptide

<400> SEQUENCE: 20

Trp Ala Ser
1

<210> SEQ ID NO 21
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 21

Gln Gln Tyr Tyr Ser Thr Pro Tyr Thr
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic peptide

<400> SEQUENCE: 22

Glu Tyr Ile Phe Asn Arg Tyr Gly
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic peptide

<400> SEQUENCE: 23

Ile Thr Val Ser Gly Thr Thr Ile
1               5

<210> SEQ ID NO 24
<211> LENGTH: 12
<212> TYPE: PRT
<213> ORGANISM: Artificial Sequence
<220> FEATURE:
<223> OTHER INFORMATION: synthetic peptide

<400> SEQUENCE: 24

Val Lys Gly Pro Phe Ser Asn Lys Asn Phe Asp Ile
1               5                   10

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25

Gln Asp Ile Ser Ile Tyr
1               5

<210> SEQ ID NO 26
<211> LENGTH: 3
<212> TYPE: PRT
<213> ORGANISM: Artificial Sequence
<220> FEATURE:
<223> OTHER INFORMATION: synthetic peptide

<400> SEQUENCE: 26

Asp Ala Ser
1

<210> SEQ ID NO 27
<211> LENGTH: 9
<212> TYPE: PRT
<213> ORGANISM: Artificial Sequence
<220> FEATURE:
<223> OTHER INFORMATION: synthetic peptide
```

<400> SEQUENCE: 27

Gln Gln His Asn Ser Arg Pro Tyr Ser
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic peptide

<400> SEQUENCE: 28

Gly Phe Ile Phe Asp Asp Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic peptide

<400> SEQUENCE: 29

Ile Ser Trp Asn Ser Gly Asn Thr
1               5

<210> SEQ ID NO 30
<211> LENGTH: 18
<212> TYPE: PRT
<213> ORGANISM: Artificial Sequence
<220> FEATURE:
<223> OTHER INFORMATION: synthetic peptide

<400> SEQUENCE: 30

Ala Lys Asp Thr Asn Ala Val Val Ile Ala Thr Ser Ser His Ala Phe
1               5                   10                  15

Asp Ile

<210> SEQ ID NO 31
<211> LENGTH: 6
<212> TYPE: PRT
<213> ORGANISM: Artificial Sequence
<220> FEATURE:
<223> OTHER INFORMATION: synthetic peptide

<400> SEQUENCE: 31

Gln Asn Ile Asn Asn Tyr
1               5

<210> SEQ ID NO 32
<211> LENGTH: 3
<212> TYPE: PRT
<213> ORGANISM: Artificial Sequence
<220> FEATURE:
<223> OTHER INFORMATION: synthetic peptide

<400> SEQUENCE: 32

Ala Ala Ser
1

<210> SEQ ID NO 33
<211> LENGTH: 9
<212> TYPE: PRT
<213> ORGANISM: Artificial Sequence
<220> FEATURE:

```
<223> OTHER INFORMATION: synthetic peptide

<400> SEQUENCE: 33

Gln Gln Ser Tyr Gly Ser Pro Tyr Thr
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic peptide

<400> SEQUENCE: 34

Gly Phe Thr Phe Asp Asp Tyr Ala
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic peptide

<400> SEQUENCE: 35

Ile Ser Trp Asn Ser Gly Asp Ile
1               5

<210> SEQ ID NO 36
<211> LENGTH: 16
<212> TYPE: PRT
<213> ORGANISM: Artificial Sequence
<220> FEATURE:
<223> OTHER INFORMATION: synthetic peptide

<400> SEQUENCE: 36

Ala Lys Asp Ile Asp Pro Leu Val Ser Gly Ala Thr Arg Phe Asp Phe
1               5                   10                  15

<210> SEQ ID NO 37
<211> LENGTH: 6
<212> TYPE: PRT
<213> ORGANISM: Artificial Sequence
<220> FEATURE:
<223> OTHER INFORMATION: synthetic peptide

<400> SEQUENCE: 37

Gln Ser Ile Ser Asn Trp
1               5

<210> SEQ ID NO 38
<211> LENGTH: 3
<212> TYPE: PRT
<213> ORGANISM: Artificial Sequence
<220> FEATURE:
<223> OTHER INFORMATION: synthetic peptide

<400> SEQUENCE: 38

Lys Ala Ser
1

<210> SEQ ID NO 39
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 39

Gln Gln Tyr Lys Ser Tyr Pro Trp Thr
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic peptide

<400> SEQUENCE: 40

Gly Tyr Arg Phe Ile Ser Tyr Trp
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic peptide

<400> SEQUENCE: 41

Ile Tyr Pro Gly Asp Ser Glu Thr
1               5

<210> SEQ ID NO 42
<211> LENGTH: 9
<212> TYPE: PRT
<213> ORGANISM: Artificial Sequence
<220> FEATURE:
<223> OTHER INFORMATION: synthetic peptide

<400> SEQUENCE: 42

Ala Arg His Ser Trp Gly Met Asp Val
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic peptide

<400> SEQUENCE: 43

Gln Gly Ile Ser Ser Ser Phe
1               5

<210> SEQ ID NO 44
<211> LENGTH: 3
<212> TYPE: PRT
<213> ORGANISM: Artificial Sequence
<220> FEATURE:
<223> OTHER INFORMATION: synthetic peptide

<400> SEQUENCE: 44

Gly Ala Ser
1

<210> SEQ ID NO 45
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 45

His His Tyr Gly Asp Ser Ile Arg Pro
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic peptide

<400> SEQUENCE: 46

Gly Val Ser Phe Gly Ser Tyr Ser
1               5

<210> SEQ ID NO 47
<211> LENGTH: 8
<212> TYPE: PRT
<213> ORGANISM: Artificial Sequence
<220> FEATURE:
<223> OTHER INFORMATION: synthetic peptide

<400> SEQUENCE: 47

Ile Ser Ser Ser Ser Ser Arg Ile
1               5

<210> SEQ ID NO 48
<211> LENGTH: 13
<212> TYPE: PRT
<213> ORGANISM: Artificial Sequence
<220> FEATURE:
<223> OTHER INFORMATION: synthetic peptide

<400> SEQUENCE: 48

Ala Arg Leu Asp Asp Phe Trp Ser Gly Tyr Ile Val Asp
1               5                   10

<210> SEQ ID NO 49
<211> LENGTH: 6
<212> TYPE: PRT
<213> ORGANISM: Artificial Sequence
<220> FEATURE:
<223> OTHER INFORMATION: synthetic peptide

<400> SEQUENCE: 49

Gln Ser Val Asp Ser Asn
1               5

<210> SEQ ID NO 50
<211> LENGTH: 3
<212> TYPE: PRT
<213> ORGANISM: Artificial Sequence
<220> FEATURE:
<223> OTHER INFORMATION: synthetic peptide

<400> SEQUENCE: 50

Arg Ala Ser
1

<210> SEQ ID NO 51
<211> LENGTH: 10
<212> TYPE: PRT
<213> ORGANISM: Artificial Sequence
<220> FEATURE:
<223> OTHER INFORMATION: synthetic peptide
```

```
<400> SEQUENCE: 51

Gln Glu Tyr Asn Thr Trp Pro Pro Tyr Thr
1               5                   10

<210> SEQ ID NO 52
<211> LENGTH: 8
<212> TYPE: PRT
<213> ORGANISM: Artificial Sequence
<220> FEATURE:
<223> OTHER INFORMATION: synthetic peptide

<400> SEQUENCE: 52

Gly Tyr Thr Phe Thr Ser Tyr Asp
1               5

<210> SEQ ID NO 53
<211> LENGTH: 8
<212> TYPE: PRT
<213> ORGANISM: Artificial Sequence
<220> FEATURE:
<223> OTHER INFORMATION: synthetic peptide

<400> SEQUENCE: 53

Met Asn Ala Asn Asn Gly Asn Thr
1               5

<210> SEQ ID NO 54
<211> LENGTH: 16
<212> TYPE: PRT
<213> ORGANISM: Artificial Sequence
<220> FEATURE:
<223> OTHER INFORMATION: synthetic peptide

<400> SEQUENCE: 54

Ala Arg Glu Leu His Asn Ser Ser Ser Gly Tyr Asn Trp Phe Asp Pro
1               5                   10                  15

<210> SEQ ID NO 55
<211> LENGTH: 12
<212> TYPE: PRT
<213> ORGANISM: Artificial Sequence
<220> FEATURE:
<223> OTHER INFORMATION: synthetic peptide

<400> SEQUENCE: 55

Gln Thr Val Leu Ser Ser Ser Asp Asn Lys Asn Tyr
1               5                   10

<210> SEQ ID NO 56
<211> LENGTH: 3
<212> TYPE: PRT
<213> ORGANISM: Artificial Sequence
<220> FEATURE:
<223> OTHER INFORMATION: synthetic peptide

<400> SEQUENCE: 56

Trp Ala Ser
1

<210> SEQ ID NO 57
<211> LENGTH: 8
<212> TYPE: PRT
<213> ORGANISM: Artificial Sequence
<220> FEATURE:
<223> OTHER INFORMATION: synthetic peptide
```

```
<400> SEQUENCE: 57

Gln Gln Tyr Phe Asn Thr Gln Thr
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic peptide

<400> SEQUENCE: 58

Gly Phe Ser Phe Ser Asp Tyr Tyr
1               5

<210> SEQ ID NO 59
<211> LENGTH: 8
<212> TYPE: PRT
<213> ORGANISM: Artificial Sequence
<220> FEATURE:
<223> OTHER INFORMATION: synthetic peptide

<400> SEQUENCE: 59

Ile Ser Ser Ser Gly Arg Thr Ile
1               5

<210> SEQ ID NO 60
<211> LENGTH: 18
<212> TYPE: PRT
<213> ORGANISM: Artificial Sequence
<220> FEATURE:
<223> OTHER INFORMATION: synthetic peptide

<400> SEQUENCE: 60

Ala Arg Thr Arg Pro Thr Ile Ala Val Ala Gly Ser Pro Leu Asn Glu
1               5                   10                  15

Asp Tyr

<210> SEQ ID NO 61
<211> LENGTH: 6
<212> TYPE: PRT
<213> ORGANISM: Artificial Sequence
<220> FEATURE:
<223> OTHER INFORMATION: synthetic peptide

<400> SEQUENCE: 61

Gln Thr Val Ser Gly Tyr
1               5

<210> SEQ ID NO 62
<211> LENGTH: 3
<212> TYPE: PRT
<213> ORGANISM: Artificial Sequence
<220> FEATURE:
<223> OTHER INFORMATION: synthetic peptide

<400> SEQUENCE: 62

Asp Ala Ser
1

<210> SEQ ID NO 63
<211> LENGTH: 11
<212> TYPE: PRT
<213> ORGANISM: Artificial Sequence
<220> FEATURE:
```

```
<223> OTHER INFORMATION: synthetic peptide

<400> SEQUENCE: 63

Gln Gln Arg Ser Asn Trp Pro Pro Gly Ile Thr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: synthetic peptide

<400> SEQUENCE: 64

Gly Gly Ser Ile Lys Arg Ser Asn Tyr Tyr
1               5                   10

<210> SEQ ID NO 65
<211> LENGTH: 7
<212> TYPE: PRT
<213> ORGANISM: Artificial Sequence
<220> FEATURE:
<223> OTHER INFORMATION: synthetic peptide

<400> SEQUENCE: 65

Leu Phe Tyr Ser Gly Ser Thr
1               5

<210> SEQ ID NO 66
<211> LENGTH: 17
<212> TYPE: PRT
<213> ORGANISM: Artificial Sequence
<220> FEATURE:
<223> OTHER INFORMATION: synthetic peptide

<400> SEQUENCE: 66

Ser Arg His Phe Val Gly Phe Ala Glu Ala Pro Pro Asp Gly Met Asp
1               5                   10                  15

Val

<210> SEQ ID NO 67
<211> LENGTH: 6
<212> TYPE: PRT
<213> ORGANISM: Artificial Sequence
<220> FEATURE:
<223> OTHER INFORMATION: synthetic peptide

<400> SEQUENCE: 67

Gln Asp Ile Ser Asn His
1               5

<210> SEQ ID NO 68
<211> LENGTH: 3
<212> TYPE: PRT
<213> ORGANISM: Artificial Sequence
<220> FEATURE:
<223> OTHER INFORMATION: synthetic peptide

<400> SEQUENCE: 68

Asp Ala Ser
1

<210> SEQ ID NO 69
<211> LENGTH: 11
<212> TYPE: PRT
<213> ORGANISM: Artificial Sequence
```

```
<220> FEATURE:
<223> OTHER INFORMATION: synthetic peptide

<400> SEQUENCE: 69

Gln Gln Tyr Asp Thr Leu Pro Leu Arg Phe Thr
1               5                   10

<210> SEQ ID NO 70
<211> LENGTH: 8
<212> TYPE: PRT
<213> ORGANISM: Artificial Sequence
<220> FEATURE:
<223> OTHER INFORMATION: synthetic peptide

<400> SEQUENCE: 70

Gly Tyr Thr Phe Thr Arg Tyr Ala
1               5

<210> SEQ ID NO 71
<211> LENGTH: 8
<212> TYPE: PRT
<213> ORGANISM: Artificial Sequence
<220> FEATURE:
<223> OTHER INFORMATION: synthetic peptide

<400> SEQUENCE: 71

Ile Asn Thr Asn Thr Gly Glu Pro
1               5

<210> SEQ ID NO 72
<211> LENGTH: 9
<212> TYPE: PRT
<213> ORGANISM: Artificial Sequence
<220> FEATURE:
<223> OTHER INFORMATION: synthetic peptide

<400> SEQUENCE: 72

Ala Gln Gln Val Ile Ala Phe Asp Val
1               5

<210> SEQ ID NO 73
<211> LENGTH: 12
<212> TYPE: PRT
<213> ORGANISM: Artificial Sequence
<220> FEATURE:
<223> OTHER INFORMATION: synthetic peptide

<400> SEQUENCE: 73

Gln Ser Leu Leu Ser Ser Ser Asn Asn Lys Asn Phe
1               5                   10

<210> SEQ ID NO 74
<211> LENGTH: 3
<212> TYPE: PRT
<213> ORGANISM: Artificial Sequence
<220> FEATURE:
<223> OTHER INFORMATION: synthetic peptide

<400> SEQUENCE: 74

Trp Ala Ser
1

<210> SEQ ID NO 75
<211> LENGTH: 10
<212> TYPE: PRT
<213> ORGANISM: Artificial Sequence
<220> FEATURE:
```

<223> OTHER INFORMATION: synthetic peptide

<400> SEQUENCE: 75

Gln Gln Tyr Tyr Ser Thr Pro Pro Tyr Ser
1               5                   10

<210> SEQ ID NO 76
<211> LENGTH: 8
<212> TYPE: PRT
<213> ORGANISM: Artificial Sequence
<220> FEATURE:
<223> OTHER INFORMATION: synthetic peptide

<400> SEQUENCE: 76

Gly Phe Thr Phe Asn Val Tyr Ser
1               5

<210> SEQ ID NO 77
<211> LENGTH: 8
<212> TYPE: PRT
<213> ORGANISM: Artificial Sequence
<220> FEATURE:
<223> OTHER INFORMATION: synthetic peptide

<400> SEQUENCE: 77

Ile Trp Tyr Asp Gly Val Asp Lys
1               5

<210> SEQ ID NO 78
<211> LENGTH: 12
<212> TYPE: PRT
<213> ORGANISM: Artificial Sequence
<220> FEATURE:
<223> OTHER INFORMATION: synthetic peptide

<400> SEQUENCE: 78

Ala Arg Gly Pro Gly Trp Ser Gly Tyr Leu Asp Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: synthetic peptide

<400> SEQUENCE: 79

Gln Ser Leu Val Tyr Ser Asp Gly Gly Thr Tyr
1               5                   10

<210> SEQ ID NO 80
<211> LENGTH: 3
<212> TYPE: PRT
<213> ORGANISM: Artificial Sequence
<220> FEATURE:
<223> OTHER INFORMATION: synthetic peptide

<400> SEQUENCE: 80

Lys Val Ser
1

<210> SEQ ID NO 81
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 81

Met Gln Ala Thr His Trp Pro His Thr
1               5

<210> SEQ ID NO 82
<211> LENGTH: 10
<212> TYPE: PRT
<213> ORGANISM: Artificial Sequence
<220> FEATURE:
<223> OTHER INFORMATION: synthetic peptide

<400> SEQUENCE: 82

Gly Gly Ser Met Ser Ser Gly Asp Tyr Tyr
1               5                   10

<210> SEQ ID NO 83
<211> LENGTH: 7
<212> TYPE: PRT
<213> ORGANISM: Artificial Sequence
<220> FEATURE:
<223> OTHER INFORMATION: synthetic peptide

<400> SEQUENCE: 83

Ile Ser Tyr Ser Gly Ser Ala
1               5

<210> SEQ ID NO 84
<211> LENGTH: 12
<212> TYPE: PRT
<213> ORGANISM: Artificial Sequence
<220> FEATURE:
<223> OTHER INFORMATION: synthetic peptide

<400> SEQUENCE: 84

Ala Arg Val Phe Ser Gly Tyr Tyr Tyr Ser Asp Tyr
1               5                   10

<210> SEQ ID NO 85
<211> LENGTH: 6
<212> TYPE: PRT
<213> ORGANISM: Artificial Sequence
<220> FEATURE:
<223> OTHER INFORMATION: synthetic peptide

<400> SEQUENCE: 85

Gln Ser Ile Ser Ser Trp
1               5

<210> SEQ ID NO 86
<211> LENGTH: 3
<212> TYPE: PRT
<213> ORGANISM: Artificial Sequence
<220> FEATURE:
<223> OTHER INFORMATION: synthetic peptide

<400> SEQUENCE: 86

Lys Ala Ser
1

<210> SEQ ID NO 87
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 87

Gln Gln Tyr Asn Thr Tyr Pro Trp Thr
1               5

<210> SEQ ID NO 88
<211> LENGTH: 8
<212> TYPE: PRT
<213> ORGANISM: Artificial Sequence
<220> FEATURE:
<223> OTHER INFORMATION: synthetic peptide

<400> SEQUENCE: 88

Gly Phe Thr Leu Ser Asn Tyr Gly
1               5

<210> SEQ ID NO 89
<211> LENGTH: 8
<212> TYPE: PRT
<213> ORGANISM: Artificial Sequence
<220> FEATURE:
<223> OTHER INFORMATION: synthetic peptide

<400> SEQUENCE: 89

Ile Leu Tyr Asp Gly Gly Asn Arg
1               5

<210> SEQ ID NO 90
<211> LENGTH: 17
<212> TYPE: PRT
<213> ORGANISM: Artificial Sequence
<220> FEATURE:
<223> OTHER INFORMATION: synthetic peptide

<400> SEQUENCE: 90

Ala Lys Asp Asp Ser Val Phe Glu Thr Asp Arg Thr Gly Thr Leu Asn
1               5                   10                  15

Tyr

<210> SEQ ID NO 91
<211> LENGTH: 6
<212> TYPE: PRT
<213> ORGANISM: Artificial Sequence
<220> FEATURE:
<223> OTHER INFORMATION: synthetic peptide

<400> SEQUENCE: 91

Gln Ser Ile Gly Ile Tyr
1               5

<210> SEQ ID NO 92
<211> LENGTH: 3
<212> TYPE: PRT
<213> ORGANISM: Artificial Sequence
<220> FEATURE:
<223> OTHER INFORMATION: synthetic peptide

<400> SEQUENCE: 92

Ala Ser Ser
1

<210> SEQ ID NO 93
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 93

Gln Gln Ser Tyr Ser Ser Pro Pro Ala
1               5

<210> SEQ ID NO 94
<211> LENGTH: 8
<212> TYPE: PRT
<213> ORGANISM: Artificial Sequence
<220> FEATURE:
<223> OTHER INFORMATION: synthetic peptide

<400> SEQUENCE: 94

Gly Phe Ala Val Asn Tyr Tyr Ala
1               5

<210> SEQ ID NO 95
<211> LENGTH: 8
<212> TYPE: PRT
<213> ORGANISM: Artificial Sequence
<220> FEATURE:
<223> OTHER INFORMATION: synthetic peptide

<400> SEQUENCE: 95

Ile Val Gly Tyr Gly Ala Thr Thr
1               5

<210> SEQ ID NO 96
<211> LENGTH: 14
<212> TYPE: PRT
<213> ORGANISM: Artificial Sequence
<220> FEATURE:
<223> OTHER INFORMATION: synthetic peptide

<400> SEQUENCE: 96

Ala Lys Leu Thr His Pro His Asp Gly Ser Ser Phe Glu Thr
1               5                   10

<210> SEQ ID NO 97
<211> LENGTH: 6
<212> TYPE: PRT
<213> ORGANISM: Artificial Sequence
<220> FEATURE:
<223> OTHER INFORMATION: synthetic peptide

<400> SEQUENCE: 97

Gln Asp Val Thr Thr Ala
1               5

<210> SEQ ID NO 98
<211> LENGTH: 3
<212> TYPE: PRT
<213> ORGANISM: Artificial Sequence
<220> FEATURE:
<223> OTHER INFORMATION: synthetic peptide

<400> SEQUENCE: 98

Trp Ala Ser
1

<210> SEQ ID NO 99
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 99

Gln Gln His Tyr Ser Thr Pro Leu Thr
1               5

<210> SEQ ID NO 100
<211> LENGTH: 10
<212> TYPE: PRT
<213> ORGANISM: Artificial Sequence
<220> FEATURE:
<223> OTHER INFORMATION: synthetic peptide

<400> SEQUENCE: 100

Gly Phe Ser Leu Ser Thr Ser Glu Val Gly
1               5                   10

<210> SEQ ID NO 101
<211> LENGTH: 7
<212> TYPE: PRT
<213> ORGANISM: Artificial Sequence
<220> FEATURE:
<223> OTHER INFORMATION: synthetic peptide

<400> SEQUENCE: 101

Ile Tyr Trp Asp Asp Asp Lys
1               5

<210> SEQ ID NO 102
<211> LENGTH: 19
<212> TYPE: PRT
<213> ORGANISM: Artificial Sequence
<220> FEATURE:
<223> OTHER INFORMATION: synthetic peptide

<400> SEQUENCE: 102

Ala His Ile Lys Ser Tyr Cys Ser Thr Ile Thr Cys Tyr Pro Thr Thr
1               5                   10                  15

Phe Asp Tyr

<210> SEQ ID NO 103
<211> LENGTH: 12
<212> TYPE: PRT
<213> ORGANISM: Artificial Sequence
<220> FEATURE:
<223> OTHER INFORMATION: synthetic peptide

<400> SEQUENCE: 103

Gln Ser Val Leu Asp Ser Ser Asn Asn Asn Tyr Tyr
1               5                   10

<210> SEQ ID NO 104
<211> LENGTH: 3
<212> TYPE: PRT
<213> ORGANISM: Artificial Sequence
<220> FEATURE:
<223> OTHER INFORMATION: synthetic peptide

<400> SEQUENCE: 104

Trp Ala Ser
1

<210> SEQ ID NO 105
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 105

Gln Gln Tyr Tyr Ser Thr Pro Trp Thr
1               5

<210> SEQ ID NO 106
<211> LENGTH: 8
<212> TYPE: PRT
<213> ORGANISM: Artificial Sequence
<220> FEATURE:
<223> OTHER INFORMATION: synthetic peptide

<400> SEQUENCE: 106

Gly Tyr Ser Phe Ser Ser Tyr Ser
1               5

<210> SEQ ID NO 107
<211> LENGTH: 8
<212> TYPE: PRT
<213> ORGANISM: Artificial Sequence
<220> FEATURE:
<223> OTHER INFORMATION: synthetic peptide

<400> SEQUENCE: 107

Ile Tyr Pro Gly Asp Ser Tyr Thr
1               5

<210> SEQ ID NO 108
<211> LENGTH: 8
<212> TYPE: PRT
<213> ORGANISM: Artificial Sequence
<220> FEATURE:
<223> OTHER INFORMATION: synthetic peptide

<400> SEQUENCE: 108

Val Arg Gly Met Ala Thr Asn Asn
1               5

<210> SEQ ID NO 109
<211> LENGTH: 11
<212> TYPE: PRT
<213> ORGANISM: Artificial Sequence
<220> FEATURE:
<223> OTHER INFORMATION: synthetic peptide

<400> SEQUENCE: 109

Gln Thr Leu Val His Ser Asp Gly Asn Thr Tyr
1               5                   10

<210> SEQ ID NO 110
<211> LENGTH: 3
<212> TYPE: PRT
<213> ORGANISM: Artificial Sequence
<220> FEATURE:
<223> OTHER INFORMATION: synthetic peptide

<400> SEQUENCE: 110

Lys Ile Ser
1

<210> SEQ ID NO 111
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 111

Met Gln Ala Thr His Phe Pro Trp Thr
1               5

<210> SEQ ID NO 112
<211> LENGTH: 8
<212> TYPE: PRT
<213> ORGANISM: Artificial Sequence
<220> FEATURE:
<223> OTHER INFORMATION: synthetic peptide

<400> SEQUENCE: 112

Gly Phe Thr Phe Arg Asn Tyr Val
1               5

<210> SEQ ID NO 113
<211> LENGTH: 8
<212> TYPE: PRT
<213> ORGANISM: Artificial Sequence
<220> FEATURE:
<223> OTHER INFORMATION: synthetic peptide

<400> SEQUENCE: 113

Ile Ser Tyr Asp Gly Asn Asn Lys
1               5

<210> SEQ ID NO 114
<211> LENGTH: 16
<212> TYPE: PRT
<213> ORGANISM: Artificial Sequence
<220> FEATURE:
<223> OTHER INFORMATION: synthetic peptide

<400> SEQUENCE: 114

Ala Arg Asp Thr Gln Thr Gln Asn Ser Asp Trp Tyr Leu Phe Gly Ala
1               5                   10                  15

<210> SEQ ID NO 115
<211> LENGTH: 6
<212> TYPE: PRT
<213> ORGANISM: Artificial Sequence
<220> FEATURE:
<223> OTHER INFORMATION: synthetic peptide

<400> SEQUENCE: 115

Gln Ser Val Phe Ile Asn
1               5

<210> SEQ ID NO 116
<211> LENGTH: 3
<212> TYPE: PRT
<213> ORGANISM: Artificial Sequence
<220> FEATURE:
<223> OTHER INFORMATION: synthetic peptide

<400> SEQUENCE: 116

Gly Ala Ser
1

<210> SEQ ID NO 117
<211> LENGTH: 10
<212> TYPE: PRT
<213> ORGANISM: Artificial Sequence
<220> FEATURE:
<223> OTHER INFORMATION: synthetic peptide
```

```
<400> SEQUENCE: 117

Gln Gln Tyr Asn Asp Trp Pro Pro Ile Thr
1               5                   10

<210> SEQ ID NO 118
<211> LENGTH: 8
<212> TYPE: PRT
<213> ORGANISM: Artificial Sequence
<220> FEATURE:
<223> OTHER INFORMATION: synthetic peptide

<400> SEQUENCE: 118

Gly Tyr Thr Phe Asn Asn His Tyr
1               5

<210> SEQ ID NO 119
<211> LENGTH: 8
<212> TYPE: PRT
<213> ORGANISM: Artificial Sequence
<220> FEATURE:
<223> OTHER INFORMATION: synthetic peptide

<400> SEQUENCE: 119

Ile Ala Pro Ser Gly Asp Asn Thr
1               5

<210> SEQ ID NO 120
<211> LENGTH: 17
<212> TYPE: PRT
<213> ORGANISM: Artificial Sequence
<220> FEATURE:
<223> OTHER INFORMATION: synthetic peptide

<400> SEQUENCE: 120

Ala Arg Asp Gln Leu Asn Arg His Ser Thr Asn Arg Gly Phe Phe Asp
1               5                   10                  15

Leu

<210> SEQ ID NO 121
<211> LENGTH: 6
<212> TYPE: PRT
<213> ORGANISM: Artificial Sequence
<220> FEATURE:
<223> OTHER INFORMATION: synthetic peptide

<400> SEQUENCE: 121

Gln Ser Val Gly Ser Tyr
1               5

<210> SEQ ID NO 122
<211> LENGTH: 3
<212> TYPE: PRT
<213> ORGANISM: Artificial Sequence
<220> FEATURE:
<223> OTHER INFORMATION: synthetic peptide

<400> SEQUENCE: 122

Asp Ala Ser
1

<210> SEQ ID NO 123
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 123

His Gln Arg Gly Asn Trp Pro Pro Ser
1               5

<210> SEQ ID NO 124
<211> LENGTH: 8
<212> TYPE: PRT
<213> ORGANISM: Artificial Sequence
<220> FEATURE:
<223> OTHER INFORMATION: synthetic peptide

<400> SEQUENCE: 124

Gly Phe Asn Phe Asp Asp Tyr Gly
1               5

<210> SEQ ID NO 125
<211> LENGTH: 8
<212> TYPE: PRT
<213> ORGANISM: Artificial Sequence
<220> FEATURE:
<223> OTHER INFORMATION: synthetic peptide

<400> SEQUENCE: 125

Ile Thr Trp Asn Ser Gly Leu Ile
1               5

<210> SEQ ID NO 126
<211> LENGTH: 17
<212> TYPE: PRT
<213> ORGANISM: Artificial Sequence
<220> FEATURE:
<223> OTHER INFORMATION: synthetic peptide

<400> SEQUENCE: 126

Ala Lys Asp Met Gly Arg Leu Tyr Thr Val Gly Trp Tyr Asn Phe His
1               5                   10                  15

Phe

<210> SEQ ID NO 127
<211> LENGTH: 6
<212> TYPE: PRT
<213> ORGANISM: Artificial Sequence
<220> FEATURE:
<223> OTHER INFORMATION: synthetic peptide

<400> SEQUENCE: 127

Leu Asn Ile Gly Thr Phe
1               5

<210> SEQ ID NO 128
<211> LENGTH: 3
<212> TYPE: PRT
<213> ORGANISM: Artificial Sequence
<220> FEATURE:
<223> OTHER INFORMATION: synthetic peptide

<400> SEQUENCE: 128

Ala Val Ser
1

<210> SEQ ID NO 129
<211> LENGTH: 11
<212> TYPE: PRT
<213> ORGANISM: Artificial Sequence
<220> FEATURE:
<223> OTHER INFORMATION: synthetic peptide
```

<400> SEQUENCE: 129

Gln Glu Ser Tyr Asn Thr Pro Glu Asp Leu Thr
1               5                   10

<210> SEQ ID NO 130
<211> LENGTH: 10
<212> TYPE: PRT
<213> ORGANISM: Artificial Sequence
<220> FEATURE:
<223> OTHER INFORMATION: synthetic peptide

<400> SEQUENCE: 130

Gly Phe Ser Leu Asn Thr Ser Gly Val Thr
1               5                   10

<210> SEQ ID NO 131
<211> LENGTH: 7
<212> TYPE: PRT
<213> ORGANISM: Artificial Sequence
<220> FEATURE:
<223> OTHER INFORMATION: synthetic peptide

<400> SEQUENCE: 131

Ile Tyr Trp Asp Gly Asp Lys
1               5

<210> SEQ ID NO 132
<211> LENGTH: 12
<212> TYPE: PRT
<213> ORGANISM: Artificial Sequence
<220> FEATURE:
<223> OTHER INFORMATION: synthetic peptide

<400> SEQUENCE: 132

Ser Tyr Thr Ser Tyr Lys Tyr Phe Asp Val Asp Val
1               5                   10

<210> SEQ ID NO 133
<211> LENGTH: 6
<212> TYPE: PRT
<213> ORGANISM: Artificial Sequence
<220> FEATURE:
<223> OTHER INFORMATION: synthetic peptide

<400> SEQUENCE: 133

Gln Ser Gly Asn Asn Tyr
1               5

<210> SEQ ID NO 134
<211> LENGTH: 3
<212> TYPE: PRT
<213> ORGANISM: Artificial Sequence
<220> FEATURE:
<223> OTHER INFORMATION: synthetic peptide

<400> SEQUENCE: 134

Asp Thr Ser
1

<210> SEQ ID NO 135
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 135

Gln Gln Arg Ser Asn Trp Pro Arg Thr
1               5

<210> SEQ ID NO 136
<211> LENGTH: 8
<212> TYPE: PRT
<213> ORGANISM: Artificial Sequence
<220> FEATURE:
<223> OTHER INFORMATION: synthetic peptide

<400> SEQUENCE: 136

Gly Tyr Thr Leu Thr Thr Tyr Pro
1               5

<210> SEQ ID NO 137
<211> LENGTH: 8
<212> TYPE: PRT
<213> ORGANISM: Artificial Sequence
<220> FEATURE:
<223> OTHER INFORMATION: synthetic peptide

<400> SEQUENCE: 137

Ile Asn Thr His Thr Gly Asn Pro
1               5

<210> SEQ ID NO 138
<211> LENGTH: 12
<212> TYPE: PRT
<213> ORGANISM: Artificial Sequence
<220> FEATURE:
<223> OTHER INFORMATION: synthetic peptide

<400> SEQUENCE: 138

Ala Arg Asp Leu Ala Val Ala Glu Tyr His Gly Tyr
1               5                   10

<210> SEQ ID NO 139
<211> LENGTH: 6
<212> TYPE: PRT
<213> ORGANISM: Artificial Sequence
<220> FEATURE:
<223> OTHER INFORMATION: synthetic peptide

<400> SEQUENCE: 139

Gln Asp Val Thr Thr Ala
1               5

<210> SEQ ID NO 140
<211> LENGTH: 3
<212> TYPE: PRT
<213> ORGANISM: Artificial Sequence
<220> FEATURE:
<223> OTHER INFORMATION: synthetic peptide

<400> SEQUENCE: 140

Trp Ala Ser
1

<210> SEQ ID NO 141
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 141

Gln Gln His Tyr Ser Thr Pro Leu Thr
1               5

<210> SEQ ID NO 142
<211> LENGTH: 8
<212> TYPE: PRT
<213> ORGANISM: Artificial Sequence
<220> FEATURE:
<223> OTHER INFORMATION: synthetic peptide

<400> SEQUENCE: 142

Gly Phe Ile Phe Asp Asp His Ala
1               5

<210> SEQ ID NO 143
<211> LENGTH: 8
<212> TYPE: PRT
<213> ORGANISM: Artificial Sequence
<220> FEATURE:
<223> OTHER INFORMATION: synthetic peptide

<400> SEQUENCE: 143

Ile Ser Trp Asn Ser Gly Asp Ile
1               5

<210> SEQ ID NO 144
<211> LENGTH: 18
<212> TYPE: PRT
<213> ORGANISM: Artificial Sequence
<220> FEATURE:
<223> OTHER INFORMATION: synthetic peptide

<400> SEQUENCE: 144

Val Lys Asp Thr Pro Tyr Cys Gly Gly Gly Cys Leu Asn Trp Phe
1               5                   10                  15

Asp Ser

<210> SEQ ID NO 145
<211> LENGTH: 11
<212> TYPE: PRT
<213> ORGANISM: Artificial Sequence
<220> FEATURE:
<223> OTHER INFORMATION: synthetic peptide

<400> SEQUENCE: 145

Gln Ser Leu Leu His Ser Asn Gly Tyr Asn Tyr
1               5                   10

<210> SEQ ID NO 146
<211> LENGTH: 3
<212> TYPE: PRT
<213> ORGANISM: Artificial Sequence
<220> FEATURE:
<223> OTHER INFORMATION: synthetic peptide

<400> SEQUENCE: 146

Leu Gly Ser
1

<210> SEQ ID NO 147
<211> LENGTH: 9
<212> TYPE: PRT
<213> ORGANISM: Artificial Sequence
<220> FEATURE:
<223> OTHER INFORMATION: synthetic peptide
```

```
<400> SEQUENCE: 147

Met Gln Thr Leu Gln Thr Pro Arg Thr
1               5

<210> SEQ ID NO 148
<211> LENGTH: 8
<212> TYPE: PRT
<213> ORGANISM: Artificial Sequence
<220> FEATURE:
<223> OTHER INFORMATION: synthetic peptide

<400> SEQUENCE: 148

Gly Phe Thr Phe Asp Asp Tyr Ala
1               5

<210> SEQ ID NO 149
<211> LENGTH: 10
<212> TYPE: PRT
<213> ORGANISM: Artificial Sequence
<220> FEATURE:
<223> OTHER INFORMATION: synthetic peptide

<400> SEQUENCE: 149

Ile Lys Ser Glu Thr Tyr Gly Gly Thr Thr
1               5                   10

<210> SEQ ID NO 150
<211> LENGTH: 19
<212> TYPE: PRT
<213> ORGANISM: Artificial Sequence
<220> FEATURE:
<223> OTHER INFORMATION: synthetic peptide

<400> SEQUENCE: 150

Ser Ile Val Val Ala Gln Val Val Arg Gly Ile Pro Leu Pro Asn Val
1               5                   10                  15

Phe Asp Ile

<210> SEQ ID NO 151
<211> LENGTH: 6
<212> TYPE: PRT
<213> ORGANISM: Artificial Sequence
<220> FEATURE:
<223> OTHER INFORMATION: synthetic peptide

<400> SEQUENCE: 151

Gln Gly Ile Gly Asn Tyr
1               5

<210> SEQ ID NO 152
<211> LENGTH: 3
<212> TYPE: PRT
<213> ORGANISM: Artificial Sequence
<220> FEATURE:
<223> OTHER INFORMATION: synthetic peptide

<400> SEQUENCE: 152

Ser Ala Ser
1

<210> SEQ ID NO 153
<211> LENGTH: 9
<212> TYPE: PRT
<213> ORGANISM: Artificial Sequence
<220> FEATURE:
<223> OTHER INFORMATION: synthetic peptide
```

<400> SEQUENCE: 153

Leu Lys Tyr His Gly Ala Pro Tyr Thr
1               5

<210> SEQ ID NO 154
<211> LENGTH: 8
<212> TYPE: PRT
<213> ORGANISM: Artificial Sequence
<220> FEATURE:
<223> OTHER INFORMATION: synthetic peptide

<400> SEQUENCE: 154

Gly Phe Thr Phe Ser Asn Tyr Val
1               5

<210> SEQ ID NO 155
<211> LENGTH: 8
<212> TYPE: PRT
<213> ORGANISM: Artificial Sequence
<220> FEATURE:
<223> OTHER INFORMATION: synthetic peptide

<400> SEQUENCE: 155

Ile Ser Tyr Asp Gly Ser Asn Lys
1               5

<210> SEQ ID NO 156
<211> LENGTH: 16
<212> TYPE: PRT
<213> ORGANISM: Artificial Sequence
<220> FEATURE:
<223> OTHER INFORMATION: synthetic peptide

<400> SEQUENCE: 156

Ala Arg Asp Thr Gln Thr Gln Ser Ser Asp Tyr Tyr Leu Phe Gly Ala
1               5                   10                  15

<210> SEQ ID NO 157
<211> LENGTH: 6
<212> TYPE: PRT
<213> ORGANISM: Artificial Sequence
<220> FEATURE:
<223> OTHER INFORMATION: synthetic peptide

<400> SEQUENCE: 157

Gln Ser Val Ile Asn Asn
1               5

<210> SEQ ID NO 158
<211> LENGTH: 3
<212> TYPE: PRT
<213> ORGANISM: Artificial Sequence
<220> FEATURE:
<223> OTHER INFORMATION: synthetic peptide

<400> SEQUENCE: 158

Gly Ala Ser
1

<210> SEQ ID NO 159
<211> LENGTH: 10
<212> TYPE: PRT
<213> ORGANISM: Artificial Sequence
<220> FEATURE:
<223> OTHER INFORMATION: synthetic peptide

```
<400> SEQUENCE: 159

Gln Gln Tyr Asn Asp Trp Pro Pro Ile Thr
1               5                   10

<210> SEQ ID NO 160
<211> LENGTH: 8
<212> TYPE: PRT
<213> ORGANISM: Artificial Sequence
<220> FEATURE:
<223> OTHER INFORMATION: synthetic peptide

<400> SEQUENCE: 160

Gly Glu Ser Phe Ser Gly Tyr Tyr
1               5

<210> SEQ ID NO 161
<211> LENGTH: 7
<212> TYPE: PRT
<213> ORGANISM: Artificial Sequence
<220> FEATURE:
<223> OTHER INFORMATION: synthetic peptide

<400> SEQUENCE: 161

Ile Asn His Ser Gly Ser Thr
1               5

<210> SEQ ID NO 162
<211> LENGTH: 20
<212> TYPE: PRT
<213> ORGANISM: Artificial Sequence
<220> FEATURE:
<223> OTHER INFORMATION: synthetic peptide

<400> SEQUENCE: 162

Ala Arg Gly Tyr Ala Asp Thr Pro Val Phe Arg Arg Ala Ala Ala Ala
1               5                   10                  15

Gly Met Asp Val
            20

<210> SEQ ID NO 163
<211> LENGTH: 6
<212> TYPE: PRT
<213> ORGANISM: Artificial Sequence
<220> FEATURE:
<223> OTHER INFORMATION: synthetic peptide

<400> SEQUENCE: 163

Gln Tyr Ile Gly Thr Phe
1               5

<210> SEQ ID NO 164
<211> LENGTH: 3
<212> TYPE: PRT
<213> ORGANISM: Artificial Sequence
<220> FEATURE:
<223> OTHER INFORMATION: synthetic peptide

<400> SEQUENCE: 164

Asp Ala Ser
1

<210> SEQ ID NO 165
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 165

Gln Gln Gly Tyr Ser Pro Leu Tyr Ser
1               5

<210> SEQ ID NO 166
<211> LENGTH: 8
<212> TYPE: PRT
<213> ORGANISM: Artificial Sequence
<220> FEATURE:
<223> OTHER INFORMATION: synthetic peptide

<400> SEQUENCE: 166

Gly Phe Gly Val Asn Asn Asn Tyr
1               5

<210> SEQ ID NO 167
<211> LENGTH: 7
<212> TYPE: PRT
<213> ORGANISM: Artificial Sequence
<220> FEATURE:
<223> OTHER INFORMATION: synthetic peptide

<400> SEQUENCE: 167

Ile Tyr Ala Gly Gly Asn Thr
1               5

<210> SEQ ID NO 168
<211> LENGTH: 14
<212> TYPE: PRT
<213> ORGANISM: Artificial Sequence
<220> FEATURE:
<223> OTHER INFORMATION: synthetic peptide

<400> SEQUENCE: 168

Ala Arg Glu Val Val Pro Thr Ala Met Gly Gly Phe Asp Leu
1               5                   10

<210> SEQ ID NO 169
<211> LENGTH: 8
<212> TYPE: PRT
<213> ORGANISM: Artificial Sequence
<220> FEATURE:
<223> OTHER INFORMATION: synthetic peptide

<400> SEQUENCE: 169

Gly Gly Ser Ile Ser Asn Tyr Tyr
1               5

<210> SEQ ID NO 170
<211> LENGTH: 7
<212> TYPE: PRT
<213> ORGANISM: Artificial Sequence
<220> FEATURE:
<223> OTHER INFORMATION: synthetic peptide

<400> SEQUENCE: 170

Met Tyr Tyr Ser Gly Ser Thr
1               5

<210> SEQ ID NO 171
<211> LENGTH: 15
<212> TYPE: PRT
<213> ORGANISM: Artificial Sequence
<220> FEATURE:
<223> OTHER INFORMATION: synthetic peptide
```

```
<400> SEQUENCE: 171

Ala Arg Ser Tyr Cys Asp Ile Ala Asn Cys Tyr Thr Phe Asp Leu
1               5                   10                  15

<210> SEQ ID NO 172
<211> LENGTH: 6
<212> TYPE: PRT
<213> ORGANISM: Artificial Sequence
<220> FEATURE:
<223> OTHER INFORMATION: synthetic peptide

<400> SEQUENCE: 172

Gln Val Thr Ser Gly Tyr
1               5

<210> SEQ ID NO 173
<211> LENGTH: 3
<212> TYPE: PRT
<213> ORGANISM: Artificial Sequence
<220> FEATURE:
<223> OTHER INFORMATION: synthetic peptide

<400> SEQUENCE: 173

Ala Ala Ser
1

<210> SEQ ID NO 174
<211> LENGTH: 11
<212> TYPE: PRT
<213> ORGANISM: Artificial Sequence
<220> FEATURE:
<223> OTHER INFORMATION: synthetic peptide

<400> SEQUENCE: 174

Gln Gln Leu Asn Ser Asn Pro Leu Val Tyr Thr
1               5                   10

<210> SEQ ID NO 175
<211> LENGTH: 8
<212> TYPE: PRT
<213> ORGANISM: Artificial Sequence
<220> FEATURE:
<223> OTHER INFORMATION: synthetic peptide

<400> SEQUENCE: 175

Gly Phe Thr Phe Ser Ser Tyr Trp
1               5

<210> SEQ ID NO 176
<211> LENGTH: 8
<212> TYPE: PRT
<213> ORGANISM: Artificial Sequence
<220> FEATURE:
<223> OTHER INFORMATION: synthetic peptide

<400> SEQUENCE: 176

Ile Asn Ser Asp Gly Ser Ser Ile
1               5

<210> SEQ ID NO 177
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 177

Leu Thr Thr Ser Arg Phe Gly Ala Phe Asp Met
1               5                   10

<210> SEQ ID NO 178
<211> LENGTH: 11
<212> TYPE: PRT
<213> ORGANISM: Artificial Sequence
<220> FEATURE:
<223> OTHER INFORMATION: synthetic peptide

<400> SEQUENCE: 178

Gln Ser Leu Leu His Ser Asn Gly Tyr Asn Tyr
1               5                   10

<210> SEQ ID NO 179
<211> LENGTH: 3
<212> TYPE: PRT
<213> ORGANISM: Artificial Sequence
<220> FEATURE:
<223> OTHER INFORMATION: synthetic peptide

<400> SEQUENCE: 179

Leu Gly Ser
1

<210> SEQ ID NO 180
<211> LENGTH: 9
<212> TYPE: PRT
<213> ORGANISM: Artificial Sequence
<220> FEATURE:
<223> OTHER INFORMATION: synthetic peptide

<400> SEQUENCE: 180

Met Gln Ala Leu Gln Thr Pro Tyr Thr
1               5

<210> SEQ ID NO 181
<211> LENGTH: 8
<212> TYPE: PRT
<213> ORGANISM: Artificial Sequence
<220> FEATURE:
<223> OTHER INFORMATION: synthetic peptide

<400> SEQUENCE: 181

Gly Tyr Thr Leu Thr Arg Phe Ala
1               5

<210> SEQ ID NO 182
<211> LENGTH: 8
<212> TYPE: PRT
<213> ORGANISM: Artificial Sequence
<220> FEATURE:
<223> OTHER INFORMATION: synthetic peptide

<400> SEQUENCE: 182

Ile Asn Thr Asn Thr Gly Asn Pro
1               5

<210> SEQ ID NO 183
<211> LENGTH: 12
<212> TYPE: PRT
<213> ORGANISM: Artificial Sequence
<220> FEATURE:
<223> OTHER INFORMATION: synthetic peptide
```

-continued

```
<400> SEQUENCE: 183

Ala Arg Asp Gly Tyr Asn His Gly Tyr Asn Asp Leu
1               5                   10

<210> SEQ ID NO 184
<211> LENGTH: 6
<212> TYPE: PRT
<213> ORGANISM: Artificial Sequence
<220> FEATURE:
<223> OTHER INFORMATION: synthetic peptide

<400> SEQUENCE: 184

Gln Ser Val Ser Ser Glu
1               5

<210> SEQ ID NO 185
<211> LENGTH: 3
<212> TYPE: PRT
<213> ORGANISM: Artificial Sequence
<220> FEATURE:
<223> OTHER INFORMATION: synthetic peptide

<400> SEQUENCE: 185

Asp Ala Ser
1

<210> SEQ ID NO 186
<211> LENGTH: 10
<212> TYPE: PRT
<213> ORGANISM: Artificial Sequence
<220> FEATURE:
<223> OTHER INFORMATION: synthetic peptide

<400> SEQUENCE: 186

Gln Gln Arg Ser Ser Trp Pro Leu Phe Thr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: synthetic peptide

<400> SEQUENCE: 187

Gly Phe Ser Leu Ser Thr Asn Gly Val Gly
1               5                   10

<210> SEQ ID NO 188
<211> LENGTH: 7
<212> TYPE: PRT
<213> ORGANISM: Artificial Sequence
<220> FEATURE:
<223> OTHER INFORMATION: synthetic peptide

<400> SEQUENCE: 188

Ile Tyr Trp Asp Asp Asp Glu
1               5

<210> SEQ ID NO 189
<211> LENGTH: 21
<212> TYPE: PRT
<213> ORGANISM: Artificial Sequence
<220> FEATURE:
<223> OTHER INFORMATION: synthetic peptide
```

<400> SEQUENCE: 189

Ala His Lys Gly Tyr Tyr Cys Ser Ser Ser Cys Tyr Ala Gly Gly
1               5                   10                  15

Lys Ala Phe Asn Ile
            20

<210> SEQ ID NO 190
<211> LENGTH: 6
<212> TYPE: PRT
<213> ORGANISM: Artificial Sequence
<220> FEATURE:
<223> OTHER INFORMATION: synthetic peptide

<400> SEQUENCE: 190

Gln Gly Ile Asn Ser Tyr
1               5

<210> SEQ ID NO 191
<211> LENGTH: 3
<212> TYPE: PRT
<213> ORGANISM: Artificial Sequence
<220> FEATURE:
<223> OTHER INFORMATION: synthetic peptide

<400> SEQUENCE: 191

Ala Ala Ser
1

<210> SEQ ID NO 192
<211> LENGTH: 9
<212> TYPE: PRT
<213> ORGANISM: Artificial Sequence
<220> FEATURE:
<223> OTHER INFORMATION: synthetic peptide

<400> SEQUENCE: 192

Gln Gln Pro Ser Ser His Pro Leu Thr
1               5

<210> SEQ ID NO 193
<211> LENGTH: 8
<212> TYPE: PRT
<213> ORGANISM: Artificial Sequence
<220> FEATURE:
<223> OTHER INFORMATION: synthetic peptide

<400> SEQUENCE: 193

Gly Tyr Thr Phe Thr Asp Tyr Thr
1               5

<210> SEQ ID NO 194
<211> LENGTH: 8
<212> TYPE: PRT
<213> ORGANISM: Artificial Sequence
<220> FEATURE:
<223> OTHER INFORMATION: synthetic peptide

<400> SEQUENCE: 194

Ile Asn Thr Lys Thr Gly Asn Pro
1               5

<210> SEQ ID NO 195
<211> LENGTH: 25
<212> TYPE: PRT
<213> ORGANISM: Artificial Sequence
<220> FEATURE:
<223> OTHER INFORMATION: synthetic peptide

<400> SEQUENCE: 195

Ala Arg Ile Arg Leu Val His Tyr Tyr Gly Ser Gly Asn Tyr Phe Lys
1               5                   10                  15

Ser Phe Gln Ser Phe Gly Met Gly Val
            20                  25

<210> SEQ ID NO 196
<211> LENGTH: 11
<212> TYPE: PRT
<213> ORGANISM: Artificial Sequence
<220> FEATURE:
<223> OTHER INFORMATION: synthetic peptide

<400> SEQUENCE: 196

Gln Thr Leu Leu His Ser Asn Gly Tyr Asn Tyr
1               5                   10

<210> SEQ ID NO 197
<211> LENGTH: 3
<212> TYPE: PRT
<213> ORGANISM: Artificial Sequence
<220> FEATURE:
<223> OTHER INFORMATION: synthetic peptide

<400> SEQUENCE: 197

Met Gly Ser
1

<210> SEQ ID NO 198
<211> LENGTH: 9
<212> TYPE: PRT
<213> ORGANISM: Artificial Sequence
<220> FEATURE:
<223> OTHER INFORMATION: synthetic peptide

<400> SEQUENCE: 198

Met Gln Gly Leu Gln Thr Pro His Thr
1               5

<210> SEQ ID NO 199
<211> LENGTH: 8
<212> TYPE: PRT
<213> ORGANISM: Artificial Sequence
<220> FEATURE:
<223> OTHER INFORMATION: synthetic peptide

<400> SEQUENCE: 199

Gly Phe Ser Phe Asp Asp Tyr Val
1               5

<210> SEQ ID NO 200
<211> LENGTH: 8
<212> TYPE: PRT
<213> ORGANISM: Artificial Sequence
<220> FEATURE:
<223> OTHER INFORMATION: synthetic peptide

<400> SEQUENCE: 200

Ile Ser Trp Asp Gly Asp Ser Thr
1               5

<210> SEQ ID NO 201
<211> LENGTH: 17

```
<212> TYPE: PRT
<213> ORGANISM: Artificial Sequence
<220> FEATURE:
<223> OTHER INFORMATION: synthetic peptide

<400> SEQUENCE: 201

Ala Arg Ser Leu Ala Asp Tyr Leu Asn Tyr Tyr His Tyr Thr Met Asp
1               5                   10                  15
Val

<210> SEQ ID NO 202
<211> LENGTH: 12
<212> TYPE: PRT
<213> ORGANISM: Artificial Sequence
<220> FEATURE:
<223> OTHER INFORMATION: synthetic peptide

<400> SEQUENCE: 202

Gln Ser Val Leu Tyr Ser Ser Ser Asn Lys Ser Tyr
1               5                   10

<210> SEQ ID NO 203
<211> LENGTH: 3
<212> TYPE: PRT
<213> ORGANISM: Artificial Sequence
<220> FEATURE:
<223> OTHER INFORMATION: synthetic peptide

<400> SEQUENCE: 203

Trp Ala Ser
1

<210> SEQ ID NO 204
<211> LENGTH: 9
<212> TYPE: PRT
<213> ORGANISM: Artificial Sequence
<220> FEATURE:
<223> OTHER INFORMATION: synthetic peptide

<400> SEQUENCE: 204

Gln Gln Tyr Tyr Ser Thr Pro Tyr Thr
1               5

<210> SEQ ID NO 205
<211> LENGTH: 8
<212> TYPE: PRT
<213> ORGANISM: Artificial Sequence
<220> FEATURE:
<223> OTHER INFORMATION: synthetic peptide

<400> SEQUENCE: 205

Gly Phe Thr Phe Ser Ala His Tyr
1               5

<210> SEQ ID NO 206
<211> LENGTH: 8
<212> TYPE: PRT
<213> ORGANISM: Artificial Sequence
<220> FEATURE:
<223> OTHER INFORMATION: synthetic peptide

<400> SEQUENCE: 206

Ile Ser Ser Arg Gly Ser Thr Ile
1               5

<210> SEQ ID NO 207
```

```
<211> LENGTH: 13
<212> TYPE: PRT
<213> ORGANISM: Artificial Sequence
<220> FEATURE:
<223> OTHER INFORMATION: synthetic peptide

<400> SEQUENCE: 207

Ala Gly Ala Ile Thr Trp Asn Asp Val Phe Phe Trp Tyr
1               5                   10

<210> SEQ ID NO 208
<211> LENGTH: 11
<212> TYPE: PRT
<213> ORGANISM: Artificial Sequence
<220> FEATURE:
<223> OTHER INFORMATION: synthetic peptide

<400> SEQUENCE: 208

Gln Ser Leu Val His Ser Asp Gly Asn Thr Tyr
1               5                   10

<210> SEQ ID NO 209
<211> LENGTH: 3
<212> TYPE: PRT
<213> ORGANISM: Artificial Sequence
<220> FEATURE:
<223> OTHER INFORMATION: synthetic peptide

<400> SEQUENCE: 209

Lys Val Ser
1

<210> SEQ ID NO 210
<211> LENGTH: 9
<212> TYPE: PRT
<213> ORGANISM: Artificial Sequence
<220> FEATURE:
<223> OTHER INFORMATION: synthetic peptide

<400> SEQUENCE: 210

Met Gln Ala Thr Gln Phe Leu Trp Thr
1               5

<210> SEQ ID NO 211
<211> LENGTH: 10
<212> TYPE: PRT
<213> ORGANISM: Artificial Sequence
<220> FEATURE:
<223> OTHER INFORMATION: synthetic peptide

<400> SEQUENCE: 211

Gly Phe Ser Leu Thr Thr Ser Gly Met Cys
1               5                   10

<210> SEQ ID NO 212
<211> LENGTH: 7
<212> TYPE: PRT
<213> ORGANISM: Artificial Sequence
<220> FEATURE:
<223> OTHER INFORMATION: synthetic peptide

<400> SEQUENCE: 212

Ile Asp Trp Asp Asp Asp Lys
1               5

<210> SEQ ID NO 213
<211> LENGTH: 21
```

```
<212> TYPE: PRT
<213> ORGANISM: Artificial Sequence
<220> FEATURE:
<223> OTHER INFORMATION: synthetic peptide

<400> SEQUENCE: 213

Ala Arg Ser Pro Pro Gly Ala Ser Val Ala Ile Leu Pro Thr Thr Lys
1               5                   10                  15

Tyr Tyr Phe Asp Ser
            20

<210> SEQ ID NO 214
<211> LENGTH: 7
<212> TYPE: PRT
<213> ORGANISM: Artificial Sequence
<220> FEATURE:
<223> OTHER INFORMATION: synthetic peptide

<400> SEQUENCE: 214

His Ser Val Thr Ser Ser Tyr
1               5

<210> SEQ ID NO 215
<211> LENGTH: 3
<212> TYPE: PRT
<213> ORGANISM: Artificial Sequence
<220> FEATURE:
<223> OTHER INFORMATION: synthetic peptide

<400> SEQUENCE: 215

Gly Ala Ser
1

<210> SEQ ID NO 216
<211> LENGTH: 10
<212> TYPE: PRT
<213> ORGANISM: Artificial Sequence
<220> FEATURE:
<223> OTHER INFORMATION: synthetic peptide

<400> SEQUENCE: 216

Gln Gln Tyr Gly Ser Ser Ala Met Tyr Thr
1               5                   10

<210> SEQ ID NO 217
<211> LENGTH: 6
<212> TYPE: PRT
<213> ORGANISM: Artificial Sequence
<220> FEATURE:
<223> OTHER INFORMATION: synthetic peptide

<400> SEQUENCE: 217

Gln Asp Val Thr Thr Ala
1               5

<210> SEQ ID NO 218
<211> LENGTH: 3
<212> TYPE: PRT
<213> ORGANISM: Artificial Sequence
<220> FEATURE:
<223> OTHER INFORMATION: synthetic peptide

<400> SEQUENCE: 218

Trp Ala Ser
1
```

```
<210> SEQ ID NO 219
<211> LENGTH: 9
<212> TYPE: PRT
<213> ORGANISM: Artificial Sequence
<220> FEATURE:
<223> OTHER INFORMATION: synthetic peptide

<400> SEQUENCE: 219

Gln Gln His Tyr Ser Thr Pro Leu Thr
1               5

<210> SEQ ID NO 220
<211> LENGTH: 8
<212> TYPE: PRT
<213> ORGANISM: Artificial Sequence
<220> FEATURE:
<223> OTHER INFORMATION: synthetic peptide

<400> SEQUENCE: 220

Gly Phe Thr Phe Gly Asn Tyr Gly
1               5

<210> SEQ ID NO 221
<211> LENGTH: 8
<212> TYPE: PRT
<213> ORGANISM: Artificial Sequence
<220> FEATURE:
<223> OTHER INFORMATION: synthetic peptide

<400> SEQUENCE: 221

Ile Trp Phe Asp Gly Ser Asn Lys
1               5

<210> SEQ ID NO 222
<211> LENGTH: 18
<212> TYPE: PRT
<213> ORGANISM: Artificial Sequence
<220> FEATURE:
<223> OTHER INFORMATION: synthetic peptide

<400> SEQUENCE: 222

Ala Arg Ala Asp Gly Tyr Cys Ser Asp Asp Ala Cys Tyr Asp Trp Phe
1               5                   10                  15

Asp Pro

<210> SEQ ID NO 223
<211> LENGTH: 8
<212> TYPE: PRT
<213> ORGANISM: Artificial Sequence
<220> FEATURE:
<223> OTHER INFORMATION: synthetic peptide

<400> SEQUENCE: 223

Gly Phe Thr Phe Ser Ser Tyr Val
1               5

<210> SEQ ID NO 224
<211> LENGTH: 8
<212> TYPE: PRT
<213> ORGANISM: Artificial Sequence
<220> FEATURE:
<223> OTHER INFORMATION: synthetic peptide

<400> SEQUENCE: 224

Ile Ser Tyr Asp Gly Ser Asn Lys
1               5
```

```
<210> SEQ ID NO 225
<211> LENGTH: 16
<212> TYPE: PRT
<213> ORGANISM: Artificial Sequence
<220> FEATURE:
<223> OTHER INFORMATION: synthetic peptide

<400> SEQUENCE: 225

Ala Arg Asp Thr Gln Thr Gln Ser Ser Asp Tyr Tyr Leu Phe Gly Ala
1               5                   10                  15

<210> SEQ ID NO 226
<211> LENGTH: 6
<212> TYPE: PRT
<213> ORGANISM: Artificial Sequence
<220> FEATURE:
<223> OTHER INFORMATION: synthetic peptide

<400> SEQUENCE: 226

Gln Ser Ile Ile Asn Asn
1               5

<210> SEQ ID NO 227
<211> LENGTH: 3
<212> TYPE: PRT
<213> ORGANISM: Artificial Sequence
<220> FEATURE:
<223> OTHER INFORMATION: synthetic peptide

<400> SEQUENCE: 227

Gly Ala Ser
1

<210> SEQ ID NO 228
<211> LENGTH: 10
<212> TYPE: PRT
<213> ORGANISM: Artificial Sequence
<220> FEATURE:
<223> OTHER INFORMATION: synthetic peptide

<400> SEQUENCE: 228

Gln Gln Tyr Asn Asp Trp Pro Pro Ile Thr
1               5                   10

<210> SEQ ID NO 229
<211> LENGTH: 8
<212> TYPE: PRT
<213> ORGANISM: Artificial Sequence
<220> FEATURE:
<223> OTHER INFORMATION: synthetic peptide

<400> SEQUENCE: 229

Ser Gly Asp Ser Met Ser Tyr Tyr
1               5

<210> SEQ ID NO 230
<211> LENGTH: 7
<212> TYPE: PRT
<213> ORGANISM: Artificial Sequence
<220> FEATURE:
<223> OTHER INFORMATION: synthetic peptide

<400> SEQUENCE: 230

Ile Phe Ile Ser Gly Asn Thr
1               5
```

```
<210> SEQ ID NO 231
<211> LENGTH: 9
<212> TYPE: PRT
<213> ORGANISM: Artificial Sequence
<220> FEATURE:
<223> OTHER INFORMATION: synthetic peptide

<400> SEQUENCE: 231

Ala Lys Gly Ser Arg Ser Phe Ile Ala
1               5

<210> SEQ ID NO 232
<211> LENGTH: 6
<212> TYPE: PRT
<213> ORGANISM: Artificial Sequence
<220> FEATURE:
<223> OTHER INFORMATION: synthetic peptide

<400> SEQUENCE: 232

Gln Asp Val Ser Ile Tyr
1               5

<210> SEQ ID NO 233
<211> LENGTH: 3
<212> TYPE: PRT
<213> ORGANISM: Artificial Sequence
<220> FEATURE:
<223> OTHER INFORMATION: synthetic peptide

<400> SEQUENCE: 233

Asp Ala Ser
1

<210> SEQ ID NO 234
<211> LENGTH: 9
<212> TYPE: PRT
<213> ORGANISM: Artificial Sequence
<220> FEATURE:
<223> OTHER INFORMATION: synthetic peptide

<400> SEQUENCE: 234

Gln Gln His Asp Asn Leu Pro Pro Thr
1               5

<210> SEQ ID NO 235
<211> LENGTH: 8
<212> TYPE: PRT
<213> ORGANISM: Artificial Sequence
<220> FEATURE:
<223> OTHER INFORMATION: synthetic peptide

<400> SEQUENCE: 235

Gly Phe Thr Phe Ser Ser Tyr Glu
1               5

<210> SEQ ID NO 236
<211> LENGTH: 8
<212> TYPE: PRT
<213> ORGANISM: Artificial Sequence
<220> FEATURE:
<223> OTHER INFORMATION: synthetic peptide

<400> SEQUENCE: 236

Ile Ser Gly Gly Gly Asp Thr Ile
1               5

<210> SEQ ID NO 237
```

```
<211> LENGTH: 13
<212> TYPE: PRT
<213> ORGANISM: Artificial Sequence
<220> FEATURE:
<223> OTHER INFORMATION: synthetic peptide

<400> SEQUENCE: 237

Ala Lys Phe Trp Asn Asp Tyr Tyr Asn Asp Phe Glu Tyr
1               5                   10

<210> SEQ ID NO 238
<211> LENGTH: 6
<212> TYPE: PRT
<213> ORGANISM: Artificial Sequence
<220> FEATURE:
<223> OTHER INFORMATION: synthetic peptide

<400> SEQUENCE: 238

Gln Ser Val Ser Ser Tyr
1               5

<210> SEQ ID NO 239
<211> LENGTH: 3
<212> TYPE: PRT
<213> ORGANISM: Artificial Sequence
<220> FEATURE:
<223> OTHER INFORMATION: synthetic peptide

<400> SEQUENCE: 239

Asp Ala Ser
1

<210> SEQ ID NO 240
<211> LENGTH: 10
<212> TYPE: PRT
<213> ORGANISM: Artificial Sequence
<220> FEATURE:
<223> OTHER INFORMATION: synthetic peptide

<400> SEQUENCE: 240

Gln Gln Arg Thr Asn Trp Pro Pro Trp Thr
1               5                   10

<210> SEQ ID NO 241
<211> LENGTH: 8
<212> TYPE: PRT
<213> ORGANISM: Artificial Sequence
<220> FEATURE:
<223> OTHER INFORMATION: synthetic peptide

<400> SEQUENCE: 241

Gly Tyr Ser Phe Thr Ser Phe Asp
1               5

<210> SEQ ID NO 242
<211> LENGTH: 8
<212> TYPE: PRT
<213> ORGANISM: Artificial Sequence
<220> FEATURE:
<223> OTHER INFORMATION: synthetic peptide

<400> SEQUENCE: 242

Met Asn Pro Asn Ser Gly Ser Ser
1               5

<210> SEQ ID NO 243
<211> LENGTH: 11
```

```
<212> TYPE: PRT
<213> ORGANISM: Artificial Sequence
<220> FEATURE:
<223> OTHER INFORMATION: synthetic peptide

<400> SEQUENCE: 243

Ala Thr Ile Thr Val Thr Gly Thr Leu Gly Phe
1               5                   10

<210> SEQ ID NO 244
<211> LENGTH: 6
<212> TYPE: PRT
<213> ORGANISM: Artificial Sequence
<220> FEATURE:
<223> OTHER INFORMATION: synthetic peptide

<400> SEQUENCE: 244

Gln Gly Ile Arg His Tyr
1               5

<210> SEQ ID NO 245
<211> LENGTH: 3
<212> TYPE: PRT
<213> ORGANISM: Artificial Sequence
<220> FEATURE:
<223> OTHER INFORMATION: synthetic peptide

<400> SEQUENCE: 245

Ala Ala Ser
1

<210> SEQ ID NO 246
<211> LENGTH: 10
<212> TYPE: PRT
<213> ORGANISM: Artificial Sequence
<220> FEATURE:
<223> OTHER INFORMATION: synthetic peptide

<400> SEQUENCE: 246

Gln Gln Leu Asn Ser Tyr Pro Pro Val Thr
1               5                   10

<210> SEQ ID NO 247
<211> LENGTH: 8
<212> TYPE: PRT
<213> ORGANISM: Artificial Sequence
<220> FEATURE:
<223> OTHER INFORMATION: synthetic peptide

<400> SEQUENCE: 247

Gly Asp Thr Phe Ser Ser Tyr Gly
1               5

<210> SEQ ID NO 248
<211> LENGTH: 8
<212> TYPE: PRT
<213> ORGANISM: Artificial Sequence
<220> FEATURE:
<223> OTHER INFORMATION: synthetic peptide

<400> SEQUENCE: 248

Ile Ile Pro Ile Val Asp Ile Thr
1               5

<210> SEQ ID NO 249
<211> LENGTH: 24
<212> TYPE: PRT
```

```
<213> ORGANISM: Artificial Sequence
<220> FEATURE:
<223> OTHER INFORMATION: synthetic peptide

<400> SEQUENCE: 249

Ala Arg Ile Ser Ala Tyr Tyr Tyr Asp Gly Ser Gly Ser Asn Pro Gly
1               5                   10                  15

Ile Thr Asp Tyr Gly Met Asp Val
            20

<210> SEQ ID NO 250
<211> LENGTH: 11
<212> TYPE: PRT
<213> ORGANISM: Artificial Sequence
<220> FEATURE:
<223> OTHER INFORMATION: synthetic peptide

<400> SEQUENCE: 250

Gln Ser Leu Leu His Ser Asn Gly Tyr Asn Tyr
1               5                   10

<210> SEQ ID NO 251
<211> LENGTH: 3
<212> TYPE: PRT
<213> ORGANISM: Artificial Sequence
<220> FEATURE:
<223> OTHER INFORMATION: synthetic peptide

<400> SEQUENCE: 251

Leu Gly Ser
1

<210> SEQ ID NO 252
<211> LENGTH: 9
<212> TYPE: PRT
<213> ORGANISM: Artificial Sequence
<220> FEATURE:
<223> OTHER INFORMATION: synthetic peptide

<400> SEQUENCE: 252

Met Gln Gly Leu Gln Thr Pro His Thr
1               5

<210> SEQ ID NO 253
<211> LENGTH: 8
<212> TYPE: PRT
<213> ORGANISM: Artificial Sequence
<220> FEATURE:
<223> OTHER INFORMATION: synthetic peptide

<400> SEQUENCE: 253

Gly Phe Ser Phe Ser Asp Tyr Tyr
1               5

<210> SEQ ID NO 254
<211> LENGTH: 7
<212> TYPE: PRT
<213> ORGANISM: Artificial Sequence
<220> FEATURE:
<223> OTHER INFORMATION: synthetic peptide

<400> SEQUENCE: 254

Ile Tyr Ser Gly Gly Ser Thr
1               5

<210> SEQ ID NO 255
```

```
<211> LENGTH: 15
<212> TYPE: PRT
<213> ORGANISM: Artificial Sequence
<220> FEATURE:
<223> OTHER INFORMATION: synthetic peptide

<400> SEQUENCE: 255

Ala Arg Ala Pro Ser Trp Gly Leu Arg Val Gly Pro Phe Asp Phe
1               5                   10                  15

<210> SEQ ID NO 256
<211> LENGTH: 6
<212> TYPE: PRT
<213> ORGANISM: Artificial Sequence
<220> FEATURE:
<223> OTHER INFORMATION: synthetic peptide

<400> SEQUENCE: 256

Arg Ser Ile Asn Ser Tyr
1               5

<210> SEQ ID NO 257
<211> LENGTH: 3
<212> TYPE: PRT
<213> ORGANISM: Artificial Sequence
<220> FEATURE:
<223> OTHER INFORMATION: synthetic peptide

<400> SEQUENCE: 257

Ala Ala Ser
1

<210> SEQ ID NO 258
<211> LENGTH: 10
<212> TYPE: PRT
<213> ORGANISM: Artificial Sequence
<220> FEATURE:
<223> OTHER INFORMATION: synthetic peptide

<400> SEQUENCE: 258

His Gln Thr Tyr Thr Thr Pro Pro Gly Thr
1               5                   10

<210> SEQ ID NO 259
<211> LENGTH: 8
<212> TYPE: PRT
<213> ORGANISM: Artificial Sequence
<220> FEATURE:
<223> OTHER INFORMATION: synthetic peptide

<400> SEQUENCE: 259

Gly Tyr Thr Phe Ser Asp Tyr Asp
1               5

<210> SEQ ID NO 260
<211> LENGTH: 8
<212> TYPE: PRT
<213> ORGANISM: Artificial Sequence
<220> FEATURE:
<223> OTHER INFORMATION: synthetic peptide

<400> SEQUENCE: 260

Ile Ser Thr Tyr Ser Gly Asp Ala
1               5

<210> SEQ ID NO 261
<211> LENGTH: 23
```

```
<212> TYPE: PRT
<213> ORGANISM: Artificial Sequence
<220> FEATURE:
<223> OTHER INFORMATION: synthetic peptide

<400> SEQUENCE: 261

Ala Arg Ala Ala His Leu Ser Tyr Asp Phe Trp Asn Gly Pro Lys Gly
1               5                   10                  15

Trp Tyr His Phe Met Asp Val
            20

<210> SEQ ID NO 262
<211> LENGTH: 6
<212> TYPE: PRT
<213> ORGANISM: Artificial Sequence
<220> FEATURE:
<223> OTHER INFORMATION: synthetic peptide

<400> SEQUENCE: 262

Gln Ser Ile Thr Thr Trp
1               5

<210> SEQ ID NO 263
<211> LENGTH: 3
<212> TYPE: PRT
<213> ORGANISM: Artificial Sequence
<220> FEATURE:
<223> OTHER INFORMATION: synthetic peptide

<400> SEQUENCE: 263

Lys Thr Ser
1

<210> SEQ ID NO 264
<211> LENGTH: 9
<212> TYPE: PRT
<213> ORGANISM: Artificial Sequence
<220> FEATURE:
<223> OTHER INFORMATION: synthetic peptide

<400> SEQUENCE: 264

Gln Gln Cys Asp Ser Asn Leu Trp Ser
1               5

<210> SEQ ID NO 265
<211> LENGTH: 8
<212> TYPE: PRT
<213> ORGANISM: Artificial Sequence
<220> FEATURE:
<223> OTHER INFORMATION: synthetic peptide

<400> SEQUENCE: 265

Gly Tyr Thr Phe Ile Asp Tyr Tyr
1               5

<210> SEQ ID NO 266
<211> LENGTH: 8
<212> TYPE: PRT
<213> ORGANISM: Artificial Sequence
<220> FEATURE:
<223> OTHER INFORMATION: synthetic peptide

<400> SEQUENCE: 266

Ile Asn Pro Asn Ser Gly Asp Thr
1               5
```

```
<210> SEQ ID NO 267
<211> LENGTH: 13
<212> TYPE: PRT
<213> ORGANISM: Artificial Sequence
<220> FEATURE:
<223> OTHER INFORMATION: synthetic peptide

<400> SEQUENCE: 267

Ala Arg Asp Pro Leu Pro Glu Thr Met Asp Ile Asp Tyr
1               5                   10

<210> SEQ ID NO 268
<211> LENGTH: 7
<212> TYPE: PRT
<213> ORGANISM: Artificial Sequence
<220> FEATURE:
<223> OTHER INFORMATION: synthetic peptide

<400> SEQUENCE: 268

Gln Ser Val Ser Ser Asn Tyr
1               5

<210> SEQ ID NO 269
<211> LENGTH: 3
<212> TYPE: PRT
<213> ORGANISM: Artificial Sequence
<220> FEATURE:
<223> OTHER INFORMATION: synthetic peptide

<400> SEQUENCE: 269

Thr Ala Ser
1

<210> SEQ ID NO 270
<211> LENGTH: 9
<212> TYPE: PRT
<213> ORGANISM: Artificial Sequence
<220> FEATURE:
<223> OTHER INFORMATION: synthetic peptide

<400> SEQUENCE: 270

Gln Gln Tyr Gly Ser Ala Pro Arg Thr
1               5

<210> SEQ ID NO 271
<211> LENGTH: 10
<212> TYPE: PRT
<213> ORGANISM: Artificial Sequence
<220> FEATURE:
<223> OTHER INFORMATION: synthetic peptide

<400> SEQUENCE: 271

Gly Asp Ser Ile Ser Thr Glu Thr Tyr Tyr
1               5                   10

<210> SEQ ID NO 272
<211> LENGTH: 7
<212> TYPE: PRT
<213> ORGANISM: Artificial Sequence
<220> FEATURE:
<223> OTHER INFORMATION: synthetic peptide

<400> SEQUENCE: 272

Ile Tyr Ala Ser Gly Ser Thr
1               5

<210> SEQ ID NO 273
```

```
<211> LENGTH: 19
<212> TYPE: PRT
<213> ORGANISM: Artificial Sequence
<220> FEATURE:
<223> OTHER INFORMATION: synthetic peptide

<400> SEQUENCE: 273

Ala Arg Glu Trp Tyr Tyr Tyr Asn Ser Ser Gly Phe Tyr Leu Glu Ala
1               5                   10                  15

Phe Asp Ile

<210> SEQ ID NO 274
<211> LENGTH: 8
<212> TYPE: PRT
<213> ORGANISM: Artificial Sequence
<220> FEATURE:
<223> OTHER INFORMATION: synthetic peptide

<400> SEQUENCE: 274

Gly Gly Ser Phe Gly Gly Tyr Tyr
1               5

<210> SEQ ID NO 275
<211> LENGTH: 7
<212> TYPE: PRT
<213> ORGANISM: Artificial Sequence
<220> FEATURE:
<223> OTHER INFORMATION: synthetic peptide

<400> SEQUENCE: 275

Ile Asn His Ser Gly Ser Thr
1               5

<210> SEQ ID NO 276
<211> LENGTH: 8
<212> TYPE: PRT
<213> ORGANISM: Artificial Sequence
<220> FEATURE:
<223> OTHER INFORMATION: synthetic peptide

<400> SEQUENCE: 276

Ala Arg Gly Pro Tyr Phe Asp Tyr
1               5

<210> SEQ ID NO 277
<211> LENGTH: 6
<212> TYPE: PRT
<213> ORGANISM: Artificial Sequence
<220> FEATURE:
<223> OTHER INFORMATION: synthetic peptide

<400> SEQUENCE: 277

Gln Ser Val Ser Ser Asp
1               5

<210> SEQ ID NO 278
<211> LENGTH: 3
<212> TYPE: PRT
<213> ORGANISM: Artificial Sequence
<220> FEATURE:
<223> OTHER INFORMATION: synthetic peptide

<400> SEQUENCE: 278

Gly Ala Ser
1
```

```
<210> SEQ ID NO 279
<211> LENGTH: 9
<212> TYPE: PRT
<213> ORGANISM: Artificial Sequence
<220> FEATURE:
<223> OTHER INFORMATION: synthetic peptide

<400> SEQUENCE: 279

Gln Gln Tyr Lys Ser Trp Pro Tyr Thr
1               5

<210> SEQ ID NO 280
<211> LENGTH: 10
<212> TYPE: PRT
<213> ORGANISM: Artificial Sequence
<220> FEATURE:
<223> OTHER INFORMATION: synthetic peptide

<400> SEQUENCE: 280

Gly Phe Ser Leu Ser Thr Ser Gly Val Gly
1               5                   10

<210> SEQ ID NO 281
<211> LENGTH: 7
<212> TYPE: PRT
<213> ORGANISM: Artificial Sequence
<220> FEATURE:
<223> OTHER INFORMATION: synthetic peptide

<400> SEQUENCE: 281

Ile Tyr Trp Asp Asp Asp Lys
1               5

<210> SEQ ID NO 282
<211> LENGTH: 13
<212> TYPE: PRT
<213> ORGANISM: Artificial Sequence
<220> FEATURE:
<223> OTHER INFORMATION: synthetic peptide

<400> SEQUENCE: 282

Ala His Leu Thr Ser Tyr Pro Ile Asn Ala Phe Asp Ile
1               5                   10

<210> SEQ ID NO 283
<211> LENGTH: 6
<212> TYPE: PRT
<213> ORGANISM: Artificial Sequence
<220> FEATURE:
<223> OTHER INFORMATION: synthetic peptide

<400> SEQUENCE: 283

His Thr Ile Ser Thr Asn
1               5

<210> SEQ ID NO 284
<211> LENGTH: 3
<212> TYPE: PRT
<213> ORGANISM: Artificial Sequence
<220> FEATURE:
<223> OTHER INFORMATION: synthetic peptide

<400> SEQUENCE: 284

Arg Ala Ser
1

<210> SEQ ID NO 285
```

```
<211> LENGTH: 8
<212> TYPE: PRT
<213> ORGANISM: Artificial Sequence
<220> FEATURE:
<223> OTHER INFORMATION: synthetic peptide

<400> SEQUENCE: 285

Gln Gln Tyr Asn Asn Trp Pro Thr
1               5

<210> SEQ ID NO 286
<211> LENGTH: 8
<212> TYPE: PRT
<213> ORGANISM: Artificial Sequence
<220> FEATURE:
<223> OTHER INFORMATION: synthetic peptide

<400> SEQUENCE: 286

Gly Glu Ser Phe Ser Gly Tyr Tyr
1               5

<210> SEQ ID NO 287
<211> LENGTH: 7
<212> TYPE: PRT
<213> ORGANISM: Artificial Sequence
<220> FEATURE:
<223> OTHER INFORMATION: synthetic peptide

<400> SEQUENCE: 287

Ile Asn His Ser Gly Ser Thr
1               5

<210> SEQ ID NO 288
<211> LENGTH: 20
<212> TYPE: PRT
<213> ORGANISM: Artificial Sequence
<220> FEATURE:
<223> OTHER INFORMATION: synthetic peptide

<400> SEQUENCE: 288

Ala Arg Gly Tyr Ala Asp Thr Pro Val Phe Arg Arg Tyr Tyr Tyr
1               5                   10                  15

Gly Met Asp Val
            20

<210> SEQ ID NO 289
<211> LENGTH: 6
<212> TYPE: PRT
<213> ORGANISM: Artificial Sequence
<220> FEATURE:
<223> OTHER INFORMATION: synthetic peptide

<400> SEQUENCE: 289

Gln Thr Val Ser Ser Lys
1               5

<210> SEQ ID NO 290
<211> LENGTH: 3
<212> TYPE: PRT
<213> ORGANISM: Artificial Sequence
<220> FEATURE:
<223> OTHER INFORMATION: synthetic peptide

<400> SEQUENCE: 290

Gly Ala Ser
1
```

```
<210> SEQ ID NO 291
<211> LENGTH: 10
<212> TYPE: PRT
<213> ORGANISM: Artificial Sequence
<220> FEATURE:
<223> OTHER INFORMATION: synthetic peptide

<400> SEQUENCE: 291

Gln Gln Tyr Asp Asn Trp Pro Pro Tyr Thr
1               5                   10

<210> SEQ ID NO 292
<211> LENGTH: 8
<212> TYPE: PRT
<213> ORGANISM: Artificial Sequence
<220> FEATURE:
<223> OTHER INFORMATION: synthetic peptide

<400> SEQUENCE: 292

Gly Phe Thr Phe Ser Asn Tyr Gly
1               5

<210> SEQ ID NO 293
<211> LENGTH: 8
<212> TYPE: PRT
<213> ORGANISM: Artificial Sequence
<220> FEATURE:
<223> OTHER INFORMATION: synthetic peptide

<400> SEQUENCE: 293

Ile Ser Gly Gly Gly Ala Ser Thr
1               5

<210> SEQ ID NO 294
<211> LENGTH: 15
<212> TYPE: PRT
<213> ORGANISM: Artificial Sequence
<220> FEATURE:
<223> OTHER INFORMATION: synthetic peptide

<400> SEQUENCE: 294

Ala Lys Gly Gly Arg Trp Asp Gly Ser Ile Ala Glu Phe Asp Tyr
1               5                   10                  15

<210> SEQ ID NO 295
<211> LENGTH: 6
<212> TYPE: PRT
<213> ORGANISM: Artificial Sequence
<220> FEATURE:
<223> OTHER INFORMATION: synthetic peptide

<400> SEQUENCE: 295

Gln Ser Val Arg Gly Asn
1               5

<210> SEQ ID NO 296
<211> LENGTH: 3
<212> TYPE: PRT
<213> ORGANISM: Artificial Sequence
<220> FEATURE:
<223> OTHER INFORMATION: synthetic peptide

<400> SEQUENCE: 296

Gly Ala Ser
1
```

```
<210> SEQ ID NO 297
<211> LENGTH: 10
<212> TYPE: PRT
<213> ORGANISM: Artificial Sequence
<220> FEATURE:
<223> OTHER INFORMATION: synthetic peptide

<400> SEQUENCE: 297

Gln Gln Tyr Asn Asn Trp Pro Leu Tyr Thr
1               5                   10

<210> SEQ ID NO 298
<211> LENGTH: 10
<212> TYPE: PRT
<213> ORGANISM: Artificial Sequence
<220> FEATURE:
<223> OTHER INFORMATION: synthetic peptide

<400> SEQUENCE: 298

Gly Ala Ser Ile Ser Ser Gly Asp Tyr Tyr
1               5                   10

<210> SEQ ID NO 299
<211> LENGTH: 7
<212> TYPE: PRT
<213> ORGANISM: Artificial Sequence
<220> FEATURE:
<223> OTHER INFORMATION: synthetic peptide

<400> SEQUENCE: 299

Ile Tyr Tyr Thr Gly Arg Thr
1               5

<210> SEQ ID NO 300
<211> LENGTH: 14
<212> TYPE: PRT
<213> ORGANISM: Artificial Sequence
<220> FEATURE:
<223> OTHER INFORMATION: synthetic peptide

<400> SEQUENCE: 300

Ala Arg Asp Arg Gly Val Arg Gly Gly Tyr Gly Ile Asp Tyr
1               5                   10

<210> SEQ ID NO 301
<211> LENGTH: 7
<212> TYPE: PRT
<213> ORGANISM: Artificial Sequence
<220> FEATURE:
<223> OTHER INFORMATION: synthetic peptide

<400> SEQUENCE: 301

Gln Ser Val Gly Ser Ser Tyr
1               5

<210> SEQ ID NO 302
<211> LENGTH: 3
<212> TYPE: PRT
<213> ORGANISM: Artificial Sequence
<220> FEATURE:
<223> OTHER INFORMATION: synthetic peptide

<400> SEQUENCE: 302

Gly Ser Ser
1

<210> SEQ ID NO 303
```

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 303

Leu Gln Tyr Ala Gly Thr Pro Arg Thr
1               5

<210> SEQ ID NO 304
<211> LENGTH: 8
<212> TYPE: PRT
<213> ORGANISM: Artificial Sequence
<220> FEATURE:
<223> OTHER INFORMATION: synthetic peptide

<400> SEQUENCE: 304

Gly Tyr Trp Phe Thr Ser Tyr Trp
1               5

<210> SEQ ID NO 305
<211> LENGTH: 8
<212> TYPE: PRT
<213> ORGANISM: Artificial Sequence
<220> FEATURE:
<223> OTHER INFORMATION: synthetic peptide

<400> SEQUENCE: 305

Ile Tyr Pro Gly Asp Ser Asp Ala
1               5

<210> SEQ ID NO 306
<211> LENGTH: 14
<212> TYPE: PRT
<213> ORGANISM: Artificial Sequence
<220> FEATURE:
<223> OTHER INFORMATION: synthetic peptide

<400> SEQUENCE: 306

Ala Arg His Ser Val Gly Glu Ala Pro Arg Gln Leu Glu Phe
1               5                   10

<210> SEQ ID NO 307
<211> LENGTH: 7
<212> TYPE: PRT
<213> ORGANISM: Artificial Sequence
<220> FEATURE:
<223> OTHER INFORMATION: synthetic peptide

<400> SEQUENCE: 307

Ala Ser Gln Ser Val Ser Arg
1               5

<210> SEQ ID NO 308
<211> LENGTH: 3
<212> TYPE: PRT
<213> ORGANISM: Artificial Sequence
<220> FEATURE:
<223> OTHER INFORMATION: synthetic peptide

<400> SEQUENCE: 308

Asp Ala Ser
1

<210> SEQ ID NO 309
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 309

Gln Gln Tyr Gly Ser Thr Pro Tyr Thr
1               5

<210> SEQ ID NO 310
<211> LENGTH: 8
<212> TYPE: PRT
<213> ORGANISM: Artificial Sequence
<220> FEATURE:
<223> OTHER INFORMATION: synthetic peptide

<400> SEQUENCE: 310

Gly Phe Thr Phe Ser Ser Tyr Ser
1               5

<210> SEQ ID NO 311
<211> LENGTH: 8
<212> TYPE: PRT
<213> ORGANISM: Artificial Sequence
<220> FEATURE:
<223> OTHER INFORMATION: synthetic peptide

<400> SEQUENCE: 311

Ile Ser Thr Thr Ser Ser Tyr Ile
1               5

<210> SEQ ID NO 312
<211> LENGTH: 11
<212> TYPE: PRT
<213> ORGANISM: Artificial Sequence
<220> FEATURE:
<223> OTHER INFORMATION: synthetic peptide

<400> SEQUENCE: 312

Ala Arg Asp Gly Val Ser Gly Ala His Asp Ile
1               5                   10

<210> SEQ ID NO 313
<211> LENGTH: 6
<212> TYPE: PRT
<213> ORGANISM: Artificial Sequence
<220> FEATURE:
<223> OTHER INFORMATION: synthetic peptide

<400> SEQUENCE: 313

Gln Ser Ile Ser Ser Tyr
1               5

<210> SEQ ID NO 314
<211> LENGTH: 3
<212> TYPE: PRT
<213> ORGANISM: Artificial Sequence
<220> FEATURE:
<223> OTHER INFORMATION: synthetic peptide

<400> SEQUENCE: 314

Ala Ala Ser
1

<210> SEQ ID NO 315
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 315

Gln Gln Thr Tyr Ser Thr Leu Trp Thr
1               5

<210> SEQ ID NO 316
<211> LENGTH: 8
<212> TYPE: PRT
<213> ORGANISM: Artificial Sequence
<220> FEATURE:
<223> OTHER INFORMATION: synthetic peptide

<400> SEQUENCE: 316

Gly Phe Thr Phe Gly Thr Tyr Ala
1               5

<210> SEQ ID NO 317
<211> LENGTH: 8
<212> TYPE: PRT
<213> ORGANISM: Artificial Sequence
<220> FEATURE:
<223> OTHER INFORMATION: synthetic peptide

<400> SEQUENCE: 317

Ile Ser Gly Ser Gly Ala Gly Thr
1               5

<210> SEQ ID NO 318
<211> LENGTH: 13
<212> TYPE: PRT
<213> ORGANISM: Artificial Sequence
<220> FEATURE:
<223> OTHER INFORMATION: synthetic peptide

<400> SEQUENCE: 318

Ala Lys Asp Asn Ser Ala Ser Val Trp Asp Leu Ala Tyr
1               5                   10

<210> SEQ ID NO 319
<211> LENGTH: 11
<212> TYPE: PRT
<213> ORGANISM: Artificial Sequence
<220> FEATURE:
<223> OTHER INFORMATION: synthetic peptide

<400> SEQUENCE: 319

His Ser Leu Leu His Thr Asn Gly Tyr Asn Tyr
1               5                   10

<210> SEQ ID NO 320
<211> LENGTH: 3
<212> TYPE: PRT
<213> ORGANISM: Artificial Sequence
<220> FEATURE:
<223> OTHER INFORMATION: synthetic peptide

<400> SEQUENCE: 320

Leu Gly Ser
1

<210> SEQ ID NO 321
<211> LENGTH: 9
<212> TYPE: PRT
<213> ORGANISM: Artificial Sequence
```

```
<220> FEATURE:
<223> OTHER INFORMATION: synthetic peptide

<400> SEQUENCE: 321

Met Gln Ala Leu Gln Thr Leu Tyr Thr
1               5

<210> SEQ ID NO 322
<211> LENGTH: 8
<212> TYPE: PRT
<213> ORGANISM: Artificial Sequence
<220> FEATURE:
<223> OTHER INFORMATION: synthetic peptide

<400> SEQUENCE: 322

Gly Phe Thr Phe Ser Asn Tyr Ala
1               5

<210> SEQ ID NO 323
<211> LENGTH: 8
<212> TYPE: PRT
<213> ORGANISM: Artificial Sequence
<220> FEATURE:
<223> OTHER INFORMATION: synthetic peptide

<400> SEQUENCE: 323

Met Ser Tyr Asp Gly Ile Asn Thr
1               5

<210> SEQ ID NO 324
<211> LENGTH: 15
<212> TYPE: PRT
<213> ORGANISM: Artificial Sequence
<220> FEATURE:
<223> OTHER INFORMATION: synthetic peptide

<400> SEQUENCE: 324

Ala Arg Asp Leu Gln Tyr Arg Gly Trp Gly Ser Gly Leu Asp Ser
1               5                   10                  15

<210> SEQ ID NO 325
<211> LENGTH: 6
<212> TYPE: PRT
<213> ORGANISM: Artificial Sequence
<220> FEATURE:
<223> OTHER INFORMATION: synthetic peptide

<400> SEQUENCE: 325

Gln Thr Ile Asn Thr Tyr
1               5

<210> SEQ ID NO 326
<211> LENGTH: 3
<212> TYPE: PRT
<213> ORGANISM: Artificial Sequence
<220> FEATURE:
<223> OTHER INFORMATION: synthetic peptide

<400> SEQUENCE: 326

Ala Ala Ser
1

<210> SEQ ID NO 327
<211> LENGTH: 9
<212> TYPE: PRT
<213> ORGANISM: Artificial Sequence
<220> FEATURE:
```

<223> OTHER INFORMATION: synthetic peptide

<400> SEQUENCE: 327

Gln Gln Thr Tyr Ser Thr Pro Phe Thr
1               5

<210> SEQ ID NO 328
<211> LENGTH: 8
<212> TYPE: PRT
<213> ORGANISM: Artificial Sequence
<220> FEATURE:
<223> OTHER INFORMATION: synthetic peptide

<400> SEQUENCE: 328

Gly Tyr Thr Phe Thr Arg Tyr Ala
1               5

<210> SEQ ID NO 329
<211> LENGTH: 8
<212> TYPE: PRT
<213> ORGANISM: Artificial Sequence
<220> FEATURE:
<223> OTHER INFORMATION: synthetic peptide

<400> SEQUENCE: 329

Ile Asn Thr Asn Thr Gly Asn Pro
1               5

<210> SEQ ID NO 330
<211> LENGTH: 13
<212> TYPE: PRT
<213> ORGANISM: Artificial Sequence
<220> FEATURE:
<223> OTHER INFORMATION: synthetic peptide

<400> SEQUENCE: 330

Ala His Ile Pro Gly Ile Ala Ala Gly Glu Met Phe Pro
1               5                   10

<210> SEQ ID NO 331
<211> LENGTH: 6
<212> TYPE: PRT
<213> ORGANISM: Artificial Sequence
<220> FEATURE:
<223> OTHER INFORMATION: synthetic peptide

<400> SEQUENCE: 331

Gln Ser Val Gly Ser Tyr
1               5

<210> SEQ ID NO 332
<211> LENGTH: 3
<212> TYPE: PRT
<213> ORGANISM: Artificial Sequence
<220> FEATURE:
<223> OTHER INFORMATION: synthetic peptide

<400> SEQUENCE: 332

Asp Val Ser
1

<210> SEQ ID NO 333
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 333

Gln His Gly Ser Asn Trp Arg Val Ala
1               5

<210> SEQ ID NO 334
<211> LENGTH: 8
<212> TYPE: PRT
<213> ORGANISM: Artificial Sequence
<220> FEATURE:
<223> OTHER INFORMATION: synthetic peptide

<400> SEQUENCE: 334

Gly Phe Thr Phe Asp Asp Tyr Ala
1               5

<210> SEQ ID NO 335
<211> LENGTH: 8
<212> TYPE: PRT
<213> ORGANISM: Artificial Sequence
<220> FEATURE:
<223> OTHER INFORMATION: synthetic peptide

<400> SEQUENCE: 335

Ile Ser Trp Asn Gly Asp Thr Val
1               5

<210> SEQ ID NO 336
<211> LENGTH: 18
<212> TYPE: PRT
<213> ORGANISM: Artificial Sequence
<220> FEATURE:
<223> OTHER INFORMATION: synthetic peptide

<400> SEQUENCE: 336

Ala Lys Asp Met Ala Ala Gly Glu Gly Asp Tyr Tyr Asn His Tyr Phe
1               5                   10                  15

Asp Pro

<210> SEQ ID NO 337
<211> LENGTH: 6
<212> TYPE: PRT
<213> ORGANISM: Artificial Sequence
<220> FEATURE:
<223> OTHER INFORMATION: synthetic peptide

<400> SEQUENCE: 337

Gln Ser Ile Ser Ser Ser
1               5

<210> SEQ ID NO 338
<211> LENGTH: 3
<212> TYPE: PRT
<213> ORGANISM: Artificial Sequence
<220> FEATURE:
<223> OTHER INFORMATION: synthetic peptide

<400> SEQUENCE: 338

Asp Ala Val
1

<210> SEQ ID NO 339
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 339

Gln Gln Arg Arg Ser Trp Leu Phe Thr
1               5

<210> SEQ ID NO 340
<211> LENGTH: 8
<212> TYPE: PRT
<213> ORGANISM: Artificial Sequence
<220> FEATURE:
<223> OTHER INFORMATION: synthetic peptide

<400> SEQUENCE: 340

Gly Phe Thr Phe Asp Asp Ser Ala
1               5

<210> SEQ ID NO 341
<211> LENGTH: 8
<212> TYPE: PRT
<213> ORGANISM: Artificial Sequence
<220> FEATURE:
<223> OTHER INFORMATION: synthetic peptide

<400> SEQUENCE: 341

Ile Ser Trp Asn Ser Asp Thr Ile
1               5

<210> SEQ ID NO 342
<211> LENGTH: 19
<212> TYPE: PRT
<213> ORGANISM: Artificial Sequence
<220> FEATURE:
<223> OTHER INFORMATION: synthetic peptide

<400> SEQUENCE: 342

Ala Lys Asp His Ser Pro Tyr Tyr Tyr Gly Tyr Arg Gly Asn Asn Trp
1               5                   10                  15

Phe Asp Ser

<210> SEQ ID NO 343
<211> LENGTH: 6
<212> TYPE: PRT
<213> ORGANISM: Artificial Sequence
<220> FEATURE:
<223> OTHER INFORMATION: synthetic peptide

<400> SEQUENCE: 343

Gln Gly Ile His Asn Tyr
1               5

<210> SEQ ID NO 344
<211> LENGTH: 3
<212> TYPE: PRT
<213> ORGANISM: Artificial Sequence
<220> FEATURE:
<223> OTHER INFORMATION: synthetic peptide

<400> SEQUENCE: 344

Ala Ala Ser
1

<210> SEQ ID NO 345
<211> LENGTH: 9
<212> TYPE: PRT
<213> ORGANISM: Artificial Sequence
```

```
<220> FEATURE:
<223> OTHER INFORMATION: synthetic peptide

<400> SEQUENCE: 345

Gln Gln Ser Tyr Ser Thr Pro Arg Thr
1               5

<210> SEQ ID NO 346
<211> LENGTH: 8
<212> TYPE: PRT
<213> ORGANISM: Artificial Sequence
<220> FEATURE:
<223> OTHER INFORMATION: synthetic peptide

<400> SEQUENCE: 346

Gly Leu Thr Leu Ser Gly Tyr Trp
1               5

<210> SEQ ID NO 347
<211> LENGTH: 8
<212> TYPE: PRT
<213> ORGANISM: Artificial Sequence
<220> FEATURE:
<223> OTHER INFORMATION: synthetic peptide

<400> SEQUENCE: 347

Ile Asn Ser Asp Gly Ser Ser Thr
1               5

<210> SEQ ID NO 348
<211> LENGTH: 8
<212> TYPE: PRT
<213> ORGANISM: Artificial Sequence
<220> FEATURE:
<223> OTHER INFORMATION: synthetic peptide

<400> SEQUENCE: 348

Thr Ile Gln Lys Val Gly Glu Ile
1               5

<210> SEQ ID NO 349
<211> LENGTH: 6
<212> TYPE: PRT
<213> ORGANISM: Artificial Sequence
<220> FEATURE:
<223> OTHER INFORMATION: synthetic peptide

<400> SEQUENCE: 349

Gln Ser Val Ser Phe Tyr
1               5

<210> SEQ ID NO 350
<211> LENGTH: 3
<212> TYPE: PRT
<213> ORGANISM: Artificial Sequence
<220> FEATURE:
<223> OTHER INFORMATION: synthetic peptide

<400> SEQUENCE: 350

Asp Ala Ser
1

<210> SEQ ID NO 351
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 351

Gln Gln Arg Ser Asn Trp Ala Trp Thr
1               5

<210> SEQ ID NO 352
<211> LENGTH: 8
<212> TYPE: PRT
<213> ORGANISM: Artificial Sequence
<220> FEATURE:
<223> OTHER INFORMATION: synthetic peptide

<400> SEQUENCE: 352

Gly Phe Thr Phe Ser Ser Tyr Ala
1               5

<210> SEQ ID NO 353
<211> LENGTH: 8
<212> TYPE: PRT
<213> ORGANISM: Artificial Sequence
<220> FEATURE:
<223> OTHER INFORMATION: synthetic peptide

<400> SEQUENCE: 353

Ile Ser Gly Ser Gly Gly Ser Thr
1               5

<210> SEQ ID NO 354
<211> LENGTH: 21
<212> TYPE: PRT
<213> ORGANISM: Artificial Sequence
<220> FEATURE:
<223> OTHER INFORMATION: synthetic peptide

<400> SEQUENCE: 354

Ala Phe Gly Gly Arg Ser Ile Pro Trp Val Leu Ser Val Ala Asp Thr
1               5                   10                  15

Thr Ala Leu Asp Tyr
            20

<210> SEQ ID NO 355
<211> LENGTH: 7
<212> TYPE: PRT
<213> ORGANISM: Artificial Sequence
<220> FEATURE:
<223> OTHER INFORMATION: synthetic peptide

<400> SEQUENCE: 355

Gln Ser Val Ser Ser Ser Tyr
1               5

<210> SEQ ID NO 356
<211> LENGTH: 3
<212> TYPE: PRT
<213> ORGANISM: Artificial Sequence
<220> FEATURE:
<223> OTHER INFORMATION: synthetic peptide

<400> SEQUENCE: 356

Gly Ala Ser
1

<210> SEQ ID NO 357
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 357

Gln Gln Tyr Gly Ser Ser Arg Gly Thr
1               5

<210> SEQ ID NO 358
<211> LENGTH: 10
<212> TYPE: PRT
<213> ORGANISM: Artificial Sequence
<220> FEATURE:
<223> OTHER INFORMATION: synthetic peptide

<400> SEQUENCE: 358

Ser Asn Val Phe Thr Ser Ser Gly Val Gly
1               5                   10

<210> SEQ ID NO 359
<211> LENGTH: 7
<212> TYPE: PRT
<213> ORGANISM: Artificial Sequence
<220> FEATURE:
<223> OTHER INFORMATION: synthetic peptide

<400> SEQUENCE: 359

Ile Tyr Gly Asp Asp Asp Lys
1               5

<210> SEQ ID NO 360
<211> LENGTH: 19
<212> TYPE: PRT
<213> ORGANISM: Artificial Sequence
<220> FEATURE:
<223> OTHER INFORMATION: synthetic peptide

<400> SEQUENCE: 360

Ala His Ser Asn Tyr Asp Phe Trp Gly Gly Phe Tyr Ile Lys Ser Tyr
1               5                   10                  15

Ile Asp Tyr

<210> SEQ ID NO 361
<211> LENGTH: 6
<212> TYPE: PRT
<213> ORGANISM: Artificial Sequence
<220> FEATURE:
<223> OTHER INFORMATION: synthetic peptide

<400> SEQUENCE: 361

Gln Ser Val Ser Ser Asn
1               5

<210> SEQ ID NO 362
<211> LENGTH: 3
<212> TYPE: PRT
<213> ORGANISM: Artificial Sequence
<220> FEATURE:
<223> OTHER INFORMATION: synthetic peptide

<400> SEQUENCE: 362

Gly Ala Ser
1

<210> SEQ ID NO 363
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 363

Gln Gln Tyr Asp Asn Trp Pro Tyr Thr
1               5

<210> SEQ ID NO 364
<211> LENGTH: 8
<212> TYPE: PRT
<213> ORGANISM: Artificial Sequence
<220> FEATURE:
<223> OTHER INFORMATION: synthetic peptide

<400> SEQUENCE: 364

Gly Gly Ser Phe Gly Gly Tyr Tyr
1               5

<210> SEQ ID NO 365
<211> LENGTH: 7
<212> TYPE: PRT
<213> ORGANISM: Artificial Sequence
<220> FEATURE:
<223> OTHER INFORMATION: synthetic peptide

<400> SEQUENCE: 365

Ile Asn His Ser Gly Ser Thr
1               5

<210> SEQ ID NO 366
<211> LENGTH: 8
<212> TYPE: PRT
<213> ORGANISM: Artificial Sequence
<220> FEATURE:
<223> OTHER INFORMATION: synthetic peptide

<400> SEQUENCE: 366

Ala Arg Gly Pro Tyr Phe Asp Tyr
1               5

<210> SEQ ID NO 367
<211> LENGTH: 7
<212> TYPE: PRT
<213> ORGANISM: Artificial Sequence
<220> FEATURE:
<223> OTHER INFORMATION: synthetic peptide

<400> SEQUENCE: 367

Gln Ser Val Ser Ser Arg Tyr
1               5

<210> SEQ ID NO 368
<211> LENGTH: 3
<212> TYPE: PRT
<213> ORGANISM: Artificial Sequence
<220> FEATURE:
<223> OTHER INFORMATION: synthetic peptide

<400> SEQUENCE: 368

Gly Ala Ser
1

<210> SEQ ID NO 369
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 369

Gln Gln Tyr Ser Ser Ser Ser Tyr Thr
1               5

<210> SEQ ID NO 370
<211> LENGTH: 8
<212> TYPE: PRT
<213> ORGANISM: Artificial Sequence
<220> FEATURE:
<223> OTHER INFORMATION: synthetic peptide

<400> SEQUENCE: 370

Gly His Ala Phe Ala Ser Tyr Tyr
1               5

<210> SEQ ID NO 371
<211> LENGTH: 8
<212> TYPE: PRT
<213> ORGANISM: Artificial Sequence
<220> FEATURE:
<223> OTHER INFORMATION: synthetic peptide

<400> SEQUENCE: 371

Ile Asn Pro Ser Gly Gly Ser Thr
1               5

<210> SEQ ID NO 372
<211> LENGTH: 17
<212> TYPE: PRT
<213> ORGANISM: Artificial Sequence
<220> FEATURE:
<223> OTHER INFORMATION: synthetic peptide

<400> SEQUENCE: 372

Ala Arg Gly Leu Tyr Ser Asn Ser Trp Ser Thr Arg Gly Val Phe Asp
1               5                   10                  15

Ile

<210> SEQ ID NO 373
<211> LENGTH: 6
<212> TYPE: PRT
<213> ORGANISM: Artificial Sequence
<220> FEATURE:
<223> OTHER INFORMATION: synthetic peptide

<400> SEQUENCE: 373

Gln Ser Val Ser Thr Tyr
1               5

<210> SEQ ID NO 374
<211> LENGTH: 3
<212> TYPE: PRT
<213> ORGANISM: Artificial Sequence
<220> FEATURE:
<223> OTHER INFORMATION: synthetic peptide

<400> SEQUENCE: 374

Gly Ala Ser
1

<210> SEQ ID NO 375
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 375

Gln Gln Tyr Gly Gly Ser Pro Phe Thr
1               5

<210> SEQ ID NO 376
<211> LENGTH: 8
<212> TYPE: PRT
<213> ORGANISM: Artificial Sequence
<220> FEATURE:
<223> OTHER INFORMATION: synthetic peptide

<400> SEQUENCE: 376

Gly Phe Thr Phe Ser Asn Tyr Ala
1               5

<210> SEQ ID NO 377
<211> LENGTH: 8
<212> TYPE: PRT
<213> ORGANISM: Artificial Sequence
<220> FEATURE:
<223> OTHER INFORMATION: synthetic peptide

<400> SEQUENCE: 377

Ile Ser Gly Ser Asp Ser Ser Thr
1               5

<210> SEQ ID NO 378
<211> LENGTH: 8
<212> TYPE: PRT
<213> ORGANISM: Artificial Sequence
<220> FEATURE:
<223> OTHER INFORMATION: synthetic peptide

<400> SEQUENCE: 378

Ala Thr Gly Gly Tyr Ser Asp Tyr
1               5

<210> SEQ ID NO 379
<211> LENGTH: 6
<212> TYPE: PRT
<213> ORGANISM: Artificial Sequence
<220> FEATURE:
<223> OTHER INFORMATION: synthetic peptide

<400> SEQUENCE: 379

Gln Gly Ile Ser Ser Trp
1               5

<210> SEQ ID NO 380
<211> LENGTH: 3
<212> TYPE: PRT
<213> ORGANISM: Artificial Sequence
<220> FEATURE:
<223> OTHER INFORMATION: synthetic peptide

<400> SEQUENCE: 380

Ala Ala Ser
1

<210> SEQ ID NO 381
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 381

Gln Gln Ala Tyr Arg Phe Pro Tyr Thr
1               5

<210> SEQ ID NO 382
<211> LENGTH: 8
<212> TYPE: PRT
<213> ORGANISM: Artificial Sequence
<220> FEATURE:
<223> OTHER INFORMATION: synthetic peptide

<400> SEQUENCE: 382

Gly Asp Ser Phe Thr Asn Tyr Trp
1               5

<210> SEQ ID NO 383
<211> LENGTH: 8
<212> TYPE: PRT
<213> ORGANISM: Artificial Sequence
<220> FEATURE:
<223> OTHER INFORMATION: synthetic peptide

<400> SEQUENCE: 383

Ile Tyr Pro Asp Asp Ser Asp Ile
1               5

<210> SEQ ID NO 384
<211> LENGTH: 16
<212> TYPE: PRT
<213> ORGANISM: Artificial Sequence
<220> FEATURE:
<223> OTHER INFORMATION: synthetic peptide

<400> SEQUENCE: 384

Ala Arg His Arg Arg Thr Ala Tyr Gln Ile Gly Asp Gly Leu Asp Ile
1               5                   10                  15

<210> SEQ ID NO 385
<211> LENGTH: 7
<212> TYPE: PRT
<213> ORGANISM: Artificial Sequence
<220> FEATURE:
<223> OTHER INFORMATION: synthetic peptide

<400> SEQUENCE: 385

Thr Ser Asn Tyr Leu Ala Trp
1               5

<210> SEQ ID NO 386
<211> LENGTH: 3
<212> TYPE: PRT
<213> ORGANISM: Artificial Sequence
<220> FEATURE:
<223> OTHER INFORMATION: synthetic peptide

<400> SEQUENCE: 386

Asp Ala Ser
1

<210> SEQ ID NO 387
<211> LENGTH: 9
<212> TYPE: PRT
<213> ORGANISM: Artificial Sequence
```

```
<220> FEATURE:
<223> OTHER INFORMATION: synthetic peptide

<400> SEQUENCE: 387

Gln Gln Tyr Arg Ser Ser Pro Tyr Thr
1               5

<210> SEQ ID NO 388
<211> LENGTH: 8
<212> TYPE: PRT
<213> ORGANISM: Artificial Sequence
<220> FEATURE:
<223> OTHER INFORMATION: synthetic peptide

<400> SEQUENCE: 388

Gly Phe Leu Phe Gly Ser Tyr Trp
1               5

<210> SEQ ID NO 389
<211> LENGTH: 8
<212> TYPE: PRT
<213> ORGANISM: Artificial Sequence
<220> FEATURE:
<223> OTHER INFORMATION: synthetic peptide

<400> SEQUENCE: 389

Ile Lys Gln Asp Gly Ser Glu Lys
1               5

<210> SEQ ID NO 390
<211> LENGTH: 11
<212> TYPE: PRT
<213> ORGANISM: Artificial Sequence
<220> FEATURE:
<223> OTHER INFORMATION: synthetic peptide

<400> SEQUENCE: 390

Ala Arg Asp Trp Pro Leu Asp Pro Leu Asp Tyr
1               5                   10

<210> SEQ ID NO 391
<211> LENGTH: 6
<212> TYPE: PRT
<213> ORGANISM: Artificial Sequence
<220> FEATURE:
<223> OTHER INFORMATION: synthetic peptide

<400> SEQUENCE: 391

Gln Ser Ile Ser Ser Phe
1               5

<210> SEQ ID NO 392
<211> LENGTH: 3
<212> TYPE: PRT
<213> ORGANISM: Artificial Sequence
<220> FEATURE:
<223> OTHER INFORMATION: synthetic peptide

<400> SEQUENCE: 392

Thr Ala Ser
1

<210> SEQ ID NO 393
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 393

Gln Gln Ser Tyr Thr Ser Pro Arg Thr
1               5

<210> SEQ ID NO 394
<211> LENGTH: 8
<212> TYPE: PRT
<213> ORGANISM: Artificial Sequence
<220> FEATURE:
<223> OTHER INFORMATION: synthetic peptide

<400> SEQUENCE: 394

Gly His Ala Phe Ala Ser Tyr Tyr
1               5

<210> SEQ ID NO 395
<211> LENGTH: 8
<212> TYPE: PRT
<213> ORGANISM: Artificial Sequence
<220> FEATURE:
<223> OTHER INFORMATION: synthetic peptide

<400> SEQUENCE: 395

Ile Asn Pro Ser Gly Gly Ser Thr
1               5

<210> SEQ ID NO 396
<211> LENGTH: 17
<212> TYPE: PRT
<213> ORGANISM: Artificial Sequence
<220> FEATURE:
<223> OTHER INFORMATION: synthetic peptide

<400> SEQUENCE: 396

Ala Arg Gly Leu Tyr Ser Asn Ser Trp Ser Thr Arg Gly Val Phe Asp
1               5                   10                  15

Ile

<210> SEQ ID NO 397
<211> LENGTH: 6
<212> TYPE: PRT
<213> ORGANISM: Artificial Sequence
<220> FEATURE:
<223> OTHER INFORMATION: synthetic peptide

<400> SEQUENCE: 397

Gln Ser Val Ser Thr Tyr
1               5

<210> SEQ ID NO 398
<211> LENGTH: 3
<212> TYPE: PRT
<213> ORGANISM: Artificial Sequence
<220> FEATURE:
<223> OTHER INFORMATION: synthetic peptide

<400> SEQUENCE: 398

Gly Ala Ser
1

<210> SEQ ID NO 399
<211> LENGTH: 9
<212> TYPE: PRT
<213> ORGANISM: Artificial Sequence
```

```
<220> FEATURE:
<223> OTHER INFORMATION: synthetic peptide

<400> SEQUENCE: 399

Gln Gln Tyr Gly Gly Ser Pro Phe Thr
1               5

<210> SEQ ID NO 400
<211> LENGTH: 8
<212> TYPE: PRT
<213> ORGANISM: Artificial Sequence
<220> FEATURE:
<223> OTHER INFORMATION: synthetic peptide

<400> SEQUENCE: 400

Gly Phe Asn Phe Gly Ser Tyr Ala
1               5

<210> SEQ ID NO 401
<211> LENGTH: 8
<212> TYPE: PRT
<213> ORGANISM: Artificial Sequence
<220> FEATURE:
<223> OTHER INFORMATION: synthetic peptide

<400> SEQUENCE: 401

Ile Ser Tyr Leu Gly Asp Asn Glu
1               5

<210> SEQ ID NO 402
<211> LENGTH: 20
<212> TYPE: PRT
<213> ORGANISM: Artificial Sequence
<220> FEATURE:
<223> OTHER INFORMATION: synthetic peptide

<400> SEQUENCE: 402

Ala Ser Arg Leu Asp Asp Tyr Tyr Asp Thr Leu Gly Tyr Gly Arg Gly
1               5                   10                  15

Ala Phe Asp Leu
            20

<210> SEQ ID NO 403
<211> LENGTH: 12
<212> TYPE: PRT
<213> ORGANISM: Artificial Sequence
<220> FEATURE:
<223> OTHER INFORMATION: synthetic peptide

<400> SEQUENCE: 403

Gln Ser Val Leu Asp Ser Asn Asn Lys Asn Tyr
1               5                   10

<210> SEQ ID NO 404
<211> LENGTH: 3
<212> TYPE: PRT
<213> ORGANISM: Artificial Sequence
<220> FEATURE:
<223> OTHER INFORMATION: synthetic peptide

<400> SEQUENCE: 404

Trp Ala Ser
1

<210> SEQ ID NO 405
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 405

Gln Gln Tyr Tyr Ser Thr Pro Asp Thr
1               5

<210> SEQ ID NO 406
<211> LENGTH: 10
<212> TYPE: PRT
<213> ORGANISM: Artificial Sequence
<220> FEATURE:
<223> OTHER INFORMATION: synthetic peptide

<400> SEQUENCE: 406

Gly Phe Ser Leu Ser Thr Asn Gly Val Gly
1               5                   10

<210> SEQ ID NO 407
<211> LENGTH: 7
<212> TYPE: PRT
<213> ORGANISM: Artificial Sequence
<220> FEATURE:
<223> OTHER INFORMATION: synthetic peptide

<400> SEQUENCE: 407

Ile Tyr Trp Asp Asp Asp Glu
1               5

<210> SEQ ID NO 408
<211> LENGTH: 21
<212> TYPE: PRT
<213> ORGANISM: Artificial Sequence
<220> FEATURE:
<223> OTHER INFORMATION: synthetic peptide

<400> SEQUENCE: 408

Ala His Lys Gly Tyr Tyr Cys Ser Ser Ser Cys Tyr Ala Gly Gly
1               5                   10                  15

Lys Ala Phe Asn Ile
            20

<210> SEQ ID NO 409
<211> LENGTH: 6
<212> TYPE: PRT
<213> ORGANISM: Artificial Sequence
<220> FEATURE:
<223> OTHER INFORMATION: synthetic peptide

<400> SEQUENCE: 409

Gln Gly Ile Asn Ser Tyr
1               5

<210> SEQ ID NO 410
<211> LENGTH: 3
<212> TYPE: PRT
<213> ORGANISM: Artificial Sequence
<220> FEATURE:
<223> OTHER INFORMATION: synthetic peptide

<400> SEQUENCE: 410

Ala Ala Ser
1
```

```
<210> SEQ ID NO 411
<211> LENGTH: 9
<212> TYPE: PRT
<213> ORGANISM: Artificial Sequence
<220> FEATURE:
<223> OTHER INFORMATION: synthetic peptide

<400> SEQUENCE: 411

Gln Gln Pro Ser Ser His Pro Leu Thr
1               5

<210> SEQ ID NO 412
<211> LENGTH: 8
<212> TYPE: PRT
<213> ORGANISM: Artificial Sequence
<220> FEATURE:
<223> OTHER INFORMATION: synthetic peptide

<400> SEQUENCE: 412

Gly Leu Thr Leu Lys Asn Tyr Ala
1               5

<210> SEQ ID NO 413
<211> LENGTH: 8
<212> TYPE: PRT
<213> ORGANISM: Artificial Sequence
<220> FEATURE:
<223> OTHER INFORMATION: synthetic peptide

<400> SEQUENCE: 413

Ile Ser Phe Asp Gly Thr Tyr Lys
1               5

<210> SEQ ID NO 414
<211> LENGTH: 24
<212> TYPE: PRT
<213> ORGANISM: Artificial Sequence
<220> FEATURE:
<223> OTHER INFORMATION: synthetic peptide

<400> SEQUENCE: 414

Ala Arg Gly Pro Gln Leu Tyr Ser His Gln Pro Ala Lys Phe Gly Asp
1               5                   10                  15

Leu Leu Phe Gly Ala Phe Asp Ile
            20

<210> SEQ ID NO 415
<211> LENGTH: 6
<212> TYPE: PRT
<213> ORGANISM: Artificial Sequence
<220> FEATURE:
<223> OTHER INFORMATION: synthetic peptide

<400> SEQUENCE: 415

Gln Asp Val Ser His Tyr
1               5

<210> SEQ ID NO 416
<211> LENGTH: 3
<212> TYPE: PRT
<213> ORGANISM: Artificial Sequence
<220> FEATURE:
<223> OTHER INFORMATION: synthetic peptide

<400> SEQUENCE: 416

Asp Thr Ser
1
```

<210> SEQ ID NO 417
<211> LENGTH: 9
<212> TYPE: PRT
<213> ORGANISM: Artificial Sequence
<220> FEATURE:
<223> OTHER INFORMATION: synthetic peptide

<400> SEQUENCE: 417

Gln Gln Tyr Asp Thr Leu Pro Leu Thr
1               5

<210> SEQ ID NO 418
<211> LENGTH: 8
<212> TYPE: PRT
<213> ORGANISM: Artificial Sequence
<220> FEATURE:
<223> OTHER INFORMATION: synthetic peptide

<400> SEQUENCE: 418

Gly Phe Thr Phe Ser Ala His Tyr
1               5

<210> SEQ ID NO 419
<211> LENGTH: 8
<212> TYPE: PRT
<213> ORGANISM: Artificial Sequence
<220> FEATURE:
<223> OTHER INFORMATION: synthetic peptide

<400> SEQUENCE: 419

Ile Ser Ser Arg Gly Ser Thr Ile
1               5

<210> SEQ ID NO 420
<211> LENGTH: 13
<212> TYPE: PRT
<213> ORGANISM: Artificial Sequence
<220> FEATURE:
<223> OTHER INFORMATION: synthetic peptide

<400> SEQUENCE: 420

Ala Gly Ala Ile Thr Trp Asn Asp Val Phe Phe Trp Tyr
1               5                   10

<210> SEQ ID NO 421
<211> LENGTH: 6
<212> TYPE: PRT
<213> ORGANISM: Artificial Sequence
<220> FEATURE:
<223> OTHER INFORMATION: synthetic peptide

<400> SEQUENCE: 421

Gln Ser Val Arg Ser Tyr
1               5

<210> SEQ ID NO 422
<211> LENGTH: 3
<212> TYPE: PRT
<213> ORGANISM: Artificial Sequence
<220> FEATURE:
<223> OTHER INFORMATION: synthetic peptide

<400> SEQUENCE: 422

Asp Ala Thr
1

<210> SEQ ID NO 423
<211> LENGTH: 9
<212> TYPE: PRT
<213> ORGANISM: Artificial Sequence
<220> FEATURE:
<223> OTHER INFORMATION: synthetic peptide

<400> SEQUENCE: 423

Gln Leu Arg Ser Thr Leu Gly Val Thr
1               5

<210> SEQ ID NO 424
<211> LENGTH: 8
<212> TYPE: PRT
<213> ORGANISM: Artificial Sequence
<220> FEATURE:
<223> OTHER INFORMATION: synthetic peptide

<400> SEQUENCE: 424

Gly Phe Thr Phe Arg Asn Tyr Trp
1               5

<210> SEQ ID NO 425
<211> LENGTH: 8
<212> TYPE: PRT
<213> ORGANISM: Artificial Sequence
<220> FEATURE:
<223> OTHER INFORMATION: synthetic peptide

<400> SEQUENCE: 425

Ile Asn Arg Asn Gly Asn Glu Lys
1               5

<210> SEQ ID NO 426
<211> LENGTH: 19
<212> TYPE: PRT
<213> ORGANISM: Artificial Sequence
<220> FEATURE:
<223> OTHER INFORMATION: synthetic peptide

<400> SEQUENCE: 426

Val Arg Asp Ser Ser Pro Ser Phe Gly Pro Gly Asn Tyr Tyr Asp Ala
1               5                   10                  15

Phe Asp Ile

<210> SEQ ID NO 427
<211> LENGTH: 6
<212> TYPE: PRT
<213> ORGANISM: Artificial Sequence
<220> FEATURE:
<223> OTHER INFORMATION: synthetic peptide

<400> SEQUENCE: 427

Gln Asp Ile Arg Asn Glu
1               5

<210> SEQ ID NO 428
<211> LENGTH: 3
<212> TYPE: PRT
<213> ORGANISM: Artificial Sequence
<220> FEATURE:
<223> OTHER INFORMATION: synthetic peptide

<400> SEQUENCE: 428

Ala Ala Ser
1

```
<210> SEQ ID NO 429
<211> LENGTH: 9
<212> TYPE: PRT
<213> ORGANISM: Artificial Sequence
<220> FEATURE:
<223> OTHER INFORMATION: synthetic peptide

<400> SEQUENCE: 429

Leu Gln Asp Phe Asn Tyr Pro Arg Thr
1               5

<210> SEQ ID NO 430
<211> LENGTH: 10
<212> TYPE: PRT
<213> ORGANISM: Artificial Sequence
<220> FEATURE:
<223> OTHER INFORMATION: synthetic peptide

<400> SEQUENCE: 430

Gly Phe Ser Leu Thr Thr Tyr Ser Met Gly
1               5                   10

<210> SEQ ID NO 431
<211> LENGTH: 7
<212> TYPE: PRT
<213> ORGANISM: Artificial Sequence
<220> FEATURE:
<223> OTHER INFORMATION: synthetic peptide

<400> SEQUENCE: 431

Ile Tyr Gly Asp Gly Val Lys
1               5

<210> SEQ ID NO 432
<211> LENGTH: 11
<212> TYPE: PRT
<213> ORGANISM: Artificial Sequence
<220> FEATURE:
<223> OTHER INFORMATION: synthetic peptide

<400> SEQUENCE: 432

Ala His Ser Ser Thr Val Asp Trp Asp Val Asp
1               5                   10

<210> SEQ ID NO 433
<211> LENGTH: 6
<212> TYPE: PRT
<213> ORGANISM: Artificial Sequence
<220> FEATURE:
<223> OTHER INFORMATION: synthetic peptide

<400> SEQUENCE: 433

Gln Ser Val Ser Ser Phe
1               5

<210> SEQ ID NO 434
<211> LENGTH: 3
<212> TYPE: PRT
<213> ORGANISM: Artificial Sequence
<220> FEATURE:
<223> OTHER INFORMATION: synthetic peptide

<400> SEQUENCE: 434

Asp Ala Ser
1
```

<210> SEQ ID NO 435
<211> LENGTH: 9
<212> TYPE: PRT
<213> ORGANISM: Artificial Sequence
<220> FEATURE:
<223> OTHER INFORMATION: synthetic peptide

<400> SEQUENCE: 435

His Gln Arg Ser Asn Trp Pro Arg Thr
1               5

<210> SEQ ID NO 436
<211> LENGTH: 8
<212> TYPE: PRT
<213> ORGANISM: Artificial Sequence
<220> FEATURE:
<223> OTHER INFORMATION: synthetic peptide

<400> SEQUENCE: 436

Gly Glu Ser Phe Ser Gly Tyr Tyr
1               5

<210> SEQ ID NO 437
<211> LENGTH: 7
<212> TYPE: PRT
<213> ORGANISM: Artificial Sequence
<220> FEATURE:
<223> OTHER INFORMATION: synthetic peptide

<400> SEQUENCE: 437

Ile Asn His Ser Gly Ser Thr
1               5

<210> SEQ ID NO 438
<211> LENGTH: 20
<212> TYPE: PRT
<213> ORGANISM: Artificial Sequence
<220> FEATURE:
<223> OTHER INFORMATION: synthetic peptide

<400> SEQUENCE: 438

Ala Arg Gly Tyr Ala Asp Thr Pro Val Phe Arg Arg Ala Ala Ala Ala
1               5                   10                  15

Gly Met Asp Val
            20

<210> SEQ ID NO 439
<211> LENGTH: 6
<212> TYPE: PRT
<213> ORGANISM: Artificial Sequence
<220> FEATURE:
<223> OTHER INFORMATION: synthetic peptide

<400> SEQUENCE: 439

Gln Arg Ile Asp Ser Trp
1               5

<210> SEQ ID NO 440
<211> LENGTH: 3
<212> TYPE: PRT
<213> ORGANISM: Artificial Sequence
<220> FEATURE:
<223> OTHER INFORMATION: synthetic peptide

<400> SEQUENCE: 440

Gln Ala Ser
1

<210> SEQ ID NO 441
<211> LENGTH: 9
<212> TYPE: PRT
<213> ORGANISM: Artificial Sequence
<220> FEATURE:
<223> OTHER INFORMATION: synthetic peptide

<400> SEQUENCE: 441

Gln Gln Tyr Lys Ser Phe Ser Tyr Thr
1               5

<210> SEQ ID NO 442
<211> LENGTH: 10
<212> TYPE: PRT
<213> ORGANISM: Artificial Sequence
<220> FEATURE:
<223> OTHER INFORMATION: synthetic peptide

<400> SEQUENCE: 442

Gly Phe Ser Leu Thr Thr Ser Gly Met Cys
1               5                   10

<210> SEQ ID NO 443
<211> LENGTH: 7
<212> TYPE: PRT
<213> ORGANISM: Artificial Sequence
<220> FEATURE:
<223> OTHER INFORMATION: synthetic peptide

<400> SEQUENCE: 443

Ile Asp Trp Asp Asp Asp Lys
1               5

<210> SEQ ID NO 444
<211> LENGTH: 21
<212> TYPE: PRT
<213> ORGANISM: Artificial Sequence
<220> FEATURE:
<223> OTHER INFORMATION: synthetic peptide

<400> SEQUENCE: 444

Ala Arg Ser Pro Pro Gly Ala Ser Val Ala Ile Leu Pro Thr Thr Lys
1               5                   10                  15

Tyr Tyr Phe Asp Ser
            20

<210> SEQ ID NO 445
<211> LENGTH: 7
<212> TYPE: PRT
<213> ORGANISM: Artificial Sequence
<220> FEATURE:
<223> OTHER INFORMATION: synthetic peptide

<400> SEQUENCE: 445

His Ser Val Thr Ser Ser Tyr
1               5

<210> SEQ ID NO 446
<211> LENGTH: 3
<212> TYPE: PRT
<213> ORGANISM: Artificial Sequence

```
<220> FEATURE:
<223> OTHER INFORMATION: synthetic peptide

<400> SEQUENCE: 446

Gly Ala Ser
1

<210> SEQ ID NO 447
<211> LENGTH: 10
<212> TYPE: PRT
<213> ORGANISM: Artificial Sequence
<220> FEATURE:
<223> OTHER INFORMATION: synthetic peptide

<400> SEQUENCE: 447

Gln Gln Tyr Gly Ser Ser Ala Met Tyr Thr
1               5                   10

<210> SEQ ID NO 448
<211> LENGTH: 8
<212> TYPE: PRT
<213> ORGANISM: Artificial Sequence
<220> FEATURE:
<223> OTHER INFORMATION: synthetic peptide

<400> SEQUENCE: 448

Gly Tyr Ile Phe Asn Arg Tyr Ala
1               5

<210> SEQ ID NO 449
<211> LENGTH: 8
<212> TYPE: PRT
<213> ORGANISM: Artificial Sequence
<220> FEATURE:
<223> OTHER INFORMATION: synthetic peptide

<400> SEQUENCE: 449

Ile Asn Thr Asn Ser Gly Asp Ala
1               5

<210> SEQ ID NO 450
<211> LENGTH: 16
<212> TYPE: PRT
<213> ORGANISM: Artificial Sequence
<220> FEATURE:
<223> OTHER INFORMATION: synthetic peptide

<400> SEQUENCE: 450

Ala Arg Asp Arg Trp Ser Ser Gly Tyr Gln Tyr Gly Leu Asp Ala
1               5                   10                  15

<210> SEQ ID NO 451
<211> LENGTH: 7
<212> TYPE: PRT
<213> ORGANISM: Artificial Sequence
<220> FEATURE:
<223> OTHER INFORMATION: synthetic peptide

<400> SEQUENCE: 451

Gln Gly Val Arg Asn Asp Tyr
1               5

<210> SEQ ID NO 452
<211> LENGTH: 3
<212> TYPE: PRT
<213> ORGANISM: Artificial Sequence
<220> FEATURE:
```

<223> OTHER INFORMATION: synthetic peptide

<400> SEQUENCE: 452

Gly Ala Ser
1

<210> SEQ ID NO 453
<211> LENGTH: 9
<212> TYPE: PRT
<213> ORGANISM: Artificial Sequence
<220> FEATURE:
<223> OTHER INFORMATION: synthetic peptide

<400> SEQUENCE: 453

Gln Gln Tyr Gly Arg Ser Pro Met Thr
1               5

<210> SEQ ID NO 454
<211> LENGTH: 8
<212> TYPE: PRT
<213> ORGANISM: Artificial Sequence
<220> FEATURE:
<223> OTHER INFORMATION: synthetic peptide

<400> SEQUENCE: 454

Gly Phe Thr Phe Lys Asp Tyr Ala
1               5

<210> SEQ ID NO 455
<211> LENGTH: 8
<212> TYPE: PRT
<213> ORGANISM: Artificial Sequence
<220> FEATURE:
<223> OTHER INFORMATION: synthetic peptide

<400> SEQUENCE: 455

Val Ser Val Asp Gly Ser Leu Gln
1               5

<210> SEQ ID NO 456
<211> LENGTH: 14
<212> TYPE: PRT
<213> ORGANISM: Artificial Sequence
<220> FEATURE:
<223> OTHER INFORMATION: synthetic peptide

<400> SEQUENCE: 456

Ala Arg Glu Phe Ser Gly Thr Asn Val Arg Cys Phe Asp Leu
1               5                   10

<210> SEQ ID NO 457
<211> LENGTH: 6
<212> TYPE: PRT
<213> ORGANISM: Artificial Sequence
<220> FEATURE:
<223> OTHER INFORMATION: synthetic peptide

<400> SEQUENCE: 457

Gln Gly Ile His Arg Trp
1               5

<210> SEQ ID NO 458
<211> LENGTH: 3
<212> TYPE: PRT
<213> ORGANISM: Artificial Sequence
<220> FEATURE:
<223> OTHER INFORMATION: synthetic peptide

<400> SEQUENCE: 458

Ala Ala Ser
1

<210> SEQ ID NO 459
<211> LENGTH: 9
<212> TYPE: PRT
<213> ORGANISM: Artificial Sequence
<220> FEATURE:
<223> OTHER INFORMATION: synthetic peptide

<400> SEQUENCE: 459

Gln Gln Gly Asn Ser Phe Pro Leu Thr
1               5

<210> SEQ ID NO 460
<211> LENGTH: 8
<212> TYPE: PRT
<213> ORGANISM: Artificial Sequence
<220> FEATURE:
<223> OTHER INFORMATION: synthetic peptide

<400> SEQUENCE: 460

Gly Gly Ser Ile Arg Ser His Tyr
1               5

<210> SEQ ID NO 461
<211> LENGTH: 7
<212> TYPE: PRT
<213> ORGANISM: Artificial Sequence
<220> FEATURE:
<223> OTHER INFORMATION: synthetic peptide

<400> SEQUENCE: 461

Ile Tyr Thr Ser Gly Thr Thr
1               5

<210> SEQ ID NO 462
<211> LENGTH: 9
<212> TYPE: PRT
<213> ORGANISM: Artificial Sequence
<220> FEATURE:
<223> OTHER INFORMATION: synthetic peptide

<400> SEQUENCE: 462

Ala Arg Gly Ser Ser Glu Val Thr Ile
1               5

<210> SEQ ID NO 463
<211> LENGTH: 6
<212> TYPE: PRT
<213> ORGANISM: Artificial Sequence
<220> FEATURE:
<223> OTHER INFORMATION: synthetic peptide

<400> SEQUENCE: 463

Gln Asp Ile Ser Asn Tyr
1               5

<210> SEQ ID NO 464
<211> LENGTH: 3
<212> TYPE: PRT
<213> ORGANISM: Artificial Sequence
<220> FEATURE:
<223> OTHER INFORMATION: synthetic peptide

```
<400> SEQUENCE: 464

Ala Ala Ser
1

<210> SEQ ID NO 465
<211> LENGTH: 9
<212> TYPE: PRT
<213> ORGANISM: Artificial Sequence
<220> FEATURE:
<223> OTHER INFORMATION: synthetic peptide

<400> SEQUENCE: 465

Gln Gln Tyr Asp Asn Leu Pro Leu Thr
1               5

<210> SEQ ID NO 466
<211> LENGTH: 8
<212> TYPE: PRT
<213> ORGANISM: Artificial Sequence
<220> FEATURE:
<223> OTHER INFORMATION: synthetic peptide

<400> SEQUENCE: 466

Gly Phe Thr Phe Ser Ser Tyr Glu
1               5

<210> SEQ ID NO 467
<211> LENGTH: 8
<212> TYPE: PRT
<213> ORGANISM: Artificial Sequence
<220> FEATURE:
<223> OTHER INFORMATION: synthetic peptide

<400> SEQUENCE: 467

Thr Asn His Ser Gly Ser Thr Ile
1               5

<210> SEQ ID NO 468
<211> LENGTH: 17
<212> TYPE: PRT
<213> ORGANISM: Artificial Sequence
<220> FEATURE:
<223> OTHER INFORMATION: synthetic peptide

<400> SEQUENCE: 468

Ala Arg Glu His Tyr Asp Ile Leu Thr Gly Phe Gly Gly Tyr Leu Asp
1               5                   10                  15

Tyr

<210> SEQ ID NO 469
<211> LENGTH: 6
<212> TYPE: PRT
<213> ORGANISM: Artificial Sequence
<220> FEATURE:
<223> OTHER INFORMATION: synthetic peptide

<400> SEQUENCE: 469

Gln Ser Val Ser Asn Asn
1               5

<210> SEQ ID NO 470
<211> LENGTH: 3
<212> TYPE: PRT
<213> ORGANISM: Artificial Sequence
<220> FEATURE:
<223> OTHER INFORMATION: synthetic peptide
```

<400> SEQUENCE: 470

Gly Ala Ser
1

<210> SEQ ID NO 471
<211> LENGTH: 10
<212> TYPE: PRT
<213> ORGANISM: Artificial Sequence
<220> FEATURE:
<223> OTHER INFORMATION: synthetic peptide

<400> SEQUENCE: 471

Gln Gln Tyr Asn Asp Trp Pro Arg Trp Thr
1               5                   10

<210> SEQ ID NO 472
<211> LENGTH: 8
<212> TYPE: PRT
<213> ORGANISM: Artificial Sequence
<220> FEATURE:
<223> OTHER INFORMATION: synthetic peptide

<400> SEQUENCE: 472

Gly Glu Ser Phe Ser Gly Tyr Tyr
1               5

<210> SEQ ID NO 473
<211> LENGTH: 7
<212> TYPE: PRT
<213> ORGANISM: Artificial Sequence
<220> FEATURE:
<223> OTHER INFORMATION: synthetic peptide

<400> SEQUENCE: 473

Ile Asn His Ser Gly Ser Thr
1               5

<210> SEQ ID NO 474
<211> LENGTH: 20
<212> TYPE: PRT
<213> ORGANISM: Artificial Sequence
<220> FEATURE:
<223> OTHER INFORMATION: synthetic peptide

<400> SEQUENCE: 474

Ala Arg Gly Tyr Ala Asp Thr Pro Val Phe Arg Arg Ala Ala Ala
1               5                   10                  15

Gly Met Asp Val
            20

<210> SEQ ID NO 475
<211> LENGTH: 6
<212> TYPE: PRT
<213> ORGANISM: Artificial Sequence
<220> FEATURE:
<223> OTHER INFORMATION: synthetic peptide

<400> SEQUENCE: 475

Gln Ser Ile Ser Ser Tyr
1               5

<210> SEQ ID NO 476
<211> LENGTH: 3
<212> TYPE: PRT
<213> ORGANISM: Artificial Sequence

```
<220> FEATURE:
<223> OTHER INFORMATION: synthetic peptide

<400> SEQUENCE: 476

Gly Ala Ser
1

<210> SEQ ID NO 477
<211> LENGTH: 8
<212> TYPE: PRT
<213> ORGANISM: Artificial Sequence
<220> FEATURE:
<223> OTHER INFORMATION: synthetic peptide

<400> SEQUENCE: 477

Leu Gln Ser Tyr Ser Ser Trp Thr
1               5

<210> SEQ ID NO 478
<211> LENGTH: 8
<212> TYPE: PRT
<213> ORGANISM: Artificial Sequence
<220> FEATURE:
<223> OTHER INFORMATION: synthetic peptide

<400> SEQUENCE: 478

Gly Phe Thr Phe Ser Ser Tyr Glu
1               5

<210> SEQ ID NO 479
<211> LENGTH: 8
<212> TYPE: PRT
<213> ORGANISM: Artificial Sequence
<220> FEATURE:
<223> OTHER INFORMATION: synthetic peptide

<400> SEQUENCE: 479

Ile Ser Gly Gly Gly Asp Thr Ile
1               5

<210> SEQ ID NO 480
<211> LENGTH: 13
<212> TYPE: PRT
<213> ORGANISM: Artificial Sequence
<220> FEATURE:
<223> OTHER INFORMATION: synthetic peptide

<400> SEQUENCE: 480

Ala Lys Phe Trp Asn Asp Tyr Tyr Asn Asp Phe Glu Tyr
1               5                   10

<210> SEQ ID NO 481
<211> LENGTH: 6
<212> TYPE: PRT
<213> ORGANISM: Artificial Sequence
<220> FEATURE:
<223> OTHER INFORMATION: synthetic peptide

<400> SEQUENCE: 481

Gln Ser Val Ser Ser Tyr
1               5

<210> SEQ ID NO 482
<211> LENGTH: 3
<212> TYPE: PRT
<213> ORGANISM: Artificial Sequence
<220> FEATURE:
```

<223> OTHER INFORMATION: synthetic peptide

<400> SEQUENCE: 482

Asp Ala Ser
1

<210> SEQ ID NO 483
<211> LENGTH: 10
<212> TYPE: PRT
<213> ORGANISM: Artificial Sequence
<220> FEATURE:
<223> OTHER INFORMATION: synthetic peptide

<400> SEQUENCE: 483

Gln Gln Arg Thr Asn Trp Pro Pro Trp Thr
1               5                   10

<210> SEQ ID NO 484
<211> LENGTH: 8
<212> TYPE: PRT
<213> ORGANISM: Artificial Sequence
<220> FEATURE:
<223> OTHER INFORMATION: synthetic peptide

<400> SEQUENCE: 484

Gly Phe Thr Phe Gly Thr Tyr Ala
1               5

<210> SEQ ID NO 485
<211> LENGTH: 8
<212> TYPE: PRT
<213> ORGANISM: Artificial Sequence
<220> FEATURE:
<223> OTHER INFORMATION: synthetic peptide

<400> SEQUENCE: 485

Ile Ser Gly Ser Gly Ala Gly Thr
1               5

<210> SEQ ID NO 486
<211> LENGTH: 13
<212> TYPE: PRT
<213> ORGANISM: Artificial Sequence
<220> FEATURE:
<223> OTHER INFORMATION: synthetic peptide

<400> SEQUENCE: 486

Ala Lys Asp Asn Ser Ala Ser Val Trp Asp Leu Ala Tyr
1               5                   10

<210> SEQ ID NO 487
<211> LENGTH: 6
<212> TYPE: PRT
<213> ORGANISM: Artificial Sequence
<220> FEATURE:
<223> OTHER INFORMATION: synthetic peptide

<400> SEQUENCE: 487

Arg Ser Ile Asn Ser Tyr
1               5

<210> SEQ ID NO 488
<211> LENGTH: 3
<212> TYPE: PRT
<213> ORGANISM: Artificial Sequence
<220> FEATURE:
<223> OTHER INFORMATION: synthetic peptide

<400> SEQUENCE: 488

Ala Ala Ser
1

<210> SEQ ID NO 489
<211> LENGTH: 10
<212> TYPE: PRT
<213> ORGANISM: Artificial Sequence
<220> FEATURE:
<223> OTHER INFORMATION: synthetic peptide

<400> SEQUENCE: 489

His Gln Thr Tyr Thr Thr Pro Pro Gly Thr
1               5                   10

<210> SEQ ID NO 490
<211> LENGTH: 8
<212> TYPE: PRT
<213> ORGANISM: Artificial Sequence
<220> FEATURE:
<223> OTHER INFORMATION: synthetic peptide

<400> SEQUENCE: 490

Gly Phe Ala Phe Ser Asp Tyr Ala
1               5

<210> SEQ ID NO 491
<211> LENGTH: 8
<212> TYPE: PRT
<213> ORGANISM: Artificial Sequence
<220> FEATURE:
<223> OTHER INFORMATION: synthetic peptide

<400> SEQUENCE: 491

Ile Ser Tyr Ala Gly Asn Asn Lys
1               5

<210> SEQ ID NO 492
<211> LENGTH: 14
<212> TYPE: PRT
<213> ORGANISM: Artificial Sequence
<220> FEATURE:
<223> OTHER INFORMATION: synthetic peptide

<400> SEQUENCE: 492

Ala Arg Pro Phe Ser Arg Gly Trp Phe Glu Gly Cys Asp Ser
1               5                   10

<210> SEQ ID NO 493
<211> LENGTH: 6
<212> TYPE: PRT
<213> ORGANISM: Artificial Sequence
<220> FEATURE:
<223> OTHER INFORMATION: synthetic peptide

<400> SEQUENCE: 493

Gln Thr Ile Asn Asp Phe
1               5

<210> SEQ ID NO 494
<211> LENGTH: 3
<212> TYPE: PRT
<213> ORGANISM: Artificial Sequence
<220> FEATURE:
<223> OTHER INFORMATION: synthetic peptide

```
<400> SEQUENCE: 494

Ser Ala Ser
1

<210> SEQ ID NO 495
<211> LENGTH: 9
<212> TYPE: PRT
<213> ORGANISM: Artificial Sequence
<220> FEATURE:
<223> OTHER INFORMATION: synthetic peptide

<400> SEQUENCE: 495

Gln Gln Ser Tyr Ile Ala Pro Leu Thr
1               5

<210> SEQ ID NO 496
<211> LENGTH: 8
<212> TYPE: PRT
<213> ORGANISM: Artificial Sequence
<220> FEATURE:
<223> OTHER INFORMATION: synthetic peptide

<400> SEQUENCE: 496

Gly Phe Thr Phe Arg Ser Tyr Ala
1               5

<210> SEQ ID NO 497
<211> LENGTH: 8
<212> TYPE: PRT
<213> ORGANISM: Artificial Sequence
<220> FEATURE:
<223> OTHER INFORMATION: synthetic peptide

<400> SEQUENCE: 497

Ile Ser Leu Asp Gly Ser His Lys
1               5

<210> SEQ ID NO 498
<211> LENGTH: 13
<212> TYPE: PRT
<213> ORGANISM: Artificial Sequence
<220> FEATURE:
<223> OTHER INFORMATION: synthetic peptide

<400> SEQUENCE: 498

Val Arg Gly Gly Trp His Glu Val Gly Ser Phe Asp Tyr
1               5                   10

<210> SEQ ID NO 499
<211> LENGTH: 7
<212> TYPE: PRT
<213> ORGANISM: Artificial Sequence
<220> FEATURE:
<223> OTHER INFORMATION: synthetic peptide

<400> SEQUENCE: 499

Gln Ser Ile Asn Ser Asn Tyr
1               5

<210> SEQ ID NO 500
<211> LENGTH: 3
<212> TYPE: PRT
<213> ORGANISM: Artificial Sequence
<220> FEATURE:
<223> OTHER INFORMATION: synthetic peptide
```

<400> SEQUENCE: 500

Ala Ala Ser
1

<210> SEQ ID NO 501
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 501

Gln Xaa Tyr Gly Asn Thr Pro Phe Thr
1               5

<210> SEQ ID NO 502
<211> LENGTH: 8
<212> TYPE: PRT
<213> ORGANISM: Artificial Sequence
<220> FEATURE:
<223> OTHER INFORMATION: synthetic peptide

<400> SEQUENCE: 502

Gly Asp Thr Phe Ser Ser Tyr Gly
1               5

<210> SEQ ID NO 503
<211> LENGTH: 8
<212> TYPE: PRT
<213> ORGANISM: Artificial Sequence
<220> FEATURE:
<223> OTHER INFORMATION: synthetic peptide

<400> SEQUENCE: 503

Ile Ile Pro Ile Val Asp Ile Thr
1               5

<210> SEQ ID NO 504
<211> LENGTH: 24
<212> TYPE: PRT
<213> ORGANISM: Artificial Sequence
<220> FEATURE:
<223> OTHER INFORMATION: synthetic peptide

<400> SEQUENCE: 504

Ala Arg Ile Ser Ala Tyr Tyr Tyr Asp Gly Ser Gly Ser Asn Pro Gly
1               5                   10                  15
Ile Thr Asp Tyr Gly Met Asp Val
            20

<210> SEQ ID NO 505
<211> LENGTH: 11
<212> TYPE: PRT
<213> ORGANISM: Artificial Sequence
<220> FEATURE:
<223> OTHER INFORMATION: synthetic peptide

<400> SEQUENCE: 505

Gln Ser Leu Leu His Ser Asn Gly Tyr Asn Tyr
1               5                   10

```
<210> SEQ ID NO 506
<211> LENGTH: 3
<212> TYPE: PRT
<213> ORGANISM: Artificial Sequence
<220> FEATURE:
<223> OTHER INFORMATION: synthetic peptide

<400> SEQUENCE: 506

Leu Gly Ser
1

<210> SEQ ID NO 507
<211> LENGTH: 9
<212> TYPE: PRT
<213> ORGANISM: Artificial Sequence
<220> FEATURE:
<223> OTHER INFORMATION: synthetic peptide

<400> SEQUENCE: 507

Met Gln Gly Leu Gln Thr Pro His Thr
1               5

<210> SEQ ID NO 508
<211> LENGTH: 8
<212> TYPE: PRT
<213> ORGANISM: Artificial Sequence
<220> FEATURE:
<223> OTHER INFORMATION: synthetic peptide

<400> SEQUENCE: 508

Gly Phe Thr Phe Ser Ser Tyr Asp
1               5

<210> SEQ ID NO 509
<211> LENGTH: 8
<212> TYPE: PRT
<213> ORGANISM: Artificial Sequence
<220> FEATURE:
<223> OTHER INFORMATION: synthetic peptide

<400> SEQUENCE: 509

Ala Trp Tyr Asp Gly Ser Asn Lys
1               5

<210> SEQ ID NO 510
<211> LENGTH: 37
<212> TYPE: PRT
<213> ORGANISM: Artificial Sequence
<220> FEATURE:
<223> OTHER INFORMATION: synthetic peptide

<400> SEQUENCE: 510

Ala Arg Gly Thr His Thr Tyr Thr Tyr Gly Tyr Arg Thr Asp Tyr Cys
1               5                   10                  15

Met Gly Val Trp Gly Thr His Thr Tyr Thr Tyr Gly Tyr Arg Thr Asp
            20                  25                  30

Tyr Cys Met Gly Val
        35

<210> SEQ ID NO 511
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 511

Gln Gly Ile Gly Asn Tyr
1               5

<210> SEQ ID NO 512
<211> LENGTH: 3
<212> TYPE: PRT
<213> ORGANISM: Artificial Sequence
<220> FEATURE:
<223> OTHER INFORMATION: synthetic peptide

<400> SEQUENCE: 512

Ser Ala Ser
1

<210> SEQ ID NO 513
<211> LENGTH: 9
<212> TYPE: PRT
<213> ORGANISM: Artificial Sequence
<220> FEATURE:
<223> OTHER INFORMATION: synthetic peptide

<400> SEQUENCE: 513

Leu Lys Tyr His Gly Ala Pro Tyr Ile
1               5

<210> SEQ ID NO 514
<211> LENGTH: 8
<212> TYPE: PRT
<213> ORGANISM: Artificial Sequence
<220> FEATURE:
<223> OTHER INFORMATION: synthetic peptide

<400> SEQUENCE: 514

Gly Tyr Ile Phe Thr Thr Tyr Thr
1               5

<210> SEQ ID NO 515
<211> LENGTH: 8
<212> TYPE: PRT
<213> ORGANISM: Artificial Sequence
<220> FEATURE:
<223> OTHER INFORMATION: synthetic peptide

<400> SEQUENCE: 515

Ile Asn Ala Gly Asn Gly Val Thr
1               5

<210> SEQ ID NO 516
<211> LENGTH: 15
<212> TYPE: PRT
<213> ORGANISM: Artificial Sequence
<220> FEATURE:
<223> OTHER INFORMATION: synthetic peptide

<400> SEQUENCE: 516

Ala Arg Ala Trp Lys Tyr Ser Ser Thr Trp Phe Tyr Tyr Asp Tyr
1               5                   10                  15

<210> SEQ ID NO 517
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 517

Gln Thr Ile Asn Asn Tyr
1               5

<210> SEQ ID NO 518
<211> LENGTH: 3
<212> TYPE: PRT
<213> ORGANISM: Artificial Sequence
<220> FEATURE:
<223> OTHER INFORMATION: synthetic peptide

<400> SEQUENCE: 518

Ala Ala Ser
1

<210> SEQ ID NO 519
<211> LENGTH: 9
<212> TYPE: PRT
<213> ORGANISM: Artificial Sequence
<220> FEATURE:
<223> OTHER INFORMATION: synthetic peptide

<400> SEQUENCE: 519

Gln Gln Ser Tyr Ser Ala Pro Phe Thr
1               5

<210> SEQ ID NO 520
<211> LENGTH: 8
<212> TYPE: PRT
<213> ORGANISM: Artificial Sequence
<220> FEATURE:
<223> OTHER INFORMATION: synthetic peptide

<400> SEQUENCE: 520

Gly Leu Thr Leu Ser Thr Asn Ala
1               5

<210> SEQ ID NO 521
<211> LENGTH: 8
<212> TYPE: PRT
<213> ORGANISM: Artificial Sequence
<220> FEATURE:
<223> OTHER INFORMATION: synthetic peptide

<400> SEQUENCE: 521

Ile Arg Gly Ser Gly Glu Ser Thr
1               5

<210> SEQ ID NO 522
<211> LENGTH: 15
<212> TYPE: PRT
<213> ORGANISM: Artificial Sequence
<220> FEATURE:
<223> OTHER INFORMATION: synthetic peptide

<400> SEQUENCE: 522

Ala Lys Ser Gly Met Gly Glu Leu Val Arg Cys Trp Phe Asp Ala
1               5                   10                  15

<210> SEQ ID NO 523
<211> LENGTH: 12
<212> TYPE: PRT
<213> ORGANISM: Artificial Sequence
<220> FEATURE:
<223> OTHER INFORMATION: synthetic peptide
```

```
<400> SEQUENCE: 523

Gln Ser Val Leu Tyr Ser Ser Asn Asn Lys Asn Tyr
1               5                   10

<210> SEQ ID NO 524
<211> LENGTH: 3
<212> TYPE: PRT
<213> ORGANISM: Artificial Sequence
<220> FEATURE:
<223> OTHER INFORMATION: synthetic peptide

<400> SEQUENCE: 524

Trp Ala Ser
1

<210> SEQ ID NO 525
<211> LENGTH: 11
<212> TYPE: PRT
<213> ORGANISM: Artificial Sequence
<220> FEATURE:
<223> OTHER INFORMATION: synthetic peptide

<400> SEQUENCE: 525

Gln Gln Tyr Tyr Ser Asn Pro Pro Pro Gly Thr
1               5                   10

<210> SEQ ID NO 526
<211> LENGTH: 10
<212> TYPE: PRT
<213> ORGANISM: Artificial Sequence
<220> FEATURE:
<223> OTHER INFORMATION: synthetic peptide

<400> SEQUENCE: 526

Gly Phe Ser Leu Thr Thr Pro Gly Val Gly
1               5                   10

<210> SEQ ID NO 527
<211> LENGTH: 7
<212> TYPE: PRT
<213> ORGANISM: Artificial Sequence
<220> FEATURE:
<223> OTHER INFORMATION: synthetic peptide

<400> SEQUENCE: 527

Ile Phe Trp Asn Asp Glu Lys
1               5

<210> SEQ ID NO 528
<211> LENGTH: 12
<212> TYPE: PRT
<213> ORGANISM: Artificial Sequence
<220> FEATURE:
<223> OTHER INFORMATION: synthetic peptide

<400> SEQUENCE: 528

Ala His Ser Arg Leu Asp Leu Trp Asn Gly Tyr Lys
1               5                   10

<210> SEQ ID NO 529
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 529

Gln Ser Leu Leu His Ile Asn Gly Tyr Thr Tyr
1               5                   10

<210> SEQ ID NO 530
<211> LENGTH: 3
<212> TYPE: PRT
<213> ORGANISM: Artificial Sequence
<220> FEATURE:
<223> OTHER INFORMATION: synthetic peptide

<400> SEQUENCE: 530

Leu Gly Ser
1

<210> SEQ ID NO 531
<211> LENGTH: 9
<212> TYPE: PRT
<213> ORGANISM: Artificial Sequence
<220> FEATURE:
<223> OTHER INFORMATION: synthetic peptide

<400> SEQUENCE: 531

Met Gln Ala Leu Gln Thr Pro Arg Thr
1               5

<210> SEQ ID NO 532
<211> LENGTH: 11
<212> TYPE: PRT
<213> ORGANISM: Artificial Sequence
<220> FEATURE:
<223> OTHER INFORMATION: synthetic peptide

<400> SEQUENCE: 532

Gln Ser Leu Val His Arg Asp Gly Asn Thr Tyr
1               5                   10

<210> SEQ ID NO 533
<211> LENGTH: 3
<212> TYPE: PRT
<213> ORGANISM: Artificial Sequence
<220> FEATURE:
<223> OTHER INFORMATION: synthetic peptide

<400> SEQUENCE: 533

Gly Val Ser
1

<210> SEQ ID NO 534
<211> LENGTH: 9
<212> TYPE: PRT
<213> ORGANISM: Artificial Sequence
<220> FEATURE:
<223> OTHER INFORMATION: synthetic peptide

<400> SEQUENCE: 534

Met Gln Ala Thr His Trp Gly Tyr Thr
1               5

<210> SEQ ID NO 535
<211> LENGTH: 8
<212> TYPE: PRT
<213> ORGANISM: Artificial Sequence
<220> FEATURE:
<223> OTHER INFORMATION: synthetic peptide
```

```
<400> SEQUENCE: 535

Arg Phe Ile Phe Ser Asn Tyr Gly
1               5

<210> SEQ ID NO 536
<211> LENGTH: 8
<212> TYPE: PRT
<213> ORGANISM: Artificial Sequence
<220> FEATURE:
<223> OTHER INFORMATION: synthetic peptide

<400> SEQUENCE: 536

Ile Arg Ser Asp Gly Ser Asn Thr
1               5

<210> SEQ ID NO 537
<211> LENGTH: 15
<212> TYPE: PRT
<213> ORGANISM: Artificial Sequence
<220> FEATURE:
<223> OTHER INFORMATION: synthetic peptide

<400> SEQUENCE: 537

Ala Lys Gly Cys Cys Gly Gly Val Pro Asp Phe Gly Leu Asp Val
1               5                   10                  15

<210> SEQ ID NO 538
<211> LENGTH: 10
<212> TYPE: PRT
<213> ORGANISM: Artificial Sequence
<220> FEATURE:
<223> OTHER INFORMATION: synthetic peptide

<400> SEQUENCE: 538

Gly Phe Ser Leu Thr Thr Pro Gly Val Gly
1               5                   10

<210> SEQ ID NO 539
<211> LENGTH: 7
<212> TYPE: PRT
<213> ORGANISM: Artificial Sequence
<220> FEATURE:
<223> OTHER INFORMATION: synthetic peptide

<400> SEQUENCE: 539

Ile Phe Trp Asn Asp Glu Lys
1               5

<210> SEQ ID NO 540
<211> LENGTH: 12
<212> TYPE: PRT
<213> ORGANISM: Artificial Sequence
<220> FEATURE:
<223> OTHER INFORMATION: synthetic peptide

<400> SEQUENCE: 540

Ala His Ser Arg Leu Asp Leu Trp Asn Gly Tyr Lys
1               5                   10

<210> SEQ ID NO 541
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 541

Gln Ser Leu Leu His Ile Asn Gly Tyr Thr Tyr
1               5                   10

<210> SEQ ID NO 542
<211> LENGTH: 3
<212> TYPE: PRT
<213> ORGANISM: Artificial Sequence
<220> FEATURE:
<223> OTHER INFORMATION: synthetic peptide

<400> SEQUENCE: 542

Leu Gly Ser
1

<210> SEQ ID NO 543
<211> LENGTH: 9
<212> TYPE: PRT
<213> ORGANISM: Artificial Sequence
<220> FEATURE:
<223> OTHER INFORMATION: synthetic peptide

<400> SEQUENCE: 543

Met Gln Ala Leu Gln Thr Pro Arg Thr
1               5

<210> SEQ ID NO 544
<211> LENGTH: 8
<212> TYPE: PRT
<213> ORGANISM: Artificial Sequence
<220> FEATURE:
<223> OTHER INFORMATION: synthetic peptide

<400> SEQUENCE: 544

Gly Tyr Thr Phe Thr Ser Tyr Asp
1               5

<210> SEQ ID NO 545
<211> LENGTH: 8
<212> TYPE: PRT
<213> ORGANISM: Artificial Sequence
<220> FEATURE:
<223> OTHER INFORMATION: synthetic peptide

<400> SEQUENCE: 545

Met Ser Pro His Thr Gly Asn Thr
1               5

<210> SEQ ID NO 546
<211> LENGTH: 16
<212> TYPE: PRT
<213> ORGANISM: Artificial Sequence
<220> FEATURE:
<223> OTHER INFORMATION: synthetic peptide

<400> SEQUENCE: 546

Gly Arg Leu Val Gly Ala Pro Leu Tyr Asn Tyr Tyr Gly Phe Asp Val
1               5                   10                  15

<210> SEQ ID NO 547
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 547

Gln Asp Ile Ser Asp Trp
1               5

<210> SEQ ID NO 548
<211> LENGTH: 3
<212> TYPE: PRT
<213> ORGANISM: Artificial Sequence
<220> FEATURE:
<223> OTHER INFORMATION: synthetic peptide

<400> SEQUENCE: 548

Ala Ala Ser
1

<210> SEQ ID NO 549
<211> LENGTH: 9
<212> TYPE: PRT
<213> ORGANISM: Artificial Sequence
<220> FEATURE:
<223> OTHER INFORMATION: synthetic peptide

<400> SEQUENCE: 549

Gln Gln Ser Ser Ser Phe Pro Leu Thr
1               5

<210> SEQ ID NO 550
<211> LENGTH: 8
<212> TYPE: PRT
<213> ORGANISM: Artificial Sequence
<220> FEATURE:
<223> OTHER INFORMATION: synthetic peptide

<400> SEQUENCE: 550

Gly Phe Ser Phe Asp Asp Tyr Gly
1               5

<210> SEQ ID NO 551
<211> LENGTH: 8
<212> TYPE: PRT
<213> ORGANISM: Artificial Sequence
<220> FEATURE:
<223> OTHER INFORMATION: synthetic peptide

<400> SEQUENCE: 551

Ile Ser Trp Asn Ser Gly Thr Ile
1               5

<210> SEQ ID NO 552
<211> LENGTH: 16
<212> TYPE: PRT
<213> ORGANISM: Artificial Sequence
<220> FEATURE:
<223> OTHER INFORMATION: synthetic peptide

<400> SEQUENCE: 552

Ala Lys Asp Phe Tyr Ala Gly Phe Gly Gly Asn Thr Ala Phe Asp Ile
1               5                   10                  15

<210> SEQ ID NO 553
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 553

Gln Gly Ile His Asn Tyr
1               5

<210> SEQ ID NO 554
<211> LENGTH: 3
<212> TYPE: PRT
<213> ORGANISM: Artificial Sequence
<220> FEATURE:
<223> OTHER INFORMATION: synthetic peptide

<400> SEQUENCE: 554

Ala Ala Ser
1

<210> SEQ ID NO 555
<211> LENGTH: 10
<212> TYPE: PRT
<213> ORGANISM: Artificial Sequence
<220> FEATURE:
<223> OTHER INFORMATION: synthetic peptide

<400> SEQUENCE: 555

Gln Gln Ser Tyr Ser Val Pro Arg Asn Thr
1               5                   10

<210> SEQ ID NO 556
<211> LENGTH: 8
<212> TYPE: PRT
<213> ORGANISM: Artificial Sequence
<220> FEATURE:
<223> OTHER INFORMATION: synthetic peptide

<400> SEQUENCE: 556

Gly Phe Thr Phe Lys Ser Tyr Gly
1               5

<210> SEQ ID NO 557
<211> LENGTH: 8
<212> TYPE: PRT
<213> ORGANISM: Artificial Sequence
<220> FEATURE:
<223> OTHER INFORMATION: synthetic peptide

<400> SEQUENCE: 557

Ile Ser Asn His Gly His Asn Lys
1               5

<210> SEQ ID NO 558
<211> LENGTH: 15
<212> TYPE: PRT
<213> ORGANISM: Artificial Sequence
<220> FEATURE:
<223> OTHER INFORMATION: synthetic peptide

<400> SEQUENCE: 558

Ala Lys Gly Leu Asn Ser Asp Tyr Asp Asn Glu Pro Phe Gly Asp
1               5                   10                  15

<210> SEQ ID NO 559
<211> LENGTH: 7
<212> TYPE: PRT
<213> ORGANISM: Artificial Sequence
<220> FEATURE:
<223> OTHER INFORMATION: synthetic peptide
```

```
<400> SEQUENCE: 559

Gln Ser Phe Asp Ser Ser Tyr
1               5

<210> SEQ ID NO 560
<211> LENGTH: 3
<212> TYPE: PRT
<213> ORGANISM: Artificial Sequence
<220> FEATURE:
<223> OTHER INFORMATION: synthetic peptide

<400> SEQUENCE: 560

Gly Ala Ser
1

<210> SEQ ID NO 561
<211> LENGTH: 9
<212> TYPE: PRT
<213> ORGANISM: Artificial Sequence
<220> FEATURE:
<223> OTHER INFORMATION: synthetic peptide

<400> SEQUENCE: 561

Gln Gln Tyr Ala Ser Thr Pro Phe Thr
1               5

<210> SEQ ID NO 562
<211> LENGTH: 10
<212> TYPE: PRT
<213> ORGANISM: Artificial Sequence
<220> FEATURE:
<223> OTHER INFORMATION: synthetic peptide

<400> SEQUENCE: 562

Gly Gly Ser Met Ser Ser Gly Asp Tyr Tyr
1               5                   10

<210> SEQ ID NO 563
<211> LENGTH: 7
<212> TYPE: PRT
<213> ORGANISM: Artificial Sequence
<220> FEATURE:
<223> OTHER INFORMATION: synthetic peptide

<400> SEQUENCE: 563

Ile Ser Tyr Ser Gly Ser Ala
1               5

<210> SEQ ID NO 564
<211> LENGTH: 12
<212> TYPE: PRT
<213> ORGANISM: Artificial Sequence
<220> FEATURE:
<223> OTHER INFORMATION: synthetic peptide

<400> SEQUENCE: 564

Ala Arg Val Phe Ser Gly Tyr Tyr Tyr Phe Asp Tyr
1               5                   10

<210> SEQ ID NO 565
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 565

Gln Ser Ile Ser Ser Trp
1               5

<210> SEQ ID NO 566
<211> LENGTH: 3
<212> TYPE: PRT
<213> ORGANISM: Artificial Sequence
<220> FEATURE:
<223> OTHER INFORMATION: synthetic peptide

<400> SEQUENCE: 566

Lys Ala Ser
1

<210> SEQ ID NO 567
<211> LENGTH: 9
<212> TYPE: PRT
<213> ORGANISM: Artificial Sequence
<220> FEATURE:
<223> OTHER INFORMATION: synthetic peptide

<400> SEQUENCE: 567

Gln Gln Tyr Asn Thr Tyr Pro Trp Thr
1               5

<210> SEQ ID NO 568
<211> LENGTH: 8
<212> TYPE: PRT
<213> ORGANISM: Artificial Sequence
<220> FEATURE:
<223> OTHER INFORMATION: synthetic peptide

<400> SEQUENCE: 568

Gly Tyr Thr Phe Thr Arg Tyr Ala
1               5

<210> SEQ ID NO 569
<211> LENGTH: 8
<212> TYPE: PRT
<213> ORGANISM: Artificial Sequence
<220> FEATURE:
<223> OTHER INFORMATION: synthetic peptide

<400> SEQUENCE: 569

Ile Asn Pro Gly Ile Gly Asn Thr
1               5

<210> SEQ ID NO 570
<211> LENGTH: 13
<212> TYPE: PRT
<213> ORGANISM: Artificial Sequence
<220> FEATURE:
<223> OTHER INFORMATION: synthetic peptide

<400> SEQUENCE: 570

Ala Arg Asp Leu Asp Leu Gly Ile Pro Thr Leu Gly Tyr
1               5                   10

<210> SEQ ID NO 571
<211> LENGTH: 12
<212> TYPE: PRT
<213> ORGANISM: Artificial Sequence
<220> FEATURE:
<223> OTHER INFORMATION: synthetic peptide
```

<400> SEQUENCE: 571

Gln Ser Leu Leu Ser Ser Ser Asn Asn Lys Asn Phe
1               5                   10

<210> SEQ ID NO 572
<211> LENGTH: 3
<212> TYPE: PRT
<213> ORGANISM: Artificial Sequence
<220> FEATURE:
<223> OTHER INFORMATION: synthetic peptide

<400> SEQUENCE: 572

Trp Ala Ser
1

<210> SEQ ID NO 573
<211> LENGTH: 10
<212> TYPE: PRT
<213> ORGANISM: Artificial Sequence
<220> FEATURE:
<223> OTHER INFORMATION: synthetic peptide

<400> SEQUENCE: 573

Gln Gln Tyr Tyr Ser Thr Pro Pro Tyr Ser
1               5                   10

<210> SEQ ID NO 574
<211> LENGTH: 8
<212> TYPE: PRT
<213> ORGANISM: Artificial Sequence
<220> FEATURE:
<223> OTHER INFORMATION: synthetic peptide

<400> SEQUENCE: 574

Gly Tyr Thr Phe Thr Arg Tyr Ala
1               5

<210> SEQ ID NO 575
<211> LENGTH: 8
<212> TYPE: PRT
<213> ORGANISM: Artificial Sequence
<220> FEATURE:
<223> OTHER INFORMATION: synthetic peptide

<400> SEQUENCE: 575

Ile Asn Thr Asn Thr Gly Glu Pro
1               5

<210> SEQ ID NO 576
<211> LENGTH: 9
<212> TYPE: PRT
<213> ORGANISM: Artificial Sequence
<220> FEATURE:
<223> OTHER INFORMATION: synthetic peptide

<400> SEQUENCE: 576

Ala Gln Gln Val Ile Ala Phe Asp Val
1               5

<210> SEQ ID NO 577
<211> LENGTH: 12
<212> TYPE: PRT
<213> ORGANISM: Artificial Sequence
<220> FEATURE:
<223> OTHER INFORMATION: synthetic peptide

```
<400> SEQUENCE: 577

Gln Ser Leu Leu Ser Ser Ser Asn Asn Lys Asn Phe
1               5                   10

<210> SEQ ID NO 578
<211> LENGTH: 3
<212> TYPE: PRT
<213> ORGANISM: Artificial Sequence
<220> FEATURE:
<223> OTHER INFORMATION: synthetic peptide

<400> SEQUENCE: 578

Trp Ala Ser
1

<210> SEQ ID NO 579
<211> LENGTH: 10
<212> TYPE: PRT
<213> ORGANISM: Artificial Sequence
<220> FEATURE:
<223> OTHER INFORMATION: synthetic peptide

<400> SEQUENCE: 579

Gln Gln Tyr Tyr Ser Thr Pro Pro Tyr Ser
1               5                   10

<210> SEQ ID NO 580
<211> LENGTH: 8
<212> TYPE: PRT
<213> ORGANISM: Artificial Sequence
<220> FEATURE:
<223> OTHER INFORMATION: synthetic peptide

<400> SEQUENCE: 580

Gly Phe Thr Phe Asn Asp Tyr Ala
1               5

<210> SEQ ID NO 581
<211> LENGTH: 8
<212> TYPE: PRT
<213> ORGANISM: Artificial Sequence
<220> FEATURE:
<223> OTHER INFORMATION: synthetic peptide

<400> SEQUENCE: 581

Ile Thr Trp Asn Gly Gly Pro Leu
1               5

<210> SEQ ID NO 582
<211> LENGTH: 16
<212> TYPE: PRT
<213> ORGANISM: Artificial Sequence
<220> FEATURE:
<223> OTHER INFORMATION: synthetic peptide

<400> SEQUENCE: 582

Ala Lys Val Tyr Cys Ser Ser Ser Thr Cys Ser Asn Ala Leu Asp Val
1               5                   10                  15

<210> SEQ ID NO 583
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 583

Gln Asp Ile Ser Ile Tyr
1               5

<210> SEQ ID NO 584
<211> LENGTH: 3
<212> TYPE: PRT
<213> ORGANISM: Artificial Sequence
<220> FEATURE:
<223> OTHER INFORMATION: synthetic peptide

<400> SEQUENCE: 584

Asp Ala Ser
1

<210> SEQ ID NO 585
<211> LENGTH: 9
<212> TYPE: PRT
<213> ORGANISM: Artificial Sequence
<220> FEATURE:
<223> OTHER INFORMATION: synthetic peptide

<400> SEQUENCE: 585

Gln Gln His Asn Ser Arg Pro Tyr Ser
1               5

<210> SEQ ID NO 586
<211> LENGTH: 10
<212> TYPE: PRT
<213> ORGANISM: Artificial Sequence
<220> FEATURE:
<223> OTHER INFORMATION: synthetic peptide

<400> SEQUENCE: 586

Gly Val Ser Ile Asn Asn Tyr Asp Tyr Tyr
1               5                   10

<210> SEQ ID NO 587
<211> LENGTH: 7
<212> TYPE: PRT
<213> ORGANISM: Artificial Sequence
<220> FEATURE:
<223> OTHER INFORMATION: synthetic peptide

<400> SEQUENCE: 587

Ile Ile Tyr Ser Gly Ser Thr
1               5

<210> SEQ ID NO 588
<211> LENGTH: 17
<212> TYPE: PRT
<213> ORGANISM: Artificial Sequence
<220> FEATURE:
<223> OTHER INFORMATION: synthetic peptide

<400> SEQUENCE: 588

Val Arg Ala Asn Leu Cys Asn Val Ala Ser Cys Tyr Tyr Tyr Phe Asp
1               5                   10                  15

Phe

<210> SEQ ID NO 589
<211> LENGTH: 6
<212> TYPE: PRT
<213> ORGANISM: Artificial Sequence
<220> FEATURE:
```

```
<223> OTHER INFORMATION: synthetic peptide

<400> SEQUENCE: 589

Gln Asp Val Thr Thr Ala
1               5

<210> SEQ ID NO 590
<211> LENGTH: 3
<212> TYPE: PRT
<213> ORGANISM: Artificial Sequence
<220> FEATURE:
<223> OTHER INFORMATION: synthetic peptide

<400> SEQUENCE: 590

Trp Ala Ser
1

<210> SEQ ID NO 591
<211> LENGTH: 9
<212> TYPE: PRT
<213> ORGANISM: Artificial Sequence
<220> FEATURE:
<223> OTHER INFORMATION: synthetic peptide

<400> SEQUENCE: 591

Gln Gln His Tyr Ser Thr Pro Leu Thr
1               5

<210> SEQ ID NO 592
<211> LENGTH: 8
<212> TYPE: PRT
<213> ORGANISM: Artificial Sequence
<220> FEATURE:
<223> OTHER INFORMATION: synthetic peptide

<400> SEQUENCE: 592

Gly Phe Thr Leu Ser Arg Tyr Asp
1               5

<210> SEQ ID NO 593
<211> LENGTH: 7
<212> TYPE: PRT
<213> ORGANISM: Artificial Sequence
<220> FEATURE:
<223> OTHER INFORMATION: synthetic peptide

<400> SEQUENCE: 593

Ile Gly Thr Ala Thr Thr Gly
1               5

<210> SEQ ID NO 594
<211> LENGTH: 15
<212> TYPE: PRT
<213> ORGANISM: Artificial Sequence
<220> FEATURE:
<223> OTHER INFORMATION: synthetic peptide

<400> SEQUENCE: 594

Tyr Cys Thr Arg Ala Met Val Arg Gly Leu Asp Ile Phe Asp Tyr
1               5                   10                  15

<210> SEQ ID NO 595
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 595

Gln Ser Val Ser Ser Lys
1               5

<210> SEQ ID NO 596
<211> LENGTH: 3
<212> TYPE: PRT
<213> ORGANISM: Artificial Sequence
<220> FEATURE:
<223> OTHER INFORMATION: synthetic peptide

<400> SEQUENCE: 596

Gly Ala Ser
1

<210> SEQ ID NO 597
<211> LENGTH: 10
<212> TYPE: PRT
<213> ORGANISM: Artificial Sequence
<220> FEATURE:
<223> OTHER INFORMATION: synthetic peptide

<400> SEQUENCE: 597

Gln Gln Tyr Asn Ser Trp Pro Met Cys Thr
1               5                   10

<210> SEQ ID NO 598
<211> LENGTH: 8
<212> TYPE: PRT
<213> ORGANISM: Artificial Sequence
<220> FEATURE:
<223> OTHER INFORMATION: synthetic peptide

<400> SEQUENCE: 598

Gly Phe Thr Phe Ser His Tyr Trp
1               5

<210> SEQ ID NO 599
<211> LENGTH: 8
<212> TYPE: PRT
<213> ORGANISM: Artificial Sequence
<220> FEATURE:
<223> OTHER INFORMATION: synthetic peptide

<400> SEQUENCE: 599

Ile Arg Pro Asp Gly Thr Thr Thr
1               5

<210> SEQ ID NO 600
<211> LENGTH: 18
<212> TYPE: PRT
<213> ORGANISM: Artificial Sequence
<220> FEATURE:
<223> OTHER INFORMATION: synthetic peptide

<400> SEQUENCE: 600

Ala Arg Asp Leu Thr Pro Gly Asp Asp Ser Ala Trp Tyr Asp Phe Phe
1               5                   10                  15

Asp Tyr

<210> SEQ ID NO 601
<211> LENGTH: 6
<212> TYPE: PRT
<213> ORGANISM: Artificial Sequence
<220> FEATURE:

<223> OTHER INFORMATION: synthetic peptide

<400> SEQUENCE: 601

Gln Pro Ile Arg Asn Glu
1               5

<210> SEQ ID NO 602
<211> LENGTH: 3
<212> TYPE: PRT
<213> ORGANISM: Artificial Sequence
<220> FEATURE:
<223> OTHER INFORMATION: synthetic peptide

<400> SEQUENCE: 602

Ala Ala Ser
1

<210> SEQ ID NO 603
<211> LENGTH: 9
<212> TYPE: PRT
<213> ORGANISM: Artificial Sequence
<220> FEATURE:
<223> OTHER INFORMATION: synthetic peptide

<400> SEQUENCE: 603

Leu Gln Asp Tyr Arg Tyr Pro Arg Thr
1               5

<210> SEQ ID NO 604
<211> LENGTH: 8
<212> TYPE: PRT
<213> ORGANISM: Artificial Sequence
<220> FEATURE:
<223> OTHER INFORMATION: synthetic peptide

<400> SEQUENCE: 604

Gly Phe Asp Leu Ser Asp Tyr Tyr
1               5

<210> SEQ ID NO 605
<211> LENGTH: 8
<212> TYPE: PRT
<213> ORGANISM: Artificial Sequence
<220> FEATURE:
<223> OTHER INFORMATION: synthetic peptide

<400> SEQUENCE: 605

Thr Ala Arg Thr Gly Ser Thr Glu
1               5

<210> SEQ ID NO 606
<211> LENGTH: 12
<212> TYPE: PRT
<213> ORGANISM: Artificial Sequence
<220> FEATURE:
<223> OTHER INFORMATION: synthetic peptide

<400> SEQUENCE: 606

Ala Arg Asp Leu Val Ser His Asp Val Phe Asp Ile
1               5                   10

<210> SEQ ID NO 607
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 607

Gln Arg Ile Ser Thr Asn
1               5

<210> SEQ ID NO 608
<211> LENGTH: 3
<212> TYPE: PRT
<213> ORGANISM: Artificial Sequence
<220> FEATURE:
<223> OTHER INFORMATION: synthetic peptide

<400> SEQUENCE: 608

Asp Ala Ser
1

<210> SEQ ID NO 609
<211> LENGTH: 9
<212> TYPE: PRT
<213> ORGANISM: Artificial Sequence
<220> FEATURE:
<223> OTHER INFORMATION: synthetic peptide

<400> SEQUENCE: 609

Gln Gln Tyr Ile Asn Trp Pro Arg Thr
1               5

<210> SEQ ID NO 610
<211> LENGTH: 330
<212> TYPE: PRT
<213> ORGANISM: Artificial Sequence
<220> FEATURE:
<223> OTHER INFORMATION: synthetic polypeptide

<400> SEQUENCE: 610

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Arg Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 611
<211> LENGTH: 8
<212> TYPE: PRT
<213> ORGANISM: Artificial Sequence
<220> FEATURE:
<223> OTHER INFORMATION: synthetic peptide

<400> SEQUENCE: 611

Gly Phe Thr Phe Ser Ser Phe Ala
1               5

<210> SEQ ID NO 612
<211> LENGTH: 8
<212> TYPE: PRT
<213> ORGANISM: Artificial Sequence
<220> FEATURE:
<223> OTHER INFORMATION: synthetic peptide

<400> SEQUENCE: 612

Ile Ser Tyr Glu Gly Lys Asn Lys
1               5

<210> SEQ ID NO 613
<211> LENGTH: 14
<212> TYPE: PRT
<213> ORGANISM: Artificial Sequence
<220> FEATURE:
<223> OTHER INFORMATION: synthetic peptide

<400> SEQUENCE: 613

Ala Arg Pro Phe Ser Met Ser Trp Phe Glu Gly Phe Glu Phe
1               5                   10

<210> SEQ ID NO 614
<211> LENGTH: 6
<212> TYPE: PRT
<213> ORGANISM: Artificial Sequence
<220> FEATURE:
<223> OTHER INFORMATION: synthetic peptide

<400> SEQUENCE: 614

Gln Asn Ile Asn Ser Phe
1               5
```

<210> SEQ ID NO 615
<211> LENGTH: 3
<212> TYPE: PRT
<213> ORGANISM: Artificial Sequence
<220> FEATURE:
<223> OTHER INFORMATION: synthetic peptide

<400> SEQUENCE: 615

Glu Ala Ser
1

<210> SEQ ID NO 616
<211> LENGTH: 9
<212> TYPE: PRT
<213> ORGANISM: Artificial Sequence
<220> FEATURE:
<223> OTHER INFORMATION: synthetic peptide

<400> SEQUENCE: 616

Gln Gln Ser Tyr Thr Ala Pro Leu Thr
1               5

<210> SEQ ID NO 617
<211> LENGTH: 8
<212> TYPE: PRT
<213> ORGANISM: Artificial Sequence
<220> FEATURE:
<223> OTHER INFORMATION: synthetic peptide

<400> SEQUENCE: 617

Gly Tyr Thr Phe Thr Asn Tyr Tyr
1               5

<210> SEQ ID NO 618
<211> LENGTH: 8
<212> TYPE: PRT
<213> ORGANISM: Artificial Sequence
<220> FEATURE:
<223> OTHER INFORMATION: synthetic peptide

<400> SEQUENCE: 618

Ile Tyr Pro Ser Gly Gly Asp Thr
1               5

<210> SEQ ID NO 619
<211> LENGTH: 17
<212> TYPE: PRT
<213> ORGANISM: Artificial Sequence
<220> FEATURE:
<223> OTHER INFORMATION: synthetic peptide

<400> SEQUENCE: 619

Ala Arg Asp His Leu Asn Arg Asp Ser Ser Ser Arg Gly Phe Met Asp
1               5                   10                  15

Tyr

<210> SEQ ID NO 620
<211> LENGTH: 6
<212> TYPE: PRT
<213> ORGANISM: Artificial Sequence
<220> FEATURE:
<223> OTHER INFORMATION: synthetic peptide

<400> SEQUENCE: 620

Gln Ser Ile Ser His Tyr
1               5

<210> SEQ ID NO 621
<211> LENGTH: 3
<212> TYPE: PRT
<213> ORGANISM: Artificial Sequence
<220> FEATURE:
<223> OTHER INFORMATION: synthetic peptide

<400> SEQUENCE: 621

Asp Ala Ser
1

<210> SEQ ID NO 622
<211> LENGTH: 9
<212> TYPE: PRT
<213> ORGANISM: Artificial Sequence
<220> FEATURE:
<223> OTHER INFORMATION: synthetic peptide

<400> SEQUENCE: 622

Gln Gln Arg Gly Thr Trp Pro Pro Ser
1               5

<210> SEQ ID NO 623
<211> LENGTH: 8
<212> TYPE: PRT
<213> ORGANISM: Artificial Sequence
<220> FEATURE:
<223> OTHER INFORMATION: synthetic peptide

<400> SEQUENCE: 623

Gly Tyr Thr Phe Thr Asn Tyr Pro
1               5

<210> SEQ ID NO 624
<211> LENGTH: 8
<212> TYPE: PRT
<213> ORGANISM: Artificial Sequence
<220> FEATURE:
<223> OTHER INFORMATION: synthetic peptide

<400> SEQUENCE: 624

Ile Asn Thr Asn Thr Gly Lys Pro
1               5

<210> SEQ ID NO 625
<211> LENGTH: 16
<212> TYPE: PRT
<213> ORGANISM: Artificial Sequence
<220> FEATURE:
<223> OTHER INFORMATION: synthetic peptide

<400> SEQUENCE: 625

Ala Arg Gly Arg Gly Ala Thr Thr Val Thr Thr Tyr Tyr Phe Asp Tyr
1               5                   10                  15

<210> SEQ ID NO 626
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 626

Gln Ser Val Ser Ser Asn
1               5

<210> SEQ ID NO 627
<211> LENGTH: 3
<212> TYPE: PRT
<213> ORGANISM: Artificial Sequence
<220> FEATURE:
<223> OTHER INFORMATION: synthetic peptide

<400> SEQUENCE: 627

Gly Ala Ser
1

<210> SEQ ID NO 628
<211> LENGTH: 10
<212> TYPE: PRT
<213> ORGANISM: Artificial Sequence
<220> FEATURE:
<223> OTHER INFORMATION: synthetic peptide

<400> SEQUENCE: 628

Gln His Tyr Ile Asn Arg Pro Gly Arg Thr
1               5                   10

<210> SEQ ID NO 629
<211> LENGTH: 8
<212> TYPE: PRT
<213> ORGANISM: Artificial Sequence
<220> FEATURE:
<223> OTHER INFORMATION: synthetic peptide

<400> SEQUENCE: 629

Gly Tyr Thr Phe Ile Ala Phe Tyr
1               5

<210> SEQ ID NO 630
<211> LENGTH: 8
<212> TYPE: PRT
<213> ORGANISM: Artificial Sequence
<220> FEATURE:
<223> OTHER INFORMATION: synthetic peptide

<400> SEQUENCE: 630

Ile Asn Pro Tyr Ser Gly Asp Thr
1               5

<210> SEQ ID NO 631
<211> LENGTH: 24
<212> TYPE: PRT
<213> ORGANISM: Artificial Sequence
<220> FEATURE:
<223> OTHER INFORMATION: synthetic peptide

<400> SEQUENCE: 631

Ala Arg Thr Val Tyr Val Asp Lys Gly Met Val Met Val Arg Arg Leu
1               5                   10                  15

Tyr Gln Tyr Phe Gly Met Asp Val
            20

<210> SEQ ID NO 632
<211> LENGTH: 7
<212> TYPE: PRT
<213> ORGANISM: Artificial Sequence
<220> FEATURE:
```

```
<223> OTHER INFORMATION: synthetic peptide

<400> SEQUENCE: 632

Gln Thr Val Ser Ser Ser Tyr
1               5

<210> SEQ ID NO 633
<211> LENGTH: 3
<212> TYPE: PRT
<213> ORGANISM: Artificial Sequence
<220> FEATURE:
<223> OTHER INFORMATION: synthetic peptide

<400> SEQUENCE: 633

Gly Ala Ser
1

<210> SEQ ID NO 634
<211> LENGTH: 10
<212> TYPE: PRT
<213> ORGANISM: Artificial Sequence
<220> FEATURE:
<223> OTHER INFORMATION: synthetic peptide

<400> SEQUENCE: 634

Gln Gln Tyr Gly Ile Ser Pro Glu Phe Thr
1               5                   10

<210> SEQ ID NO 635
<211> LENGTH: 8
<212> TYPE: PRT
<213> ORGANISM: Artificial Sequence
<220> FEATURE:
<223> OTHER INFORMATION: synthetic peptide

<400> SEQUENCE: 635

Gly Phe Thr Phe Ser Asp Tyr Tyr
1               5

<210> SEQ ID NO 636
<211> LENGTH: 8
<212> TYPE: PRT
<213> ORGANISM: Artificial Sequence
<220> FEATURE:
<223> OTHER INFORMATION: synthetic peptide

<400> SEQUENCE: 636

Ile Ser Ser Ser Gly Ser Thr Leu
1               5

<210> SEQ ID NO 637
<211> LENGTH: 15
<212> TYPE: PRT
<213> ORGANISM: Artificial Sequence
<220> FEATURE:
<223> OTHER INFORMATION: synthetic peptide

<400> SEQUENCE: 637

Ala Arg Ala Glu Arg Ile Val Gly Ser Val Gln Thr Pro Phe Ile
1               5                   10                  15

<210> SEQ ID NO 638
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 638

Gln Ser Leu Val Tyr Arg Asp Gly Asn Thr Tyr
1               5                   10

<210> SEQ ID NO 639
<211> LENGTH: 3
<212> TYPE: PRT
<213> ORGANISM: Artificial Sequence
<220> FEATURE:
<223> OTHER INFORMATION: synthetic peptide

<400> SEQUENCE: 639

Lys Val Ser
1

<210> SEQ ID NO 640
<211> LENGTH: 8
<212> TYPE: PRT
<213> ORGANISM: Artificial Sequence
<220> FEATURE:
<223> OTHER INFORMATION: synthetic peptide

<400> SEQUENCE: 640

Met Gln Gly Thr Asp Ser Phe Thr
1               5

<210> SEQ ID NO 641
<211> LENGTH: 8
<212> TYPE: PRT
<213> ORGANISM: Artificial Sequence
<220> FEATURE:
<223> OTHER INFORMATION: synthetic peptide

<400> SEQUENCE: 641

Gly Phe Thr Phe Ser Asp Tyr Phe
1               5

<210> SEQ ID NO 642
<211> LENGTH: 8
<212> TYPE: PRT
<213> ORGANISM: Artificial Sequence
<220> FEATURE:
<223> OTHER INFORMATION: synthetic peptide

<400> SEQUENCE: 642

Ile Ser Asp Asn Gly Asn Thr Ile
1               5

<210> SEQ ID NO 643
<211> LENGTH: 13
<212> TYPE: PRT
<213> ORGANISM: Artificial Sequence
<220> FEATURE:
<223> OTHER INFORMATION: synthetic peptide

<400> SEQUENCE: 643

Ala Arg Gly Leu Tyr Ile Gln Ser Asp Ala Phe Asp Leu
1               5                   10

<210> SEQ ID NO 644
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 644

Gln Gly Leu Ser Asn Ser
1               5

<210> SEQ ID NO 645
<211> LENGTH: 3
<212> TYPE: PRT
<213> ORGANISM: Artificial Sequence
<220> FEATURE:
<223> OTHER INFORMATION: synthetic peptide

<400> SEQUENCE: 645

Ala Ala Ser
1

<210> SEQ ID NO 646
<211> LENGTH: 10
<212> TYPE: PRT
<213> ORGANISM: Artificial Sequence
<220> FEATURE:
<223> OTHER INFORMATION: synthetic peptide

<400> SEQUENCE: 646

Gln Gln Tyr Tyr Asn Thr Pro Pro Ile Thr
1               5                   10

<210> SEQ ID NO 647
<211> LENGTH: 8
<212> TYPE: PRT
<213> ORGANISM: Artificial Sequence
<220> FEATURE:
<223> OTHER INFORMATION: synthetic peptide

<400> SEQUENCE: 647

Gly Tyr Asn Phe Thr Asn Tyr Trp
1               5

<210> SEQ ID NO 648
<211> LENGTH: 8
<212> TYPE: PRT
<213> ORGANISM: Artificial Sequence
<220> FEATURE:
<223> OTHER INFORMATION: synthetic peptide

<400> SEQUENCE: 648

Ile Tyr Pro Gly Asp Ser Asp Ser
1               5

<210> SEQ ID NO 649
<211> LENGTH: 27
<212> TYPE: PRT
<213> ORGANISM: Artificial Sequence
<220> FEATURE:
<223> OTHER INFORMATION: synthetic peptide

<400> SEQUENCE: 649

Ala Arg Arg Pro Arg Glu Gln Leu Gly Arg Leu Leu Leu Gly Asp Val
1               5                   10                  15

Val Pro His Gly Arg Asn Asp Ala Phe Asp Ile
            20                  25

<210> SEQ ID NO 650
<211> LENGTH: 6
<212> TYPE: PRT
<213> ORGANISM: Artificial Sequence
<220> FEATURE:

```
<223> OTHER INFORMATION: synthetic peptide

<400> SEQUENCE: 650

Gln Ser Ile Ser Thr Tyr
1               5

<210> SEQ ID NO 651
<211> LENGTH: 3
<212> TYPE: PRT
<213> ORGANISM: Artificial Sequence
<220> FEATURE:
<223> OTHER INFORMATION: synthetic peptide

<400> SEQUENCE: 651

Ser Ala Ser
1

<210> SEQ ID NO 652
<211> LENGTH: 9
<212> TYPE: PRT
<213> ORGANISM: Artificial Sequence
<220> FEATURE:
<223> OTHER INFORMATION: synthetic peptide

<400> SEQUENCE: 652

Gln Gln Ser Tyr Gly Thr Leu Trp Thr
1               5

<210> SEQ ID NO 653
<211> LENGTH: 8
<212> TYPE: PRT
<213> ORGANISM: Artificial Sequence
<220> FEATURE:
<223> OTHER INFORMATION: synthetic peptide

<400> SEQUENCE: 653

Gly Phe Asn Phe Asn Ile Phe Pro
1               5

<210> SEQ ID NO 654
<211> LENGTH: 8
<212> TYPE: PRT
<213> ORGANISM: Artificial Sequence
<220> FEATURE:
<223> OTHER INFORMATION: synthetic peptide

<400> SEQUENCE: 654

Ile Ser Asp Asp Val Thr Lys Lys
1               5

<210> SEQ ID NO 655
<211> LENGTH: 20
<212> TYPE: PRT
<213> ORGANISM: Artificial Sequence
<220> FEATURE:
<223> OTHER INFORMATION: synthetic peptide

<400> SEQUENCE: 655

Ala Arg Ala Ser Gly Trp Gln Arg Thr Gly Thr Lys Tyr Tyr Tyr Tyr
1               5                   10                  15
Gly Met Asp Val
            20

<210> SEQ ID NO 656
<211> LENGTH: 6
<212> TYPE: PRT
```

-continued

<213> ORGANISM: Artificial Sequence
<220> FEATURE:
<223> OTHER INFORMATION: synthetic peptide

<400> SEQUENCE: 656

Gln Asp Ile Ser Asn Asn
1               5

<210> SEQ ID NO 657
<211> LENGTH: 3
<212> TYPE: PRT
<213> ORGANISM: Artificial Sequence
<220> FEATURE:
<223> OTHER INFORMATION: synthetic peptide

<400> SEQUENCE: 657

Asp Ala Ser
1

<210> SEQ ID NO 658
<211> LENGTH: 9
<212> TYPE: PRT
<213> ORGANISM: Artificial Sequence
<220> FEATURE:
<223> OTHER INFORMATION: synthetic peptide

<400> SEQUENCE: 658

Leu Gln Tyr Asp Asn Leu Pro Tyr Ser
1               5

<210> SEQ ID NO 659
<211> LENGTH: 8
<212> TYPE: PRT
<213> ORGANISM: Artificial Sequence
<220> FEATURE:
<223> OTHER INFORMATION: synthetic peptide

<400> SEQUENCE: 659

Gly Phe Ile Phe Lys Thr Tyr Gly
1               5

<210> SEQ ID NO 660
<211> LENGTH: 8
<212> TYPE: PRT
<213> ORGANISM: Artificial Sequence
<220> FEATURE:
<223> OTHER INFORMATION: synthetic peptide

<400> SEQUENCE: 660

Ile Trp Tyr Asp Gly Ser Asn Glu
1               5

<210> SEQ ID NO 661
<211> LENGTH: 18
<212> TYPE: PRT
<213> ORGANISM: Artificial Sequence
<220> FEATURE:
<223> OTHER INFORMATION: synthetic peptide

<400> SEQUENCE: 661

Ala Arg Asp Glu Ala Val Gly Pro Tyr Gln Tyr Ala Ala Glu Tyr Phe
1               5                   10                  15

His His

<210> SEQ ID NO 662
<211> LENGTH: 6

```
<212> TYPE: PRT
<213> ORGANISM: Artificial Sequence
<220> FEATURE:
<223> OTHER INFORMATION: synthetic peptide

<400> SEQUENCE: 662

Lys Ser Val Thr Ser Asn
1               5

<210> SEQ ID NO 663
<211> LENGTH: 3
<212> TYPE: PRT
<213> ORGANISM: Artificial Sequence
<220> FEATURE:
<223> OTHER INFORMATION: synthetic peptide

<400> SEQUENCE: 663

Gly Ala Ser
1

<210> SEQ ID NO 664
<211> LENGTH: 8
<212> TYPE: PRT
<213> ORGANISM: Artificial Sequence
<220> FEATURE:
<223> OTHER INFORMATION: synthetic peptide

<400> SEQUENCE: 664

Gln Gln Tyr Asn Asn Trp Leu Thr
1               5

<210> SEQ ID NO 665
<211> LENGTH: 8
<212> TYPE: PRT
<213> ORGANISM: Artificial Sequence
<220> FEATURE:
<223> OTHER INFORMATION: synthetic peptide

<400> SEQUENCE: 665

Gly Phe Thr Phe Ser Ser Ser Ala
1               5

<210> SEQ ID NO 666
<211> LENGTH: 8
<212> TYPE: PRT
<213> ORGANISM: Artificial Sequence
<220> FEATURE:
<223> OTHER INFORMATION: synthetic peptide

<400> SEQUENCE: 666

Ile Ser Ser Asp Gly Thr Tyr Lys
1               5

<210> SEQ ID NO 667
<211> LENGTH: 12
<212> TYPE: PRT
<213> ORGANISM: Artificial Sequence
<220> FEATURE:
<223> OTHER INFORMATION: synthetic peptide

<400> SEQUENCE: 667

Ala Lys Ser Gly Trp Glu Leu His Pro Phe Gly Val
1               5                   10

<210> SEQ ID NO 668
<211> LENGTH: 6
<212> TYPE: PRT
```

```
<213> ORGANISM: Artificial Sequence
<220> FEATURE:
<223> OTHER INFORMATION: synthetic peptide

<400> SEQUENCE: 668

Gln Ser Val Ser Ser Asn
1               5

<210> SEQ ID NO 669
<211> LENGTH: 3
<212> TYPE: PRT
<213> ORGANISM: Artificial Sequence
<220> FEATURE:
<223> OTHER INFORMATION: synthetic peptide

<400> SEQUENCE: 669

Gly Ala Ser
1

<210> SEQ ID NO 670
<211> LENGTH: 10
<212> TYPE: PRT
<213> ORGANISM: Artificial Sequence
<220> FEATURE:
<223> OTHER INFORMATION: synthetic peptide

<400> SEQUENCE: 670

Gln His Tyr Ile Asn Arg Pro Gly Arg Thr
1               5                   10

<210> SEQ ID NO 671
<211> LENGTH: 8
<212> TYPE: PRT
<213> ORGANISM: Artificial Sequence
<220> FEATURE:
<223> OTHER INFORMATION: synthetic peptide

<400> SEQUENCE: 671

Gly Gly Ser Ile Ser Gly Tyr Phe
1               5

<210> SEQ ID NO 672
<211> LENGTH: 7
<212> TYPE: PRT
<213> ORGANISM: Artificial Sequence
<220> FEATURE:
<223> OTHER INFORMATION: synthetic peptide

<400> SEQUENCE: 672

Val His Tyr Ser Gly Ser Thr
1               5

<210> SEQ ID NO 673
<211> LENGTH: 11
<212> TYPE: PRT
<213> ORGANISM: Artificial Sequence
<220> FEATURE:
<223> OTHER INFORMATION: synthetic peptide

<400> SEQUENCE: 673

Ala Arg Ala Ser Thr Ser Gly Gly Phe Asp Pro
1               5                   10

<210> SEQ ID NO 674
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 674

Gln Ser Val Ser Ser Asn
1               5

<210> SEQ ID NO 675
<211> LENGTH: 3
<212> TYPE: PRT
<213> ORGANISM: Artificial Sequence
<220> FEATURE:
<223> OTHER INFORMATION: synthetic peptide

<400> SEQUENCE: 675

Gly Ala Ser
1

<210> SEQ ID NO 676
<211> LENGTH: 10
<212> TYPE: PRT
<213> ORGANISM: Artificial Sequence
<220> FEATURE:
<223> OTHER INFORMATION: synthetic peptide

<400> SEQUENCE: 676

Gln His Tyr Ile Asn Arg Pro Gly Arg Thr
1               5                   10

<210> SEQ ID NO 677
<211> LENGTH: 8
<212> TYPE: PRT
<213> ORGANISM: Artificial Sequence
<220> FEATURE:
<223> OTHER INFORMATION: synthetic peptide

<400> SEQUENCE: 677

Gly Phe Thr Phe Ser Ser Tyr Ala
1               5

<210> SEQ ID NO 678
<211> LENGTH: 8
<212> TYPE: PRT
<213> ORGANISM: Artificial Sequence
<220> FEATURE:
<223> OTHER INFORMATION: synthetic peptide

<400> SEQUENCE: 678

Ile Ser Pro Ser Gly Ser Thr Ile
1               5

<210> SEQ ID NO 679
<211> LENGTH: 13
<212> TYPE: PRT
<213> ORGANISM: Artificial Sequence
<220> FEATURE:
<223> OTHER INFORMATION: synthetic peptide

<400> SEQUENCE: 679

Val Arg Gly Val Tyr Val Gln Ser Asp Ala Phe Asp Ile
1               5                   10

<210> SEQ ID NO 680
<211> LENGTH: 6
<212> TYPE: PRT
<213> ORGANISM: Artificial Sequence
<220> FEATURE:
```

```
<223> OTHER INFORMATION: synthetic peptide

<400> SEQUENCE: 680

Gln Gly Ile Ser Tyr Ser
1               5

<210> SEQ ID NO 681
<211> LENGTH: 3
<212> TYPE: PRT
<213> ORGANISM: Artificial Sequence
<220> FEATURE:
<223> OTHER INFORMATION: synthetic peptide

<400> SEQUENCE: 681

Ala Ala Ser
1

<210> SEQ ID NO 682
<211> LENGTH: 10
<212> TYPE: PRT
<213> ORGANISM: Artificial Sequence
<220> FEATURE:
<223> OTHER INFORMATION: synthetic peptide

<400> SEQUENCE: 682

Gln Gln Tyr Tyr Ser Thr Pro Pro Ile Thr
1               5                   10

<210> SEQ ID NO 683
<211> LENGTH: 8
<212> TYPE: PRT
<213> ORGANISM: Artificial Sequence
<220> FEATURE:
<223> OTHER INFORMATION: synthetic peptide

<400> SEQUENCE: 683

Gly Val Thr Phe Ser Asp Tyr Asp
1               5

<210> SEQ ID NO 684
<211> LENGTH: 8
<212> TYPE: PRT
<213> ORGANISM: Artificial Sequence
<220> FEATURE:
<223> OTHER INFORMATION: synthetic peptide

<400> SEQUENCE: 684

Ile Arg Ser Ser Gly Gly Thr Thr
1               5

<210> SEQ ID NO 685
<211> LENGTH: 10
<212> TYPE: PRT
<213> ORGANISM: Artificial Sequence
<220> FEATURE:
<223> OTHER INFORMATION: synthetic peptide

<400> SEQUENCE: 685

Val Arg Asp Lys Asp Gly Val Phe Asp Tyr
1               5                   10

<210> SEQ ID NO 686
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 686

Gln Asp Ile Ser Ser Trp
1               5

<210> SEQ ID NO 687
<211> LENGTH: 3
<212> TYPE: PRT
<213> ORGANISM: Artificial Sequence
<220> FEATURE:
<223> OTHER INFORMATION: synthetic peptide

<400> SEQUENCE: 687

Lys Ala Ser
1

<210> SEQ ID NO 688
<211> LENGTH: 10
<212> TYPE: PRT
<213> ORGANISM: Artificial Sequence
<220> FEATURE:
<223> OTHER INFORMATION: synthetic peptide

<400> SEQUENCE: 688

Gln Gln Tyr Asn Thr Tyr Pro His Ser Thr
1               5                   10

<210> SEQ ID NO 689
<211> LENGTH: 8
<212> TYPE: PRT
<213> ORGANISM: Artificial Sequence
<220> FEATURE:
<223> OTHER INFORMATION: synthetic peptide

<400> SEQUENCE: 689

Gly Phe Thr Phe Ser Asp Tyr Tyr
1               5

<210> SEQ ID NO 690
<211> LENGTH: 8
<212> TYPE: PRT
<213> ORGANISM: Artificial Sequence
<220> FEATURE:
<223> OTHER INFORMATION: synthetic peptide

<400> SEQUENCE: 690

Ile Ser Ile Ser Gly Ser Thr Ile
1               5

<210> SEQ ID NO 691
<211> LENGTH: 13
<212> TYPE: PRT
<213> ORGANISM: Artificial Sequence
<220> FEATURE:
<223> OTHER INFORMATION: synthetic peptide

<400> SEQUENCE: 691

Ala Arg Gly Ile Tyr His Gln Ser Asp Ala Phe Asp Ile
1               5                   10

<210> SEQ ID NO 692
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 692

Gln Gly Ile Ser Asn Ser
1               5

<210> SEQ ID NO 693
<211> LENGTH: 3
<212> TYPE: PRT
<213> ORGANISM: Artificial Sequence
<220> FEATURE:
<223> OTHER INFORMATION: synthetic peptide

<400> SEQUENCE: 693

Ala Ala Ser
1

<210> SEQ ID NO 694
<211> LENGTH: 10
<212> TYPE: PRT
<213> ORGANISM: Artificial Sequence
<220> FEATURE:
<223> OTHER INFORMATION: synthetic peptide

<400> SEQUENCE: 694

Gln Gln Tyr Tyr Ser Thr Pro Pro Ile Thr
1               5                   10

<210> SEQ ID NO 695
<211> LENGTH: 8
<212> TYPE: PRT
<213> ORGANISM: Artificial Sequence
<220> FEATURE:
<223> OTHER INFORMATION: synthetic peptide

<400> SEQUENCE: 695

Gly Tyr Thr Leu Ser Thr Tyr Pro
1               5

<210> SEQ ID NO 696
<211> LENGTH: 8
<212> TYPE: PRT
<213> ORGANISM: Artificial Sequence
<220> FEATURE:
<223> OTHER INFORMATION: synthetic peptide

<400> SEQUENCE: 696

Ile Asn Thr Tyr Thr Gly Asp Pro
1               5

<210> SEQ ID NO 697
<211> LENGTH: 9
<212> TYPE: PRT
<213> ORGANISM: Artificial Sequence
<220> FEATURE:
<223> OTHER INFORMATION: synthetic peptide

<400> SEQUENCE: 697

Val Arg Gln Lys Asp Pro Phe Asp Tyr
1               5

<210> SEQ ID NO 698
<211> LENGTH: 7
<212> TYPE: PRT
<213> ORGANISM: Artificial Sequence
<220> FEATURE:
<223> OTHER INFORMATION: synthetic peptide
```

```
<400> SEQUENCE: 698

His Thr Val Ser Ser Val Tyr
1               5

<210> SEQ ID NO 699
<211> LENGTH: 3
<212> TYPE: PRT
<213> ORGANISM: Artificial Sequence
<220> FEATURE:
<223> OTHER INFORMATION: synthetic peptide

<400> SEQUENCE: 699

Gly Ala Ser
1

<210> SEQ ID NO 700
<211> LENGTH: 12
<212> TYPE: PRT
<213> ORGANISM: Artificial Sequence
<220> FEATURE:
<223> OTHER INFORMATION: synthetic peptide

<400> SEQUENCE: 700

Gln Gln Tyr Ala Ile Ser Pro Pro Pro Met Tyr Thr
1               5                   10

<210> SEQ ID NO 701
<211> LENGTH: 8
<212> TYPE: PRT
<213> ORGANISM: Artificial Sequence
<220> FEATURE:
<223> OTHER INFORMATION: synthetic peptide

<400> SEQUENCE: 701

Gly Phe Thr Phe Arg Asp Tyr Trp
1               5

<210> SEQ ID NO 702
<211> LENGTH: 8
<212> TYPE: PRT
<213> ORGANISM: Artificial Sequence
<220> FEATURE:
<223> OTHER INFORMATION: synthetic peptide

<400> SEQUENCE: 702

Ile Asn Arg Asn Gly Asn Glu Lys
1               5

<210> SEQ ID NO 703
<211> LENGTH: 19
<212> TYPE: PRT
<213> ORGANISM: Artificial Sequence
<220> FEATURE:
<223> OTHER INFORMATION: synthetic peptide

<400> SEQUENCE: 703

Val Arg Asp Asn Ser Pro Ser Phe Gly Pro Gly Asn Tyr Tyr Asp Ala
1               5                   10                  15

Phe Asp Ile

<210> SEQ ID NO 704
<211> LENGTH: 6
<212> TYPE: PRT
<213> ORGANISM: Artificial Sequence
<220> FEATURE:
```

<223> OTHER INFORMATION: synthetic peptide

<400> SEQUENCE: 704

Gln Asp Ile Arg Asn Glu
1               5

<210> SEQ ID NO 705
<211> LENGTH: 3
<212> TYPE: PRT
<213> ORGANISM: Artificial Sequence
<220> FEATURE:
<223> OTHER INFORMATION: synthetic peptide

<400> SEQUENCE: 705

Ala Ala Ser
1

<210> SEQ ID NO 706
<211> LENGTH: 9
<212> TYPE: PRT
<213> ORGANISM: Artificial Sequence
<220> FEATURE:
<223> OTHER INFORMATION: synthetic peptide

<400> SEQUENCE: 706

Leu Gln Asp Tyr Asn Tyr Pro Arg Thr
1               5

<210> SEQ ID NO 707
<211> LENGTH: 8
<212> TYPE: PRT
<213> ORGANISM: Artificial Sequence
<220> FEATURE:
<223> OTHER INFORMATION: synthetic peptide

<400> SEQUENCE: 707

Gly Tyr Thr Phe Thr Ser Tyr Ala
1               5

<210> SEQ ID NO 708
<211> LENGTH: 8
<212> TYPE: PRT
<213> ORGANISM: Artificial Sequence
<220> FEATURE:
<223> OTHER INFORMATION: synthetic peptide

<400> SEQUENCE: 708

Ile Asn Thr Asn Thr Gly Asn Pro
1               5

<210> SEQ ID NO 709
<211> LENGTH: 17
<212> TYPE: PRT
<213> ORGANISM: Artificial Sequence
<220> FEATURE:
<223> OTHER INFORMATION: synthetic peptide

<400> SEQUENCE: 709

Ala Arg Glu His Leu Val Ala Leu Glu Tyr Tyr Tyr Tyr Gly Val Asp
1               5                   10                  15

Val

<210> SEQ ID NO 710
<211> LENGTH: 6
<212> TYPE: PRT
<213> ORGANISM: Artificial Sequence

```
<220> FEATURE:
<223> OTHER INFORMATION: synthetic peptide

<400> SEQUENCE: 710

Gln Arg Ile Ser Asn Tyr
1               5

<210> SEQ ID NO 711
<211> LENGTH: 3
<212> TYPE: PRT
<213> ORGANISM: Artificial Sequence
<220> FEATURE:
<223> OTHER INFORMATION: synthetic peptide

<400> SEQUENCE: 711

Ala Ala Ser
1

<210> SEQ ID NO 712
<211> LENGTH: 9
<212> TYPE: PRT
<213> ORGANISM: Artificial Sequence
<220> FEATURE:
<223> OTHER INFORMATION: synthetic peptide

<400> SEQUENCE: 712

Gln Gln Ser Tyr Ser Val Pro Leu Thr
1               5

<210> SEQ ID NO 713
<211> LENGTH: 8
<212> TYPE: PRT
<213> ORGANISM: Artificial Sequence
<220> FEATURE:
<223> OTHER INFORMATION: synthetic peptide

<400> SEQUENCE: 713

Arg Phe Ile Phe Ser Asn Phe Gly
1               5

<210> SEQ ID NO 714
<211> LENGTH: 8
<212> TYPE: PRT
<213> ORGANISM: Artificial Sequence
<220> FEATURE:
<223> OTHER INFORMATION: synthetic peptide

<400> SEQUENCE: 714

Ile Arg Ser Asp Gly Ser Asn Glu
1               5

<210> SEQ ID NO 715
<211> LENGTH: 15
<212> TYPE: PRT
<213> ORGANISM: Artificial Sequence
<220> FEATURE:
<223> OTHER INFORMATION: synthetic peptide

<400> SEQUENCE: 715

Ala Lys Gly Cys Cys Gly Gly Val Pro Asp Phe Gly Leu Asp Val
1               5                   10                  15

<210> SEQ ID NO 716
<211> LENGTH: 11
<212> TYPE: PRT
<213> ORGANISM: Artificial Sequence
<220> FEATURE:
```

```
<223> OTHER INFORMATION: synthetic peptide

<400> SEQUENCE: 716

Gln Ser Leu Val His Arg Asp Gly Ser Thr Tyr
1               5                   10

<210> SEQ ID NO 717
<211> LENGTH: 3
<212> TYPE: PRT
<213> ORGANISM: Artificial Sequence
<220> FEATURE:
<223> OTHER INFORMATION: synthetic peptide

<400> SEQUENCE: 717

Gln Val Ser
1

<210> SEQ ID NO 718
<211> LENGTH: 9
<212> TYPE: PRT
<213> ORGANISM: Artificial Sequence
<220> FEATURE:
<223> OTHER INFORMATION: synthetic peptide

<400> SEQUENCE: 718

Met Gln Ala Thr His Trp Gly Tyr Thr
1               5

<210> SEQ ID NO 719
<211> LENGTH: 8
<212> TYPE: PRT
<213> ORGANISM: Artificial Sequence
<220> FEATURE:
<223> OTHER INFORMATION: synthetic peptide

<400> SEQUENCE: 719

Gly Tyr Thr Leu Ser Thr Tyr Pro
1               5

<210> SEQ ID NO 720
<211> LENGTH: 8
<212> TYPE: PRT
<213> ORGANISM: Artificial Sequence
<220> FEATURE:
<223> OTHER INFORMATION: synthetic peptide

<400> SEQUENCE: 720

Ile Asn Thr Tyr Thr Gly Asp Pro
1               5

<210> SEQ ID NO 721
<211> LENGTH: 9
<212> TYPE: PRT
<213> ORGANISM: Artificial Sequence
<220> FEATURE:
<223> OTHER INFORMATION: synthetic peptide

<400> SEQUENCE: 721

Val Arg Gln Lys Asp Pro Phe Asp Tyr
1               5

<210> SEQ ID NO 722
<211> LENGTH: 6
<212> TYPE: PRT
<213> ORGANISM: Artificial Sequence
<220> FEATURE:
<223> OTHER INFORMATION: synthetic peptide
```

-continued

```
<400> SEQUENCE: 722

Gln Asp Val Thr Thr Ala
1               5

<210> SEQ ID NO 723
<211> LENGTH: 3
<212> TYPE: PRT
<213> ORGANISM: Artificial Sequence
<220> FEATURE:
<223> OTHER INFORMATION: synthetic peptide

<400> SEQUENCE: 723

Trp Ala Ser
1

<210> SEQ ID NO 724
<211> LENGTH: 9
<212> TYPE: PRT
<213> ORGANISM: Artificial Sequence
<220> FEATURE:
<223> OTHER INFORMATION: synthetic peptide

<400> SEQUENCE: 724

Gln Gln His Tyr Ser Thr Pro Leu Thr
1               5

<210> SEQ ID NO 725
<211> LENGTH: 8
<212> TYPE: PRT
<213> ORGANISM: Artificial Sequence
<220> FEATURE:
<223> OTHER INFORMATION: synthetic peptide

<400> SEQUENCE: 725

Gly Phe Thr Phe Ser Asp Tyr Tyr
1               5

<210> SEQ ID NO 726
<211> LENGTH: 8
<212> TYPE: PRT
<213> ORGANISM: Artificial Sequence
<220> FEATURE:
<223> OTHER INFORMATION: synthetic peptide

<400> SEQUENCE: 726

Ile Ser Thr Ser Gly Ser Thr Met
1               5

<210> SEQ ID NO 727
<211> LENGTH: 13
<212> TYPE: PRT
<213> ORGANISM: Artificial Sequence
<220> FEATURE:
<223> OTHER INFORMATION: synthetic peptide

<400> SEQUENCE: 727

Ala Arg Gly Ile Tyr Tyr Gln Ser Asp Ala Phe Asp Ile
1               5                   10

<210> SEQ ID NO 728
<211> LENGTH: 6
<212> TYPE: PRT
<213> ORGANISM: Artificial Sequence
<220> FEATURE:
<223> OTHER INFORMATION: synthetic peptide
```

```
-continued

<400> SEQUENCE: 728

Gln Gly Ile Ser Asn Ser
1               5

<210> SEQ ID NO 729
<211> LENGTH: 3
<212> TYPE: PRT
<213> ORGANISM: Artificial Sequence
<220> FEATURE:
<223> OTHER INFORMATION: synthetic peptide

<400> SEQUENCE: 729

Ala Ala Ser
1

<210> SEQ ID NO 730
<211> LENGTH: 10
<212> TYPE: PRT
<213> ORGANISM: Artificial Sequence
<220> FEATURE:
<223> OTHER INFORMATION: synthetic peptide

<400> SEQUENCE: 730

Gln Gln Tyr Tyr Ser Thr Pro Pro Met Thr
1               5                   10

<210> SEQ ID NO 731
<211> LENGTH: 8
<212> TYPE: PRT
<213> ORGANISM: Artificial Sequence
<220> FEATURE:
<223> OTHER INFORMATION: synthetic peptide

<400> SEQUENCE: 731

Gly Phe Thr Phe Ser Ser Ser Ala
1               5

<210> SEQ ID NO 732
<211> LENGTH: 8
<212> TYPE: PRT
<213> ORGANISM: Artificial Sequence
<220> FEATURE:
<223> OTHER INFORMATION: synthetic peptide

<400> SEQUENCE: 732

Ile Ser Ser Asp Gly Thr Tyr Lys
1               5

<210> SEQ ID NO 733
<211> LENGTH: 12
<212> TYPE: PRT
<213> ORGANISM: Artificial Sequence
<220> FEATURE:
<223> OTHER INFORMATION: synthetic peptide

<400> SEQUENCE: 733

Ala Lys Ser Gly Trp Glu Leu His Pro Phe Gly Val
1               5                   10

<210> SEQ ID NO 734
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 734

Gln Asp Val Thr Thr Ala
1               5

<210> SEQ ID NO 735
<211> LENGTH: 3
<212> TYPE: PRT
<213> ORGANISM: Artificial Sequence
<220> FEATURE:
<223> OTHER INFORMATION: synthetic peptide

<400> SEQUENCE: 735

Trp Ala Ser
1

<210> SEQ ID NO 736
<211> LENGTH: 9
<212> TYPE: PRT
<213> ORGANISM: Artificial Sequence
<220> FEATURE:
<223> OTHER INFORMATION: synthetic peptide

<400> SEQUENCE: 736

Gln Gln His Tyr Ser Thr Pro Leu Thr
1               5

<210> SEQ ID NO 737
<211> LENGTH: 8
<212> TYPE: PRT
<213> ORGANISM: Artificial Sequence
<220> FEATURE:
<223> OTHER INFORMATION: synthetic peptide

<400> SEQUENCE: 737

Gly Tyr Thr Phe Thr Ser Ser Tyr
1               5

<210> SEQ ID NO 738
<211> LENGTH: 8
<212> TYPE: PRT
<213> ORGANISM: Artificial Sequence
<220> FEATURE:
<223> OTHER INFORMATION: synthetic peptide

<400> SEQUENCE: 738

Ile Tyr Pro Ser Gly Gly Asn Thr
1               5

<210> SEQ ID NO 739
<211> LENGTH: 17
<212> TYPE: PRT
<213> ORGANISM: Artificial Sequence
<220> FEATURE:
<223> OTHER INFORMATION: synthetic peptide

<400> SEQUENCE: 739

Ala Arg Asp His Leu Asn Arg Asp Ser Thr Ser Arg Gly Phe Ile Asp
1               5                   10                  15

Ser

<210> SEQ ID NO 740
<211> LENGTH: 6
<212> TYPE: PRT
<213> ORGANISM: Artificial Sequence
<220> FEATURE:
```

<223> OTHER INFORMATION: synthetic peptide

<400> SEQUENCE: 740

Gln Ser Val Gly Asn Tyr
1               5

<210> SEQ ID NO 741
<211> LENGTH: 3
<212> TYPE: PRT
<213> ORGANISM: Artificial Sequence
<220> FEATURE:
<223> OTHER INFORMATION: synthetic peptide

<400> SEQUENCE: 741

Asp Ala Ser
1

<210> SEQ ID NO 742
<211> LENGTH: 9
<212> TYPE: PRT
<213> ORGANISM: Artificial Sequence
<220> FEATURE:
<223> OTHER INFORMATION: synthetic peptide

<400> SEQUENCE: 742

Glu Gln Arg Gly Asp Trp Pro Leu Thr
1               5

<210> SEQ ID NO 743
<211> LENGTH: 10
<212> TYPE: PRT
<213> ORGANISM: Artificial Sequence
<220> FEATURE:
<223> OTHER INFORMATION: synthetic peptide

<400> SEQUENCE: 743

Gly Gly Ser Ile Ser Ser Asp Ile Tyr Tyr
1               5                   10

<210> SEQ ID NO 744
<211> LENGTH: 7
<212> TYPE: PRT
<213> ORGANISM: Artificial Sequence
<220> FEATURE:
<223> OTHER INFORMATION: synthetic peptide

<400> SEQUENCE: 744

Ile Tyr Tyr Ser Gly Ser Thr
1               5

<210> SEQ ID NO 745
<211> LENGTH: 14
<212> TYPE: PRT
<213> ORGANISM: Artificial Sequence
<220> FEATURE:
<223> OTHER INFORMATION: synthetic peptide

<400> SEQUENCE: 745

Ala Arg Arg Gly Glu Trp Leu Arg Leu Gly Tyr Phe Asp Tyr
1               5                   10

<210> SEQ ID NO 746
<211> LENGTH: 7
<212> TYPE: PRT
<213> ORGANISM: Artificial Sequence
<220> FEATURE:
<223> OTHER INFORMATION: synthetic peptide

<400> SEQUENCE: 746

Gln Ser Val Ser Ser Tyr
1               5

<210> SEQ ID NO 747
<211> LENGTH: 3
<212> TYPE: PRT
<213> ORGANISM: Artificial Sequence
<220> FEATURE:
<223> OTHER INFORMATION: synthetic peptide

<400> SEQUENCE: 747

Gly Ala Ser
1

<210> SEQ ID NO 748
<211> LENGTH: 9
<212> TYPE: PRT
<213> ORGANISM: Artificial Sequence
<220> FEATURE:
<223> OTHER INFORMATION: synthetic peptide

<400> SEQUENCE: 748

Gln Gln Tyr Gly Ser Ser Pro Trp Thr
1               5

<210> SEQ ID NO 749
<211> LENGTH: 8
<212> TYPE: PRT
<213> ORGANISM: Artificial Sequence
<220> FEATURE:
<223> OTHER INFORMATION: synthetic peptide

<400> SEQUENCE: 749

Gly Gly Ser Ile Ser Gly Tyr Phe
1               5

<210> SEQ ID NO 750
<211> LENGTH: 7
<212> TYPE: PRT
<213> ORGANISM: Artificial Sequence
<220> FEATURE:
<223> OTHER INFORMATION: synthetic peptide

<400> SEQUENCE: 750

Val His Tyr Ser Gly Ser Thr
1               5

<210> SEQ ID NO 751
<211> LENGTH: 11
<212> TYPE: PRT
<213> ORGANISM: Artificial Sequence
<220> FEATURE:
<223> OTHER INFORMATION: synthetic peptide

<400> SEQUENCE: 751

Ala Arg Ala Ser Thr Ser Gly Gly Phe Asp Pro
1               5                   10

<210> SEQ ID NO 752
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 752

Gln Gly Ile Arg Asn Asp
1               5

<210> SEQ ID NO 753
<211> LENGTH: 3
<212> TYPE: PRT
<213> ORGANISM: Artificial Sequence
<220> FEATURE:
<223> OTHER INFORMATION: synthetic peptide

<400> SEQUENCE: 753

Ala Ala Ser
1

<210> SEQ ID NO 754
<211> LENGTH: 9
<212> TYPE: PRT
<213> ORGANISM: Artificial Sequence
<220> FEATURE:
<223> OTHER INFORMATION: synthetic peptide

<400> SEQUENCE: 754

Leu Gln His Asn Ser Tyr Pro Tyr Thr
1               5

<210> SEQ ID NO 755
<211> LENGTH: 8
<212> TYPE: PRT
<213> ORGANISM: Artificial Sequence
<220> FEATURE:
<223> OTHER INFORMATION: synthetic peptide

<400> SEQUENCE: 755

Gly Phe Ser Phe Ser Asn Tyr Glu
1               5

<210> SEQ ID NO 756
<211> LENGTH: 8
<212> TYPE: PRT
<213> ORGANISM: Artificial Sequence
<220> FEATURE:
<223> OTHER INFORMATION: synthetic peptide

<400> SEQUENCE: 756

Ile Ser Ser Gly Ser Ser Tyr Arg
1               5

<210> SEQ ID NO 757
<211> LENGTH: 18
<212> TYPE: PRT
<213> ORGANISM: Artificial Sequence
<220> FEATURE:
<223> OTHER INFORMATION: synthetic peptide

<400> SEQUENCE: 757

Val Arg Asp Glu Asp Tyr Arg Asn Gly Ser Arg His Tyr Asp Gly Leu
1               5                   10                  15

His Val

<210> SEQ ID NO 758
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 758

Gln Gly Ile Arg Asn Asp
1               5

<210> SEQ ID NO 759
<211> LENGTH: 3
<212> TYPE: PRT
<213> ORGANISM: Artificial Sequence
<220> FEATURE:
<223> OTHER INFORMATION: synthetic peptide

<400> SEQUENCE: 759

Ala Ala Ser
1

<210> SEQ ID NO 760
<211> LENGTH: 9
<212> TYPE: PRT
<213> ORGANISM: Artificial Sequence
<220> FEATURE:
<223> OTHER INFORMATION: synthetic peptide

<400> SEQUENCE: 760

Leu Gln Asp Tyr Asn Tyr Pro Arg Thr
1               5

<210> SEQ ID NO 761
<211> LENGTH: 8
<212> TYPE: PRT
<213> ORGANISM: Artificial Sequence
<220> FEATURE:
<223> OTHER INFORMATION: synthetic peptide

<400> SEQUENCE: 761

Gly Phe Thr Phe Ser Ser Ser Ala
1               5

<210> SEQ ID NO 762
<211> LENGTH: 8
<212> TYPE: PRT
<213> ORGANISM: Artificial Sequence
<220> FEATURE:
<223> OTHER INFORMATION: synthetic peptide

<400> SEQUENCE: 762

Ile Ser Ser Asp Gly Thr Tyr Lys
1               5

<210> SEQ ID NO 763
<211> LENGTH: 12
<212> TYPE: PRT
<213> ORGANISM: Artificial Sequence
<220> FEATURE:
<223> OTHER INFORMATION: synthetic peptide

<400> SEQUENCE: 763

Ala Lys Ser Gly Trp Glu Leu His Pro Phe Gly Val
1               5                   10

<210> SEQ ID NO 764
<211> LENGTH: 12
<212> TYPE: PRT
<213> ORGANISM: Artificial Sequence
<220> FEATURE:
<223> OTHER INFORMATION: synthetic peptide

```
<400> SEQUENCE: 764

Gln Ser Val Leu Tyr Ser Ser Asn Asn Lys Asn Tyr
1               5                   10

<210> SEQ ID NO 765
<211> LENGTH: 3
<212> TYPE: PRT
<213> ORGANISM: Artificial Sequence
<220> FEATURE:
<223> OTHER INFORMATION: synthetic peptide

<400> SEQUENCE: 765

Trp Ala Ser
1

<210> SEQ ID NO 766
<211> LENGTH: 10
<212> TYPE: PRT
<213> ORGANISM: Artificial Sequence
<220> FEATURE:
<223> OTHER INFORMATION: synthetic peptide

<400> SEQUENCE: 766

Gln Gln Tyr Tyr Ser Thr Leu Pro Leu Thr
1               5                   10

<210> SEQ ID NO 767
<211> LENGTH: 8
<212> TYPE: PRT
<213> ORGANISM: Artificial Sequence
<220> FEATURE:
<223> OTHER INFORMATION: synthetic peptide

<400> SEQUENCE: 767

Gly Phe Thr Phe Arg Asp Tyr Trp
1               5

<210> SEQ ID NO 768
<211> LENGTH: 8
<212> TYPE: PRT
<213> ORGANISM: Artificial Sequence
<220> FEATURE:
<223> OTHER INFORMATION: synthetic peptide

<400> SEQUENCE: 768

Ile Asn Arg Asn Gly Asn Glu Lys
1               5

<210> SEQ ID NO 769
<211> LENGTH: 19
<212> TYPE: PRT
<213> ORGANISM: Artificial Sequence
<220> FEATURE:
<223> OTHER INFORMATION: synthetic peptide

<400> SEQUENCE: 769

Val Arg Asp Asn Ser Pro Pro Phe Gly Pro Gly Asn Tyr Tyr Asp Ala
1               5                   10                  15
Leu Asp Ile

<210> SEQ ID NO 770
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 770

Gln Asp Ile Arg Asn Glu
1               5

<210> SEQ ID NO 771
<211> LENGTH: 3
<212> TYPE: PRT
<213> ORGANISM: Artificial Sequence
<220> FEATURE:
<223> OTHER INFORMATION: synthetic peptide

<400> SEQUENCE: 771

Ala Ala Ser
1

<210> SEQ ID NO 772
<211> LENGTH: 9
<212> TYPE: PRT
<213> ORGANISM: Artificial Sequence
<220> FEATURE:
<223> OTHER INFORMATION: synthetic peptide

<400> SEQUENCE: 772

Leu Gln Asp Tyr Asn Tyr Pro Arg Thr
1               5

<210> SEQ ID NO 773
<211> LENGTH: 8
<212> TYPE: PRT
<213> ORGANISM: Artificial Sequence
<220> FEATURE:
<223> OTHER INFORMATION: synthetic peptide

<400> SEQUENCE: 773

Gly Phe Thr Phe Lys Asp Tyr Trp
1               5

<210> SEQ ID NO 774
<211> LENGTH: 8
<212> TYPE: PRT
<213> ORGANISM: Artificial Sequence
<220> FEATURE:
<223> OTHER INFORMATION: synthetic peptide

<400> SEQUENCE: 774

Ile Asn Arg Asn Gly Asn Glu Lys
1               5

<210> SEQ ID NO 775
<211> LENGTH: 19
<212> TYPE: PRT
<213> ORGANISM: Artificial Sequence
<220> FEATURE:
<223> OTHER INFORMATION: synthetic peptide

<400> SEQUENCE: 775

Val Arg Asp Ser Ser Pro Ser Phe Gly Pro Gly Asn Tyr Tyr Asp Ala
1               5                   10                  15

Phe Asp Ile

<210> SEQ ID NO 776
<211> LENGTH: 6
<212> TYPE: PRT
<213> ORGANISM: Artificial Sequence
<220> FEATURE:

<223> OTHER INFORMATION: synthetic peptide

<400> SEQUENCE: 776

Gln Asp Ile Arg Asn Glu
1               5

<210> SEQ ID NO 777
<211> LENGTH: 3
<212> TYPE: PRT
<213> ORGANISM: Artificial Sequence
<220> FEATURE:
<223> OTHER INFORMATION: synthetic peptide

<400> SEQUENCE: 777

Ala Ala Ser
1

<210> SEQ ID NO 778
<211> LENGTH: 9
<212> TYPE: PRT
<213> ORGANISM: Artificial Sequence
<220> FEATURE:
<223> OTHER INFORMATION: synthetic peptide

<400> SEQUENCE: 778

Leu Gln Asp Tyr Asn Tyr Pro Arg Thr
1               5

<210> SEQ ID NO 779
<211> LENGTH: 8
<212> TYPE: PRT
<213> ORGANISM: Artificial Sequence
<220> FEATURE:
<223> OTHER INFORMATION: synthetic peptide

<400> SEQUENCE: 779

Gly Tyr Thr Phe Thr Asp Tyr Tyr
1               5

<210> SEQ ID NO 780
<211> LENGTH: 8
<212> TYPE: PRT
<213> ORGANISM: Artificial Sequence
<220> FEATURE:
<223> OTHER INFORMATION: synthetic peptide

<400> SEQUENCE: 780

Ile Ser Pro Lys Ser Gly Gly Thr
1               5

<210> SEQ ID NO 781
<211> LENGTH: 19
<212> TYPE: PRT
<213> ORGANISM: Artificial Sequence
<220> FEATURE:
<223> OTHER INFORMATION: synthetic peptide

<400> SEQUENCE: 781

Thr Arg Asp Asn Tyr Asn Ser Trp Arg Gly Pro Asp Phe Tyr Thr Gly
1               5                   10                  15

Val Asp Val

<210> SEQ ID NO 782
<211> LENGTH: 6
<212> TYPE: PRT
<213> ORGANISM: Artificial Sequence
<220> FEATURE:
<223> OTHER INFORMATION: synthetic peptide

<400> SEQUENCE: 782

Gln Ser Val Ser Ser Tyr
1               5

<210> SEQ ID NO 783
<211> LENGTH: 3
<212> TYPE: PRT
<213> ORGANISM: Artificial Sequence
<220> FEATURE:
<223> OTHER INFORMATION: synthetic peptide

<400> SEQUENCE: 783

Asn Ala Ser
1

<210> SEQ ID NO 784
<211> LENGTH: 9
<212> TYPE: PRT
<213> ORGANISM: Artificial Sequence
<220> FEATURE:
<223> OTHER INFORMATION: synthetic peptide

<400> SEQUENCE: 784

Gln Gln Arg Ser Ser Leu Gly Leu Ser
1               5

<210> SEQ ID NO 785
<211> LENGTH: 8
<212> TYPE: PRT
<213> ORGANISM: Artificial Sequence
<220> FEATURE:
<223> OTHER INFORMATION: synthetic peptide

<400> SEQUENCE: 785

Gly Tyr Thr Phe Thr Gly Tyr Tyr
1               5

<210> SEQ ID NO 786
<211> LENGTH: 8
<212> TYPE: PRT
<213> ORGANISM: Artificial Sequence
<220> FEATURE:
<223> OTHER INFORMATION: synthetic peptide

<400> SEQUENCE: 786

Ile Asp Pro Asn Gly Gly Asp Thr
1               5

<210> SEQ ID NO 787
<211> LENGTH: 18
<212> TYPE: PRT
<213> ORGANISM: Artificial Sequence
<220> FEATURE:
<223> OTHER INFORMATION: synthetic peptide

<400> SEQUENCE: 787

Ala Arg Asp Arg Ala Gly Ser Val Trp Phe Arg Gly Val Tyr Phe Phe
1               5                   10                  15

Asp Ala

<210> SEQ ID NO 788
<211> LENGTH: 6
<212> TYPE: PRT

```
<213> ORGANISM: Artificial Sequence
<220> FEATURE:
<223> OTHER INFORMATION: synthetic peptide

<400> SEQUENCE: 788

Gln Asp Val His Tyr Tyr
1               5

<210> SEQ ID NO 789
<211> LENGTH: 3
<212> TYPE: PRT
<213> ORGANISM: Artificial Sequence
<220> FEATURE:
<223> OTHER INFORMATION: synthetic peptide

<400> SEQUENCE: 789

Gly Val Ser
1

<210> SEQ ID NO 790
<211> LENGTH: 10
<212> TYPE: PRT
<213> ORGANISM: Artificial Sequence
<220> FEATURE:
<223> OTHER INFORMATION: synthetic peptide

<400> SEQUENCE: 790

Gln Gln Tyr Ser Asn Trp Pro Pro Gly Ala
1               5                   10

<210> SEQ ID NO 791
<211> LENGTH: 8
<212> TYPE: PRT
<213> ORGANISM: Artificial Sequence
<220> FEATURE:
<223> OTHER INFORMATION: synthetic peptide

<400> SEQUENCE: 791

Gly Phe Ser Phe Ser Asn Tyr Gly
1               5

<210> SEQ ID NO 792
<211> LENGTH: 8
<212> TYPE: PRT
<213> ORGANISM: Artificial Sequence
<220> FEATURE:
<223> OTHER INFORMATION: synthetic peptide

<400> SEQUENCE: 792

Ile Ser Tyr Asp Gly Asn Asn Ile
1               5

<210> SEQ ID NO 793
<211> LENGTH: 7
<212> TYPE: PRT
<213> ORGANISM: Artificial Sequence
<220> FEATURE:
<223> OTHER INFORMATION: synthetic peptide

<400> SEQUENCE: 793

Val Lys Ala Gly Gly Phe Ser
1               5

<210> SEQ ID NO 794
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 794

Gln Gly Ile Arg Ser Ala
1               5

<210> SEQ ID NO 795
<211> LENGTH: 3
<212> TYPE: PRT
<213> ORGANISM: Artificial Sequence
<220> FEATURE:
<223> OTHER INFORMATION: synthetic peptide

<400> SEQUENCE: 795

Asp Ala Ser
1

<210> SEQ ID NO 796
<211> LENGTH: 9
<212> TYPE: PRT
<213> ORGANISM: Artificial Sequence
<220> FEATURE:
<223> OTHER INFORMATION: synthetic peptide

<400> SEQUENCE: 796

Gln His Phe Ser Thr Tyr Pro Tyr Thr
1               5

<210> SEQ ID NO 797
<211> LENGTH: 8
<212> TYPE: PRT
<213> ORGANISM: Artificial Sequence
<220> FEATURE:
<223> OTHER INFORMATION: synthetic peptide

<400> SEQUENCE: 797

Gly Tyr Ser Leu Thr Arg Tyr Tyr
1               5

<210> SEQ ID NO 798
<211> LENGTH: 8
<212> TYPE: PRT
<213> ORGANISM: Artificial Sequence
<220> FEATURE:
<223> OTHER INFORMATION: synthetic peptide

<400> SEQUENCE: 798

Ile Ser Pro Ser Gly Gly Gly Thr
1               5

<210> SEQ ID NO 799
<211> LENGTH: 16
<212> TYPE: PRT
<213> ORGANISM: Artificial Sequence
<220> FEATURE:
<223> OTHER INFORMATION: synthetic peptide

<400> SEQUENCE: 799

Ala Arg Asp Ala Cys Ser Gly Gly Ser Cys Tyr Thr Pro Phe Asp Tyr
1               5                   10                  15

<210> SEQ ID NO 800
<211> LENGTH: 6
<212> TYPE: PRT
<213> ORGANISM: Artificial Sequence
<220> FEATURE:
```

<223> OTHER INFORMATION: synthetic peptide

<400> SEQUENCE: 800

Gln Ser Val Ser Ser Asn
1               5

<210> SEQ ID NO 801
<211> LENGTH: 3
<212> TYPE: PRT
<213> ORGANISM: Artificial Sequence
<220> FEATURE:
<223> OTHER INFORMATION: synthetic peptide

<400> SEQUENCE: 801

Gly Ala Ser
1

<210> SEQ ID NO 802
<211> LENGTH: 9
<212> TYPE: PRT
<213> ORGANISM: Artificial Sequence
<220> FEATURE:
<223> OTHER INFORMATION: synthetic peptide

<400> SEQUENCE: 802

Gln Gln Tyr Asn Asn Trp Pro Arg Thr
1               5

<210> SEQ ID NO 803
<211> LENGTH: 8
<212> TYPE: PRT
<213> ORGANISM: Artificial Sequence
<220> FEATURE:
<223> OTHER INFORMATION: synthetic peptide

<400> SEQUENCE: 803

Gly Phe Ser Phe Ser Asp His Tyr
1               5

<210> SEQ ID NO 804
<211> LENGTH: 10
<212> TYPE: PRT
<213> ORGANISM: Artificial Sequence
<220> FEATURE:
<223> OTHER INFORMATION: synthetic peptide

<400> SEQUENCE: 804

Ile Arg Asn Lys Ala Lys Asp Tyr Ser Thr
1               5                   10

<210> SEQ ID NO 805
<211> LENGTH: 18
<212> TYPE: PRT
<213> ORGANISM: Artificial Sequence
<220> FEATURE:
<223> OTHER INFORMATION: synthetic peptide

<400> SEQUENCE: 805

Thr Arg Val Asn Tyr Tyr Asp Arg Ser Gly Trp Ser Leu Asp Ala Phe
1               5                   10                  15

Asp Ile

<210> SEQ ID NO 806
<211> LENGTH: 6
<212> TYPE: PRT
<213> ORGANISM: Artificial Sequence

```
<220> FEATURE:
<223> OTHER INFORMATION: synthetic peptide

<400> SEQUENCE: 806

Gln Gly Ile Ser Asn Ser
1               5

<210> SEQ ID NO 807
<211> LENGTH: 3
<212> TYPE: PRT
<213> ORGANISM: Artificial Sequence
<220> FEATURE:
<223> OTHER INFORMATION: synthetic peptide

<400> SEQUENCE: 807

Ala Ala Ser
1

<210> SEQ ID NO 808
<211> LENGTH: 10
<212> TYPE: PRT
<213> ORGANISM: Artificial Sequence
<220> FEATURE:
<223> OTHER INFORMATION: synthetic peptide

<400> SEQUENCE: 808

Gln Gln Tyr Tyr Ser Thr Pro Pro Ile Thr
1               5                   10

<210> SEQ ID NO 809
<211> LENGTH: 8
<212> TYPE: PRT
<213> ORGANISM: Artificial Sequence
<220> FEATURE:
<223> OTHER INFORMATION: synthetic peptide

<400> SEQUENCE: 809

Gly Phe Ser Phe Ser Asn Tyr Glu
1               5

<210> SEQ ID NO 810
<211> LENGTH: 8
<212> TYPE: PRT
<213> ORGANISM: Artificial Sequence
<220> FEATURE:
<223> OTHER INFORMATION: synthetic peptide

<400> SEQUENCE: 810

Ile Ser Ser Gly Ser Ser Tyr Arg
1               5

<210> SEQ ID NO 811
<211> LENGTH: 9
<212> TYPE: PRT
<213> ORGANISM: Artificial Sequence
<220> FEATURE:
<223> OTHER INFORMATION: synthetic peptide

<400> SEQUENCE: 811

Ala Arg Arg Trp His Gly Ile Asp Ile
1               5

<210> SEQ ID NO 812
<211> LENGTH: 6
<212> TYPE: PRT
<213> ORGANISM: Artificial Sequence
<220> FEATURE:
```

```
<223> OTHER INFORMATION: synthetic peptide

<400> SEQUENCE: 812

Gln Asp Ile Arg Ser Asp
1               5

<210> SEQ ID NO 813
<211> LENGTH: 3
<212> TYPE: PRT
<213> ORGANISM: Artificial Sequence
<220> FEATURE:
<223> OTHER INFORMATION: synthetic peptide

<400> SEQUENCE: 813

Ala Ala Ser
1

<210> SEQ ID NO 814
<211> LENGTH: 9
<212> TYPE: PRT
<213> ORGANISM: Artificial Sequence
<220> FEATURE:
<223> OTHER INFORMATION: synthetic peptide

<400> SEQUENCE: 814

Leu Gln Asp Phe Asn Tyr Pro Arg Ile
1               5

<210> SEQ ID NO 815
<211> LENGTH: 8
<212> TYPE: PRT
<213> ORGANISM: Artificial Sequence
<220> FEATURE:
<223> OTHER INFORMATION: synthetic peptide

<400> SEQUENCE: 815

Gly Tyr Thr Phe Ser Arg Tyr Ala
1               5

<210> SEQ ID NO 816
<211> LENGTH: 8
<212> TYPE: PRT
<213> ORGANISM: Artificial Sequence
<220> FEATURE:
<223> OTHER INFORMATION: synthetic peptide

<400> SEQUENCE: 816

Ile Asn Thr Asn Thr Gly Glu Pro
1               5

<210> SEQ ID NO 817
<211> LENGTH: 18
<212> TYPE: PRT
<213> ORGANISM: Artificial Sequence
<220> FEATURE:
<223> OTHER INFORMATION: synthetic peptide

<400> SEQUENCE: 817

Ala Arg Asp Gly Thr Leu Arg Ser Ala Asp Gly Glu Thr Ser Ala Phe
1               5                   10                  15

Asp Ile

<210> SEQ ID NO 818
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 818

Gln Gly Ile Ser Asn Ser
1               5

<210> SEQ ID NO 819
<211> LENGTH: 3
<212> TYPE: PRT
<213> ORGANISM: Artificial Sequence
<220> FEATURE:
<223> OTHER INFORMATION: synthetic peptide

<400> SEQUENCE: 819

Ala Ala Ser
1

<210> SEQ ID NO 820
<211> LENGTH: 10
<212> TYPE: PRT
<213> ORGANISM: Artificial Sequence
<220> FEATURE:
<223> OTHER INFORMATION: synthetic peptide

<400> SEQUENCE: 820

Gln Gln Tyr Tyr Ser Thr Pro Pro Ile Thr
1               5                   10

<210> SEQ ID NO 821
<211> LENGTH: 8
<212> TYPE: PRT
<213> ORGANISM: Artificial Sequence
<220> FEATURE:
<223> OTHER INFORMATION: synthetic peptide

<400> SEQUENCE: 821

Gly Phe Thr Phe Ser Ser Tyr Gly
1               5

<210> SEQ ID NO 822
<211> LENGTH: 8
<212> TYPE: PRT
<213> ORGANISM: Artificial Sequence
<220> FEATURE:
<223> OTHER INFORMATION: synthetic peptide

<400> SEQUENCE: 822

Ile Trp Leu Asp Gly Thr Asn Lys
1               5

<210> SEQ ID NO 823
<211> LENGTH: 19
<212> TYPE: PRT
<213> ORGANISM: Artificial Sequence
<220> FEATURE:
<223> OTHER INFORMATION: synthetic peptide

<400> SEQUENCE: 823

Ala Arg Arg Gly Phe His Tyr Asp Ser Ser Gly Tyr Tyr Tyr Gly
1               5                   10                  15

Met Asp Val

<210> SEQ ID NO 824
<211> LENGTH: 11
<212> TYPE: PRT
```

```
<213> ORGANISM: Artificial Sequence
<220> FEATURE:
<223> OTHER INFORMATION: synthetic peptide

<400> SEQUENCE: 824

Gln Ser Leu Leu His Ser Asn Gly Tyr Asn Tyr
1               5                   10

<210> SEQ ID NO 825
<211> LENGTH: 3
<212> TYPE: PRT
<213> ORGANISM: Artificial Sequence
<220> FEATURE:
<223> OTHER INFORMATION: synthetic peptide

<400> SEQUENCE: 825

Leu Gly Ser
1

<210> SEQ ID NO 826
<211> LENGTH: 10
<212> TYPE: PRT
<213> ORGANISM: Artificial Sequence
<220> FEATURE:
<223> OTHER INFORMATION: synthetic peptide

<400> SEQUENCE: 826

Met Gln Ala Leu Gln Thr Pro Pro Phe Thr
1               5                   10

<210> SEQ ID NO 827
<211> LENGTH: 8
<212> TYPE: PRT
<213> ORGANISM: Artificial Sequence
<220> FEATURE:
<223> OTHER INFORMATION: synthetic peptide

<400> SEQUENCE: 827

Gly Val Thr Phe Ser Asp Tyr Asp
1               5

<210> SEQ ID NO 828
<211> LENGTH: 8
<212> TYPE: PRT
<213> ORGANISM: Artificial Sequence
<220> FEATURE:
<223> OTHER INFORMATION: synthetic peptide

<400> SEQUENCE: 828

Ile Arg Ser Ser Gly Gly Thr Thr
1               5

<210> SEQ ID NO 829
<211> LENGTH: 10
<212> TYPE: PRT
<213> ORGANISM: Artificial Sequence
<220> FEATURE:
<223> OTHER INFORMATION: synthetic peptide

<400> SEQUENCE: 829

Val Arg Asp Lys Asp Gly Val Phe Asp Tyr
1               5                   10

<210> SEQ ID NO 830
<211> LENGTH: 12
<212> TYPE: PRT
<213> ORGANISM: Artificial Sequence
```

```
<220> FEATURE:
<223> OTHER INFORMATION: synthetic peptide

<400> SEQUENCE: 830

Gln Ser Val Leu Tyr Ser Ser Asn Asn Lys Asn Tyr
1               5                   10

<210> SEQ ID NO 831
<211> LENGTH: 3
<212> TYPE: PRT
<213> ORGANISM: Artificial Sequence
<220> FEATURE:
<223> OTHER INFORMATION: synthetic peptide

<400> SEQUENCE: 831

Trp Ala Ser
1

<210> SEQ ID NO 832
<211> LENGTH: 8
<212> TYPE: PRT
<213> ORGANISM: Artificial Sequence
<220> FEATURE:
<223> OTHER INFORMATION: synthetic peptide

<400> SEQUENCE: 832

Gln Gln Tyr Tyr Arg Thr Pro Leu
1               5

<210> SEQ ID NO 833
<211> LENGTH: 8
<212> TYPE: PRT
<213> ORGANISM: Artificial Sequence
<220> FEATURE:
<223> OTHER INFORMATION: synthetic peptide

<400> SEQUENCE: 833

Gly Phe Thr Phe Ser Ser Tyr Ala
1               5

<210> SEQ ID NO 834
<211> LENGTH: 8
<212> TYPE: PRT
<213> ORGANISM: Artificial Sequence
<220> FEATURE:
<223> OTHER INFORMATION: synthetic peptide

<400> SEQUENCE: 834

Ile Ser Pro Ser Gly Ser Thr Ile
1               5

<210> SEQ ID NO 835
<211> LENGTH: 13
<212> TYPE: PRT
<213> ORGANISM: Artificial Sequence
<220> FEATURE:
<223> OTHER INFORMATION: synthetic peptide

<400> SEQUENCE: 835

Val Arg Gly Val Tyr Val Gln Ser Asp Ala Phe Asp Ile
1               5                   10

<210> SEQ ID NO 836
<211> LENGTH: 6
<212> TYPE: PRT
<213> ORGANISM: Artificial Sequence
<220> FEATURE:
```

<223> OTHER INFORMATION: synthetic peptide

<400> SEQUENCE: 836

Gln Gly Ile Ser Asn Ser
1               5

<210> SEQ ID NO 837
<211> LENGTH: 3
<212> TYPE: PRT
<213> ORGANISM: Artificial Sequence
<220> FEATURE:
<223> OTHER INFORMATION: synthetic peptide

<400> SEQUENCE: 837

Ala Ala Ser
1

<210> SEQ ID NO 838
<211> LENGTH: 10
<212> TYPE: PRT
<213> ORGANISM: Artificial Sequence
<220> FEATURE:
<223> OTHER INFORMATION: synthetic peptide

<400> SEQUENCE: 838

Gln Gln Tyr Tyr Ser Thr Pro Pro Ile Thr
1               5                   10

<210> SEQ ID NO 839
<211> LENGTH: 8
<212> TYPE: PRT
<213> ORGANISM: Artificial Sequence
<220> FEATURE:
<223> OTHER INFORMATION: synthetic peptide

<400> SEQUENCE: 839

Gly Tyr Thr Phe Thr Thr Tyr Ala
1               5

<210> SEQ ID NO 840
<211> LENGTH: 8
<212> TYPE: PRT
<213> ORGANISM: Artificial Sequence
<220> FEATURE:
<223> OTHER INFORMATION: synthetic peptide

<400> SEQUENCE: 840

Ile Asn Thr Asn Thr Gly Asn Pro
1               5

<210> SEQ ID NO 841
<211> LENGTH: 14
<212> TYPE: PRT
<213> ORGANISM: Artificial Sequence
<220> FEATURE:
<223> OTHER INFORMATION: synthetic peptide

<400> SEQUENCE: 841

Ala Arg Asp Arg Tyr Ser Ser Ser Trp Tyr Gln Phe Asp Pro
1               5                   10

<210> SEQ ID NO 842
<211> LENGTH: 6
<212> TYPE: PRT
<213> ORGANISM: Artificial Sequence
<220> FEATURE:
<223> OTHER INFORMATION: synthetic peptide

<400> SEQUENCE: 842

Gln Gly Ile Ser Asn Ser
1               5

<210> SEQ ID NO 843
<211> LENGTH: 3
<212> TYPE: PRT
<213> ORGANISM: Artificial Sequence
<220> FEATURE:
<223> OTHER INFORMATION: synthetic peptide

<400> SEQUENCE: 843

Ala Ala Ser
1

<210> SEQ ID NO 844
<211> LENGTH: 10
<212> TYPE: PRT
<213> ORGANISM: Artificial Sequence
<220> FEATURE:
<223> OTHER INFORMATION: synthetic peptide

<400> SEQUENCE: 844

Gln Gln Tyr Asn Thr Tyr Pro His Ser Thr
1               5                   10

<210> SEQ ID NO 845
<211> LENGTH: 8
<212> TYPE: PRT
<213> ORGANISM: Artificial Sequence
<220> FEATURE:
<223> OTHER INFORMATION: synthetic peptide

<400> SEQUENCE: 845

Gly Phe Thr Phe Ser Asn Tyr Asp
1               5

<210> SEQ ID NO 846
<211> LENGTH: 7
<212> TYPE: PRT
<213> ORGANISM: Artificial Sequence
<220> FEATURE:
<223> OTHER INFORMATION: synthetic peptide

<400> SEQUENCE: 846

Ile Asp Thr Ser Gly Asn Thr
1               5

<210> SEQ ID NO 847
<211> LENGTH: 16
<212> TYPE: PRT
<213> ORGANISM: Artificial Sequence
<220> FEATURE:
<223> OTHER INFORMATION: synthetic peptide

<400> SEQUENCE: 847

Val Arg Leu Gly Gly Tyr Ile Gly Asn Asp Arg Asp Ala Phe Asp Ile
1               5                   10                  15

<210> SEQ ID NO 848
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 848

Gln Asp Ile Ser Ser Trp
1               5

<210> SEQ ID NO 849
<211> LENGTH: 3
<212> TYPE: PRT
<213> ORGANISM: Artificial Sequence
<220> FEATURE:
<223> OTHER INFORMATION: synthetic peptide

<400> SEQUENCE: 849

Lys Ala Ser
1

<210> SEQ ID NO 850
<211> LENGTH: 10
<212> TYPE: PRT
<213> ORGANISM: Artificial Sequence
<220> FEATURE:
<223> OTHER INFORMATION: synthetic peptide

<400> SEQUENCE: 850

Gln Gln Tyr Asn Thr Tyr Pro His Ser Thr
1               5                   10

<210> SEQ ID NO 851
<211> LENGTH: 8
<212> TYPE: PRT
<213> ORGANISM: Artificial Sequence
<220> FEATURE:
<223> OTHER INFORMATION: synthetic peptide

<400> SEQUENCE: 851

Gly Tyr Thr Phe Ile Ser Tyr Gly
1               5

<210> SEQ ID NO 852
<211> LENGTH: 8
<212> TYPE: PRT
<213> ORGANISM: Artificial Sequence
<220> FEATURE:
<223> OTHER INFORMATION: synthetic peptide

<400> SEQUENCE: 852

Ile Ser Ala Lys Asn Gly Asn Thr
1               5

<210> SEQ ID NO 853
<211> LENGTH: 10
<212> TYPE: PRT
<213> ORGANISM: Artificial Sequence
<220> FEATURE:
<223> OTHER INFORMATION: synthetic peptide

<400> SEQUENCE: 853

Ala Arg Asp Arg Thr Gly Thr Leu Asp Ser
1               5                   10

<210> SEQ ID NO 854
<211> LENGTH: 12
<212> TYPE: PRT
<213> ORGANISM: Artificial Sequence
<220> FEATURE:
<223> OTHER INFORMATION: synthetic peptide
```

<400> SEQUENCE: 854

Gln Asp Ile Lys Lys Phe Leu Asn Trp Tyr Gln Gln
1               5                   10

<210> SEQ ID NO 855
<211> LENGTH: 3
<212> TYPE: PRT
<213> ORGANISM: Artificial Sequence
<220> FEATURE:
<223> OTHER INFORMATION: synthetic peptide

<400> SEQUENCE: 855

Asp Ala Phe
1

<210> SEQ ID NO 856
<211> LENGTH: 9
<212> TYPE: PRT
<213> ORGANISM: Artificial Sequence
<220> FEATURE:
<223> OTHER INFORMATION: synthetic peptide

<400> SEQUENCE: 856

Gln Gln Tyr Asp Ile Leu Pro Tyr Thr
1               5

<210> SEQ ID NO 857
<211> LENGTH: 8
<212> TYPE: PRT
<213> ORGANISM: Artificial Sequence
<220> FEATURE:
<223> OTHER INFORMATION: synthetic peptide

<400> SEQUENCE: 857

Gly Tyr Thr Phe Ile Ser Tyr Gly
1               5

<210> SEQ ID NO 858
<211> LENGTH: 8
<212> TYPE: PRT
<213> ORGANISM: Artificial Sequence
<220> FEATURE:
<223> OTHER INFORMATION: synthetic peptide

<400> SEQUENCE: 858

Ile Ser Ala Lys Ser Gly Asn Thr
1               5

<210> SEQ ID NO 859
<211> LENGTH: 10
<212> TYPE: PRT
<213> ORGANISM: Artificial Sequence
<220> FEATURE:
<223> OTHER INFORMATION: synthetic peptide

<400> SEQUENCE: 859

Ala Arg Asp Arg Thr Gly Thr Leu Asp Ser
1               5                   10

<210> SEQ ID NO 860
<211> LENGTH: 6
<212> TYPE: PRT
<213> ORGANISM: Artificial Sequence
<220> FEATURE:
<223> OTHER INFORMATION: synthetic peptide

<400> SEQUENCE: 860

Gln Ser Ile Asp Asp Tyr
1               5

<210> SEQ ID NO 861
<211> LENGTH: 3
<212> TYPE: PRT
<213> ORGANISM: Artificial Sequence
<220> FEATURE:
<223> OTHER INFORMATION: synthetic peptide

<400> SEQUENCE: 861

Ala Ala Ser
1

<210> SEQ ID NO 862
<211> LENGTH: 9
<212> TYPE: PRT
<213> ORGANISM: Artificial Sequence
<220> FEATURE:
<223> OTHER INFORMATION: synthetic peptide

<400> SEQUENCE: 862

Gln Gln Thr Tyr Gly Thr Ser Ile Thr
1               5

<210> SEQ ID NO 863
<211> LENGTH: 8
<212> TYPE: PRT
<213> ORGANISM: Artificial Sequence
<220> FEATURE:
<223> OTHER INFORMATION: synthetic peptide

<400> SEQUENCE: 863

Gly Phe Ile Phe Gly Asp Phe Ala
1               5

<210> SEQ ID NO 864
<211> LENGTH: 10
<212> TYPE: PRT
<213> ORGANISM: Artificial Sequence
<220> FEATURE:
<223> OTHER INFORMATION: synthetic peptide

<400> SEQUENCE: 864

Ile Arg Ser Gln Ala His Gly Gly Thr Thr
1               5                   10

<210> SEQ ID NO 865
<211> LENGTH: 18
<212> TYPE: PRT
<213> ORGANISM: Artificial Sequence
<220> FEATURE:
<223> OTHER INFORMATION: synthetic peptide

<400> SEQUENCE: 865

Thr Arg Glu Gly Val Val Val Ala Ala Arg Tyr Tyr Tyr Ile Met
1               5                   10                  15

Asp Val

<210> SEQ ID NO 866
<211> LENGTH: 6
<212> TYPE: PRT
<213> ORGANISM: Artificial Sequence
<220> FEATURE:
<223> OTHER INFORMATION: synthetic peptide

<400> SEQUENCE: 866

His Asn Ile Ser Arg Tyr
1               5

<210> SEQ ID NO 867
<211> LENGTH: 3
<212> TYPE: PRT
<213> ORGANISM: Artificial Sequence
<220> FEATURE:
<223> OTHER INFORMATION: synthetic peptide

<400> SEQUENCE: 867

Ala Ala Ser
1

<210> SEQ ID NO 868
<211> LENGTH: 9
<212> TYPE: PRT
<213> ORGANISM: Artificial Sequence
<220> FEATURE:
<223> OTHER INFORMATION: synthetic peptide

<400> SEQUENCE: 868

Gln Gln Asn Tyr Arg Thr Pro Arg Thr
1               5

<210> SEQ ID NO 869
<211> LENGTH: 8
<212> TYPE: PRT
<213> ORGANISM: Artificial Sequence
<220> FEATURE:
<223> OTHER INFORMATION: synthetic peptide

<400> SEQUENCE: 869

Gly Phe Ala Phe Asn Tyr Tyr Asp
1               5

<210> SEQ ID NO 870
<211> LENGTH: 8
<212> TYPE: PRT
<213> ORGANISM: Artificial Sequence
<220> FEATURE:
<223> OTHER INFORMATION: synthetic peptide

<400> SEQUENCE: 870

Ile Lys Pro Gly Gly Gly Asn Thr
1               5

<210> SEQ ID NO 871
<211> LENGTH: 12
<212> TYPE: PRT
<213> ORGANISM: Artificial Sequence
<220> FEATURE:
<223> OTHER INFORMATION: synthetic peptide

<400> SEQUENCE: 871

Ala Arg Gln Leu Tyr Gly Asn Ser Phe Phe Asp Tyr
1               5                   10

<210> SEQ ID NO 872
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 872

Gln Gly Ile Ser Asn Ser
1               5

<210> SEQ ID NO 873
<211> LENGTH: 3
<212> TYPE: PRT
<213> ORGANISM: Artificial Sequence
<220> FEATURE:
<223> OTHER INFORMATION: synthetic peptide

<400> SEQUENCE: 873

Ala Ala Ser
1

<210> SEQ ID NO 874
<211> LENGTH: 10
<212> TYPE: PRT
<213> ORGANISM: Artificial Sequence
<220> FEATURE:
<223> OTHER INFORMATION: synthetic peptide

<400> SEQUENCE: 874

Gln Gln Tyr Tyr Ser Thr Pro Pro Ile Thr
1               5                   10

<210> SEQ ID NO 875
<211> LENGTH: 8
<212> TYPE: PRT
<213> ORGANISM: Artificial Sequence
<220> FEATURE:
<223> OTHER INFORMATION: synthetic peptide

<400> SEQUENCE: 875

Gly Phe Thr Phe Arg Asp Tyr Trp
1               5

<210> SEQ ID NO 876
<211> LENGTH: 8
<212> TYPE: PRT
<213> ORGANISM: Artificial Sequence
<220> FEATURE:
<223> OTHER INFORMATION: synthetic peptide

<400> SEQUENCE: 876

Ile Asn Arg Asn Gly Asn Glu Lys
1               5

<210> SEQ ID NO 877
<211> LENGTH: 19
<212> TYPE: PRT
<213> ORGANISM: Artificial Sequence
<220> FEATURE:
<223> OTHER INFORMATION: synthetic peptide

<400> SEQUENCE: 877

Val Arg Asp Ser Ser Pro Ser Phe Gly Pro Gly Asn Tyr Tyr Asp Ala
1               5                   10                  15

Phe Asp Ile

<210> SEQ ID NO 878
<211> LENGTH: 6
<212> TYPE: PRT
<213> ORGANISM: Artificial Sequence
<220> FEATURE:
<223> OTHER INFORMATION: synthetic peptide
```

<400> SEQUENCE: 878

Gln Asp Ile Arg Asn Glu
1               5

<210> SEQ ID NO 879
<211> LENGTH: 3
<212> TYPE: PRT
<213> ORGANISM: Artificial Sequence
<220> FEATURE:
<223> OTHER INFORMATION: synthetic peptide

<400> SEQUENCE: 879

Ala Ala Ser
1

<210> SEQ ID NO 880
<211> LENGTH: 9
<212> TYPE: PRT
<213> ORGANISM: Artificial Sequence
<220> FEATURE:
<223> OTHER INFORMATION: synthetic peptide

<400> SEQUENCE: 880

Leu Gln Asp Tyr Asn Tyr Pro Arg Thr
1               5

<210> SEQ ID NO 881
<211> LENGTH: 8
<212> TYPE: PRT
<213> ORGANISM: Artificial Sequence
<220> FEATURE:
<223> OTHER INFORMATION: synthetic peptide

<400> SEQUENCE: 881

Gly Tyr Thr Phe Ile Asp Tyr Tyr
1               5

<210> SEQ ID NO 882
<211> LENGTH: 8
<212> TYPE: PRT
<213> ORGANISM: Artificial Sequence
<220> FEATURE:
<223> OTHER INFORMATION: synthetic peptide

<400> SEQUENCE: 882

Ile Asn Pro Lys Ser Gly Ala Thr
1               5

<210> SEQ ID NO 883
<211> LENGTH: 12
<212> TYPE: PRT
<213> ORGANISM: Artificial Sequence
<220> FEATURE:
<223> OTHER INFORMATION: synthetic peptide

<400> SEQUENCE: 883

Ser Thr Phe Trp Asp Gly Val Asp Ala Phe Asp Val
1               5                   10

<210> SEQ ID NO 884
<211> LENGTH: 6
<212> TYPE: PRT
<213> ORGANISM: Artificial Sequence
<220> FEATURE:
<223> OTHER INFORMATION: synthetic peptide -continued

```
<400> SEQUENCE: 884

Gln Ser Val Ser Ser Tyr
1               5

<210> SEQ ID NO 885
<211> LENGTH: 3
<212> TYPE: PRT
<213> ORGANISM: Artificial Sequence
<220> FEATURE:
<223> OTHER INFORMATION: synthetic peptide

<400> SEQUENCE: 885

Asp Thr Ser
1

<210> SEQ ID NO 886
<211> LENGTH: 10
<212> TYPE: PRT
<213> ORGANISM: Artificial Sequence
<220> FEATURE:
<223> OTHER INFORMATION: synthetic peptide

<400> SEQUENCE: 886

Leu Gln Arg Arg Asn Trp Pro Pro Phe Thr
1               5                   10

<210> SEQ ID NO 887
<211> LENGTH: 8
<212> TYPE: PRT
<213> ORGANISM: Artificial Sequence
<220> FEATURE:
<223> OTHER INFORMATION: synthetic peptide

<400> SEQUENCE: 887

Gly Phe Ser Phe Ser Asn Tyr Glu
1               5

<210> SEQ ID NO 888
<211> LENGTH: 8
<212> TYPE: PRT
<213> ORGANISM: Artificial Sequence
<220> FEATURE:
<223> OTHER INFORMATION: synthetic peptide

<400> SEQUENCE: 888

Ile Ser Ser Gly Ser Ser Tyr Arg
1               5

<210> SEQ ID NO 889
<211> LENGTH: 9
<212> TYPE: PRT
<213> ORGANISM: Artificial Sequence
<220> FEATURE:
<223> OTHER INFORMATION: synthetic peptide

<400> SEQUENCE: 889

Ala Arg Arg Trp His Gly Leu Asp Ile
1               5

<210> SEQ ID NO 890
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 890

Gln Ser Leu Leu His Ile Asn Gly Tyr Asn Tyr
1               5                   10

<210> SEQ ID NO 891
<211> LENGTH: 3
<212> TYPE: PRT
<213> ORGANISM: Artificial Sequence
<220> FEATURE:
<223> OTHER INFORMATION: synthetic peptide

<400> SEQUENCE: 891

Leu Gly Ser
1

<210> SEQ ID NO 892
<211> LENGTH: 9
<212> TYPE: PRT
<213> ORGANISM: Artificial Sequence
<220> FEATURE:
<223> OTHER INFORMATION: synthetic peptide

<400> SEQUENCE: 892

Met Gln Ala Leu Gln Thr Pro Trp Thr
1               5

<210> SEQ ID NO 893
<211> LENGTH: 8
<212> TYPE: PRT
<213> ORGANISM: Artificial Sequence
<220> FEATURE:
<223> OTHER INFORMATION: synthetic peptide

<400> SEQUENCE: 893

Gly Phe Ile Phe Ser Ser Thr Gly
1               5

<210> SEQ ID NO 894
<211> LENGTH: 8
<212> TYPE: PRT
<213> ORGANISM: Artificial Sequence
<220> FEATURE:
<223> OTHER INFORMATION: synthetic peptide

<400> SEQUENCE: 894

Ile Gly Arg Asp Gly Asn Tyr Lys
1               5

<210> SEQ ID NO 895
<211> LENGTH: 14
<212> TYPE: PRT
<213> ORGANISM: Artificial Sequence
<220> FEATURE:
<223> OTHER INFORMATION: synthetic peptide

<400> SEQUENCE: 895

Ile Leu Ser Ser Ala Leu Val Pro Gly Ala Thr Phe Asp Lys
1               5                   10

<210> SEQ ID NO 896
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 896

Gln Ser Ile Ser Thr Ser
1               5

<210> SEQ ID NO 897
<211> LENGTH: 3
<212> TYPE: PRT
<213> ORGANISM: Artificial Sequence
<220> FEATURE:
<223> OTHER INFORMATION: synthetic peptide

<400> SEQUENCE: 897

Thr Ala Ser
1

<210> SEQ ID NO 898
<211> LENGTH: 10
<212> TYPE: PRT
<213> ORGANISM: Artificial Sequence
<220> FEATURE:
<223> OTHER INFORMATION: synthetic peptide

<400> SEQUENCE: 898

Cys Gln Gln Ser Tyr Ser Val Pro Tyr Thr
1               5                   10

<210> SEQ ID NO 899
<211> LENGTH: 8
<212> TYPE: PRT
<213> ORGANISM: Artificial Sequence
<220> FEATURE:
<223> OTHER INFORMATION: synthetic peptide

<400> SEQUENCE: 899

Gly Phe Thr Phe Arg Ser Phe Glu
1               5

<210> SEQ ID NO 900
<211> LENGTH: 7
<212> TYPE: PRT
<213> ORGANISM: Artificial Sequence
<220> FEATURE:
<223> OTHER INFORMATION: synthetic peptide

<400> SEQUENCE: 900

Ile Ser Val Gly Ala Asn Pro
1               5

<210> SEQ ID NO 901
<211> LENGTH: 12
<212> TYPE: PRT
<213> ORGANISM: Artificial Sequence
<220> FEATURE:
<223> OTHER INFORMATION: synthetic peptide

<400> SEQUENCE: 901

Val Arg Lys Ile Pro Gly Thr Ser His Phe Asp Tyr
1               5                   10

<210> SEQ ID NO 902
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 902

Gln Ser Val Ser Ser Tyr
1               5

<210> SEQ ID NO 903
<211> LENGTH: 3
<212> TYPE: PRT
<213> ORGANISM: Artificial Sequence
<220> FEATURE:
<223> OTHER INFORMATION: synthetic peptide

<400> SEQUENCE: 903

Asp Ala Ser
1

<210> SEQ ID NO 904
<211> LENGTH: 9
<212> TYPE: PRT
<213> ORGANISM: Artificial Sequence
<220> FEATURE:
<223> OTHER INFORMATION: synthetic peptide

<400> SEQUENCE: 904

Gln His Phe Ser Thr Tyr Pro Tyr Thr
1               5

<210> SEQ ID NO 905
<211> LENGTH: 8
<212> TYPE: PRT
<213> ORGANISM: Artificial Sequence
<220> FEATURE:
<223> OTHER INFORMATION: synthetic peptide

<400> SEQUENCE: 905

Gly Gly Ile Phe Ser Asn Tyr Ala
1               5

<210> SEQ ID NO 906
<211> LENGTH: 8
<212> TYPE: PRT
<213> ORGANISM: Artificial Sequence
<220> FEATURE:
<223> OTHER INFORMATION: synthetic peptide

<400> SEQUENCE: 906

Phe Ile Pro Ile Val Asn Ile Gly
1               5

<210> SEQ ID NO 907
<211> LENGTH: 17
<212> TYPE: PRT
<213> ORGANISM: Artificial Sequence
<220> FEATURE:
<223> OTHER INFORMATION: synthetic peptide

<400> SEQUENCE: 907

Ala Arg Asp Leu Glu Ala Ala Asn Ser Val Ile Leu Pro Arg Leu Phe
1               5                   10                  15

Tyr

<210> SEQ ID NO 908
<211> LENGTH: 6
<212> TYPE: PRT
<213> ORGANISM: Artificial Sequence
<220> FEATURE:
```

```
<223> OTHER INFORMATION: synthetic peptide

<400> SEQUENCE: 908

Gln Gly Ile Ser Asn Ser
1               5

<210> SEQ ID NO 909
<211> LENGTH: 3
<212> TYPE: PRT
<213> ORGANISM: Artificial Sequence
<220> FEATURE:
<223> OTHER INFORMATION: synthetic peptide

<400> SEQUENCE: 909

Ala Ala Ser
1

<210> SEQ ID NO 910
<211> LENGTH: 10
<212> TYPE: PRT
<213> ORGANISM: Artificial Sequence
<220> FEATURE:
<223> OTHER INFORMATION: synthetic peptide

<400> SEQUENCE: 910

Gln Gln Tyr Tyr Ser Thr Pro Pro Ile Thr
1               5                   10

<210> SEQ ID NO 911
<211> LENGTH: 8
<212> TYPE: PRT
<213> ORGANISM: Artificial Sequence
<220> FEATURE:
<223> OTHER INFORMATION: synthetic peptide

<400> SEQUENCE: 911

Gly Phe Thr Leu Ser Asp His Tyr
1               5

<210> SEQ ID NO 912
<211> LENGTH: 10
<212> TYPE: PRT
<213> ORGANISM: Artificial Sequence
<220> FEATURE:
<223> OTHER INFORMATION: synthetic peptide

<400> SEQUENCE: 912

Ser Arg Asn Lys Ala Lys Thr Tyr Thr Thr
1               5                   10

<210> SEQ ID NO 913
<211> LENGTH: 18
<212> TYPE: PRT
<213> ORGANISM: Artificial Sequence
<220> FEATURE:
<223> OTHER INFORMATION: synthetic peptide

<400> SEQUENCE: 913

Thr Arg Pro Gly Tyr Phe Asp Arg Ser Gly Asp Ser Phe Asp Ala Leu
1               5                   10                  15

Asp Ile

<210> SEQ ID NO 914
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 914

Gln Gly Ile Arg Ser Ala
1               5

<210> SEQ ID NO 915
<211> LENGTH: 3
<212> TYPE: PRT
<213> ORGANISM: Artificial Sequence
<220> FEATURE:
<223> OTHER INFORMATION: synthetic peptide

<400> SEQUENCE: 915

Asp Ala Ser
1

<210> SEQ ID NO 916
<211> LENGTH: 9
<212> TYPE: PRT
<213> ORGANISM: Artificial Sequence
<220> FEATURE:
<223> OTHER INFORMATION: synthetic peptide

<400> SEQUENCE: 916

Gln His Phe Ser Thr Tyr Pro Tyr Thr
1               5

<210> SEQ ID NO 917
<211> LENGTH: 8
<212> TYPE: PRT
<213> ORGANISM: Artificial Sequence
<220> FEATURE:
<223> OTHER INFORMATION: synthetic peptide

<400> SEQUENCE: 917

Gly Phe Ser Phe Ser Asn Tyr Glu
1               5

<210> SEQ ID NO 918
<211> LENGTH: 8
<212> TYPE: PRT
<213> ORGANISM: Artificial Sequence
<220> FEATURE:
<223> OTHER INFORMATION: synthetic peptide

<400> SEQUENCE: 918

Ile Ser Thr Ile Arg Pro Tyr Ile
1               5

<210> SEQ ID NO 919
<211> LENGTH: 19
<212> TYPE: PRT
<213> ORGANISM: Artificial Sequence
<220> FEATURE:
<223> OTHER INFORMATION: synthetic peptide

<400> SEQUENCE: 919

Ala Arg Asp Ala Phe Thr Ser Thr Ser Tyr Asp Gly Phe Ser Gly Asn
1               5                   10                  15

Phe Asp Tyr

<210> SEQ ID NO 920
<211> LENGTH: 6
<212> TYPE: PRT
```

```
<213> ORGANISM: Artificial Sequence
<220> FEATURE:
<223> OTHER INFORMATION: synthetic peptide

<400> SEQUENCE: 920

Gln Gly Ile Arg Ser Ala
1               5

<210> SEQ ID NO 921
<211> LENGTH: 3
<212> TYPE: PRT
<213> ORGANISM: Artificial Sequence
<220> FEATURE:
<223> OTHER INFORMATION: synthetic peptide

<400> SEQUENCE: 921

Asp Ala Ser
1

<210> SEQ ID NO 922
<211> LENGTH: 9
<212> TYPE: PRT
<213> ORGANISM: Artificial Sequence
<220> FEATURE:
<223> OTHER INFORMATION: synthetic peptide

<400> SEQUENCE: 922

Gln His Phe Ser Thr Tyr Pro Tyr Thr
1               5

<210> SEQ ID NO 923
<211> LENGTH: 8
<212> TYPE: PRT
<213> ORGANISM: Artificial Sequence
<220> FEATURE:
<223> OTHER INFORMATION: synthetic peptide

<400> SEQUENCE: 923

Gly Phe Thr Phe Thr Asp Tyr Tyr
1               5

<210> SEQ ID NO 924
<211> LENGTH: 8
<212> TYPE: PRT
<213> ORGANISM: Artificial Sequence
<220> FEATURE:
<223> OTHER INFORMATION: synthetic peptide

<400> SEQUENCE: 924

Ile Ser Pro Ser Gly Ser Thr Ile
1               5

<210> SEQ ID NO 925
<211> LENGTH: 13
<212> TYPE: PRT
<213> ORGANISM: Artificial Sequence
<220> FEATURE:
<223> OTHER INFORMATION: synthetic peptide

<400> SEQUENCE: 925

Ala Arg Gly Ile Tyr Tyr Gln Ser Asp Ala Phe Asp Thr
1               5                   10

<210> SEQ ID NO 926
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 926

Gln Val Ile Arg Asn Ser
1               5

<210> SEQ ID NO 927
<211> LENGTH: 3
<212> TYPE: PRT
<213> ORGANISM: Artificial Sequence
<220> FEATURE:
<223> OTHER INFORMATION: synthetic peptide

<400> SEQUENCE: 927

Ala Ala Ser
1

<210> SEQ ID NO 928
<211> LENGTH: 10
<212> TYPE: PRT
<213> ORGANISM: Artificial Sequence
<220> FEATURE:
<223> OTHER INFORMATION: synthetic peptide

<400> SEQUENCE: 928

Gln Gln Tyr Tyr Ser Thr Pro Pro Ile Thr
1               5                   10

<210> SEQ ID NO 929
<211> LENGTH: 8
<212> TYPE: PRT
<213> ORGANISM: Artificial Sequence
<220> FEATURE:
<223> OTHER INFORMATION: synthetic peptide

<400> SEQUENCE: 929

Gly Phe Thr Phe Thr Ser Tyr Ala
1               5

<210> SEQ ID NO 930
<211> LENGTH: 8
<212> TYPE: PRT
<213> ORGANISM: Artificial Sequence
<220> FEATURE:
<223> OTHER INFORMATION: synthetic peptide

<400> SEQUENCE: 930

Ile Ser Tyr Asn Gly Arg Asn Lys
1               5

<210> SEQ ID NO 931
<211> LENGTH: 14
<212> TYPE: PRT
<213> ORGANISM: Artificial Sequence
<220> FEATURE:
<223> OTHER INFORMATION: synthetic peptide

<400> SEQUENCE: 931

Val Arg Ser Met Gly Asp Phe Asp Trp Leu Leu Thr Asp Tyr
1               5                   10

<210> SEQ ID NO 932
<211> LENGTH: 6
<212> TYPE: PRT
<213> ORGANISM: Artificial Sequence
<220> FEATURE:
```

```
<223> OTHER INFORMATION: synthetic peptide

<400> SEQUENCE: 932

Gln Ser Val Ser Thr His
1               5

<210> SEQ ID NO 933
<211> LENGTH: 3
<212> TYPE: PRT
<213> ORGANISM: Artificial Sequence
<220> FEATURE:
<223> OTHER INFORMATION: synthetic peptide

<400> SEQUENCE: 933

Asp Ala Ser
1

<210> SEQ ID NO 934
<211> LENGTH: 8
<212> TYPE: PRT
<213> ORGANISM: Artificial Sequence
<220> FEATURE:
<223> OTHER INFORMATION: synthetic peptide

<400> SEQUENCE: 934

Gln Gln Tyr Asn Thr Trp Pro Arg
1               5

<210> SEQ ID NO 935
<211> LENGTH: 8
<212> TYPE: PRT
<213> ORGANISM: Artificial Sequence
<220> FEATURE:
<223> OTHER INFORMATION: synthetic peptide

<400> SEQUENCE: 935

Gly Val Thr Phe Ser Asp Tyr Asp
1               5

<210> SEQ ID NO 936
<211> LENGTH: 8
<212> TYPE: PRT
<213> ORGANISM: Artificial Sequence
<220> FEATURE:
<223> OTHER INFORMATION: synthetic peptide

<400> SEQUENCE: 936

Ile Arg Ser Ser Gly Gly Thr Thr
1               5

<210> SEQ ID NO 937
<211> LENGTH: 10
<212> TYPE: PRT
<213> ORGANISM: Artificial Sequence
<220> FEATURE:
<223> OTHER INFORMATION: synthetic peptide

<400> SEQUENCE: 937

Val Arg Asp Lys Asp Gly Val Phe Asp Tyr
1               5                   10

<210> SEQ ID NO 938
<211> LENGTH: 7
<212> TYPE: PRT
<213> ORGANISM: Artificial Sequence
<220> FEATURE:
<223> OTHER INFORMATION: synthetic peptide
```

<400> SEQUENCE: 938

Gln Ser Val Thr Arg Thr Phe
1               5

<210> SEQ ID NO 939
<211> LENGTH: 3
<212> TYPE: PRT
<213> ORGANISM: Artificial Sequence
<220> FEATURE:
<223> OTHER INFORMATION: synthetic peptide

<400> SEQUENCE: 939

Asp Ala Ser
1

<210> SEQ ID NO 940
<211> LENGTH: 9
<212> TYPE: PRT
<213> ORGANISM: Artificial Sequence
<220> FEATURE:
<223> OTHER INFORMATION: synthetic peptide

<400> SEQUENCE: 940

Gln Gln Tyr Gly Thr Ser Pro Leu Thr
1               5

<210> SEQ ID NO 941
<211> LENGTH: 8
<212> TYPE: PRT
<213> ORGANISM: Artificial Sequence
<220> FEATURE:
<223> OTHER INFORMATION: synthetic peptide

<400> SEQUENCE: 941

Gly Phe Thr Phe Ser His Tyr Trp
1               5

<210> SEQ ID NO 942
<211> LENGTH: 8
<212> TYPE: PRT
<213> ORGANISM: Artificial Sequence
<220> FEATURE:
<223> OTHER INFORMATION: synthetic peptide

<400> SEQUENCE: 942

Ile Asn Gly Asn Gly Gly Ala Thr
1               5

<210> SEQ ID NO 943
<211> LENGTH: 12
<212> TYPE: PRT
<213> ORGANISM: Artificial Sequence
<220> FEATURE:
<223> OTHER INFORMATION: synthetic peptide

<400> SEQUENCE: 943

Val Gly Gly Ser Asn Asp Trp Val Gly Ile Asp Tyr
1               5                   10

<210> SEQ ID NO 944
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 944

Gln Ser Ile Arg Thr Phe
1               5

<210> SEQ ID NO 945
<211> LENGTH: 3
<212> TYPE: PRT
<213> ORGANISM: Artificial Sequence
<220> FEATURE:
<223> OTHER INFORMATION: synthetic peptide

<400> SEQUENCE: 945

Asp Ala Ser
1

<210> SEQ ID NO 946
<211> LENGTH: 9
<212> TYPE: PRT
<213> ORGANISM: Artificial Sequence
<220> FEATURE:
<223> OTHER INFORMATION: synthetic peptide

<400> SEQUENCE: 946

Gln Gln Ser Tyr Ser Ser Pro Leu Thr
1               5

<210> SEQ ID NO 947
<211> LENGTH: 8
<212> TYPE: PRT
<213> ORGANISM: Artificial Sequence
<220> FEATURE:
<223> OTHER INFORMATION: synthetic peptide

<400> SEQUENCE: 947

Gly Tyr Thr Phe Ile Asp Tyr Phe
1               5

<210> SEQ ID NO 948
<211> LENGTH: 8
<212> TYPE: PRT
<213> ORGANISM: Artificial Sequence
<220> FEATURE:
<223> OTHER INFORMATION: synthetic peptide

<400> SEQUENCE: 948

Ile Tyr Pro Lys Ser Gly Glu Thr
1               5

<210> SEQ ID NO 949
<211> LENGTH: 14
<212> TYPE: PRT
<213> ORGANISM: Artificial Sequence
<220> FEATURE:
<223> OTHER INFORMATION: synthetic peptide

<400> SEQUENCE: 949

Ala Arg Asp Ile Ala Pro Thr Gly Ala Trp Trp Phe Asp Ser
1               5                   10

<210> SEQ ID NO 950
<211> LENGTH: 7
<212> TYPE: PRT
<213> ORGANISM: Artificial Sequence
<220> FEATURE:
<223> OTHER INFORMATION: synthetic peptide
```

<400> SEQUENCE: 950

Gln Met Leu Ser Ser Ser Arg
1               5

<210> SEQ ID NO 951
<211> LENGTH: 3
<212> TYPE: PRT
<213> ORGANISM: Artificial Sequence
<220> FEATURE:
<223> OTHER INFORMATION: synthetic peptide

<400> SEQUENCE: 951

Gly Ala Ser
1

<210> SEQ ID NO 952
<211> LENGTH: 8
<212> TYPE: PRT
<213> ORGANISM: Artificial Sequence
<220> FEATURE:
<223> OTHER INFORMATION: synthetic peptide

<400> SEQUENCE: 952

Gln Gln Tyr Gly Ser Pro Arg Thr
1               5

<210> SEQ ID NO 953
<211> LENGTH: 8
<212> TYPE: PRT
<213> ORGANISM: Artificial Sequence
<220> FEATURE:
<223> OTHER INFORMATION: synthetic peptide

<400> SEQUENCE: 953

Gly Tyr Thr Phe Ile Ser Tyr Gly
1               5

<210> SEQ ID NO 954
<211> LENGTH: 8
<212> TYPE: PRT
<213> ORGANISM: Artificial Sequence
<220> FEATURE:
<223> OTHER INFORMATION: synthetic peptide

<400> SEQUENCE: 954

Ile Ser Ala Lys Asn Gly Asn Thr
1               5

<210> SEQ ID NO 955
<211> LENGTH: 10
<212> TYPE: PRT
<213> ORGANISM: Artificial Sequence
<220> FEATURE:
<223> OTHER INFORMATION: synthetic peptide

<400> SEQUENCE: 955

Ala Arg Asp Arg Thr Gly Thr Leu Asp Ser
1               5                   10

<210> SEQ ID NO 956
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 956

Gln Ser Ile Ser Asp Phe
1               5

<210> SEQ ID NO 957
<211> LENGTH: 3
<212> TYPE: PRT
<213> ORGANISM: Artificial Sequence
<220> FEATURE:
<223> OTHER INFORMATION: synthetic peptide

<400> SEQUENCE: 957

Thr Ala Ser
1

<210> SEQ ID NO 958
<211> LENGTH: 9
<212> TYPE: PRT
<213> ORGANISM: Artificial Sequence
<220> FEATURE:
<223> OTHER INFORMATION: synthetic peptide

<400> SEQUENCE: 958

Gln Gln Ser Tyr Ser Ala Pro Leu Thr
1               5

<210> SEQ ID NO 959
<211> LENGTH: 8
<212> TYPE: PRT
<213> ORGANISM: Artificial Sequence
<220> FEATURE:
<223> OTHER INFORMATION: synthetic peptide

<400> SEQUENCE: 959

Gly Tyr Thr Phe Ile Ala Phe Tyr
1               5

<210> SEQ ID NO 960
<211> LENGTH: 8
<212> TYPE: PRT
<213> ORGANISM: Artificial Sequence
<220> FEATURE:
<223> OTHER INFORMATION: synthetic peptide

<400> SEQUENCE: 960

Ile Asn Pro Tyr Ser Gly Asp Thr
1               5

<210> SEQ ID NO 961
<211> LENGTH: 24
<212> TYPE: PRT
<213> ORGANISM: Artificial Sequence
<220> FEATURE:
<223> OTHER INFORMATION: synthetic peptide

<400> SEQUENCE: 961

Ala Arg Thr Val Tyr Val Asp Lys Gly Met Val Met Val Arg Arg Leu
1               5                   10                  15

Tyr Gln Tyr Phe Gly Met Asp Val
            20

<210> SEQ ID NO 962
<211> LENGTH: 7
<212> TYPE: PRT
<213> ORGANISM: Artificial Sequence
<220> FEATURE:
```

```
<223> OTHER INFORMATION: synthetic peptide

<400> SEQUENCE: 962

Gln Ser Ile Ser Asn Asn Phe
1               5

<210> SEQ ID NO 963
<211> LENGTH: 3
<212> TYPE: PRT
<213> ORGANISM: Artificial Sequence
<220> FEATURE:
<223> OTHER INFORMATION: synthetic peptide

<400> SEQUENCE: 963

Ala Ser Ser
1

<210> SEQ ID NO 964
<211> LENGTH: 9
<212> TYPE: PRT
<213> ORGANISM: Artificial Sequence
<220> FEATURE:
<223> OTHER INFORMATION: synthetic peptide

<400> SEQUENCE: 964

Gln Gln Tyr Gly Thr Ser Pro Ala Thr
1               5

<210> SEQ ID NO 965
<211> LENGTH: 8
<212> TYPE: PRT
<213> ORGANISM: Artificial Sequence
<220> FEATURE:
<223> OTHER INFORMATION: synthetic peptide

<400> SEQUENCE: 965

Gly Phe Ile Phe Lys Thr Tyr Gly
1               5

<210> SEQ ID NO 966
<211> LENGTH: 8
<212> TYPE: PRT
<213> ORGANISM: Artificial Sequence
<220> FEATURE:
<223> OTHER INFORMATION: synthetic peptide

<400> SEQUENCE: 966

Ile Trp Tyr Asp Gly Ser Asn Glu
1               5

<210> SEQ ID NO 967
<211> LENGTH: 18
<212> TYPE: PRT
<213> ORGANISM: Artificial Sequence
<220> FEATURE:
<223> OTHER INFORMATION: synthetic peptide

<400> SEQUENCE: 967

Ala Arg Asp Glu Ala Val Gly Pro Tyr Gln Tyr Ala Ala Glu Tyr Phe
1               5                   10                  15

His His

<210> SEQ ID NO 968
<211> LENGTH: 11
<212> TYPE: PRT
<213> ORGANISM: Artificial Sequence
```

```
<220> FEATURE:
<223> OTHER INFORMATION: synthetic peptide

<400> SEQUENCE: 968

Gln Ser Leu Leu His Gly Asn Gly Tyr Asn Phe
1               5                   10

<210> SEQ ID NO 969
<211> LENGTH: 3
<212> TYPE: PRT
<213> ORGANISM: Artificial Sequence
<220> FEATURE:
<223> OTHER INFORMATION: synthetic peptide

<400> SEQUENCE: 969

Leu Gly Ser
1

<210> SEQ ID NO 970
<211> LENGTH: 9
<212> TYPE: PRT
<213> ORGANISM: Artificial Sequence
<220> FEATURE:
<223> OTHER INFORMATION: synthetic peptide

<400> SEQUENCE: 970

Met Gln Ala Leu Gln Thr Pro Trp Thr
1               5

<210> SEQ ID NO 971
<211> LENGTH: 8
<212> TYPE: PRT
<213> ORGANISM: Artificial Sequence
<220> FEATURE:
<223> OTHER INFORMATION: synthetic peptide

<400> SEQUENCE: 971

Gly Phe Thr Phe Ser Gly His Tyr
1               5

<210> SEQ ID NO 972
<211> LENGTH: 10
<212> TYPE: PRT
<213> ORGANISM: Artificial Sequence
<220> FEATURE:
<223> OTHER INFORMATION: synthetic peptide

<400> SEQUENCE: 972

Ile Arg Asp Gln Pro His Lys Tyr Ser Thr
1               5                   10

<210> SEQ ID NO 973
<211> LENGTH: 18
<212> TYPE: PRT
<213> ORGANISM: Artificial Sequence
<220> FEATURE:
<223> OTHER INFORMATION: synthetic peptide

<400> SEQUENCE: 973

Ala Arg Ala Pro Phe Tyr Asp Thr Thr Gly Tyr Ser Leu Asp Ala Leu
1               5                   10                  15

Asp Ile

<210> SEQ ID NO 974
<211> LENGTH: 6
<212> TYPE: PRT
```

<213> ORGANISM: Artificial Sequence
<220> FEATURE:
<223> OTHER INFORMATION: synthetic peptide

<400> SEQUENCE: 974

Gln Ser Val Ser Ser Asn
1               5

<210> SEQ ID NO 975
<211> LENGTH: 3
<212> TYPE: PRT
<213> ORGANISM: Artificial Sequence
<220> FEATURE:
<223> OTHER INFORMATION: synthetic peptide

<400> SEQUENCE: 975

Gly Ala Ser
1

<210> SEQ ID NO 976
<211> LENGTH: 10
<212> TYPE: PRT
<213> ORGANISM: Artificial Sequence
<220> FEATURE:
<223> OTHER INFORMATION: synthetic peptide

<400> SEQUENCE: 976

Gln His Tyr Ile Asn Arg Pro Gly Arg Thr
1               5                   10

<210> SEQ ID NO 977
<211> LENGTH: 8
<212> TYPE: PRT
<213> ORGANISM: Artificial Sequence
<220> FEATURE:
<223> OTHER INFORMATION: synthetic peptide

<400> SEQUENCE: 977

Gly Phe Ser Phe Ser Asn Tyr Glu
1               5

<210> SEQ ID NO 978
<211> LENGTH: 8
<212> TYPE: PRT
<213> ORGANISM: Artificial Sequence
<220> FEATURE:
<223> OTHER INFORMATION: synthetic peptide

<400> SEQUENCE: 978

Ile Ser Ser Gly Ser Ser Tyr Arg
1               5

<210> SEQ ID NO 979
<211> LENGTH: 12
<212> TYPE: PRT
<213> ORGANISM: Artificial Sequence
<220> FEATURE:
<223> OTHER INFORMATION: synthetic peptide

<400> SEQUENCE: 979

Ala Arg Gln Asp Asn Ser Gly Arg Pro Phe Ser His
1               5                   10

<210> SEQ ID NO 980
<211> LENGTH: 6
<212> TYPE: PRT
<213> ORGANISM: Artificial Sequence

```
<220> FEATURE:
<223> OTHER INFORMATION: synthetic peptide

<400> SEQUENCE: 980

Gln Gly Ile Ser Asn Ser
1               5

<210> SEQ ID NO 981
<211> LENGTH: 3
<212> TYPE: PRT
<213> ORGANISM: Artificial Sequence
<220> FEATURE:
<223> OTHER INFORMATION: synthetic peptide

<400> SEQUENCE: 981

Ala Ala Ser
1

<210> SEQ ID NO 982
<211> LENGTH: 10
<212> TYPE: PRT
<213> ORGANISM: Artificial Sequence
<220> FEATURE:
<223> OTHER INFORMATION: synthetic peptide

<400> SEQUENCE: 982

Gln Gln Tyr Tyr Ser Thr Pro Pro Ile Thr
1               5                   10

<210> SEQ ID NO 983
<211> LENGTH: 8
<212> TYPE: PRT
<213> ORGANISM: Artificial Sequence
<220> FEATURE:
<223> OTHER INFORMATION: synthetic peptide

<400> SEQUENCE: 983

Gly Phe Thr Phe Ser Ser His Ala
1               5

<210> SEQ ID NO 984
<211> LENGTH: 8
<212> TYPE: PRT
<213> ORGANISM: Artificial Sequence
<220> FEATURE:
<223> OTHER INFORMATION: synthetic peptide

<400> SEQUENCE: 984

Ile Ser Tyr Asp Gly Ser Asn Lys
1               5

<210> SEQ ID NO 985
<211> LENGTH: 10
<212> TYPE: PRT
<213> ORGANISM: Artificial Sequence
<220> FEATURE:
<223> OTHER INFORMATION: synthetic peptide

<400> SEQUENCE: 985

Val Arg Trp Val Ala Tyr Tyr Phe Asp Asn
1               5                   10

<210> SEQ ID NO 986
<211> LENGTH: 7
<212> TYPE: PRT
<213> ORGANISM: Artificial Sequence
<220> FEATURE:
```

```
<223> OTHER INFORMATION: synthetic peptide

<400> SEQUENCE: 986

Gln Ser Val Ser Ser Ser
1               5

<210> SEQ ID NO 987
<211> LENGTH: 3
<212> TYPE: PRT
<213> ORGANISM: Artificial Sequence
<220> FEATURE:
<223> OTHER INFORMATION: synthetic peptide

<400> SEQUENCE: 987

Gly Thr Ser
1

<210> SEQ ID NO 988
<211> LENGTH: 10
<212> TYPE: PRT
<213> ORGANISM: Artificial Sequence
<220> FEATURE:
<223> OTHER INFORMATION: synthetic peptide

<400> SEQUENCE: 988

Gln Tyr Tyr Gly Ser Leu Pro Pro Ile Thr
1               5                   10

<210> SEQ ID NO 989
<211> LENGTH: 8
<212> TYPE: PRT
<213> ORGANISM: Artificial Sequence
<220> FEATURE:
<223> OTHER INFORMATION: synthetic peptide

<400> SEQUENCE: 989

Gly Asp Ser Ile Ser Ser Tyr Tyr
1               5

<210> SEQ ID NO 990
<211> LENGTH: 7
<212> TYPE: PRT
<213> ORGANISM: Artificial Sequence
<220> FEATURE:
<223> OTHER INFORMATION: synthetic peptide

<400> SEQUENCE: 990

Ile Ser Tyr Thr Gly Ser Thr
1               5

<210> SEQ ID NO 991
<211> LENGTH: 14
<212> TYPE: PRT
<213> ORGANISM: Artificial Sequence
<220> FEATURE:
<223> OTHER INFORMATION: synthetic peptide

<400> SEQUENCE: 991

Ala Arg Leu Gly Tyr Ser His Pro Tyr Trp Tyr Phe Asp Leu
1               5                   10

<210> SEQ ID NO 992
<211> LENGTH: 6
<212> TYPE: PRT
<213> ORGANISM: Artificial Sequence
<220> FEATURE:
<223> OTHER INFORMATION: synthetic peptide
```

```
<400> SEQUENCE: 992

Gln Ser Ile Ser Asn Phe
1               5

<210> SEQ ID NO 993
<211> LENGTH: 3
<212> TYPE: PRT
<213> ORGANISM: Artificial Sequence
<220> FEATURE:
<223> OTHER INFORMATION: synthetic peptide

<400> SEQUENCE: 993

Ala Ala Ser
1

<210> SEQ ID NO 994
<211> LENGTH: 10
<212> TYPE: PRT
<213> ORGANISM: Artificial Sequence
<220> FEATURE:
<223> OTHER INFORMATION: synthetic peptide

<400> SEQUENCE: 994

Gln Gln Ser Tyr Ser Pro Pro Leu Ile Thr
1               5                   10

<210> SEQ ID NO 995
<211> LENGTH: 8
<212> TYPE: PRT
<213> ORGANISM: Artificial Sequence
<220> FEATURE:
<223> OTHER INFORMATION: synthetic peptide

<400> SEQUENCE: 995

Gly Phe Thr Phe Ser Arg Tyr Trp
1               5

<210> SEQ ID NO 996
<211> LENGTH: 8
<212> TYPE: PRT
<213> ORGANISM: Artificial Sequence
<220> FEATURE:
<223> OTHER INFORMATION: synthetic peptide

<400> SEQUENCE: 996

Ile Glu Ala Asp Gly Ser Val Lys
1               5

<210> SEQ ID NO 997
<211> LENGTH: 18
<212> TYPE: PRT
<213> ORGANISM: Artificial Sequence
<220> FEATURE:
<223> OTHER INFORMATION: synthetic peptide

<400> SEQUENCE: 997

Ala Arg Asp Ala Asn Tyr His Asp Gly Ser Ala Tyr Tyr Asp Ala Phe
1               5                   10                  15

Asp Val

<210> SEQ ID NO 998
<211> LENGTH: 6
<212> TYPE: PRT
<213> ORGANISM: Artificial Sequence
<220> FEATURE:
```

<223> OTHER INFORMATION: synthetic peptide

<400> SEQUENCE: 998

Gln Ala Ile Arg Asn Asp
1               5

<210> SEQ ID NO 999
<211> LENGTH: 3
<212> TYPE: PRT
<213> ORGANISM: Artificial Sequence
<220> FEATURE:
<223> OTHER INFORMATION: synthetic peptide

<400> SEQUENCE: 999

Gly Ala Ser
1

<210> SEQ ID NO 1000
<211> LENGTH: 9
<212> TYPE: PRT
<213> ORGANISM: Artificial Sequence
<220> FEATURE:
<223> OTHER INFORMATION: synthetic peptide

<400> SEQUENCE: 1000

Leu Gln Asp Tyr Asn Tyr Pro Arg Thr
1               5

<210> SEQ ID NO 1001
<211> LENGTH: 8
<212> TYPE: PRT
<213> ORGANISM: Artificial Sequence
<220> FEATURE:
<223> OTHER INFORMATION: synthetic peptide

<400> SEQUENCE: 1001

Gly Tyr Ser Phe Ser Ala His Ala
1               5

<210> SEQ ID NO 1002
<211> LENGTH: 8
<212> TYPE: PRT
<213> ORGANISM: Artificial Sequence
<220> FEATURE:
<223> OTHER INFORMATION: synthetic peptide

<400> SEQUENCE: 1002

Ile Asn Gly Gly Asn Gly Asn Thr
1               5

<210> SEQ ID NO 1003
<211> LENGTH: 21
<212> TYPE: PRT
<213> ORGANISM: Artificial Sequence
<220> FEATURE:
<223> OTHER INFORMATION: synthetic peptide

<400> SEQUENCE: 1003

Ala Arg His Leu Pro Glu Pro Trp Asn Tyr Tyr Asp Ser Ser Gly Tyr
1               5                   10                  15

Phe Gly Phe Asp Tyr
            20

<210> SEQ ID NO 1004
<211> LENGTH: 6
<212> TYPE: PRT

```
<213> ORGANISM: Artificial Sequence
<220> FEATURE:
<223> OTHER INFORMATION: synthetic peptide

<400> SEQUENCE: 1004

Gln Ser Val Ser Asn Tyr
1               5

<210> SEQ ID NO 1005
<211> LENGTH: 3
<212> TYPE: PRT
<213> ORGANISM: Artificial Sequence
<220> FEATURE:
<223> OTHER INFORMATION: synthetic peptide

<400> SEQUENCE: 1005

Tyr Thr Ser
1

<210> SEQ ID NO 1006
<211> LENGTH: 9
<212> TYPE: PRT
<213> ORGANISM: Artificial Sequence
<220> FEATURE:
<223> OTHER INFORMATION: synthetic peptide

<400> SEQUENCE: 1006

Gln Gln Arg Tyr Asn Trp Pro Leu Thr
1               5

<210> SEQ ID NO 1007
<211> LENGTH: 8
<212> TYPE: PRT
<213> ORGANISM: Artificial Sequence
<220> FEATURE:
<223> OTHER INFORMATION: synthetic peptide

<400> SEQUENCE: 1007

Gly Phe Thr Phe Ser Asp Tyr Tyr
1               5

<210> SEQ ID NO 1008
<211> LENGTH: 8
<212> TYPE: PRT
<213> ORGANISM: Artificial Sequence
<220> FEATURE:
<223> OTHER INFORMATION: synthetic peptide

<400> SEQUENCE: 1008

Ile Ser Gly Ser Gly Lys Ile Thr
1               5

<210> SEQ ID NO 1009
<211> LENGTH: 15
<212> TYPE: PRT
<213> ORGANISM: Artificial Sequence
<220> FEATURE:
<223> OTHER INFORMATION: synthetic peptide

<400> SEQUENCE: 1009

Ala Arg Val Gln Gly Glu Gln Trp Arg Gly Leu His Phe Asp Ser
1               5                   10                  15

<210> SEQ ID NO 1010
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 1010

Gln Asp Ile Ser Asn Tyr
1               5

<210> SEQ ID NO 1011
<211> LENGTH: 3
<212> TYPE: PRT
<213> ORGANISM: Artificial Sequence
<220> FEATURE:
<223> OTHER INFORMATION: synthetic peptide

<400> SEQUENCE: 1011

Asp Ala Ser
1

<210> SEQ ID NO 1012
<211> LENGTH: 8
<212> TYPE: PRT
<213> ORGANISM: Artificial Sequence
<220> FEATURE:
<223> OTHER INFORMATION: synthetic peptide

<400> SEQUENCE: 1012

Gln His Arg Ser Asn Trp Pro Ala
1               5

<210> SEQ ID NO 1013
<211> LENGTH: 8
<212> TYPE: PRT
<213> ORGANISM: Artificial Sequence
<220> FEATURE:
<223> OTHER INFORMATION: synthetic peptide

<400> SEQUENCE: 1013

Gly Phe Arg Phe Gly Asp Tyr Ala
1               5

<210> SEQ ID NO 1014
<211> LENGTH: 8
<212> TYPE: PRT
<213> ORGANISM: Artificial Sequence
<220> FEATURE:
<223> OTHER INFORMATION: synthetic peptide

<400> SEQUENCE: 1014

Ile Asn Trp Asp Ser Gly Asp Ile
1               5

<210> SEQ ID NO 1015
<211> LENGTH: 23
<212> TYPE: PRT
<213> ORGANISM: Artificial Sequence
<220> FEATURE:
<223> OTHER INFORMATION: synthetic peptide

<400> SEQUENCE: 1015

Ala Lys Asp Ser Gly Trp Leu Arg Arg Gly Asp Tyr Asp Thr Ser Gly
1               5                   10                  15

Phe Tyr Gly Pro Ile Asp Tyr
            20

<210> SEQ ID NO 1016
<211> LENGTH: 6
```

```
<212> TYPE: PRT
<213> ORGANISM: Artificial Sequence
<220> FEATURE:
<223> OTHER INFORMATION: synthetic peptide

<400> SEQUENCE: 1016

Gln Tyr Ile Ser Thr Tyr
1               5

<210> SEQ ID NO 1017
<211> LENGTH: 3
<212> TYPE: PRT
<213> ORGANISM: Artificial Sequence
<220> FEATURE:
<223> OTHER INFORMATION: synthetic peptide

<400> SEQUENCE: 1017

Ser Ala Ser
1

<210> SEQ ID NO 1018
<211> LENGTH: 9
<212> TYPE: PRT
<213> ORGANISM: Artificial Sequence
<220> FEATURE:
<223> OTHER INFORMATION: synthetic peptide

<400> SEQUENCE: 1018

Gln Gln Ser Tyr Gly Thr Leu Leu Thr
1               5
```